(12) United States Patent
Stephan et al.

(10) Patent No.: US 9,092,391 B2
(45) Date of Patent: Jul. 28, 2015

(54) GENETIC ANALYSIS SYSTEMS AND METHODS

(75) Inventors: Dietrich A. Stephan, Phoenix, AZ (US); Melissa Floren Filippone, New York, NY (US); Jennifer Wessel, San Francisco, CA (US); Michele Cargill, Orinda, CA (US); Eran Halperin, Berkeley, CA (US)

(73) Assignee: Navigenics, Inc., Carlsbad, CA (US)

( * ) Notice: Subject to any disclaimer, the term of this patent is extended or adjusted under 35 U.S.C. 154(b) by 1060 days.

(21) Appl. No.: 12/516,915

(22) PCT Filed: Nov. 30, 2007

(86) PCT No.: PCT/US2007/086138
§ 371 (c)(1),
(2), (4) Date: Jun. 24, 2010

(87) PCT Pub. No.: WO2008/067551
PCT Pub. Date: Jun. 5, 2008

(65) Prior Publication Data
US 2010/0293130 A1    Nov. 18, 2010

Related U.S. Application Data

(63) Continuation of application No. 11/781,679, filed on Jul. 23, 2007, now abandoned.

(60) Provisional application No. 60/868,066, filed on Nov. 30, 2006, provisional application No. 60/951,123, filed on Jul. 20, 2007, provisional application No. 60/972,198, filed on Sep. 13, 2007, provisional application No. 60/985,622, filed on Nov. 5, 2007, provisional application No. 60/989,685, filed on Nov. 21, 2007.

(51) Int. Cl.
*G01N 33/50* (2006.01)
*G06F 19/18* (2011.01)
*G06F 19/28* (2011.01)

(52) U.S. Cl.
CPC ........... *G06F 19/18* (2013.01); *G06F 19/28* (2013.01)

(58) Field of Classification Search
None
See application file for complete search history.

(56) References Cited

U.S. PATENT DOCUMENTS

| | | | |
|---|---|---|---|
| 5,612,179 | A | 3/1997 | Simons |
| 5,958,684 | A | 9/1999 | Van Leeuwen et al. |
| 6,640,211 | B1 | 10/2003 | Holden |
| 6,703,228 | B1 | 3/2004 | Landers et al. |
| 6,955,883 | B2 | 10/2005 | Margus et al. |
| 7,072,794 | B2 | 7/2006 | Wittkowski |
| 7,401,026 | B2 | 7/2008 | Holden |
| 2002/0095585 | A1 | 7/2002 | Scott |
| 2002/0128860 | A1 | 9/2002 | Leveque et al. |
| 2002/0133495 | A1* | 9/2002 | Rienhoff et al. ............. 707/100 |
| 2002/0187474 | A1 | 12/2002 | Comings et al. |
| 2003/0040002 | A1 | 2/2003 | Ledley |
| 2003/0046110 | A1 | 3/2003 | Gogolak |
| 2003/0054381 | A1 | 3/2003 | Affourtit et al. |
| 2003/0104453 | A1 | 6/2003 | Pickar et al. |
| 2003/0108938 | A1 | 6/2003 | Pickar et al. |
| 2003/0135096 | A1 | 7/2003 | Dodds |
| 2003/0208454 | A1 | 11/2003 | Rienhoff et al. |
| 2003/0219776 | A1 | 11/2003 | Lalouel et al. |
| 2004/0002818 | A1 | 1/2004 | Kulp et al. |
| 2004/0115701 | A1 | 6/2004 | Comings et al. |
| 2004/0121320 | A1 | 6/2004 | DePhillipo et al. |
| 2005/0037366 | A1 | 2/2005 | Gut et al. |
| 2005/0064476 | A1 | 3/2005 | Huang et al. |
| 2005/0177397 | A1 | 8/2005 | Kane |
| 2005/0196770 | A1 | 9/2005 | Cox et al. |
| 2005/0209787 | A1 | 9/2005 | Waggener et al. |
| 2005/0214811 | A1* | 9/2005 | Margulies et al. ............... 435/6 |
| 2005/0243551 | A1 | 11/2005 | Onishi et al. |
| 2005/0272054 | A1 | 12/2005 | Cargill et al. |
| 2006/0046256 | A1 | 3/2006 | Halldorsson et al. |
| 2006/0051763 | A1 | 3/2006 | Loukola et al. |
| 2006/0160074 | A1 | 7/2006 | Dorn et al. |
| 2006/0166224 | A1 | 7/2006 | Norviel |
| 2006/0184489 | A1 | 8/2006 | Weiner et al. |
| 2006/0188875 | A1 | 8/2006 | Cox et al. |
| 2006/0240428 | A1 | 10/2006 | Itakura et al. |
| 2006/0257888 | A1 | 11/2006 | Zabeau et al. |
| 2006/0278241 | A1 | 12/2006 | Ruano |
| 2007/0122824 | A1 | 5/2007 | Tucker et al. |
| 2007/0196344 | A1 | 8/2007 | Osborne et al. |

(Continued)

FOREIGN PATENT DOCUMENTS

| | | |
|---|---|---|
| CA | 2671267 | 6/2008 |
| EP | 1684202 A1 | 7/2006 |

(Continued)

OTHER PUBLICATIONS

Amundsen et al., Genetic analysis of the CD28/CTLA4/ICOS (CELIAC3) region in coeliac disease, Tissue Antigens, published online Oct. 20, 2004, vol. 64, Issue 5, pp. 593-599.*

(Continued)

*Primary Examiner* — Jason Sims

(57) ABSTRACT

The present invention provides methods of determining a Genetic Composite Index score by assessing the association between an individual's genotype and at least one disease or condition. The assessment comprises comparing an individual's genomic profile with a database of medically relevant genetic variations that have been established to associate with at least one disease or condition.

21 Claims, 87 Drawing Sheets

(56) References Cited

U.S. PATENT DOCUMENTS

| | | |
|---|---|---|
| 2007/0254289 A1 | 11/2007 | Li et al. |
| 2008/0004848 A1 | 1/2008 | Avey |
| 2008/0108713 A1* | 5/2008 | Begovich et al. ............. 514/789 |
| 2008/0131887 A1 | 6/2008 | Stephan et al. |
| 2008/0261220 A1* | 10/2008 | Cracauer et al. ................. 435/6 |
| 2009/0099789 A1 | 4/2009 | Stephan et al. |
| 2009/0182579 A1 | 7/2009 | Liu |
| 2009/0198519 A1 | 8/2009 | Mcnamar |
| 2010/0042438 A1 | 2/2010 | Moore et al. |
| 2010/0070455 A1 | 3/2010 | Halperin et al. |

FOREIGN PATENT DOCUMENTS

| | | |
|---|---|---|
| GB | 2444410 | 6/2008 |
| JP | 200067139 | 3/2000 |
| JP | 2002107366 A | 4/2002 |
| JP | 2006500016 | 1/2006 |
| JP | 2010522537 | 7/2010 |
| WO | WO 96/32502 A1 | 10/1996 |
| WO | WO-01/16860 | 3/2001 |
| WO | WO 01/16860 A2 | 3/2001 |
| WO | WO-01/26029 | 4/2001 |
| WO | WO 01/26029 A2 | 4/2001 |
| WO | WO 01/16860 A3 | 6/2001 |
| WO | WO 01/26029 A3 | 3/2002 |
| WO | WO 02/063415 A2 | 8/2002 |
| WO | WO 02/086663 A2 | 10/2002 |
| WO | WO 02/086663 A3 | 5/2003 |
| WO | WO 02/063415 A3 | 8/2003 |
| WO | WO-2004/020968 | 3/2004 |
| WO | WO 2004/072887 A2 | 8/2004 |
| WO | WO-2004/109551 | 12/2004 |
| WO | WO 2004/072887 A3 | 12/2005 |
| WO | WO-2006/008045 | 1/2006 |
| WO | WO-2006/053955 | 5/2006 |
| WO | WO 2006/065658 A2 | 6/2006 |
| WO | WO 2006/065658 A3 | 11/2007 |
| WO | WO 2008/067551 A2 | 6/2008 |
| WO | WO 2008/067551 A3 | 12/2008 |
| WO | WO 2009/023360 A2 | 2/2009 |
| WO | WO 2009/023360 A3 | 8/2009 |

OTHER PUBLICATIONS

Office action dated Feb. 15, 2011 for U.S. Appl. No. 11/781,679.
Office action dated Mar. 30, 2010 for U.S. Appl. No. 11/781,679.
Office action dated Jun. 15, 2009 for U.S. Appl. No. 11/781,679.
Office action dated Sep. 13, 2011 for U.S. Appl. No. 12/239,718.
Office action dated Nov. 15, 2011 for U.S. Appl. No. 12/538,064.
International preliminary report on patentability dated Feb. 17, 2011 for PCT Application No. US09/053216.
International search report dated Jan. 4, 2010 for PCT Application No. US2009/56720.
Jin, et al. Combined effects of HLA-Cw6 and cigarette smoking in psoriasis vulgaris: a hospital-based case-control study in China. J Eur Acad Dermatol Venereol. Feb. 2009;23(2):132-7.
Demchuck, et al. A statistical model for assessing genetic susceptibility as a risk factor in multifactorial diseases: lessons from occupational asthma. Environ Health Perspect. Feb. 2007;115(2):231-4.
Office action with search report dated Apr. 12, 2011 for Taiwanese application 096148586. (in Chinese with English summary).
Office action dated Mar. 28, 2012 for U.S. Appl. No. 11/781,679.
Office action dated Apr. 11, 2012 for U.S. Appl. No. 12/239,718.
Singapore search report and written opinion dated May 20, 2011 for Singapore Application No. 200903655-9.
Arking, et al. A common genetic variant in the NOS1 regulator NOS1AP modulates cardiac repolarization. Nature Genet. 2006; 38(6): 644-651.
Baker, et al. Association of an extended haplotype in the tau gene with progressive supranuclear palsy. Hum Molec Genet. 1999; 8(4): 711-5.
Begovich, et al. A Missense Single-Nucleotide Polymorphism in a Gene Encoding a Protein Tyrosine Phosphatase (PTPN22) is Associated with Rheumatoid Arthritis. Am. J. Hum. Genet. 2004; 75: 330-337.
Bertina, et al. Mutation in blood coagulation factor V associated with resistance to activated protein C. Nature. 1994; 369(6475): 64-67.
Bottini, et al. A functional variant of lymphoid tyrosine phosphatase is associated with type I diabetes. Nature Genet. 2004; 36(4): 337-338.
Brenner, S. Common sense for our genomes. Nature. 2007; 449: 783-784.
Breslin, et al. Monozygotic twins with Crohn's disease and ulcerative colitis: a unique case report. Gut. 1997; 41: 557-560.
Casas, et al. Endothelial Nitric Oxide Synthase Genotype and Ischemic Heart Disease: Meta-Analysis of 26 Studies Involving 23028 Subjects. Circulation. 2004; 109: 1359-1365.
Coon, et al. A High Density Whole-Genome Association Study Reveals that APOE is the Major Susceptibility Gene for Sporadic Late-Onset Alzheimer's Disease. Psychiatry. 2007; 68:4: 613-618.
Corder, et al. Gene dose of apolipoprotein E type 4 allele and the risk of Alzheimer's disease in late onset families. Science. 1993; 261: 921-923.
Cox, et al. A common coding variant in CASP8 is associated with breast cancer risk. Nature Genetics. 2007; 39(3): 352-358, 688.
Crocq, et al. Association between schizophrenia and homozygosity at the dopamine D3 receptor gene. J Med Genet. 1992; 29: 858-860.
Dequervain, et al. Indentification of a genetic cluster influencing memory performance and hippocampal activity in humans. PNAS 2006; 103(11): 4270-4274.
Doh-Ura, et al. Pro→Leu change at position 102 of prion protein is the most common but not the sole mutation related to Gerstmann-Sträussler syndrome. Biochem Biophys Res Commun. 1989; 163(2): 974-979.
Duerr, et al. A genome-wide association study identifies IL23R as an inflammatory bowel disease gene. Science. 2006; 314(5804): 1461-1463.
Dunsworth, et al. Heterogeneity of insulin-dependent diabetes—new evidence. Clin Genet. 1982; 21: 233-236.
Easton, et al. Genome-wide association study identifies novel breast cancer susceptibility loci. Nature. 2007; 447(28): 1087-1095.
Farrer, et al. Effects of age, sex, and ethnicity on the association between apolipoprotein E genotype and Alzheimer's disease. A meta-analysis. JAMA. 1997; 278(16): 1349-1356.
Fernandez-Arquero, et al. Primary association of a TNF gene polymorphism with susceptibility to multiple sclerosis. Neurology. 1999; 53: 1361-1363.
Frayling, et al. A Common Variant in the FTO Gene is Associated with Body Mass Index and Predisposes to Childhood and Adult Obesity. Scienceexpress. 2007; 1-5 and four unnumbered pages.
Gatz, et al. Role of Genese and Environments for Explaining Alzheimer Disease. Arch Gen Psychiatry. 2006; 63: 168-174.
Graham, et al. A common haplotype of interferon regulatory factor 5 (IRF5) regulates splicing and expression and is associated with increased risk of systemic lupus erythematosus. Nature Genet. 2006; 38: 550-555.
Grant, et al. Reduced bone density and osteoporosis associated with a polymorphic Sp1 binding site in the collagen type I α 1 gene. Nature Genet. 1996; 14: 203-205.
Grant, et al. Variant of transcription factor 7-like 2 (TCF7L2) gene confers risk of type 2 diabetes. Nature Genet. 2006; 38: 320-323.
Greco, et al. The first large population based twin study of coeliac disease. Gut. 2002; 50: 624-628.
Green, et al. The association of HLA-linked genes with systemic lupus erythematosus. Ann Hum Genet. 1986; 50: 93-96.
Greenbaum, et al. Islet cell antibody-positive relatives with human leukocyte antigen DQA1*0102, DQB1*0602: Identification by the diabetes prevention trial-type 1. J Clin Endocr Metab. 2000; 85(3): 1255-1260.
Gregersen, et al. Functional epistasis on a common MHC haplotype associated with multiple sclerosis. Nature. 2006; 443: 574-577.
Gudmundsson, et al. Genome-wide association study identifies a second prostate cancer susceptibility variant at 8q24. Nature Genetics. 2007; 1-7.

(56) References Cited

OTHER PUBLICATIONS

Haddad, et al. The Genetics of Age-Related Macular Degeneration: A Review of Progress to Date. Survey of Ophthalmology. 2006; 51(4): 316-363.

Haiman, et al. Multiple regions within 8q24 independently affect risk for prostate cancer. Nature Genetics. 2007; 1-7.

Healey, et al. A common variant in BRCA2 is associated with both breast cancer risk and prenatal viability. Nature Genet. 2000; 26: 362-364.

Helgadottir, et al. A common variant on chromosome 9p21 affects the risk of myocardial infarction. Science. 2007; 316(5830):1491-1493.

Heward, et al. Linkage disequilibrium between the human leukocyte antigen class II region of the major histocompatibility complex and Graves' disease: Replication using a population case control and family-based study. J Clin Endocr Metab. 1998; 83(10): 3394-3397.

Hinds, et al. Whole-genome patterns of common DNA variation in three human populations. Science. 2005; 307(5712): 1072-1079.

Hugot, et al. Association of NOD2 leucine-rich repeat variants with susceptibility to Crohn's disease. Nature. 2001; 411: 599-603.

Hunt, et al. A common CTLA4 haplotype associated with coeliac disease. European Journal of Human Genetics. 2005; 440-444.

International Hapmap Consortium. A haplotype of the human genome. Nature. 2005; 437(7036): 1299-1320.

Klein, et al. Complement factor H polymorphism in age-related macular degeneration. Science. 2005; 308: 385-389.

Kubo, et al. A nonsynonymous SNP in PRKCH (protein kinase C η) increases the risk of cerebral infarction. Nature Genetics. 2007; 39(2): 212-217.

Laken, et al. Familial colorectal cancer in Ashkenazim due to a hypermutable tract in APC. Nature Genet. 1997; 17: 79-83.

Lichtenstein, et al. Environmental and Heritable Factors in the Causation of Cancer. The New England Journal of Medicine. 2000; 343(2): 78-85.

Locatelli, et al. The Heritability of Breast Cancer: a Bayesian Correlated Frailty Model Applied to Swedish Twins Data. Twin Research. 2003; 7(2): 182-191.

MacGregor, et al. Characterizing the Quantitative Genetic Contribution to Rheumatoid Arthritis Using Data From Twins. Arthritis & Rheumatism. 2000; 43(1): 30-37.

Maller, et al. Common variation in three genes, including a noncoding variant in CFH strongly influences risk of age-related macular degeneration. Nature Genetics. 2006; 38(9): 1055-1059.

McGuffin, et al. The Heritability of Bipolar Affective Disorder and the Genetic Relationship to Unipolar Depression. Arch Gen Psychiatry. 2003; 60: 497-502.

McPherson, et al. A Common Allele on Chromosome 9 Associated with Coronary Heart Disease. Science. 2007; 316: 1488-1491.

Michou, et al. Validation of the reshaped shared epitope HLA-DRB1 classification in rheumatoid arthritis. Arthritis Res Ther. 2006; 8(3): 1-6.

Miyamoto, et al. A functional polymorphism in the 5' UTR of GDF5 is associated with susceptibility to osteoarthritis. Nature Genetics. 2007; 39(4): 529-533.

Nisticò, et al. The CTLA-4 gene region of chromosome 2q33 is linked to, and associated with, type 1 diabetes. Hum Molec Genet. 1996; 5: 1075-1080.

Nisticò, et al., Concordance, disease progression, and heritability of coeliac disease in Italian twins. Gut. 2006; 55: 803-808.

Page, et al. Heredity and Prostate Cancer: A Study of World War II Veteran Twins. The Prostate. 1997; 33: 240-245.

Page, et al. Primary Osteoarthritis of the Hip in Monozygotic and Dizygotic Male Twins. Twin Research. 2003; 6(2): 147-151.

Papassotiropoulos, et al. Common Kibra alleles are associated with human memory performance. Science. 2006; 314: 475-478.

Pugliese, et al. The insulin gene is transcribed in the human thymus and transcription levels correlate with allelic variation at the INS VNTR-IDDM2 susceptibility locus for type 1 diabetes. Nature Genet. 1997; 15: 293-297.

Reiman, et al. GAB2 Alleles Modify Alzheimer's Risk in APOE g4 Carriers. Neuron. 2007; 54: 713-720.

Roberts, et al. Personalized Genomic Medicine: a Future Prerequisite for the Prevention of Coronary Artery Disease. Am Heart Hosp J. 2006; 4: 222-227.

Samson, et al. Resistance to HIV-1 infection in caucasian individuals-bearing mutant alleles of the CCR-5 chemokine receptor gene. Nature. 1996; 382: 722-725.

Scott, et al. A Genome-Wide Association Study of Type 2 Diabetes in Finns Detects Multiple Susceptibility Variants. Science. 2007; 316: 1341-1345.

Sladek, et al. A genome-wide association study identifies novel risk loci for type 2 diabetes. Nature. 2007; 445: 881-885.

Smyth, et al. A genome-wide association study of nonsynonymous SNPs identifies a type 1 diabetes locus in the interferon-induced helicase (IFIH1) region. Nature Genet. 2006; 38: 617-619.

Stacey, et al. Common variants on chromosomes 2q35 and 16q12 confer susceptibility to estrogen receptor-positive breast cancer. Nature Genetics. 2007; 39: 865-869.

Steinthorsdottir, et al. A variant in CDKAL1 influences insulin response and risk of type 2 diabetes. Nature Genetics. 2007; 39(6): 770-775.

Tambs, et al. Genetic and Environmental Contributions to the Variance of the Body Mass Index in a Norwegian Sample of First- and Second-Degree Relatives. American Journal of Human Biology. 1991; 3: 257-267.

Thorisson, et al. A User's Guide to the International HapMap Project Web Site. International Haplotype Map Project. 2003; 1-11.

Topol, et al. Single Nucleotide Polymorphisms in Multiple Novel Thrombosponding Genes May Be Associated With Familial Premature Myocardial Infarction. Circulation. 2001; 104: 2641-2644.

Van Heel, et al. A genome-wide association study for celiac disease identifies risk variants in the region harboring IL2 and IL21. Nature Genetics. 2007; 39(7): 827-829.

Van Tilburg, et al. Defining the genetic contribution of type 2 diabetes mellitus. J. Med. Genet. 2001; 38: 569-578.

Walsh, et al. An integrated haplotype map of the human major histocompatibility complex. Am J Hum Genet. 2003; 73: 580-590.

Wellcome Trust Case Control Consortium, The Genome-wide association study of 14,000 cases of seven common diseases and 3,000 shared controls. Nature. 2007; 447: 661-678.

Witte, J. S. Multiple prostate cancer risk variants on 8q24. Nature Genetics. 2007; 39(5): 579-580.

Yeager, et al. Genome-wide association study of prostate cancer identifies a second risk locus at 8q24, Nature Genetics. 2007; 1-5.

Yoshida, et al. Determination of genotypes of human aldehyde dehydrogenase ALDH2 locus. Am J Hum Genet. 1983; 35: 1107-1116.

Zdravkovic, S. Coronary Heart Disease in Swedish Twins: Quantitative Genetic Studies. Karolinska Institutet. 2006; 1-39.

Zeggini, et al. Replication of Genome-Wide Association Signals in UK Samples Reveals Risk Loci for Type 2 Diabetes. 2007; 316: 1336-1341.

Zhai, et al. Genetic influence on the progression of radiographic knee osteoarthritis: a longitudinal twin study. OsteoArthritis and Cartilage. 2007; 15(2): 222-225.

European search report and search opinion dated Aug. 4, 2011 for Application No. 08834463.7.

Goddard, et al. Linkage disequilibrium and allele-frequency distributions for 114 single-nucleotide polymorphisms in five populations. Am J Hum Genet. Jan. 2000;66(1):216-34.

Lazarus, et al. Single-nucleotide polymorphisms in the interleukin-10 gene: differences in frequencies, linkage disequilibrium patterns, and haplotypes in three United States ethnic groups. Genomics. Aug. 2002;80(2):223-8.

Lo, et al. GABRB2 association with schizophrenia: commonalities and differences between ethnic groups and clinical subtypes. Biol Psychiatry. Mar. 1, 2007;61(5):653-60. Epub Sep. 1, 2006.

Nuchnoi, et al. Linkage disequilibrium structure of the 5q31-33 region in a Thai population. J Hum Genet. 2008;53(9):850-6. Epub Jun. 24, 2008.

Office action dated Aug. 24, 2011 for EP Application No. 09792478. 1.

(56) References Cited

OTHER PUBLICATIONS

Rao, et al. Single nucleotide polymorphisms in alcohol dehydrogenase genes among some Indian populations. Am J Hum Biol. May-Jun. 2007;19(3):338-44.

European search report and opinion dated Oct. 20, 2010 for Application No. 07854875.7.

Hamosh, et al. Online Mendelian Inheritance in Man (OMIM). Hum Mutat. 2000;15(1):57-61.

Padhukasahasram, et al. Presymptomatic risk assessment for chronic non-communicable diseases. PLoS One. Dec. 31, 2010;5(12):e14338.

Discovery Vitality HealthyFood Catalogue. Feb. 2009. Available at https://healthyfood.prezence.co.za/Discovery_Vitality_HealthyFood_Catalog.pdf. Accessed Aug. 13, 2009.

Discovery Vitality program, "HealthyFood Overview." Available at https://www.discovery.co.za/memberf.jhtml?p_brand_css=/StyleSheets/screen_vitality.css &p_content=/content/view_content.jhtml&p_template=1&p_alias=indv_discovery_vitality&p_path=healthyfood/healthyfood_overview/healthyfood.xml. Accessed Aug. 13, 2009.

Discovery Vitality program, "How to Earn Points." Available at https://www.discovery.co.za/memberf.jhtml?p_brand_css=/StyleSheets/screen_vitality.css&p_content=/content/view_content.jhtml&p_template=5&p_alias=indv_discovery_vitality_howto&p_path=how_to_earn_points.xml&p_children=how_to_earn_points_contents. Accessed Aug. 13, 2009.

Discovery Vitality program, "Other preventive screening tests." Available at https://www.discovery.co.za/index_login.jhtml?p_content=/content/view_content.jhtml&p_alias=indv_discovery_vitality_howto&p_path=how_to_earn_points_contents/vitality_screenings_other.xml&p_brand_css=/StyleSheets/screen_vitality.css. Accessed Aug. 13, 2009.

Discovery Vitality program, "Virgin Life Care HealthZone." Available at https://www.discovery.co.za/index_login.jhtml?p_content=/content/view_content.jhtml&p_alias=indv_discovery_vitality_howto&p_path=how_to_earn_points_contents/virgin_life_care_healthzones.xml&p_brand_css=/StyleSheets/screen_vitality.css. Accessed Aug. 13, 2009.

Discovery Vitality program, "Vitality Fitness Assessment." Available at https://www.discovery.co.za/index_login.jhtml?p_content=/content/view_content.jhtml&p_alias=indv_discovery_vitality_howto&p_path=how_to_earn_points_contents/vitality_fitness_assessment.xml&p_brand_css=/StyleSheets/screen_vitality.css. Accessed Aug. 13, 2009.

Discovery Vitality program, "Vitality Nutrition Assessment." Available at https://www.discovery.co.za/index_login.jhtml?p_content=/content/view_content.jhtml&p_alias=indv_discovery_vitality_howto&p_path=how_to_earn_points_contents/nutrition_assesment.xml&p_brand_css=/StyleSheets/screen_vitality.css. Accessed Aug. 13, 2009.

Discovery Vitality program, "Vitality pharmacy screenings." Available at https://www.discovery.co.za/index_login.jhtml?p_content=/content/view_content.jhtml&p_alias=indv_discovery_vitality_howto&p_path=how_to_earn_points_contents/vitality_pharmacy_screenings.xml&p_brand_css=/StyleSheets/screen_vitality.css. Accessed Aug. 13, 2009.

Discovery Vitality program, "Vitality's online Nutrition Centre." Available at https://www.discovery.co.za/index_login.jhtml?p_content=/content/view_content.jhtml &p_alias=indv_discovery_vitality_howto&p_path=how_to_earn_points_contents/nutrition_centre.xml&p_brand_css=/StyleSheets/screen_vitality.css. Accessed Aug. 13, 2009.

Discovery Vitality program, "Vitality's online Stress Centre." Available at https://www.discovery.co.za/index_login.jhtml?p_content=/content/view_content.jhtml&p_alias=indv_discovery_vitality_howto&p_path=how_to_earn_points_contents/stress_management_centre.xml&p_brand_css=/StyleSheets/screen_vitality.css. Accessed Aug. 13, 2009.

Discovery Vitality program, "What is Vitality?" Available at https://www.discovery.co.za/index_login.jhtml?p_brand_css=/StyleSheets/screen_vitality.css&p_content=/content/view_content.jhtml&p_template=1&p_alias=indv_discovery_vitality&p_path=what_is_vitality/what_is_vitality.xml. Accessed Aug. 13, 2009.

Hilton Breakfast color-coded guide. Available at http://www.hilton.com/en/hi/promotions/hiltonbreakfast/index.jhtml?cid=OH,HH,houwc,BreakfastF. Accessed Aug. 13, 2009.

International search report dated Jan. 9, 2009 for PCT Application No. US08/78035.

International search report dated Oct. 1, 2008 for PCT Application No. US07/86138.

International search report dated Oct. 2, 2009 for PCT Application No. US09/053216.

Search Report dated Feb. 29, 2008 for Application No. GB 0723512.0.

Lewis, C., "Genetic association studies: Design, analysis and interpretation", *Briefings in Bioinformatics*, vol. 3(2), Jun. 2002, 146-153.

"Subscription" Google Dictionary, http://www.google.com/search?q=subscription+definition&sourceid=ie7 &rls=com.microsoft: en-us: IE-SearchBox&ie=&oe= (last visited Nov. 1, 2012).

* cited by examiner

| Short Phenotype Name | Locus | Gene (anchaloc on B36) | Gender applicability (F, M, B) | Test SNP | CHR | B3S Location | Test Risk Allele (plus, R) | Test NonRisk Allele (plus, N) | Ethnicity Race-distr |
|---|---|---|---|---|---|---|---|---|---|
| AD | AD_1 | APOE | B | rs4420638 | chr19 | 50114785 | G | A | CEU |
| BC | BC_1 | FGFR2 | F | rs2981582 | chr10 | 123342306 | T | C | CEU/AS |
| BC | BC_2 | TNRC9 | F | rs3803662 | chr16 | 51143841 | T | C | CEU/AS |
| BC | BC_3 | MAP3K1 | F | rs4700485 | chr5 | 56067640 | G | A | CEU/AS |
| BC | BC_4 | LSP1 | F | rs3817198 | chr11 | 1865581 | C | T | CEU/AS |
| BC | BC_5 | CASP8 | F | rs17468277 | chr2 | 201857833 | C | T | CEU |
| BCERP | BCERP_1 | chr2.217614077 | F | rs6721996 | chr2 | 217614076 | G | A | CEU |
| BCERP | BCERP_2 | TNRC9 | F | rs3803662 | chr16 | 51143841 | T | C | CEU |
| BMIOB | BMIOB_1 | FTO | B | rs9939609 | chr16 | 52378027 | A | T | CEU |
| BMIOW | BMIOW_1 | FTO | B | rs9939609 | chr16 | 52378027 | A | T | CEU |
| BP | BP_1 | PALB2 | B | rs420259 | chr16 | 23541526 | T | C | CEU |
| CD | CD_1 | chr10.101277754 | B | rs1088365 | chr10 | 101277754 | G | A | CEU |
| CD | CD_2 | PTGER4 | B | rs17234657 | chr5 | 404037265 | G | T | CEU |
| CD | CD_3 | ATG16L1 | B | rs10210302 | chr2 | 2338223577 | T | C | CEU |
| CD | CD_4 | BSN | B | rs9858542 | chr3 | 49676986 | A | G | CEU |
| CD | CD_5 | IL23R | B | rs11805303 | chr1 | 67448103 | T | C | CEU |
| CD | CD_6 | IRGM | B | rs1000113 | chr5 | 150220268 | T | C | CEU |
| CD | CD_7 | NOD2 (CARD15) | B | rs17221417 | chr16 | 49297082 | G | C | CEU |
| CD | CD_8 | PTPN2 | B | rs2542151 | chr18 | 12769946 | G | T | CEU |
| CD | CD_9 | ZNF365 | B | rs10761659 | chr10 | 64115569 | G | A | CEU |
| CeID | CeID_1 | IL2-IL22 Locus | B | rs6840978 | chr4 | 123774157 | C | T | CEU |
| CeID | CeID_2 | HLA-DQ2.5cis | B | rs2187668 | chr6 | 32713862 | A | G | CEU |
| CeID | CeID_3 | CTLA4 | B | rs11571315 | chr2 | 204442732 | A | G | CEU |
| EMI | EMI_1 | THBS4 | B | rs1866389 | chr5 | 79397020 | C | G | CEU |

FIG. 4A

| Short Phenotype Name | Locus | Gene (anchaloc on B36) | Gender applicability (F, M, B) | Test SNP | CHR | B3S Location | Test Risk Allele (plus, R) | Test NonRisk Allele (plus, N) | Ethnicity Race-distr |
|---|---|---|---|---|---|---|---|---|---|
| EMI | EMI_2 | 9p21 | B | rs1333049 | chr9 | 22114476 | C | G | CEU |
| MI | MI_1 | 9p21 | B | rs1333049 | chr9 | 22114476 | C | G | CEU |
| OAK | OAK_1 | GDF5 | B | rs4911178 | chr20 | 33489396 | A | G | CHB |
| PC | PC_1 | 8q24_R1 | M | rs9643226 | chr8 | 128563663 | C | G | CEU |
| PC | PC_2 | 8q24_R3 | M | rs6983267 | chr8 | 128482487 | G | T | CEU |
| RA | RA_1 | PTPN22 | B | rs6679677 | chr1 | 114105330 | A | C | CEU |
| RA | RA_2 | MHC | B | rs6457617 | chr6 | 32771828 | C | G | CEU |
| T2D | T2D_1 | CDKAL1 | B | rs7754840 | chr6 | 20769228 | C | A | CEU |
| T2D | T2D_10 | TCF7L2 | B | rs4506565 | chr10 | 114746030 | T | A | CHB |
| T2D | T2D_2 | CDKAL1 | B | rs7756992 | chr6 | 20787687 | G | A | CEU |
| T2D | T2D_2 | CDKAL1 | B | rs7756992 | chr6 | 20787687 | G | A | CEU |
| T2D | T2D_3 | CDKN2A/B | B | rs10811661 | chr9 | 22124093 | T | C | CEU |
| T2D | T2D_4 | Chr11.41871942 | B | rs12804210 | chr11 | 41871941 | T | C | CEU |
| T2D | T2D_5 | FTO | B | rs8050136 | chr16 | 52373775 | A | C | CEU |
| T2D | T2D_6 | HHEX | B | rs1111875 | chr10 | 94452861 | G | A | CEU |
| T2D | T2D_7 | IGF2BP2 | B | rs4402960 | chr3 | 186994380 | T | G | CEU |
| T2D | T2D_8 | KCNJ11 | B | rs5215 | chr11 | 17366147 | C | T | CEU |
| T2D | T2D_9 | PPARG | B | rs1801282 | chr3 | 12368124 | C | G | CEU |
| AMD | AMD_1 | GRK5 | B | rs1537576 | chr10 | 39926059 | C | G | CEU |
| AMD | AMD_2 | LOC387715 | B | rs10490924 | chr10 | 124204438 | C | A | CEU |
| AMD | AMD_3 | CFH | B | rs10737680 | chr1 | 194946078 | C | A | CEU |
| AMD | AMD_4 | CFB-C2 | B | rs541862 | chr6 | 32024930 | A | G | CEU |

FIG. 4B

| Short Phenotype Name | Gene (or chr.loc on B36) | Functional on published SNP | Published Risk allele (plus) | Published Non Risk allele (plus) | UNITS for effect estimate | Effect Estimate | Genotypic risk: risk homoz (RR vs NN) | Genotypic risk heteroz (RN vs NN) |
|---|---|---|---|---|---|---|---|---|
| AD | APOE | rs429358 & rs7412 (ApoE2/3/4 SNPs) | C | T | OR (95% CI) | genotypic | 21.59 (9.88, 47.21) | 5.02 (3.72, 6.77) |
| BC | FGFR2 | rs2981582 | T | C | OR (95% CI) | genotypic | 1.63 (1.51, 1.72) | 1.23 (1.18, 1.28) |
| BC | TNRC9 | rs3803662 | T | C | OR (95% CI) | genotypic | 1.39 (1.26, 1.45) | 1.23 (1.18, 1.29) |
| BC | MAP3K1 | rs889312 | C | A | OR (95% CI) | genotypic | 1.13 (1.09, 1.18) | 1.13 (1.10, 1.16) |
| BC | LSP1 | rs3817198 | C | T | OR (95% CI) | genotypic | 1.17 (1.08, 1.25) | 1.06 (1.02, 1.11) |
| BC | CASP8 | rs1045485 | G | C | OR (95% CI) | genotypic | 1.35 (1.04, 1.18) | 1.12 (1.15, .61) |
| BCERP | chr2.217614077 | rs13387042 | A | G | OR (95% CI) | genotypic | 1.44 (1.30, 1.58) | 1.11 (1.03, 1.20) |
| BCERP | TNRC9 | rs3803662 | T | C | OR (95% CI) | genotypic | 1.64 (1.45, 1.85) | 1.27 (1.19, 1.36) |
| BMIOB | FTO | rs9939609 | A | T | OR (95% CI) | genotypic | 1.74 (1.60, 1.89) | 1.31 (1.23, 1.39) |
| BMIOW | FTO | rs9939609 | A | T | OR (95% CI) | genotypic | 1.42 (1.32, 1.52) | 1.17 (1.11, 1.23) |
| BP | PALB2 | rs420259 | T | C | OR (95% CI) | genotypic | 2.07 (1.60, 2.69) | 2.08 (1.60, 2.71) |
| CD | chr10.101277754 | rs1083365 | G | A | OR (95% CI) | genotypic | 1.62 (1.37, 1.92) | 1.21 (1.03, 1.39) |
| CD | PTGER4 | rs17234657 | G | T | OR (95% CI) | genotypic | 2.32 (1.59, 3.39) | 1.54 (1.34, 1.76) |
| CD | ATG16L1 | rs10210302 | T | C | OR (95% CI) | genotypic | 1.85 (1.56, 2.21) | 1.19 (1.01, 1.41) |
| CD | BSN | rs9858542 | A | G | OR (95% CI) | genotypic | 1.84 (1.49, 2.26) | 1.09 (0.96, 1.24) |
| CD | IL23R | rs11805303 | T | C | OR (95% CI) | genotypic | 1.86 (1.54, 2.24) | 1.39 (1.22, 1.58) |
| CD | IRGM | rs10000113 | C | T | OR (95% CI) | genotypic | 1.92 (0.92, 4.00) | 1.54 (1.31, 1.82) |
| CD | NOD2 (CARD15) | rs17221417 | G | C | OR (95% CI) | genotypic | 1.92 (1.58, 2.34) | 1.29 (1.13, 1.46) |
| CD | PTPN2 | rs2542151 | G | T | OR (95% CI) | genotypic | 2.01 (1.46, 2.76) | 1.3 (1.13, 1.48) |
| CD | ZNF365 | rs10761659 | C | A | OR (95% CI) | genotypic | 1.55 (1.30, 1.84) | 1.23 (1.05, 1.45) |
| CeID | IL2-IL22 locus | rs6840978 | T | | OR (95% CI) | allelic | | |
| CeID | HLA-DQ2.5cis | rs2187668 | A | G | OR (95% CI) | allelic | | |
| CeID | CTLA4 | rs231779 | T | C | OR (95% CI) | allelic | | |

FIG. 4C

| Short Phenotype Name | Gene (or chr.loc on B36) | Functional on published SNP | Published Risk allele (plus) | Published Non Risk allele (plus) | UNITS for effect estimate | Effect Estimate | Genotypic risk: risk homoz (RR vs NN) | Genotypic risk heteroz (RN vs NN) |
|---|---|---|---|---|---|---|---|---|
| EMI | THBS4 | rs1866389 | C | G | OR (95% CI) | genotypic | 1.64 (0.75, 3.57) | 1.85 (1.28, 2.67) |
| EMI | 9p21 | rs10757278 | G | A | OR (95% CI) | genotypic | 2.08 (1.69, 2.58) | 1.56 (1.32, 1.85) |
| MI | 9p21 | rs10757278 | G | A | OR (95% CI) | genotypic | 1.72 (1.45, 2.03) | 1.28 (1.14, 1.45) |
| OAK | GDF5 | rs143383 | T | C | OR (95% CI) | genotypic | 2.04 (1.16, 3.58) | 1.27 (0.71, 2.28) |
| PC | 8q24_R1 | rs1447295 | A | C | OR (95% CI) | genotypic | 1.43 (1.29, 1.59) | 2.23 (1.58, 3.14) |
| PC | 8q24_R3 | rs6983267 | G | T | OR (95% CI) | genotypic | 1.26 (1.13, 1.41) | 1.58 (1.40, 1.78) |
| RA | PTPN22 | rs6679677 | A | C | OR (95% CI) | genotypic | 3.32 (1.93, 5.59) | 1.98 (1.72, 2.27) |
| RA | MHC | rs6457617 | T | C | OR (95% CI) | genotypic | 5.21 (4.31, 6.30) | 2.36 (1.97, 2.84) |
| T2D | CDKAL1 | rs7754840 | C | G | OR (95% CI) | genotypic | 1.34 (1.23, 1.47) | 1.33 (1.22, 1.45) |
| T2D | TCF7L2 | rs4506565 | T | A | OR (95% CI) | genotypic | 1.88 (1.56, 2.27) | 1.36 (1.20, 1.54) |
| T2D | CDKAL1 | rs7756992 | G | A | OR (95% CI) | genotypic | 1.52 (1.21, 1.90) | 1.27 (1.05, 1.55) |
| T2D | CDKAL1 | rs7756992 | G | A | OR (95% CI) | genotypic | 1.50 (1.31, 1.72) | 1.15 (1.06, 1.24) |
| T2D | CDKN2A/B | rs10811661 | T | C | OR (95% CI) | genotypic | 1.39 (1.13, 1.71) | 1.16 (0.94, 1.43) |
| T2D | Chr11.41871942 | rs9300039 | C | A | OR (95% CI) | genotypic | 2.61 (1.33, 5.11) | 1.80 (0.91, 3.57) |
| T2D | FTO | rs8050136 | A | C | OR (95% CI) | genotypic | 1.49 (1.33, 1.68) | 1.15 (1.06, 1.26) |
| T2D | HHEX | rs1111875 | G | A | OR (95% CI) | genotypic | 1.20 (1.10, 1.31) | 1.06 (0.98, 1.16) |
| T2D | IGF2BP2 | rs4402960 | T | G | OR (95% CI) | genotypic | 1.21 (1.10, 1.34) | 1.16 (1.09, 1.24) |
| T2D | KCNJ11 | rs5219 | T | C | OR (95% CI) | genotypic | 1.22 (1.04, 1.44) | 1.12 (0.98, 1.28) |
| T2D | PPARG | rs1801282 | C | G | OR (95% CI) | genotypic | 1.53 (1.08, 2.16) | 1.30 (0.91, 1.86) |
| AMD | GRK5 | rs1537576 | T | G | OR (n/a CI) | genotypic | | |
| AMD | LOC387715 | rs10490924 | T | G | OR (n/a CI) | genotypic | 1.9 | n/a |
| AMD | CFH | rs10737680 | C | A | OR (n/a CI) | genotypic | 2.7 | 7.60 |
| AMD | CFB-C2 | rs641153 | C | T | OR (n/a CI) | genotypic | 9.5 | 3.10 |

FIG. 4D

| Short Phenotype Name | Gene (or chr.loc on B36) | Genotypic risk: nonrisk homoz (NN vs NN) | Carrier Risk (RR or RN - vs NN) | Allelic Risk (R vs N) | Seminal publication | DIRECT or TAG SNP | Test SNP RR freq in HapMap CEU | Test SNP RN freq in HapMap CEU |
|---|---|---|---|---|---|---|---|---|
| AD | APOE | 1 | 6.34 (4.76, 8.44) | | Coon et al., J. Clin. Psychiatry 68:613-618 (2007) | TAG | 3% | 30% |
| BC | FGFR2 | 1.00 | | | Easton et al., Nature 447:1087-1093 (2007) | DIRECT | 22% | 40% |
| BC | TNRC9 | 1.00 | | | Easton et al., Nature 447:1087-1093 (2007) | DIRECT | 12% | 37% |
| BC | MAP3K1 | 1.00 | | | Easton et al., Nature 447:1087-1093 (2007) | TAG | 47% | 45% |
| BC | LSP1 | 1.00 | | | Easton et al., Nature 447:1087-1093 (2007) | DIRECT | 8% | 52% |
| BC | CASP8 | 1.00 | | | Cox et al., Nat. Genet. 39:352-358 (2007) | TAG | 77% | 22% |
| BCERP | chr2.217614077 | 1.00 | | | Stacey et al., Nat. Genet. 39:865-869 (2007) | TAG | 40% | 45% |
| BCERP | TNRC9 | 1.00 | | | Stacey et al., Nat. Genet. 39:865-869 (2007) | DIRECT | 12% | 37% |
| BMIOB | FTO | 1.00 | | | Frayling et al., Science 316:889-894 (2007) | DIRECT | 12% | 67% |
| BMIOW | FTO | 1.00 | | | Frayling et al., Science 316:889-894 (2007) | DIRECT | 12% | 67% |
| BP | PALB2 | 1.00 | | | Wellcome Trust Case Control Consortium (WTCCC) Nature 447:661-678 (2007) | DIRECT | 67% | 27% |
| CD | chr10.101277754 | 1.00 | | | Wellcome Trust Case Control Consortium (WTCCC) Nature 447:661-678 (2007) | DIRECT | 30% | 40% |
| CD | PTGER4 | 1.00 | | | Wellcome Trust Case Control Consortium (WTCCC) Nature 447:661-678 (2007) | DIRECT | 7% | 20% |
| CD | ATG16L1 | 1.00 | | | Wellcome Trust Case Control Consortium (WTCCC) Nature 447:661-678 (2007) | DIRECT | 30% | 50% |
| CD | BSN | 1.00 | | | Wellcome Trust Case Control Consortium (WTCCC) Nature 447:661-678 (2007) | DIRECT | 3% | 42% |
| CD | IL23R | 1.00 | | | Wellcome Trust Case Control Consortium (WTCCC) Nature 447:661-678 (2007) | DIRECT | 10% | 38% |

FIG. 4E

| Short Phenotype Name | Gene (or chr.loc on B36) | Genotypic risk: norrisk homoz (NN) vs NN) | Carrier Risk (RR or RN vs NN) | Allelic Risk (R vs N) | Seminal publication | DIRECT or TAG SNP | Test SNP RR freq in HapMap CEU | Test SNP RN freq in HapMap CEU |
|---|---|---|---|---|---|---|---|---|
| CD | IRGM | 1.00 | | | Wellcome Trust Case Control Consortium (WTCCC) Nature 447:661-678 (2007) | DIRECT | 0% | 7% |
| CD | NOD2 (CARD15) | 1.00 | | | Wellcome Trust Case Control Consortium (WTCCC) Nature 447:661-678 (2007) | DIRECT | 10% | 52% |
| CD | PTPN2 | 1.00 | | | Wellcome Trust Case Control Consortium (WTCCC) Nature 447:661-678 (2007) | DIRECT | 5% | 28% |
| CD | ZNF365 | 1.00 | | | Wellcome Trust Case Control Consortium (WTCCC) Nature 447:661-678 (2007) | DIRECT | 23% | 63% |
| CelD | IL2-IL22 locus | | | 1.42 (1.28-1.59) | van Heel et al., Nat. Genet. 39:827-829 (2007) | DIRECT | 55% | 42% |
| CelD | HLA-DQ2.5cis | | | 7.04 (6.08-8.15) | van Heel Nat Genet 39:827 (2007) | DIRECT | 0% | 18% |
| CelD | CTLA4 | | | 1.24 (1.04-1.49) | Hunt et al., Eur. J. Hum. Genet. 13:440-444 (2005) | TAG | 8% | 58% |
| EMI | THBS4 | 1.00 | | | Topol et al., Circulation 104:2641-6544 (2001) (main reference) | DIRECT | 53% | 37% |
| EMI | 9b21 | 1.00 | | | Helgadottir et al., Science 316:1491-1493 (2007); subset from McPherson et al., Science 316:1488-1491 (2007) | TAG | 22% | 55% |
| MI | 9b21 | 1.00 | | | Helgadottir et al., Science 316:1491-1493 (2007); subset from McPherson et al., Science 316:1488-1491 (2007) | TAG | 22% | 55% |
| OAK | GDF5 | 1.00 | | | Miyamoto et al., Nat. Genet. 39:529-533 (2007) | TAG | 42% | 47% |
| PC | 8q24_R1 | 1.00 | | | Yeager et., Nat. Genet. 39:64-649 (2007) | TAG | 0% | 13% |
| PC | 8q24_R3 | 1.00 | | | Yeager et., Nat. Genet. 39:64-649 (2007) | DIRECT | 18% | 55% |
| RA | PTPN22 | 1.00 | | | Wellcome Trust Case Control Consortium (WTCCC) Nature 447:661-678 (2007) | DIRECT | 0% | 28% |
| RA | MHC | 1.00 | | | Wellcome Trust Case Control Consortium (WTCCC) Nature 447:661-678 (2007) | DIRECT | 22% | 57% |
| T2D | CDKAL1 | 1.00 | | | Scott et al., Science 316:1341-1345 (2007); Zeggini Science 316:1336-1341 (2007) | DIRECT | 8% | 45% |

FIG. 4F

| Short Phenotype Name | Gene (or chr.loc on B36) | Genotypic risk: nonrisk homoz (NN vs NN) | Carrier Risk (RR or RN - vs NN) | Allelic Risk (R vs N) | Seminal publication | DIRECT or TAG SNP | Test SNP RR freq in HapMap CEU | Test SNP RN freq in HapMap CEU |
|---|---|---|---|---|---|---|---|---|
| T2D | TCF7L2 | 1.00 | | | Wellcome Trust Case Control Consortium (WTCCC) Nature 447:661-678 (2007) | DIRECT | 9% | 37% |
| T2D | CDKAL1 | 1.00 | | | Steinthorsdottir et al., Nat. Genet. 39:770-775 (2007). | DIRECT | 8% | 33% |
| T2D | CDKAL1 | 1.00 | | | Steinthorsdottir et al., Nat. Genet. 39:770-775 (2007). | DIRECT | 8% | 33% |
| T2D | CDKN2A/B | 1.00 | | | Scott et al., Science 316:1341-1345 (2007); Zeggini et al., Science 316:1336-1341 (2007) | DIRECT | 67% | 25% |
| T2D | Chr11.41871942 | 1.00 | | | Scott et al., Science 316:1341-1345 (2007); | TAG | 78% | 22% |
| T2D | FTO | 1.00 | | | Scott et al., Science 316:1341-1345 (2007); | DIRECT | 12% | 67% |
| T2D | HHEX | 1.00 | | | Scott et al., Science 316:1341-1345 (2007); | DIRECT | 32% | 48% |
| T2D | IGF2BP2 | 1.00 | | | Scott et al., Science 316:1341-1345 (2007); | DIRECT | 12% | 35% |
| T2D | KCNJ11 | 1.00 | | | Scott et al., Science 316:1341-1345 (2007); | TAG | 10% | 62% |
| T2D | PPARG | 1.00 | | | Scott et al., Science 316:1341-1345 (2007); | DIRECT | 87% | 12% |
| AMD | GRK5 | | 1.59 | | Jakobsdottir et al., Am. J. Hum. Genet. 77:389-407 (2005) | TAG | 27% | 50% |
| AMD | LOC387715 | 1.00 | | | Maller et al., Nat. Genet. 38:1055-1059 (2006) | DIRECT | 2.00% | 40% |
| AMD | CFH | 1.00 | | | Maller et al., Nat. Genet. 38:1055-1059 (2006) | DIRECT | 22% | 38% |
| AMD | CFB-C2 | 1.00 | | | Maller et al., Nat. Genet. 38:1055-1059 (2006) | TAG | 0% | 12% |

FIG. 4G

| Short Phenotype Name | Gene (or chr.loc on B36) | Test SNP-NN freq in HapMap CEU | Test SNP-RR freq in HapMap CHB | Test SNP-RN freq in HapMap CHB | Test SNP-NN freq in HapMap CHB | Test SNP RR freq in HapMap YRI | Test SNP RN freq in HapMap YRI | Test SNP NN freq in HapMap YRI | Test SNP RR freq in HapMap JAP | Test SNP RN freq in HapMap JAP | Test SNP NN freq in HapMap JAP |
|---|---|---|---|---|---|---|---|---|---|---|---|
| AD | APOE | 67% | 0% | 24% | 76% | 2% | 27% | 72% | 2% | 13% | 84% |
| BC | FGFR2 | 38% | 9% | 42% | 49% | 28% | 47% | 25% | 4% | 31% | 64% |
| BC | TNRC9 | 52% | 49% | 44% | 7% | 22% | 63% | 15% | 33% | 44% | 22% |
| BC | MAP3K1 | 8% | 27% | 42% | 31% | 53% | 42% | 5% | 13% | 64% | 22% |
| BC | LSP1 | 40% | 2% | 16% | 82% | 0% | 25% | 75% | 0% | 29% | 71% |
| BC | CASP8 | 2% | 100% | 0% | 0% | 2% | 37% | 62% | 100% | 0% | 0% |
| BCERP | chr2.217614077 | 15% | 0% | 27% | 73% | 67% | 27% | 7% | 4% | 13% | 82% |
| BCERP | TNRC9 | 52% | 49% | 44% | 7% | 75% | 25% | 0% | 33% | 44% | 22% |
| BMIOB | FTO | 22% | 0% | 24% | 76% | 25% | 53% | 22% | 7% | 20% | 73% |
| BMIOW | FTO | 22% | 0% | 24% | 76% | 25% | 53% | 22% | 7% | 20% | 73% |
| BP | PALB2 | 7% | 40% | 44% | 16% | 5% | 42% | 53% | 42% | 49% | 9% |
| CD | chr10.101277754 | 40% | 31% | 47% | 22% | 25% | 48% | 27% | 27% | 47% | 27% |
| CD | PTGER4 | 73% | 0% | 0% | 100% | 0% | 3% | 97% | 0% | 0% | 100% |
| CD | ATG16L1 | 20% | 16% | 47% | 38% | 8% | 38% | 53% | 0% | 33% | 67% |
| CD | BSN | 55% | 0% | 9% | 91% |  |  |  | 0% | 16% | 84% |
| CD | IL23R | 52% | 29% | 49% | 22% | 5% | 47% | 48% | 36% | 49% | 16% |
| CD | IRGM | 93% | 13% | 49% | 38% | 7% | 43% | 50% | 21% | 39% | 41% |
| CD | NOD2 (CARD15) | 38% | 0% | 0% | 100% | 0% | 0% | 100% | 0% | 0% | 100% |
| CD | PTPN2 | 67% | 2% | 33% | 64% | 28% | 47% | 25% | 0% | 16% | 84% |
| CD | ZNF365 | 13% | 71% | 24% | 4% | 0% | 3% | 97% | 49% | 44% | 7% |
| CelD | IL2-IL22 locus | 3% | 84% | 16% | 0% | 82% | 16% | 2% | 77% | 21% | 2% |
| CelD | HLA-DQ2.5cis | 82% | 0% | 13% | 87% | 0% | 5% | 95% | 0% | 17% | 83% |

FIG. 4H

| Short Phenotype Name | Gene (or chr.loc on B36) | Test SNP-NN freq in Hap Map CEU | Test SNP-RR freq in Hap Map CHB | Test SNP-RN freq in Hap Map CHB | Test SNP-NN freq in Hap Map CHB | Test SNP RR freq in Hap Map YRI | Test SNP RN freq in Hap Map YRI | Test SNP NN freq in Hap Map YRI | Test SNP RR freq in Hap Map JAP | Test SNP RN freq in Hap Map JAP | Test SNP NN freq in Hap Map JAP |
|---|---|---|---|---|---|---|---|---|---|---|---|
| CelD | CTLA4 | 33% | 47% | 42% | 11% | 40% | 49% | 11% | 27% | 50% | 23% |
| EMI | THBS4 | 10% | 96% | 4% | 0% | 85% | 15% | 0% | 84% | 16% | 0% |
| EMI | 9p21 | 23% | 22% | 51% | 27% | 2% | 32% | 67% | 27% | 48% | 25% |
| MI | 9p21 | 23% | 22% | 51% | 27% | 2% | 32% | 67% | 27% | 48% | 25% |
| OAK | GDF5 | 12% | 58% | 36% | 7% | 17% | 60% | 23% | 51% | 44% | 4% |
| PC | 8q24 R1 | 87% | 2% | 13% | 84% | 3% | 22% | 75% | 4% | 31% | 64% |
| PC | 8q24 R3 | 27% | 11% | 56% | 33% | 97% | 3% | 0% | 11% | 46% | 43% |
| RA | PTPN22 | 72% | 0% | 0% | 100% | 18% | 43% | 38% | 0% | 0% | 100% |
| RA | MHC | 22% | 31% | 42% | 27% | 0% | 0% | 100% | 30% | 49% | 21% |
| T2D | CDKAL1 | 47% | 16% | 51% | 33% | 48% | 37% | 15% | 16% | 44% | 40% |
| T2D | TCF7L2 | 54% | 0% | 4% | 96% | 22% | 61% | 17% | 0% | 4% | 96% |
| T2D | CDKAL1 | 58% | 22% | 49% | 29% | 42% | 43% | 15% | 23% | 48% | 30% |
| T2D | CDKAL1 | 58% | 22% | 49% | 29% | 42% | 43% | 15% | 23% | 48% | 30% |
| T2D | CDKN2A/B | 8% | 43% | 33% | 24% | 100% | 0% | 0% | 29% | 56% | 16% |
| T2D | Chr11.41871942 | 0% | 60% | 33% | 7% | 70% | 28% | 2% | 47% | 51% | 2% |
| T2D | FTO | 22% | 0% | 24% | 76% | 23% | 47% | 30% | 7% | 20% | 73% |
| T2D | HHEX | 20% | 7% | 51% | 42% | 75% | 22% | 3% | 21% | 41% | 39% |
| T2D | IGF2BP2 | 53% | 4% | 36% | 60% | 30% | 50% | 20% | 13% | 36% | 51% |
| T2D | KCNJ11 | 28% | 11% | 49% | 40% | 0% | 2% | 98% | 9% | 47% | 44% |
| T2D | PPARG | 2% | 96% | 4% | 0% | 100% | 0% | 0% | 89% | 11% | 0% |
| AMD | GRK5 | 23% | 76% | 20% | 4% | 82% | 18% | 0% | 66% | 21% | 13% |
| AMD | LOC387715 | 58% | 16% | 62% | 22% | 8% | 45% | 47% | 20% | 47% | 33% |
| AMD | CFH | 40% | 22% | 42% | 36% | 32% | 52% | 17% | 13% | 53% | 33% |
| AMD | CFB-C2 | 88% | n/a | n/a | n/a | 2% | 17% | 81% | n/a | n/a | n/a |

FIG. 4I

| Short Phenotype Name | Locus | Gene (or chr.loc on B36) | Gender Applicability (F-M-B) | TEST SNP | CHR | Test Risk allele (plus, R) | Test Non Risk allele (plus, N) | Ethnicity/ Race distr | Functional or published SNP | UNITS for effect estimate |
|---|---|---|---|---|---|---|---|---|---|---|
| PC | PC_1 PC_2 | 8q24_R1\|8q24_R3 | M | rs9643226\|rs6983267 | chr8 | C\|G | G\|T | CEU | rs1447295\|rs6983267 | OR (95% CI) |

| Gene or chr.loc on B36 | UNITS for effect estimate | 2locus_ genotypic affect NNRN | 2locus_ genotypic effect RRRR | 2locus_ genotypic effect RRRN | 2locus_ genotypic effect RNRR | 2locus_ genotypic effect RNRN | 2locus_ genotypic effect RNNN | Gene (or chr.loc on B36) |
|---|---|---|---|---|---|---|---|---|
| 8q24_R1\|8q24_R3 | OR (95% CI) | 1.24 (1.17, 1.32) | 3.17 (2.55, 3.94) | 2.55 (2.10, 3.09) | 2.05 (1.70, 2.46) | 2.22 (1.91, 2.57) | 1.78 (1.60, 1.98) | 1.43 (1.30, 1.57) | 8q24_R1\|8q24_R3 |

| 2locus genotypic affect NNRR | 2locus genotypic affect NNRN | 2locus genotypic affect NNNN | Seminal publication |
|---|---|---|---|
| 1.55 (1.37, 1.75) | 1.24 (1.17, 1.32) | 1 | Yeager et, Nat. Genet. 39:64-649 (2007) |

FIG. 4J

| Short Phenotype Name | Locus | LOCUS_ETH | Gene (or chr.loc on B36) | Gender applicability (F, M, B) | TEST SNP | Test Risk allele (plus $R_j$) | Test NonRisk allele (plus $N_j$) | Ethnicity/Race-distr | Functional or published SNP |
|---|---|---|---|---|---|---|---|---|---|
| AMD | AMD_2_3_4 | AMD_2_3_4_CEU | LOC387715\|CFH\|CFB-C2 | B | rs10490924\|rs10737680\|rs541862 | T\|C\|A | G\|A\|G | CEU | rs10490924\|rs10737680\|rs641153 |

| CHR | UNITS for effect estimate | Effect $R_1R_1R_2R_2R_3R_3$ | Effect $R_1R_1R_2R_2N_3$ | Effect $R_1R_1R_2N_2N_3$ | Effect $R_1R_1N_2N_2N_3$ | Effect $R_1R_1R_2R_2R_3$ | Effect $R_1R_1R_2N_2R_3$ | Effect $R_1R_1N_2N_2R_3$ | Effect $R_1N_1R_2R_2R_3$ |
|---|---|---|---|---|---|---|---|---|---|
| chr10\|chr1\|chrB | OR (n/a CI) | 285 | 154 | 154 | 92.5 | 49.8 | 49.8 | 30 | 70.8 |

| Effect $R_1N_1R_2R_2N_3$ | Effect $R_1N_1R_2N_2N_3$ | Effect $R_1N_1N_2N_2N_3$ | Effect $R_1N_1R_2R_2R_3$ | Effect $R_1N_1R_2N_2R_3$ | Effect $R_1N_1N_2N_2R_3$ | Effect $N_1N_1R_2R_2R_3$ | Effect $N_1N_1R_2N_2R_3$ | Effect $N_1N_1N_2N_2R_3$ |
|---|---|---|---|---|---|---|---|---|
| 38.1 | 38.1 | 23 | 12.4 | 12.4 | 7.5 | 9.5 | 4 | |

| Effect $N_1N_1R_2R_2N_3$ | Effect $N_1N_1R_2N_2N_3$ | Effect $N_1N_1N_2N_2N_3$ | Seminal publication |
|---|---|---|---|
| 5.7 | 3.1 | 1.9 | Maller et al., Nat. Genet. 38:1055-1059 (2006) |
| 17.6 | 9.5 | 1.9 | |
| 16.2 | 16.2 | 3.1 | |
| 16.2 | 4 | | |

FIG. 4K

| Abbreviation | What Does it stand for? |
|---|---|
| CEU | European/Caucasian ethnicity |
| CHB | Chinese ethnicity |
| JAP | Japanese ethnicity |
| YRI | Yoruban ethnicity |
| R | risk allele |
| N | non-risk allele |
| CC | case control study design |
| | |
| Ethnicity | |
| C(H) | Han Chinese ethnicity |
| E | European |
| J | Japanese |
| L | Latine |
| NA-P | Native American-Pima Indians |
| H | Hawaiian |
| Af | African |
| As | Asian |
| | |
| Countries | |
| CH | Switzerland |
| Dk | Denmark |
| FI | Finland |
| GH | Ghana |
| IS | Iceland |
| IT | italy |
| KR | Korea |
| NG | Nigeria |
| NL | Netherlands |
| GB | United Kingdom |
| FR | France |
| ES | Spain |
| SE | Sweden |
| TH | Thailand |
| TW | Taiwan |
| US | United States |

FIG. 4L

| Short Phenotype Name | Phenotype | Heritability | Reference |
|---|---|---|---|
| AMD | Age Related Macular Degeneration | 0.71[1] | Haddad et al., Survey of Opthalmology. 51:316 -363 (2006) |
| AD | Alzheimer's Disease | 0.79[2] | Gatz et al., Arch of Gen. Psychiatry. 63:168-174 (2006) |
| T2D | Diabetes, Type 2 | 0.80 | van Tilburg et al., J. Med. Genet. 38:569-578 (2001) |
| EMEM | Episodic Memory (Short-term) | 0.50 | de Quervain et al., Proc. Natl. Acad. Sci. USA 103:4270-4274 (2006). |
| MI | Myocardial infarction | 0.57 (M), 0.38 (F) | Zdravkovic, Karolinska Inst. 2006. http://diss.kib.ki.se/2006/91-7140-771-5/ |
| EMI | Myocardial infarction (early onset M<45, F<50) | 0.63 | Roberts and Stewart, Am. Heart Hosp. J. 4:222-227 (2006) |
| EMI | Myocardial infarction (early onset M<50, F<60) | 0.63 | Roberts and Stewart, Am. Heart Hosp. J. 4:222-227 (2006) |
| BMIOB | Body Mass Index, obesity endpoint (BMI 30kg/m$^2$) | 0.40 | Tambs et al., Am. J. Hum. Biol. 3:257-267 (1991) |
| BMIOW | Body mass index, overweight endpoint (BMI>25kg/m$^2$) | 0.40 | Tambs et al., Am. J. Hum. Biol. 3:257-267 (1991) |
| BC | Breast Cancer | 0.30 | Locatelli et al., Twin Res. 7:182-191 (2004). |
| CD | Crohn's Disease (inflammatory bowel disease) | 0.58 | Breslin et al., Gut 41:557-560 (1997) |
| BP | Bipolar Disorder | 0.75 | McGuffin et al., Arch. Gen. Psych. 60:497-502 (2003) |
| BCERP | Breast Caner, ER positive | n/a | |
| OAH | osteoarthritis, hip joint | 0.61 (radiograph vs. self report) | Page et al., Twin Res. 6:147-151 (2003) |
| OAK | osteoarthritis, knee joint | 0.63 (radiograph) | Zhai et al., Osteoarthritis Cartilage 15:222-225 (2007) |
| RA | rheumatoid arthritis | 0.53 | MacGregor et al., Arthritis Rheum. 2000, 43:30-37 (2000). |
| CelD | Celiac Disease | 0.70 | Nistico et al., Gut 55:803-808 (2006) |
| PC | Prostate Cancer | 0.27 | Page et al., Prostate 33:240-245 (1997) |
| | Colorectal cancer | 0.35 | Lichtenstein et al., N. Engl. J. Med. 343:78-85 (2000) |

[1] MC-1-5 grade of maculopathy, her estimate for grades 4 and 5 "advanced disease", AMD
[2] Adjusted for age

FIG. 4M

| Phenotype | Gene | Minor allele | Ethnicity/ Race (1) | Country (2) | Functional or published SNP | Effect estimate in homoz (3) | Effect estimate in heteroz (3) | Effect estimate in carriers (3,4) | Seminal publication |
|---|---|---|---|---|---|---|---|---|---|
| Age Related Macular Degeration | CFH | C | E | US | rs1329428 | NA | NA | 6.2 (2.9, 13)* | Klein et al., Science 308:385-389 (2005) |
| Alzheimer's Disease (conditional on carrying the APOE4 allele) | GAB2 | T | E | US | rs2373115 | | | 4.06 (2.81, 14.69)* multiplied by the APOE4 risk | Reiman et al., Neuron 54:713-720 (2007) |
| Cardiac repolarization (QT interval) | NOS1AP | G | E | US | rs10494366 | | 0.1±0.6** | GG: 2.7±1.0, GT:0.1±0.6, TT:-1.3±0.6** | Arking et al., Nat. Genet. 38:644-651 (2006) |
| Cerebral infarction | PRKCH | A | As | JP, CN | rs2230500 | 1.56 (1.03, 2.37) | 1.28 (1.07, 1.54) | 1.31 (1.11, 1.56) | Kubo et al., Nat. Genet. 39:212-217 (2007). |
| Crohn's Disease (inflammatory bowel disease) | IL23R | A | E | US | rs11209026 | | | 0.26 (0.15, 0.43)* | Duerr et al., Science 314:1461-1463 (2006) |
| Diabetes, Type 1 | CTLA4 | G | E | IT | rs231775 | | | 1.79 (1.20, 2.69)* | Nistico et al., Hum. Molec. Genet. 5:1075-1080 (1996) |

FIG. 5A

| Phenotype | Gene | Minor allele | Ethnicity/Race (1) | Country (2) | Functional or published SNP | Effect estimate in homoz (3) | Effect estimate in heteroz (3) | Effect estimate in carriers (3,4) | Seminal publication |
|---|---|---|---|---|---|---|---|---|---|
| Diabetes, Type 2 | IGF2BP2 | T | E | US | rs4402960 | | | 1.18 (1.08, 1.28)* | Scott et al., Science 316:1341-1345 (2007) |
| Diabetes, Type 2 | IGF2BP2 | T | | GB | rs4402960 | | | 1.11 (1.05, 1.16)* | Scott et al., Science 316:1341-1345 (2007) |
| Diabetes, Type 2 | KCNJ11 | T | E | US | rs5219 | | | 1.11 (1.02, 1.21)* | Scott et al., Science 316:1341-1345 (2007) |
| Diabetes, Type 2 | KCNJ11 | T | | UK | rs5219 | | | 1.13 (1.07, 1.19)* | Scott et al., Science 316:1341-1345 (2007) |
| Diabetes, Type 2 | SLC30A8 | C | E | US | rs13266634 | | | 1.18 (1.09, 1.29)* | Scott et al., Science 316:1341-1345 (2007) |
| Diabetes, Type 2 | SLC30A8 | C | | UK | rs13266634 | | | 1.12 (1.05, 1.18)* | Scott et al., Science 316:1341-1345 (2007) |
| Diabetes, Type 2 | TCF7L2 | T | E | FR | rs7903146 | 2.77 (2.27, 3.27)* | 1.65 (1.46, 1.84)* | 1.83 (1.64, 2.05)* | Sladek et al., Nature 445:881-885 (2007); Grant et al. Nat. Genet. 38:320-323 (2006) |
| Episodic Memory (short term) | WWC1 (KIBRA) | T | E | CH | rs1070145 | NA | NA | 9.4+0.2 (24% better word recall)*** | Papassotiropoulos et al., Science 314:475-478 (2006) |
| Prostate cancer | 8q24 region 1 | A | E | US | rs1447295 | 1.42 (1.29, 1.59)* | 2.23 (1.58, 3.14)* | | Yeager et al. Nat Genet. 39:645-9064 (2007); meta-analysis Witte et al. Nat. Genet. 39:579-580 (2007) |

FIG. 5B

| Phenotype | Gene | Minor allele | Ethnicity/Race (1) | Country (2) | Functional or published SNP | Effect estimate in homoz (3) | Effect estimate in heteroz (3) | Effect estimate in carriers (3,4) | Seminal publication |
|---|---|---|---|---|---|---|---|---|---|
| Prostate cancer | 8q24 region 1 | A | | IS | rs1447295 | | | 1.71 (1.49, 1.95)* | Gudmundsson et al., Nat. Genet. 39:631-637 (2007); meta-analysis Witte et al., Nat. Genet. 39:579-580 (2007) |
| Prostate cancer | 8q24 region 1 | A | | ES | rs1447295 | | | 1.44 (1.07,1.94)* | Gudmundsson et al., Nat. Genet. 39:631-637 (2007); meta-analysis Witte et al., Nat. Genet. 39:579-580 (2007) |
| Prostate cancer | 8q24 region 1 | A | | NL | rs1447295 | | | 1.39 (1.09,1.78)* | Gudmundsson et al., Nat. Genet. 39:631-637 (2007); meta-analysis Witte et al., Nat. Genet. 39:579-580 (2007) |
| Prostate cancer | 8q24 region 1 | A | A | US | rs1447295 | | | 1.25 (1.06,1.49)* | Haiman et al., Nat. Genet. 39:638-644 (2007); meta-analysis Witte et al., Nat. Genet. 39:579-580 (2007) |
| Prostate cancer | 8q24 region 1 | A | J | US | rs1447295 | | | 1.49 (1.23,1.81)* | Haiman et al., Nat. Genet. 39:638-644 (2007); meta-analysis Witte et al., Nat. Genet. 39:579-580 (2007) |
| Prostate cancer | 8q24 region 1 | A | H | US | rs1447295 | | | 2.55 (1.33,4.89)* | Haiman et al., Nat. Genet. 39:638-644 (2007); meta-analysis Witte et al., Nat. Genet. 39:579-580 (2007) |

FIG. 5C

| Phenotype | Gene | Minor allele | Ethnicity/ Race (1) | Country (2) | Functional or published SNP | Effect estimate in homoz (3) | Effect estimate in heteroz (3) | Effect estimate in carriers (3,4) | Seminal publication |
|---|---|---|---|---|---|---|---|---|---|
| Prostate cancer | 8q24 region 1 | A | L | US | rs1447295 | | | 1.98 (1.49, 2.61)* | Haiman et al., Nat. Genet. 39:638-644 (2007); meta-analysis Witte et al., Nat. Genet. 39:579-580 (2007) |
| Prostate cancer | 8q24 region 2/HapC | A | E | US | rs16901979 | | | 1.44 (1.21, 1.70)* | Gudmundsson et al., Nat. Genet. 39:631-637 (2007); meta-analysis Witte et al. Nat. Genet. 39:579-580 (2007) |
| Prostate cancer | 8q24 region 2/HapC | A | E | IS | rs16901979 | | | 2.08 (1.66, 2.60)* | Gudmundsson et al., Nat. Genet. 39:631-637 (2007); meta-analysis Witte et al. Nat. Genet. 39:579-580 (2007) |
| Prostate cancer | 8q24 region 2/HapC | A | E | ES | rs16901979 | | | 2.13 (1.34, 3.40)* | Gudmundsson et al., Nat. Genet. 39:631-637 (2007); meta-analysis Witte et al. Nat. Genet. 39:579-580 (2007) |
| Prostate cancer | 8q24 region 2/HapC | A | E | NL | rs16901979 | | | 1.85 (1.05, 3.27)* | Gudmundsson et al., Nat. Genet. 39:631-637 (2007); meta-analysis Witte et al. Nat. Genet. 39:579-580 (2007) |
| Prostate cancer | 8q24 region 2/HapC | A | A | US | rs16901979 | | | 1.34 (1.18, 1.53)* | Haiman et al., Nat. Genet. 39:638-644 (2007); meta-analysis Witte et al., Nat. Genet. 39:579-580 (2007) |

FIG. 5D

| Phenotype | Gene | Minor allele | Ethnicity/Race (1) | Country (2) | Functional or published SNP | Effect estimate in homoz (3) | Effect estimate in heteroz (3) | Effect estimate in carriers (3,4) | Seminal publication |
|---|---|---|---|---|---|---|---|---|---|
| Prostate cancer | 8q24 region 2/HapC | A | J | US | rs16901979 | | | 1.78 (1.47, 2.15)* | Haiman et al., Nat. Genet. 39:638-644 (2007); meta-analysis Witte et al. Nat. Genet. 39:579-580 (2007) |
| Prostate cancer | 8q24 region 2/HapC | A | H | US | rs16901979 | | | 3.17 (1.87, 5.36)* | Haiman et al., Nat. Genet. 39:638-644 (2007); meta-analysis Witte et al. Nat. Genet. 39:579-580 (2007) |
| Prostate cancer | 8q24 region 2/HapC | A | L | US | rs16901979 | | | 1.99 (1.34, 2.96)* | Haiman et al., Nat. Genet. 39:638-644 (2007); meta-analysis Witte et al. Nat. Genet. 39:579-580 (2007) |
| Prostate cancer | 8q24 region 3 | G | E | US | rs6983267 | 1.26 (1.13, 1.41)* | 1.58 (1.40, 1.78)* | | Yeager et al., Nat. Genet. 39:645-9064 (2007); meta-analysis Witte et al. Nat. Genet. 39:579-580 (2007) |
| Prostate cancer | 8q24 region 3 | G | A | US | rs6983267 | | | 1.33 (1.17, 1.75)* | Haiman et al., Nat. Genet. 39:638-644 (2007); meta-analysis Witte et al. Nat. Genet. 39:579-580 (2007) |
| Prostate cancer | 8q24 region 3 | G | J | US | rs6983267 | | | 1.23 (1.04, 2.46)* | Haiman et al., Nat. Genet. 39:638-644 (2007); meta-analysis Witte et al. Nat. Genet. 39:579-580 (2007) |
| Prostate cancer | 8q24 region 3 | G | H | US | rs6983267 | | | 1.38 (0.89, 2.14)* | Haiman et al., Nat. Genet. 39:638-644 (2007); meta-analysis Witte et al. Nat. Genet. 39:579-580 (2007) |

FIG. 5E

| Phenotype | Gene | Minor allele | Ethnicity/ Race (1) | Country (2) | Functional or published SNP | Effect estimate in homoz (3) | Effect estimate in heteroz (3) | Effect estimate in carriers (3,4) | Seminal publication |
|---|---|---|---|---|---|---|---|---|---|
| Prostate cancer | 8q24 region 3 | G | L | US | rs6983267 | | | 1.29 (1.07, 1.56)* | Haiman et al., Nat. Genet. 39:638-644 (2007); meta-analysis Witte et al., Nat. Genet. 39:579-580 (2007) |
| Rheumatoid arthritis | PTPN22 | T | E | US | rs2476601 | 2.26 (0.56, 9.14)* | 1.69 (1.23, 2.32)* | 1.71 (1.25, 2.34)* | Begovich et al., Am. J. Hum. Genet. 75:330-337 (2004) |

FIG. 5F

| Phenotype | Gene | Direct or Tag SNP | Covered by | r2 (single or multi) | Risk Haplo/Diplotypes (Tag GT = Risk GT) | Other allele | Remarks |
|---|---|---|---|---|---|---|---|
| Age Related Macular Degeration | CFH | Tag | rs10737680 | 1 | AA=CC; AC=CT; CC=TT | T | 3.68% PP; 30%PP of >75 yo; 0.07% PI; other possible identifiers: haplotype Y402H, rs1061170 |
| Alzheimer's Disease (conditional on carrying the APOE4 allele) | GAB2 | Direct | | | | | |
| Cardiac repolarization (QT interval) | NOS1AP | Tag | rs12733821 | 1 | GG=GG; GC=GT; CC=TT | G | |
| Cerebral infarction | PRKCH | Tag | | | | T | |
| Crohn's Disease (inflammatory bowel disease) | IL23R | Direct | | | | G | 0.18% population prevalence |
| Diabetes, Type 1 | CTLA4 | Direct | | | | A | 0.12% PP(5); 0.01% PI(6) |
| Diabetes, Type 2 | IGF2BP2 | Direct | | | | G | |
| Diabetes, Type 2 | IGF2BP2 | Direct | | | | G | |
| Diabetes, Type 2 | KCNJ11 | | | | | T | |
| Diabetes, Type 2 | KCNJ11 | | | | | T | |

FIG. 5G

| Phenotype | Gene | Direct or Tag SNP | Covered by | r2 (single or multi) | Risk Haplo/Diplotypes (Tag GT = Risk GT) | Other allele | Remarks |
|---|---|---|---|---|---|---|---|
| Diabetes, Type 2 | SLC30A8 | | | | | C | |
| Diabetes, Type 2 | SLC30A8 | | | | | C | (ii); 5.88% PP; 0.29% PI; other possible identifiers: haplotype DG10S478, rs12255372 |
| Diabetes, Type 2 | TCF7L2 | Tag | rs4506565 | 0.92 | TT=TT (9.1%); TA=TC (35.2%); AA=CC (52.3%); // TA=CC (2.3%); TT=CT (1.1%) | | |
| Episodic Memory (short term) | WWC1 (KIBRA) | Direct | | | | C | >45 avg age of onset |
| Prostate cancer | 8q24 region 1 | Tag | rs9643226 | 1.000 | GG=CC; GG=CA; CC=AA | C | 9% PAR (7) |
| Prostate cancer | 8q24 region 1 | Tag | rs9643226 | 1.000 | GG=CC; GG=CA; CC=AA | C | |
| Prostate cancer | 8q24 region 1 | Tag | rs9643226 | 1.000 | GG=CC; GG=CA; CC=AA | C | |
| Prostate cancer | 8q24 region 1 | Tag | rs9643226 | 1.000 | GG=CC; GG=CA; CC=AA | C | |
| Prostate cancer | 8q24 region 1 | Tag | rs9643226 | 1.000 | GG=CC; GG=CA; CC=AA | C | |
| Prostate cancer | 8q24 region 1 | Tag | rs9643226 | 1.000 | GG=CC; GG=CA; CC=AA | C | |
| Prostate cancer | 8q24 region 1 | Tag | rs9643226 | 1.000 | GG=CC; GG=CA; CC=AA | C | |
| Prostate cancer | 8q24 region 2/HapC | Direct | | | | C | |

FIG. 5H

| Phenotype | Gene | Direct or Tag SNP | Covered by | r2 (single or multi) | Risk Haplo/Diplotypes (Tag GT = Risk GT) | Other allele | Remarks |
|---|---|---|---|---|---|---|---|
| Prostate cancer | 8q24 region 2/HapC | Direct | | | | C | |
| Prostate cancer | 8q24 region 2/HapC | Direct | | | | C | |
| Prostate cancer | 8q24 region 2/HapC | Direct | | | | C | |
| Prostate cancer | 8q24 region 2/HapC | Direct | | | | C | |
| Prostate cancer | 8q24 region 2/HapC | Direct | | | | C | |
| Prostate cancer | 8q24 region 2/HapC | Direct | | | | C | |
| Prostate cancer | 8q24 region 2/HapC | Direct | | | | C | |
| Prostate cancer | 8q24 region 3 | Tag | rs10505477 | 0.935 | TT=GG; TC=GT; CC=TT | T | 21% PAR |
| Prostate cancer | 8q24 region 3 | Tag | rs10505477 | 0.935 | TT=GG; TC=GT; CC=TT | T | |
| Prostate cancer | 8q24 region 3 | Tag | rs10505477 | 0.935 | TT=GG; TC=GT; CC=TT | T | |
| Prostate cancer | 8q24 region 3 | Tag | rs10505477 | 0.935 | TT=GG; TC=GT; CC=TT | T | |
| Prostate cancer | 8q24 region 3 | Tag | rs10505477 | 0.935 | TT=GG; TC=GT; CC=TT | T | |

FIG. 5I

| Phenotype | Gene | Direct or Tag SNP | Covered by | r2 (single or multi) | Risk Haplo/Diplotypes (Tag GT = Risk GT) | Other allele | Remarks |
|---|---|---|---|---|---|---|---|
| Rheumatoid arthritis | PTPN22 | Tag | rs6679677 | | AA=TT; AC=TC; CC=CC | C | 1% PP |

Notes:
(1) Ancestry: C(H)=Han Chinese, E=European, J=Japanese, L=Latino, H=Hawaiian, A=African
(2) DK=Denmark, FI=Finland, GH=Ghana, IS=Iceland, IT=Italy, NG=Nigeria, NL=Netherlands, GB=United Kingdom, FR=France, ES=Spain, SE=Sweden, CH=Switzerland, US=United States.
(3) Due to the different study designs, effect estimates are reported as follows:
*Odds ratio (95% confidence interval).
**Difference from mean+/-standard error for each genotype level.
***Mean+/-standard error
****Hazard ratio (95% confidence interval). An overall effect estimate is reported if multiple populations are reported in the cited publication, when available.
Effect estimates adjusted for covariates are reported, when available.
(4) Carriers=Homozygotes + heterozygotes
(5) PP=population prevalence (USA=300M)
(6) PI=population incidence (USA)
(7) PAR=population attributable risk

FIG. 5J

| Phenotype | Gene | Haplotype | Identifying SNPs | Average age of onset | Population Prevalence (USA = 300M people) | Population Incidence (USA) | No. copies of at-risk allele (% of population) | Estimated Relative Risk. Increase (het) | Modified age of onset (het) |
|---|---|---|---|---|---|---|---|---|---|
| Alcoholism | ALDH2 | GLU504LYS | rs671 | >30 | 5.55% (16.65M) | | | | |
| Alzheimer's Disease | ApoE | ApoE-e4 | rs11083750 | >65 | 1.47% (4M) will rise to 5% (16M) by 2050; 50% at 85 | | 73% | 0.5-1.0 | 84 |
| Breast Cancer | BRCA2 | N372H | rs144848 | | 0.08% (240k) | 0.08% (240k) | | | |
| Celiac Disease | HLA-DQA1 | 201 | rs4988889(T)+r s2858331(T) | | 0.4% (1.2M) | | | | |
| Colon Cancer | APC | I1307K | rs28933380 | | 0.05% (150k) | 0.035% (106k/yr) | | | |
| coronary heart disease | eNOS | | rs1799983 | | | | | | |
| coronary heart disease | MTHFR | | rs1801133 | | | | | | |
| coronary heart disease | APOB | Ins/Del/Sp1/ EcoR1 | | | | | | | |
| Creutzfeld-Jakob | PRNP | M129V | rs1799990 | | 0% (20) | 0% (20/yr) | | | |
| Crohn's Disease (inflammatory bowel disease) | CARD15 | n/a | rs2066845 & rs2066844 | | 0.18% (540k) | | | | |
| Cystic Fibrosis | CFTR | deltaF508 | various | | 0.01% (30k) | 0.009% (2.5k) | | | |

FIG. 6A

| Phenotype | Gene | Haplotype | Identifying SNPs | Average age of onset | Population Prevalence (USA = 300M people) | Population Incidence (USA) | No. copies of at-risk allele (% of population) | Estimated Relative Risk Increase (het) | Modified age of onset (het) |
|---|---|---|---|---|---|---|---|---|---|
| Diabetes Type 1 | HLA-DR | DRB1*0301 | rs2040410 | | 0.12% (360k) | 0.01% (30k/yr) | | | |
| Diabetes Type 1 | HLA-DQ | Multiple Haplotypes (protective/not) | various | | 0.12% (360k) | 0.01% (30k/yr) | | | |
| Diabetes Type 1 | INS | class 1 VNTR | n/a | | 0.12% (360k) | 0.01% (30k/yr) | | | |
| Diabetes Type 1 | CTLA4 | | rs231775 | | 0.12% (360k) | 0.01% (30k/yr) | | | |
| Diabetes Type 1 | PTPN22 | R620W | rs2476601 | | 0.12% (360k) | 0.01% (30k/yr) | | | |
| Diabetes Type 1 | IFIH1 | A946T | rs1990760 | | 0.12% (360k) | 0.01% (30k/yr) | | | |
| Episodic Memory | CAMTA1 | | rs4908449 | | | | | | |
| Lupus | IRF5 | | rs2004640 | | 0.51% (1.53M) | | | | |
| Multiple Sclerosis | HLA-DRB | B801/DRB1/ 0301/DQA1/ 0501 | rs3197630©+rs 4639334© | | 1.12% (3.6M) | | | | |
| Multiple Sclerosis | HLA-DQA1 | 102 | rs9264286©+r s6457594(a)+ RS7451962© | | 0.14% (420k) | | | | |
| Multiple Sclerosis | HLA-DRB | drb1 | RS3135388 | | 0.14% (420k) | | | | |

FIG. 6B

| Phenotype | Gene | Haplotype | Identifying SNPs | Average age of onset | Population Prevalence (USA = 300M people) | Population Incidence (USA) | No. copies of at-risk allele 1% of population) | Estimation Relative Risk. Increase (het) | Modified age of onset (het) |
|---|---|---|---|---|---|---|---|---|---|
| Osteoporosis | COL1A1 | Sp1 | rs1800012 | | 10.29% (30.87M) | | | | |
| Progressive supra-nuclear palsy | MAPT | H1 | various | 60 | | 0.004% (12k) | | | |
| Protective against Alzheimer's Disease | ApoE | ApoE-e2 | | >65 | 1.47% (4M) will rise to 5% (16M) by 2050; 50% at 85 | | | 1.0-24.0 | |
| Protective against HIV infection | CCR5 | d32 | n/a | >14 | 0.33% (990k) | 0.01% (30k) | | | |
| Psoriasis | HLA-C | 602 | rs887466(G)+ rs4379333© | | 2.02% (6.06M) | | | | |
| Rheumatoid arthritis | HLA-DRB | DRB1 | various | | 1% (3M) | | | | |
| Schizophrenia | DRD3 | SER9GLY | rs6280 | | 0.81% (2.43M) | | | | |
| Systemic Lupus SLE | HLA-DRB1 | 1501 | rs3135388 | | 0.51% (1.53M) | | | | |
| Thrombosis | factor V Leiden | R506Q | rs6025 | >50 | 0.1% (300k) | 0.1% (300k) | 96% | 1 | >50 |

FIG. 6C

| Phenotype | Gene | heterozygous for at-risk allele (% of population) | Estimated relative risk Increase (het) | Modified age of onset (het) | homozygous for at-risk allele (% of population) | Estimated relative risk Increase (homo) | Modified age of onset (homo) | Seminal Publication |
|---|---|---|---|---|---|---|---|---|
| Alcoholism | ALDH2 | | 0.2 | | | | | Yoshida et al., Am. J. Hum. Genet. 35:1107-1116 (1983) |
| Alzheimer's Disease | ApoE | 24% | 3.0-5.0 | 75 | 3% | 24 | 68 | Corder et al., Science 261:921-923 (1993) |
| Breast Cancer | BRCA2 | | 1.3 | | | | | Healey et al., Nat. Genet. 26:362-364 (2000) |
| Celiac Disease | HLA-DQA1 | | 7 | | | | | Greco et al., Gut 50:624-628 (2002) |
| Colon Cancer | APC | | 2 | | | | | Laken et al., Nat. Genet. 17:79-83 (1997) |
| coronary heart disease | eNOS | | | | | | | Casas et al., Circulation 109:1359-1365 (2004) |
| coronary heart disease | MTHFR | | | | | | | |
| coronary heart disease | APOB | | | | | | | |
| Creutzfeld-Jakob | PRNP | | 0.65 | | | | | Doh-ura et al., Biochem. Biophys. Res. Commun. 163:974-979 (1989) |
| Crohn's Disease (inflammatory bowel disease) | CARD15 | | 3-5 | | | | | Hugot et al., Nature 411:559-603 (2001) |
| Cystic Fibrosis | CFTR | | | | | | | |
| Diabetes Type 1 | HLA-DR | | 4-5 | | | | | Dunsworth et al., Clin. Genet. 21:233-236 (1982) |

FIG. 6D

| Phenotype | Gene | heterozygous for at-risk allele (% of population) | Estimated relative risk Increase (het) | Modified age of onset (het) | homozygous for at-risk allele (% of population) | Estimated relative risk Increase (homo) | Modified age of onset (homo) | Seminal Publication |
|---|---|---|---|---|---|---|---|---|
| Diabetes Type 1 | HLA-DQ | | n/a | | | | | Greenbaum et al. J. Clin. Endocr. Metab. 85:1255-1260 (2000) |
| Diabetes Type 1 | INS | | 1.5-2 | | | | | Pugliese et al., Nature 15:293-297 (1997) |
| Diabetes Type 1 | CTLA4 | | 1.4-15 | | | | | Nistico et al., Hum. Molec. Genet. 5:1075-1080 (1996) |
| Diabetes Type 1 | PTPN22 | | 1.7 | | | | | Bottini et al., Nat. Genet. 36:337-338 (2004) |
| Diabetes Type 1 | IFIH1 | | 0.8 | | | | | Smyth et al., Nat. Genet. 38:617-619 (2006) |
| Episodic Memory | CAMTA1 | | | | | | | |
| Lupus | IRF5 | | 1.8 | | | | | Graham et al., Nat. Genet. 38:550-555 (2006) |
| Multiple Sclerosis | HLA-DRB | | 2.5 | | | | | Heward et al., J. Clin. Endocr. Metab. 83:3394-3397 (1998) |
| Multiple Sclerosis | HLA-DQA1 | | 4 | | | | | Fernandez-Arquero et al., Neurology 53:1361-1363 (1999) |
| Multiple Sclerosis | HLA-DRB | | 4 | | | | | Gregersen et al., Nature 443:574-577 (2006) |

FIG. 6E

| Phenotype | Gene | heterozygous for at-risk allele (% of population) | Estimated relative risk Increase (het) | Modified age of onset (het) | homozygous for at-risk allele (% of population) | Estimated relative risk Increase (homo) | Modified age of onset (homo) | Seminal Publication |
|---|---|---|---|---|---|---|---|---|
| Osteoporosis | COL1A1 | | 1.6 | | | | | Grant et al., Nat. Genet. 14:203-205 (1996) |
| Progressive supra-nuclear palsy | MAPT | | 3.5 | | | | | Baker et al., Hum. Molec. Genet. 8:711-715 (1999) |
| Protective against Alzheimer's Disease | ApoE | | 0.6-3 | | 1% | 0.5 | >84 | Farrer et al., JAMA 278:1349-1356 (1997) |
| Protective against HIV infection | CCR5 | | n/a | | | | | Samson et al., Nature 382:722-725 (1996) |
| Psoriasis | HLA-C | | 5 | | | | | Walsh et al., Am. J. Hum. Genet. 73:580-590 (2003) |
| Rheumatoid arthritis | HLA-DRB | | 2-4 | | | | | Michou et al., Arthritis Res. Ther. 8(:R79 (2006) |
| Schizophrenia | DRD3 | | 1.7 | | | | | Crocq et al., J. Med. Genet. 29:858-860 (1992) |
| Systemic Lupus SLE | HLA-DRB1 | | 4.5 | | | | | Green et al., Ann. Hum. Genet. 50:93-96 (1986) |
| Thrombosis | factor V Leiden | 3% | 7 | <50 | <1% | 80 | <50 | Bertina et al., Nature 369:64-67 (1994) |

FIG. 6F

Report for JOHN DOE
Premium Subscription: Gold Member
Unlimited Access
Option: Quick View for Single Phenotype PHENOTYPE: Alzheimers
CORRELATION: POSITIVE
Estimated relative risk increase: 24
Predicted age of onset: 68
Actionable: YES QUICK FACTS
Medical:
  Symptoms: Increasing and persistent forgetfulness, difficulties with abstract thinking, difficulty finding the right word, disorientation, loss of judgment, difficulty performing familiar tasks, personality changes
  Pre-symptomatic treatment: statins, exercise, vitamins, mental activity
  Drug treatments for symptoms: cholinesterase inhibitors (Exelon, Eminyl, Aricept), memantine (Namenda)
  *For further medical information click here.*

Genomic:
  Quick facts:
  Population prevalence (US) 1.47%
  Gene: ApoE
  *For further medical information click here.*

Personal Information
DOB: March 23, 1947
Ethnicity: Caucasian
Medical History: *click here*
Family History: *click here*

Current Options:

( Contact a physician or genetic counselor now )

( Schedule a generic counselor appointment )

[ Send genomic and phenotype profile to J. Doe's physician ]

Back to Main Page

Your Estimated Lifetime Risk

| Risk level | Condition name | Your estimated lifetime risk | Average lifetime risk | Above or below average | Genotype percentile |
|---|---|---|---|---|---|
| 25-50% | Heart attack | 49.1% | 42.4% | ⇦ | 49 |
| | Obesity | 43.4% | 48.9% | ⇨ | 32 |
| | Prostate cancer | 25.3% | 17.4% | ⇦ | 93 |
| 10-25% | Diabetes, type 2 | 16.2% | 25.3% | ⇨ | 11 |
| | Macular degeneration | 11.2% | 12.0% | ⇨ | 48 |
| 1-10% | Colon cancer | 5.4% | 6.0% | ⇨ | 13 |
| | Alzheimer's disease | 3.7% | 9.1% | ⇨ | 33 |
| | Glaucoma | 2.8% | 4.0% | ⇨ | 61 |
| 0-1% | Rheumatoid arthritis | 0.6% | 2.0% | ⇨ | 7 |
| | Crohn's disease | 0.4% | 0.2% | ⇦ | 94 |
| | Celiac disease | 0.2% | 0.5% | ⇨ | 9 |

Filter: 
⦿ Show all
○ Show conditions with elevated risk (your estimated risk is above average)
○ Show conditions with reduced risk (your estimated risk is below average)

FIG. 16A

| Conditions | Summary | What you can do | Your DNA | About prostate cancer |
|---|---|---|---|---|

▨ Heart attack
▨ Obesity
☑ Prostate cancer

☐ Diabetes, type 2
☐ Macular degeneration
▨ Colon cancer
▨ Alzheimer's disease
▨ Glaucoma
▨ Rheumatoid arthritis
▨ Crohn's disease
▨ Celiac disease

Your estimated risk

▨ 25.3% Your estimated lifetime risk of prostate cancer is 25.3 percent.
The average lifetime risk in the U.S. population is 17.4 percent.

How common is it?
Prostate cancer is the second most common cancer affecting American men. About 2 million men have prostate cancer or have had it in the past.

Impact
If caught early, when the cancer is limited to the prostate and surrounding area, long-term survival rates are close to 100 percent.

For a detailed analysis of the findings, see Your DNA.

What you can do
For detailed recommendations on reducing your risk of prostate cancer, see What you can do.

Learn more about the condition
Prostate cancer affects a gland whose main function is to produce seminal fluid. Since the cancer typically grows very slowly, many men live for years with the disease.

For more information about prostate cancer, see About prostrate cancer. 🔗MayoClinic.com

Taking control
You can influence some of the non-genetic factors that contribute to prostate cancer.

Causes of prostate cancer

Environment and behavior 58% | Genetic 42%

Some known non-genetic risk factors
The risk of prostate cancer may be increased by:
- Advancing age
- Being overweight
- A diet high in red meat
- Inactivity

FIG. 16B

Conditions

- Heart attack
- Obesity
- Prostate cancer
- Diabetes, type 2
- Macular degeneration
- Colon cancer
- Alzheimer's disease
- Glaucoma
- Rheumatoid arthritis
- Crohn's disease
- Celiac disease

| Summary | What you can do | Your DNA | About prostate cancer |

Your results

Navigenics scanned your genome for 4 genetic markers that are believed to increase a person's risk of prostate cancer.

The scan show that you have 2 of the markers.
Your estimated lifetime risk of prostate cancer is 25.3 percent.
The average lifetime risk in the U.S. population is 17.4 percent.

> Your results do not mean that you have prostate cancer, or that you definitely will develop it. There may be other genetic factors that have not yet been identified that you could modify your risk. Lifestyle and behavior are also important contributors to prostate cancer, and researchers believe there are steps you can take that may prevent or delay the disease.
> See What you can do.

The table below shows details about your risk markers.

| Published SNP | Test SNP | Accuracy | Risk Allele | Your Genotype | Odds Ratio | Citation |
|---|---|---|---|---|---|---|
| rs1447295 | rs9643226 | 99.0% | C | GG | 1 | Yeagar. NatGen 39:645. 2007 |
| rs16901979 | rs16901979 | 99.5% | A | AC | 1.79 | Gudmundsson. NatGen 39:631. 2007 |
| rs1859962 | rs17765344 | 100.0% | A | AA | 1.45 | Gudmundsson. NatGen 39:977. 2007 |
| rs6983267 | rs6983267 | 100.0% | G | TT | 1 | Yeagar. NatGen 39:645. 2007 |

Notes
Roll over column headers to see explanations of the information contained in each column.

*The odds ratio was calculated for each allele.

To learn how we arrived at your estimates, see How we estimate risk.

FIG. 17A

Conditions

- Heart attack
- Obesity
- Prostate cancer
- Diabetes, type 2
- Macular degeneration
- Colon cancer
- Alzheimer's disease
- Glaucoma
- Rheumatoid arthritis
- Crohn's disease
- Celiac disease

| Summary | What you can do | Your DNA | About prostate cancer |

Your estimated risk

0.4% — Your estimated lifetime risk of Crohn's disease is 0.4 percent. The average lifetime risk in the U.S. population is 0.2 percent.

How common is it?
About half a million people in the United States have Crohn's disease.

Impact
Crohn's disease can lead to a variety of symptoms, including diarrhea, abdominal cramping and pain.

For a detailed analysis of the findings, see Your DNA.

What you can do
For detailed recommendations on how to be aware of early signs of Crohn's disease see What you can do.

Learn more about the condition
Crohn's disease is a chronic condition that causes inflammation in the gastrointestinal tract. It is most often found in the ileum, the lower part of the small intestine, and is one of several types of inflammatory bowel disease For more information about Crohn's disease, see About Crohn's disease. MayoClinic.com

Genes and the environment
Environmental factors also may contribute to Crohn's disease.

Causes of Crohn's disease

- Environment and behavior 20%
- Genetic 80%

Some known non-genetic risk factors The risk of Crohn's disease may be increased by:
- Living in the developed world
- Living in northern climates
- Living in urban areas

FIG. 17B

Conditions
- Heart attack
- Obesity
- Prostate cancer
- Diabetes, type 2
- Macular degeneration
- Colon cancer
- Alzheimer's disease
- Glaucoma
- Rheumatoid arthritis
- Crohn's disease
- Celiac disease

| Summary | What you can do | Your DNA | About prostate cancer |

Your results

Navigenics scanned your genome for 9 genetic markers believed to increase a person's risk of Crohn's disease. The table below shows which markers we found in your DNA.

The scan show that you have 6 of the markers.
Your estimated lifetime risk of Crohn's disease is 0.4 percent.
The average lifetime risk in the U.S. population is 0.2 percent.

Your results do not mean that you have Crohn's disease, or that you definitely will develop it. There may be other genetic factors that have not yet been identified that you could modify your risk. However, you can be alert for early signs of the disease.

See What you can do.

The table below shows details about your risk markers.

| Published SNP | Test SNP | Accuracy | Risk Allele | Your Genotype | Odds Ratio | Citation |
|---|---|---|---|---|---|---|
| rs1000113 | rs1000113 | 100.0% | T | TT | 1.92 | WTCCC. Nature 447:661. 2007 |
| rs10210302 | rs10210302 | 100.0% | T | TT | 1.85 | WTCCC. Nature 447:661. 2007 |
| rs10761659 | rs10761659 | 100.0% | G | GG | 1.55 | WTCCC. Nature 447:661. 2007 |
| rs10883365 | rs10883365 | 100.0% | G | AG | 1.2 | WTCCC. Nature 447:661. 2007 |
| rs11805303 | rs11805303 | 100.0% | T | TC | 1.39 | WTCCC. Nature 447:661. 2007 |
| rs17221417 | rs17221417 | 100.0% | G | CC | 1 | WTCCC. Nature 447:661. 2007 |
| rs17234657 | rs17234657 | 100.0% | G | TT | 1 | WTCCC. Nature 447:661. 2007 |
| rs2542151 | rs2542151 | 100.0% | G | TT | 1 | WTCCC. Nature 447:661. 2007 |
| rs9858542 | rs9858542 | 100.0% | A | GA | 1.09 | WTCCC. Nature 447:661. 2007 |

Notes
Roll over column headers to see explanations of the information contained in each column.

2 test SNPs, missing HLA locus (8 OR for RR, 2 for RN)
Lifetime risk of MS = 0.5%, 20% is +/-0.10%

FIG. 21A

Multilocus Rules

| Short Disease Name | Locus | Gene (or chr.loc on B36) | Gender applicability (F,M,B) | TEST SNP | Test Risk allele (plus, R) | Test NonRisk allele (plus, N) | Ethnicity/ Race-distr | UNITS for effect estimate | Effect Estimate | Effect R1R1R2R2 | Effect R1R1R2N2 | Effect R1R1N2N2 |
|---|---|---|---|---|---|---|---|---|---|---|---|---|
| PC | PC_1 PC_2 | 8q24_R1 8q24_R3 | M | rs4242384 rs6983267 | C\|G | A\|T | CEU | OR (95% CI) | genotypic | 3.17 | 2.55 | 2.05 |
| HEM | HEM_1 HEM_2 | HFE | B | rs1800562 rs129128 | A\|C | G\|T | CEU | OR (95% CI) | | | | 4383 |

FIG. 21B

| CI R1R1R2 R2 | CI R1R1R2 N2 | CI R1R1N2 N2 | Effect R1N1R2 R2 | Effect R1N1R2 N2 | Effect R1N1N2 N2 | CI R1N1R2 R2 | CI R1N1R2 N2 | CI R1N1N2 N2 | Effect N1N1R2 R2 | Effect N1N1R2 N2 | Effect N1N1N2 N2 | CI N1N1R2 R2 | CI N1N1R2 N2 |
|---|---|---|---|---|---|---|---|---|---|---|---|---|---|
| 2.55, 3.94 | 2.10, 3.09 | 1.70, 2.46 | 2.22 | 1.78 | 1.43 | 1.91, 2.57 | 1.60, 1.98 | 1.30, 1.57 | 1.55 | 1.24 | 1 | 1.37, 1.75 | 1.17, 1.32 |
|  |  | 1374, 10000 |  | 32 | 4.1 |  | 18.5, 55.4 | 2.9, 5.8 | 5.7 | 1.9 | 1 | 3.2, 10.1 | 1.5, 2.5 |

FIG. 22A

| Condition | SubType | Locus | Gene (or chr.loc on B36) | Gender applicability (F,M,B) | TEST SNP | B36 Chr | B36 location | Test Risk allele (plus, R) | Test NonRisk allele (plus, N) | Ethnicity/ Race-distr |
|---|---|---|---|---|---|---|---|---|---|---|
| AD | | AD_1 | APOE | B | rs4420638 | chr19 | 50114786 | G | A | CEU |
| AMD | | AMD_2 | LOC387715 | B | rs10490924 | chr10 | 124204438 | T | G | CEU |
| AMD | | AMD_3 | CFH | B | rs10737680 | chr1 | 194946078 | A | C | CEU |
| AMD | | AMD_4 | CFB-C2 | B | rs541862 | chr6 | 32024930 | T | C | CEU |
| BC | | BC_1 | FGFR2 | F | rs2981582 | chr10 | 123342307 | A | G | CEU |
| BC | | BC_3 | MAP3K1 | F | rs4700485 | chr5 | 56069964 | A | G | CEU |
| BC | | BC_4 | LSP1 | F | rs3817198 | chr11 | 1865582 | C | T | CEU |
| BC | | BC_5 | CASP8 | F | rs17468277 | chr2 | 201862445 | C | T | CEU |
| BC | BCERP | BC_6 | chr2.217614077 | F | rs6721996 | chr2 | 217617708 | G | A | CEU |
| BC | | BC_6 | chr2.217614077 | F | rs6721996 | chr2 | 217617708 | G | A | CEU |
| BC | BCERP | BC_7 | TNRC9 | F | rs3803662 | chr16 | 51143842 | A | G | CEU |
| BC | | BC_7 | TNRC9 | F | rs3803662 | chr16 | 51143842 | A | G | CEU |
| BMIOB | | BMIOB_1 | FTO | B | rs9939609 | chr16 | 52378028 | A | T | CEU |
| BMIOB | | BMIOB_2 | GPR74 | B | rs9291171 | chr4 | 73200490 | G | A | CEU |
| CD | | CD_1 | chr10.101277754 | B | rs10883365 | chr10 | 101277754 | G | A | CEU |
| CD | | CD_2 | PTGER4 | B | rs17234657 | chr5 | 40437266 | G | T | CEU |
| CD | | CD_3 | ATG16L1 | B | rs10210302 | chr2 | 233823578 | T | C | CEU |
| CD | | CD_4 | BSN | B | rs9858542 | chr3 | 49676987 | A | G | CEU |
| CD | | CD_5 | IL23R | B | rs11805303 | chr1 | 67448104 | T | C | CEU |
| CD | | CD_6 | IRGM | B | rs1000113 | chr5 | 150220269 | T | C | CEU |
| CD | | CD_7 | NOD2 (CARD15) | B | rs17221417 | chr16 | 49297083 | G | A | CEU |
| CD | | CD_8 | PTPN2 | B | rs2542151 | chr18 | 12769947 | G | T | CEU |
| CD | | CD_9 | ZNF365 | B | rs10761659 | chr10 | 64115570 | G | A | CEU |
| CelD | | CelD_1 | IL2-IL22 locus | B | rs6840978 | chr4 | 123774157 | C | T | CEU |

FIG. 22A (cont.)

| Condition | SubType | Locus | Gene (or chr.loc on B36) | Gender applicability (F,M,B) | TEST SNP | B36 Chr | B36 location | Test Risk allele (plus, R) | Test NonRisk allele (plus, N) | Ethnicity/ Race-distr |
|---|---|---|---|---|---|---|---|---|---|---|
| CeID | | CeID_2 | HLA-DQ2.5cis | B | rs2187668 | chr6 | 32713862 | T | C | CEU |
| CeID | | CeID_3 | CTLA4 | B | rs11571315 | chr2 | 204439146 | T | C | CEU |
| CRC | | CRC_1 | 8q24_R3 | B | rs6983267 | chr8 | 128482487 | G | T | CEU |
| GD | | GD_1 | CTLA4 | B | rs3087243 | chr2 | 204447164 | G | A | CEU |
| HEM | | HEM_1 | HFE | B | rs1800562 | chr6 | 26201120 | A | G | CEU |
| HEM | | HEM_2 | HFE | B | rs129128 | chr6 | 26233321 | C | T | CEU |
| MI | | MI_1 | THBS4 | B | rs1866389 | chr5 | 79397021 | G | C | CEU |
| MI | | MI_2 | 9p21 | B | rs1333049 | chr9 | 22115503 | C | G | CEU |
| MI | | MI_3 | MTHFD1L | B | rs6922269 | chr6 | 151294678 | A | G | CEU |
| MS | | MS_1 | IL7R | B | rs6897932 | chr5 | 35910332 | C | T | CEU |
| MS | | MS_2 | IL2R | B | rs12722489 | chr10 | 6142018 | C | T | CEU |
| OA | OAK | OA_1 | GDF5 | B | rs4911178 | chr20 | 33416034 | A | G | CHB |
| PC | | PC_1 | 8q24_R1 | M | rs4242384 | chr8 | 128587736 | C | A | CEU |
| PC | | PC_2 | 8q24_R3 | M | rs6983267 | chr8 | 128482487 | G | T | CEU |
| PC | | PC_3 | 8q24_R2 | M | rs16901979 | chr8 | 128194098 | A | C | CEU |
| PC | | PC_3 | 8q24_R2 | M | rs16901979 | chr8 | 128194098 | A | C | AfrAm |
| PC | | PC_4 | TCF2 | B | rs17765344 | chr17 | 66618469 | A | G | CEU |
| PS | | PS_1 | IL12B | B | rs6859018 | chr5 | 158669570 | G | A | CEU |
| PS | | PS_2 | IL23R | B | rs11209026 | chr1 | 67478546 | G | A | CEU |
| RA | | RA_1 | PTPN22 | B | rs6679677 | chr1 | 114105331 | A | C | CEU |
| RA | RA RFpos | RA_1 | PTPN22 | B | rs6679677 | chr1 | 114105331 | A | C | CEU |
| RA | | RA_2 | MHC | B | rs6457617 | chr6 | 32771829 | T | C | CEU |
| RA | | RA_3 | PADI4 | B | rs11203367 | chr1 | 17530203 | T | C | CEU |
| RA | | RA_3 | PADI4 | B | rs11203367 | chr1 | 17530203 | T | C | AS |

FIG. 22A (cont.)

| Condition | SubType | Locus | Gene (or chr.loc on B36) | Gender applicability (F,M,B) | TEST SNP | B36 Chr | B36 location | Test Risk allele (plus, R) | Test NonRisk allele (plus, N) | Ethnicity/ Race-distr |
|---|---|---|---|---|---|---|---|---|---|---|
| RLS | | RLS_1 | MEIS1 | B | rs2300478 | chr2 | 66634957 | G | T | CEU |
| RLS | | RLS_2 | MAP2k5_LBXCOR1 | B | rs1026732 | chr15 | 65882139 | G | A | CEU |
| RLS | PLMS | RLS_3 | BTBD9 | B | rs6904723 | chr6 | 38544295 | A | C | CEU |
| RLS | | RLS_3 | BTBD9 | B | rs9296249 | chr6 | 38473819 | T | C | CEU |
| SLE | | SLE_1 | IRF5 | B | rs12531711 | chr7 | 128404702 | G | A | CEU |
| T2D | | T2D_10 | TCF7L2 | B | rs4506565 | chr10 | 114746031 | T | A | CEU |
| T2D | | T2D_11 | WFS1 | B | rs10012946 | chr4 | 6344251 | C | T | CEU |
| T2D | | T2D_2 | CDKAL1 | B | rs7756992 | chr6 | 20787688 | G | A | CEU |
| T2D | | T2D_2 | CDKAL1 | B | rs7756992 | chr6 | 20787688 | G | A | CHB |
| T2D | | T2D_3 | CDKN2A/B | B | rs10811661 | chr9 | 22124094 | T | C | CEU |
| T2D | | T2D_4 | Chr11.41871942 | B | rs12288738 | chr11 | 41868875 | T | C | CEU |
| T2D | | T2D_5 | FTO | B | rs8050136 | chr16 | 52373776 | A | C | CEU |
| T2D | | T2D_6 | HHEX | B | rs1111875 | chr10 | 94452862 | C | T | CEU |
| T2D | | T2D_7 | IGF2BP2 | B | rs4402960 | chr3 | 186994381 | T | G | CEU |
| T2D | | T2D_8 | KCNJ11 | B | rs5215 | chr11 | 17365206 | C | T | CEU |
| T2D | | T2D_9 | PPARG | B | rs1801282 | chr3 | 12368125 | C | G | CEU |
| XFG | | XFG_1 | LOXL1 | B | rs2165241 | chr15 | 72009255 | T | C | CEU |

FIG. 22B

| Condition | Published SNP | Published Risk allele (plus) | Published Non Risk allele (plus) | Units for Effect Estimate | Effect Estimate | Genotypic risk: risk homoz (RR vs NN) | RR confidence interval | Genotypic risk: risk heteroz (RN vs NN) | RN confidence interval | Genotypic risk: nonrisk homoz (NN vs NN) | Carrier Risk (RR or RN vs NN) |
|---|---|---|---|---|---|---|---|---|---|---|---|
| AD | rs4420638 | G | A | OR (95% CI) | genotypic | 17.99 | 8.95, 36.19 | 4.00 | 3.00, 5.34 | 1.00 | |
| AMD | rs10490924 | T | G | OR (95% CI) | genotypic | 10.57 | | 2.72 | | 1.00 | |
| AMD | rs1410996 | G | A | OR (95% CI) | allelic | | | | | | |
| AMD | rs641153 | G | A | OR (95% CI) | genotypic | 6.98 | 0.72, 67.50 | 2.33 | 0.23, 23.25 | 1.00 | |
| BC | rs2981582 | A | G | OR (95% CI) | genotypic | 1.63 | 1.53, 1.72 | 1.23 | 1.18, 1.28 | 1.00 | |
| BC | rs889312 | C | A | OR (95% CI) | genotypic | 1.27 | 1.19, 1.36 | 1.13 | 1.09, 1.18 | 1.00 | |
| BC | rs3817198 | C | T | OR (95% CI) | genotypic | 1.17 | 1.08, 1.25 | 1.06 | 1.02, 1.11 | 1.00 | |
| BC | rs1045485 | G | C | OR (95% CI) | genotypic | 1.35 | 1.15, 1.61 | 1.12 | 1.06, 1.18 | 1.00 | |
| BC | rs13387042 | A | G | OR (95% CI) | allelic | | | | | | |
| BC | rs13387042 | A | G | OR (95% CI) | genotypic | 1.44 | 1.30, 1.58 | 1.11 | 1.03, 1.20 | 1.00 | |
| BC | rs3803662 | A | G | OR (95% CI) | allelic | | | | | | |
| BC | rs3803662 | A | G | OR (95% CI) | genotypic | 1.64 | 1.45, 1.85 | 1.27 | 1.19, 1.36 | 1.00 | |
| BMIOB | rs9939609 | A | T | OR (95% CI) | genotypic | 1.74 | 1.60, 1.89 | 1.31 | 1.23, 1.39 | 1.00 | |
| BMIOB | rs9291171 | G | A | OR (95% CI) | genotypic | 1.53 | 1.12, 2.10 | 1.24 | 1.04, 1.47 | 1.00 | |
| CD | rs10883365 | G | A | OR (95% CI) | genotypic | 1.62 | 1.37, 1.92 | 1.20 | 1.03, 1.39 | 1.00 | |
| CD | rs17234657 | G | T | OR (95% CI) | genotypic | 2.32 | 1.59, 3.39 | 1.54 | 1.34, 1.76 | 1.00 | |
| CD | rs10210302 | T | C | OR (95% CI) | genotypic | 1.85 | 1.56, 2.21 | 1.19 | 1.01, 1.41 | 1.00 | |
| CD | rs9858542 | A | G | OR (95% CI) | genotypic | 1.84 | 1.49, 2.26 | 1.09 | 0.96, 1.24 | 1.00 | |
| CD | rs11805303 | T | C | OR (95% CI) | genotypic | 1.86 | 1.54, 2.24 | 1.39 | 1.22, 1.58 | 1.00 | |
| CD | rs1000113 | T | C | OR (95% CI) | genotypic | 1.92 | 0.92, 4.00 | 1.54 | 1.31, 1.82 | 1.00 | |
| CD | rs17221417 | G | C | OR (95% CI) | genotypic | 1.92 | 1.58, 2.34 | 1.29 | 1.13, 1.46 | 1.00 | |
| CD | rs2542151 | G | T | OR (95% CI) | genotypic | 2.01 | 1.46, 2.76 | 1.30 | 1.13, 1.48 | 1.00 | |
| CD | rs10761659 | G | A | OR (95% CI) | genotypic | 1.55 | 1.30, 1.84 | 1.23 | 1.05, 1.45 | 1.00 | |
| CelD | rs6840978 | C | T | OR (95% CI) | allelic | | | | | | |

FIG. 22B (cont.)

| Condition | Published SNP | Published Risk allele (plus) | Published Non Risk allele (plus) | Units for Effect Estimate | Effect Estimate | Genotypic risk: risk homoz (RR vs NN) | RR confidence interval | Genotypic risk: risk heteroz (RN vs NN) | RN confidence interval | Genotypic risk: nonrisk homoz (NN vs NN) | Carrier Risk (RR or RN vs NN) |
|---|---|---|---|---|---|---|---|---|---|---|---|
| CeID | rs2187668 | T | C | OR (95% CI) | allelic | | | | | | |
| CeID | rs231779 | T | C | OR (95% CI) | allelic | | | | | | |
| CRC | rs6983267 | G | T | OR (95% CI) | genotypic | 1.47 | 1.25, 1.74 | 1.04 | 0.90, 1.20 | 1 | |
| GD | rs3087243 | G | A | OR (95% CI) | genotypic | 2.32 | 1.71, 3.15 | 1.59 | 1.19, 2.13 | 1 | |
| HEM | rs1800562 | A | G | | multilocus | | | | | | |
| HEM | rs1799945 | G | C | | multilocus | | | | | | |
| MI | rs1866389 | G | C | OR (95% CI) | genotypic | 3.07 | 1.32, 7.13 | 1.16 | 0.78, 1.73 | 1.00 | |
| MI | rs10757278 | G | A | OR (95% CI) | genotypic | 1.72 | 1.45, 2.03 | 1.28 | 1.14, 1.45 | 1.00 | |
| MI | rs6922269 | A | G | OR (95% CI) | genotypic | 1.53 | 1.28, 1.83 | 1.23 | 1.11, 1.36 | 1 | |
| MS | rs6897932 | C | T | OR (95% CI) | genotypic | 1.8 | 1.37, 2.35 | 1.46 | 1.11, 1.92 | 1 | |
| MS | rs12722489 | C | T | OR (95% CI) | genotypic | 1.37 | 1.03, 1.80 | 1.06 | 0.80, 1.41 | 1 | |
| OA | rs143383 | A | G | OR (95% CI) | genotypic | 2.04 | 1.16, 3.58 | 1.27 | 0.71, 2.28 | 1.00 | |
| PC | rs1447295 | A | C | OR (95% CI) | genotypic | 2.23 | 1.58, 3.14 | 1.43 | 1.29, 1.59 | 1.00 | |
| PC | rs6983267 | G | T | OR (95% CI) | genotypic | 1.58 | 1.40, 1.78 | 1.26 | 1.13, 1.41 | 1.00 | |
| PC | rs16901979 | A | C | OR (95% CI) | allelic | | | | | | |
| PC | rs16901979 | A | C | OR (95% CI) | allelic | | | | | | |
| PC | rs1859962 | G | T | OR (95% CI) | genotypic | 1.45 | 1.29, 1.62 | 1.33 | 1.21, 1.44 | 1.00 | |
| PS | rs3212227 | T | G | OR (95% CI) | genotypic | 2.55 | 1.52, 4.28 | 1.47 | 0.86, 2.5 | 1 | |
| PS | rs11209026 | G | A | OR (95% CI) | allelic | | | | | | |
| RA | rs2476601 | A | G | OR (95% CI) | genotypic | 2.26 | 0.56, 9.14 | 1.69 | 1.23, 2.32 | 1.00 | |
| RA | rs2476601 | A | G | OR (95% CI) | carrier | | | | | | 1.71 |
| RA | rs6457617 | T | C | OR (95% CI) | genotypic | 5.21 | 4.31, 6.30 | 2.36 | 1.97, 2.84 | 1.00 | |
| RA | rs2240340 | T | C | OR (95% CI) | genotypic | 2.1 | 1.66, 2.66 | 1.12 | 0.91, 1.98 | 1 | |
| RA | rs2240340 | T | C | OR (95% CI) | genotypic | 3.19 | 2.52, 4.03 | 1.32 | 1.14, 1.53 | 1 | |

FIG. 22B (cont.)

| Condition | Published SNP | Published Risk allele (plus) | Published Non Risk allele (plus) | Units for Effect Estimate | Effect Estimate | Genotypic risk: risk homoz (RR vs NN) | RR confidence interval | Genotypic risk: risk heteroz (RN vs NN) | RN confidence interval | Genotypic risk: nonrisk homoz (NN vs NN) | Carrier Risk (RR or RN vs NN) |
|---|---|---|---|---|---|---|---|---|---|---|---|
| RLS | rs2300478 | G | T | OR (95% CI) | genotypic | 3.32 | 2.64, 4.18 | 1.82 | 1.59, 2.09 | 1 | |
| RLS | rs1026732 | G | A | OR (95% CI) | genotypic | 2.08 | 1.62, 2.66 | 1.44 | 1.12, 1.86 | 1 | |
| RLS | rs6904723 | A | C | OR (95% CI) | genotypic | 2.58 | 1.78, 3.74 | 1.86 | 1.30, 2.67 | 1 | |
| RLS | rs9296249 | T | C | OR (95% CI) | genotypic | 2.85 | 1.93, 4.20 | 1.67 | 1.45, 1.92 | 1 | |
| SLE | rs2070197 | C | T | OR (95% CI) | allelic | | | | | | |
| T2D | rs4506565 | T | A | OR (95% CI) | genotypic | 1.88 | 1.56, 2.27 | 1.36 | 1.20, 1.54 | 1.00 | |
| T2D | rs10010131 | G | A | OR (95% CI) | genotypic | 1.19 | 1.10, 1.30 | 1.03 | 0.95, 1.12 | 1 | |
| T2D | rs7756992 | G | A | OR (95% CI) | genotypic | 1.5 | 1.31, 1.72 | 1.15 | 1.06, 1.24 | 1.00 | |
| T2D | rs7756992 | G | A | OR (95% CI) | genotypic | 1.52 | 1.21, 1.90 | 1.27 | 1.05, 1.55 | 1.00 | |
| T2D | rs10811661 | T | C | OR (95% CI) | genotypic | 1.39 | 1.13, 1.71 | 1.16 | 0.94, 1.43 | 1.00 | |
| T2D | rs9300039 | C | A | OR (95% CI) | genotypic | 2.61 | 1.33, 5.11 | 1.80 | 0.91, 3.57 | 1.00 | |
| T2D | rs8050136 | A | C | OR (95% CI) | genotypic | 1.49 | 1.33, 1.68 | 1.15 | 1.06, 1.26 | 1.00 | |
| T2D | rs1111875 | C | T | OR (95% CI) | genotypic | 1.2 | 1.10, 1.31 | 1.06 | 0.98, 1.16 | 1.00 | |
| T2D | rs4402960 | T | G | OR (95% CI) | genotypic | 1.21 | 1.10, 1.34 | 1.16 | 1.09, 1.24 | 1.00 | |
| T2D | rs5219 | T | C | OR (95% CI) | genotypic | 1.22 | 1.04, 1.44 | 1.12 | 0.98, 1.28 | 1.00 | |
| T2D | rs1801282 | C | G | OR (95% CI) | genotypic | 1.53 | 1.08, 2.16 | 1.30 | 0.91, 1.86 | 1.00 | |
| XFG | rs2165241 | T | C | OR (95% CI) | genotypic | 16.54 | 9.40, 29.11 | 3.72 | 2.07, 6.68 | 1 | |

FIG. 22C

| Condition | RR or RN confidence interval | Allelic Risk (R vs N) | R confidence interval | Seminal publication | DIRECT or TAG SNP | Published SNP B36 Chr | Published SNP B36 Location | Published Minor allele (plus) | Published Major allele (plus) | Test SNP accuracy Rate |
|---|---|---|---|---|---|---|---|---|---|---|
| AD | | | | Coon. J Clin Psychiatry 68:4. 2007 | TAG | chr19 | 50114786 | G | A | 100.0% |
| AMD | | | | Jakobsdottir. AJHG 77:389. 2005 | DIRECT | chr10 | 124204438 | T | G | 99.5% |
| AMD | | 3.16 | | Maller. NatGen 38:1055. 2007 | TAG | chr1 | 194963556 | A | G | 100.0% |
| AMD | | | | Gold. Nat Genet 38:45. 2006. | TAG | chr6 | 32022159 | A | G | 100.0% |
| BC | | | | Easton. Nature 447:1087. 2007 | DIRECT | chr10 | 123342307 | A | G | 100.0% |
| BC | | | | Easton. Nature 447:1087. 2007 | TAG | chr5 | 56067641 | C | A | 100.0% |
| BC | | | | Easton. Nature 447:1087. 2007 | DIRECT | chr11 | 1865582 | C | T | 100.0% |
| BC | | | | Cox. NatGen 39:352. 2007. | TAG | chr2 | 201857834 | C | G | 100.0% |
| BC | | 1.22 | 1.14, 1.31 | Stacey. NatGen 39:865. 2007 | TAG | chr2 | 217614077 | G | A | 100.0% |
| BC | | 1.2 | 1.14, 1.26 | Stacey. NatGen 39:865. 2007 | TAG | chr2 | 217614077 | G | A | 100.0% |
| BC | | 1.32 | 1.22, 1.42 | Stacey. NatGen 39:865. 2007 | DIRECT | chr16 | 51143842 | A | G | 100.0% |
| BC | | 1.28 | 1.21, 1.35 | Stacey. NatGen 39:865. 2007 | DIRECT | chr16 | 51143842 | A | G | 100.0% |
| BMIOB | | | | Frayling. Science 316:889. 2007 | DIRECT | chr16 | 52378028 | A | T | 100.0% |
| BMIOB | | | | Dahlman. AJHG 80:1115. 2007. | DIRECT | chr4 | 73200490 | G | A | 100.0% |
| CD | | | | WTCCC. Nature 447:661. 2007 | DIRECT | chr10 | 101277754 | G | A | 100.0% |
| CD | | | | WTCCC. Nature 447:661. 2007 | DIRECT | chr5 | 40437266 | G | T | 100.0% |
| CD | | | | WTCCC. Nature 447:661. 2007 | DIRECT | chr2 | 233823578 | C | T | 100.0% |
| CD | | | | WTCCC. Nature 447:661. 2007 | DIRECT | chr3 | 49676987 | A | G | 100.0% |
| CD | | | | WTCCC. Nature 447:661. 2007 | DIRECT | chr1 | 67448104 | T | C | 100.0% |
| CD | | | | WTCCC. Nature 447:661. 2007 | DIRECT | chr5 | 150220269 | T | C | 100.0% |
| CD | | | | WTCCC. Nature 447:661. 2007 | TAG | chr16 | 49297083 | G | T | 100.0% |
| CD | | | | WTCCC. Nature 447:661. 2007 | DIRECT | chr18 | 12769947 | G | C | 100.0% |
| CD | | | | WTCCC. Nature 447:661. 2007 | DIRECT | chr10 | 64115570 | A | G | 100.0% |
| CeID | | 1.42 | 1.28, 1.59 | van Heel. Nat Genet 39:827. 2007 | DIRECT | chr4 | 123774157 | T | C | 100.0% |

FIG. 22C (cont.)

| Condition | RR or RN confidence interval | Allelic Risk (R vs N) | R confidence interval | Seminal publication | DIRECT or TAG SNP | Published SNP B36 Chr | Published SNP B36 Location | Published Minor allele (plus) | Published Major allele (plus) | Test SNP accuracy Rate |
|---|---|---|---|---|---|---|---|---|---|---|
| CelD |  | 7.04 | 6.08, 8.15 | van Heel. Nat Genet 39:827. 2007 | DIRECT | chr6 | 32713862 | T | C | 100.0% |
| CelD |  | 1.24 | 1.04, 1.49 | Hunt. EJHG 13:440. 2005; van Heel. Nat Genet 39:827. 2007 | TAG | chr2 | 204442732 | T | C | 100.0% |
| CRC |  |  |  | Haiman. NatGen July 8, 2007 | DIRECT | chr8 | 128482487 | G | T | 100.0% |
| GD |  |  |  | Ueda. Nature 423:506. 2003 | DIRECT | chr2 | 204447164 | A | G | 100.0% |
| HEM |  |  |  | Burke. Gen Med 2:271. 2000 | DIRECT | chr6 | 26201120 | A | G | 100.0% |
| HEM |  |  |  | Burke. Gen Med 2:271. 2000 | TAG | chr6 | 26199158 | G | C | 100.0% |
| MI |  |  |  | Wessel. AHJ 147:905. 2004 | DIRECT | chr5 | 79397021 | C | G | 100.0% |
| MI |  |  |  | Helgadottir. Science 316:1491. 2007. | TAG | chr9 | 22114477 | G | A | 100.0% |
| MI |  |  |  | Samani. NEJM July 2007 | DIRECT | chr6 | 151294678 | A | G | 100.0% |
| MS |  |  |  | Gregory. NatGen AOP 7/29/07 | DIRECT | chr5 | 35910332 | T | C | 100.0% |
| MS |  |  |  | Intl MS Cons. NEJM 7/29/07 | DIRECT | chr10 | 6142018 | T | C | 100.0% |
| OA |  |  |  | Miyamoto. NatGen 39:539 2007 | TAG | chr20 | 33489397 | G | A | 100.0% |
| PC |  |  |  | Yeagar. NatGen 39:645. 2007 | TAG | chr8 | 128554220 | A | C | 100.0% |
| PC |  |  |  | Yeagar. NatGen 39:645. 2007 | DIRECT | chr8 | 128482487 | G | T | 100.0% |
| PC |  | 1.79 | 1.53, 2.11 | Gudmundsson. NatGen 39:631. 2007 | DIRECT | chr8 | 128194098 | A | C | 99.5% |
| PC |  | 1.34 | 1.09, 1.64 | Gudmundsson. NatGen 39:631. 2007 | DIRECT | chr8 | 128194098 | A | C | 99.5% |
| PC |  |  |  | Gudmundsson. NatGen 39:977. 2007 | TAG | chr17 | 66620348 | G | T | 100.0% |
| PS |  |  |  | Cargill. AJHG 80:273. 2007 | TAG | chr5 | 158675528 | G | T | 98.9% |
| PS |  | 1.59 | 1.27, 2.00 | Cargill. AJHG 80:273. 2007 | DIRECT | chr1 | 67478546 | A | G | 100.0% |
| RA |  |  |  | Begovich. AJHG. 75:330. 2004 | TAG | chr1 | 114179091 | A | G | 100.0% |
| RA | 1.25, 2.34 |  |  | Begovich. AJHG. 75:330. 2004 | TAG | chr1 | 114179091 | A | G | 100.0% |
| RA |  |  |  | WTCCC. Nature 447:661. 2007 | DIRECT | chr6 | 32771829 | T | C | 100.0% |
| RA |  |  |  | Lee. RheumInt 27:827. 2007 | TAG | chr1 | 17535226 | T | C | 100.0% |

FIG. 22C (cont.)

| Condition | RR or RN confidence interval | Allelic Risk (R vs N) | R confidence interval | Seminal publication | DIRECT or TAG SNP | Published SNP B36 Chr | Published SNP B36 Location | Published Minor allele (plus) | Published Major allele (plus) | Test SNP accuracy Rate |
|---|---|---|---|---|---|---|---|---|---|---|
| RA | | | | Lee. Rheum Int 27:827. 2007 | TAG | chr1 | 17535226 | T | C | 100.0% |
| RLS | | | | Winkelman. Nat Genet July 2007. | DIRECT | chr2 | 66634957 | G | T | 100.0% |
| RLS | | | | Winkelman. Nat Genet July 2007. | DIRECT | chr15 | 65882139 | A | G | 100.0% |
| RLS | | | | Stefansson. NEJM 357. July 18, 2007 | DIRECT | chr6 | 38544295 | C | A | 100.0% |
| RLS | | | | Winkelman. Nat Genet July 2007. | DIRECT | chr6 | 38473819 | C | T | 100.0% |
| SLE | | 2.04 | 1.52, 2.74 | Graham. PNAS 104:6758. 2007 | TAG | chr7 | 128376236 | C | T | 100.0% |
| T2D | | | | WTCCC. Nature 447:661. 2007 | DIRECT | chr10 | 114746031 | T | A | 100.0% |
| T2D | | | | Sandhu. NatGen July 1 2007. | TAG | chr4 | 6343816 | A | G | 100.0% |
| T2D | | | | Steinthorsdottir. Nat Genet 39:770. 2007. | DIRECT | chr6 | 20787688 | G | A | 100.0% |
| T2D | | | | Steinthorsdottir. Nat Genet 39:770. 2007. | DIRECT | chr6 | 20787688 | G | A | 100.0% |
| T2D | | | | Scott. Science 316.1341. 2007; Zeggini. Science 316:1336. 2007 | DIRECT | chr9 | 22124094 | C | T | 100.0% |
| T2D | | | | Scott. Science 316.1341. 2007. | TAG | chr11 | 41871942 | A | C | 100.0% |
| T2D | | | | Zeggini. Science 316:1336. 2007 | DIRECT | chr16 | 52373776 | A | C | 100.0% |
| T2D | | | | Scott. Science 316.1341. 2007. | DIRECT | chr10 | 94452862 | T | C | 100.0% |
| T2D | | | | Scott. Science 316.1341. 2007. | DIRECT | chr3 | 186994381 | T | G | 100.0% |
| T2D | | | | Scott. Science 316.1341. 2007. | TAG | chr11 | 17366148 | T | C | 100.0% |
| T2D | | | | Scott. Science 316.1341. 2007. | DIRECT | chr3 | 12368125 | G | C | 100.0% |
| XFG | | | | Thorleifsson. Science Express Aug 9, 2007 | DIRECT | chr15 | 72009255 | T | C | 100.0% |

FIG. 23A

| Name | Condition or SubType | Disease | Product Disease Name | Gender applicability of the condition | Product | Overall Heritability | Male Heritability | Female Heritability | Heritability Condition | Heritability Reference |
|---|---|---|---|---|---|---|---|---|---|---|
| AD | Condition | Alzheimer's Disease | Alzheimer's Disease | B | FandF | 0.62 | | | Alzheimer's Disease | The Genetic Basis of Common Diseases, 2ed. Ed: R. King, J. Rotter, A. Motulsky, 2002 |
| AMD | Condition | Age Related Macular Degeneration | macular degeneration | B | FandF | 0.67 | | | Macular degeneration (stage 3-5) | Haddad. Survey of Opthalmology 51:316. 2006 |
| BC | Condition | Breast Cancer | breast cancer | F | FandF | | | 0.27 | Breast Cancer | Lichtenstein. NEJM 343:78. 2000 |
| BCERP | SubType | breast cancer, estrogen receptor positive | | | | | | | | |

FIG. 23A (cont.)

| Name | Condition or SubType | Disease | Product Disease Name | Gender applicability of the condition | Product | Overall Heritability | Male Heritability | Female Heritability | Heritability Condition | Heritability Reference |
|---|---|---|---|---|---|---|---|---|---|---|
| BMIOB | Condition | Body Mass Index, obesity endpoint (BMI≥30kg/m²) | obesity | B | FandF | 0.67 | | | BMI | The Genetic Basis of Common Diseases, 2ed. Ed: R. King, J. Rotter, A. Motulsky, 2002 |
| CD | Condition | Crohn's disease | Crohn's disease | B | FandF | 0.80 | | | Crohn's disease | Tysk. Gut 29:990. 1988 |
| CelD | Condition | Celiac disease | celiac disease | B | FandF | 0.57 | | | Celiac disease | Nistico. Gut 55:803. 2006 |
| CRC | Condition | Colorectal cancer | colon cancer | B | FandF | 0.35 | | | Colon cancer | Lichtenstein. NEJM 343:78. 2000 |
| GD | Condition | Graves' disease | Graves' disease | B | | 0.64 | | | Graves' disease | Brix. J Clin Endocrinol Metab 86:930. 2001 |

FIG. 23A (cont.)

| Name | Condition or SubType | Disease | Product Disease Name | Gender applicability of the condition | Product | Overall Heritability | Male Heritability | Female Heritability | Heritability Condition | Heritability Reference |
|---|---|---|---|---|---|---|---|---|---|---|
| HEM | Condition | hemochromatosis | hemochromatosis | B | | | | | | The Genetic Basis of Common Diseases, 2ed. Ed: R. King, J. Rotter, A. Motulsky, 2002 |
| MI | Condition | Myocardial infarction | heart attack | B | FandF | | 0.57 | 0.38 | Death from MI | Zdravkovic. J Int Med 252:247. 2002. |
| MS | Condition | Multiple Sclerosis | multiple sclerosis | B | | 0.48 | | | multiple sclerosis | Ebers. NEJM 315:150. 1986 |
| OA | Condition | osteoarthritis | osteoarthritis | B | | | | 0.54 | osteoarthritis | Spector. BMJ 312:940. 1996 |
| PC | Condition | Prostate Cancer | prostate cancer | M | FandF | | 0.42 | | prostate cancer | Lichtenstein. NEJM 343:78. 2000 |

FIG. 23A (cont.)

| Name | Condition or SubType | Disease | Product Disease Name | Gender applicability of the condition | Product | Overall Heritability | Male Heritability | Female Heritability | Heritability Condition | Heritability Reference |
|---|---|---|---|---|---|---|---|---|---|---|
| PLMS | SubType | Periodic Limb Movements in Sleep with restless leg syndrome (majority subset) | | | | | | | | |
| PS | Condition | Psoriasis | psoriasis | B | | 0.65 | | | psoriasis | Watson. Arch Dermatol 105:197. 1972. |
| RA | Condition | rheumatoid arthritis | rheumatoid arthritis | B | FandF | 0.53 | | | rheumatoid arthritis | MacGregor. Arthritis Rheumatism 43:30. 2000 |
| RA_RF pos | SubType | Rheumatoid arthritis, RF factor positive | | | | | | | | |
| RLS | Condition | Restless Leg Syndrome | restless leg syndrome | B | | 0.60 | | | restless leg syndrome | Chen. AJHG 74:876. 2004. |

FIG. 23A (cont.)

| Name | Condition or SubType | Disease | Product Disease Name | Gender applicability of the condition | Product | Overall Heritability | Male Heritability | Female Heritability | Heritability Condition | Heritability Reference |
|---|---|---|---|---|---|---|---|---|---|---|
| SLE | Condition | Systemic lupus erythamatosus | lupus | B | | 0.62 | | | lupus | The Genetic Basis of Common Diseases, 2ed. Ed: R. King, J. Rotter, A. Motulsky, 2002 |
| T2D | Condition | Diabetes, Type 2 | diabetes, type 2 | B | FandF | 0.64 | | | Diabetes, type 2 | The Genetic Basis of Common Diseases, 2ed. Ed: R. King, J. Rotter, A. Motulsky, 2002 |
| XFG | Condition | exfoliation glaucoma | glaucoma | B | FandF | 0.13 | | | Open angle glaucoma | Teikari. Acta Opthalmol 65:175. 1987. |

FIG. 23B

| Name | Overall Prev | Male Prevalence | Female Prevalence | Prevalence to use in GCI AND GCI+ and copy | Prevalence Reference | Overall LTR | Male LTR | Female LTR | LTR Reference | Age category for LTR | LTR curator |
|---|---|---|---|---|---|---|---|---|---|---|---|
| AD | 0.015 | 0.0117 | 0.0300 | overall | Neurology 42:115 1992 | | 0.091 | 0.172 | Seshadri S, Beiser A, Kelly-Hayes M, Kase CS, Au R, Kannel WB, Wolf PA. The lifetime risk of stroke: estimates from the Framingham Study. Stroke. 2006 Feb;37(2):345-50. Epub 2006 Jan 5 | 65-74 | JW |
| AMD | 0.0147 | 0.0103 | 0.0180 | overall | Archives of Opth. 122:564. 2004. | 0.12 | | | Klaver CC, Wolfs RC, Assink JJ, van Duijn CM, Hofman A, de Jong PT. Genetic risk of age-related maculopathy. Population-based familial aggregation study. Arch Ophthalmol. 1998 Dec;116(12):1646-51. | | DS |
| BC | 0.0083 | 0.0001 | 0.0082 | female | SEER Cancer Statistics Review 1975-2003, National Cancer Institute | | | 0.1315 | SEER Cancer Statistics Review 1975-2003, National Cancer Institute, http://seer.cancer.gov/csr/1975_2003/results_merged/topic_lifetime_risk.pdf | | JW |
| BCERP BMIOB | 0.2390 | 0.2420 | 0.2350 | overall | MMWR September 15, 2006 / 55(36); 985-988 | | 0.489 | 0.456 | Vasan RS, Pencina MJ, Cobain M, Freiberg MS, D'Agostino RB. Estimated risks for developing obesity in the Framingham Heart Study. Ann Intern Med. 2005 Oct 4;143(7):473-80. | 40-49 | JW |
| CD | 0.0015 | | | overall | www.cdc.gov/foodborne/publications/24_ashford_2001.pdf | 0.002 | | | | | DS |
| CeID | 0.0067 | | | overall | http://digestive.niddk.nih.gov/ddiseases/pubs/celiac/#7 | 0.005 | | | | | DS |

FIG. 23B (cont.)

| Name | Overall Prev | Male Prevalence | Female Prevalence | Prevalence to use in GCI AND GCI+ and copy | Prevalence Reference | Overall LTR | Male LTR | Female LTR | LTR Reference | Age category for LTR | LTR curator |
|---|---|---|---|---|---|---|---|---|---|---|---|
| CRC | 0.0037 | 0.0036 | 0.0038 | overall | SEER Cancer Statistics Review 1975-2003, National Cancer Institute | | 0.0599 | 0.0541 | SEER Cancer Statistics Review 1975-2003, National Cancer Institute, http://seer.cancer.gov/csr/1975_2003/results_merged/topic_lifetime_risk.pdf | 40-49 | JW |
| GD | 0.0147 | 0.0023 | 0.0270 | overall | Inherited Basis of Common Disease | | | | | | |
| HEM | 0.0033 | | | overall | http://ghr.nlm.nih.gov/condition=hemochromatosis | | | | | | |
| MI | 0.0400 | 0.0550 | 0.0290 | overall | MMWR February 16, 2007 / 56(06);113-118 | | 0.424 | 0.249 | Lloyd-Jones DM, Lancet 1999 | 40-49 | JW |
| MS | 0.0010 | | | overall | "No one knows exactly how many people have MS. It is believed that, currently, there are approximately 250,000 to 350,000 people in the United States with MS diagnosed by a physician." www.ninds.nih.gov/disorders/multiple_sclerosis/detail_multiple_sclerosis.htm#80483215 | | | | | | |
| OA | 0.0950 | 0.0680 | 0.1140 | overall | Arth and Rheum 41:778 1998 | 0.24 | | | | | DS |
| PC | | 0.0133 | | male | SEER Cancer Statistics Review 1975-2003, National Cancer Institute | | 0.1735 | | SEER Cancer Statistics Review 1975-2003, National Cancer Institute, http://seer.cancer.gov/csr/1975_2003/results_merged/topic_lifetime_risk.pdf | 40-49 | JW |
| PLMS | | | | | | 0.08 | | | | | DS |

FIG. 23B (cont.)

| Name | Overall Prev | Male Prevalence | Female Prevalence | Prevalence to use in GCI AND GCI+ and copy | Prevalence Reference | Overall LTR | Male LTR | Female LTR | LTR Reference | Age category for LTR | LTR curator |
|---|---|---|---|---|---|---|---|---|---|---|---|
| PS | 0.0220 | | | overall | "Psoriasis is a chronic (long-lasting) skin disease of scaling and inflammation that affects 2 to 2.6 percent of the United States population, or between 5.8 and 7.5 million people." www.niams.nih.gov/hi/topics/psoriasis/psoriasis.htm | 0.04 | | | | | DS |
| RA | 0.0110 | 0.0070 | 0.0140 | overall | Arth and Rheum 42:415 1999 | 0.02 | | | | | DS |
| RA_RFpos | | | | | | | | | | | |
| RLS | 0.1060 | 0.0990 | 0.0112 | overall | Sleep Med. 7:545 2006 | 0.1 | | | | | DS |
| SLE | 0.0010 | 0.0001 | 0.0020 | overall | Arth and Rheum 41:778 1998 | 0.0014 | | | | | DS |
| T2D | 0.0740 | 0.0780 | 0.0710 | overall | CDC. 2005 NH survey. | | 0.253 | 0.277 | Narayan KM, Boyle JP, Thompson TJ, Sorensen SW, Williamson DF. Lifetime risk for diabetes mellitus in the United States.JAMA. 2003 Oct 8; 290(14):1884-90. | 40-49 | JW |
| XFG | 0.0190 | | | overall | http://www.nei.nih.gov/eyedata/pbd_tables.asp | 0.04 | | | | | DS |

FIG. 24

Glossary

| Abbreviation | What Does it stand for? |
|---|---|
| CEU | European/Caucasian ethnicity |
| CHB | Chinese ethnicity |
| JAP | Japanese ethnicity |
| YRI | Yoruban ethnicity |
| R | risk allele |
| N | non-risk allele |
| CC | case control study design |
| | |
| Ethnicity | |
| C(H) | Han Chinese ethnicity |
| E | European |
| J | Japanese |
| L | Latino |
| NA-P | Native American-Pima Indians |
| H | Hawaiian |
| Af | African |
| As | Asian |
| AfrAm | African Americans |
| JapAm | Japanese Americans |
| EurAm | European Americans |
| Ash | Ashkenazi |
| | |
| Countries | |
| CH | Switzerland |
| Dk | Denmark |
| FI | Finland |
| GH | Ghana |
| IS | Iceland |
| IT | Italy |
| KR | Korea |
| NG | Nigeria |
| NL | Netherlands |
| GB | United Kingdom |
| FR | France |
| ES | Spain |
| SE | Sweden |
| TH | Thailand |
| TW | Taiwan |
| US | United States |
| DE | Germany |
| CA | Canada |
| BE | Belgium |

FIG. 25A

| Condition | Sub Type | Locus | Gene (or chr.loc on B36) | TEST SNP | B36 Chr | B36 location | Test Risk allele (plus, R) | Test Non Risk allele (plus, N) | Ethnicity/Race-distr |
|---|---|---|---|---|---|---|---|---|---|
| AD | | AD_1 | APOE | rs4420638 | chr19 | 50114786 | G | A | CEU |
| AMD | | AMD_1 | C3-R80G | | | | | | CEU |
| AMD | | AMD_5 | CFH-Y402H | | | | | | CEU |
| AMD | | AMD_6 | C2-E318D | | | | | | CEU |
| AMD | | AMD_3 | CFH | rs10737680 | chr1 | 194946078 | A | C | CEU |
| AMD | | AMD_2 | LOC387715-S69A | rs10490924 | chr10 | 124204438 | T | G | CEU |
| AMD | | AMD_4 | CFB | rs541862 | chr6 | 32024930 | T | C | CEU |
| BC | BCERP | BC_6 | chr2.217614077 | rs6721996 | chr2 | 217617708 | G | A | CEU |
| BC | BCERP | BC_7 | TNRC9 | rs3803662 | chr10 | 51143842 | A | G | CEU |
| BC | | BC_1 | FGFR2 | rs2981582 | chr2 | 123342307 | A | G | CEU |
| BC | | BC_3 | MAP3KL | rs4700485 | chr5 | 56069964 | A | G | CEU |
| BC | | BC_4 | LSPL | rs3817198 | chr11 | 1865582 | C | T | CEU |
| BC | | BC_5 | CASP8 | rs17468277 | chr2 | 201862445 | C | T | CEU |
| BC | | BC_6 | chr2.217614077 | rs6721996 | chr2 | 217617708 | G | A | CEU |
| BC | | BC_7 | TNRC9 | rs3803662 | chr16 | 51143842 | A | G | CEU |
| BMIOB | | BMIOB_1 | FTO | rs9939609 | chr16 | 52378028 | A | T | CEU |
| BMIOB | | BMIOB_2 | GPR74 | rs9291171 | chr4 | 73200490 | G | A | CEU |
| CD | | CD_10 | NOD2 (CARD15) | | | | | | CEU |
| CD | | CD_11 | NOD2 (CARD15) | | | | | | CEU |
| CD | | CD_1 | chr10.101277754 | rs10883365 | chr10 | 101277754 | G | A | CEU |
| CD | | CD_2 | PTGER4 | rs17234657 | chr5 | 40437266 | G | T | CEU |
| CD | | CD_3 | ATG16L1 | rs10210302 | chr2 | 233823578 | T | C | CEU |
| CD | | CD_4 | BSN | rs9858542 | chr3 | 49676987 | A | G | CEU |
| CD | | CD_5 | IL23R | rs11805303 | chr1 | 67448104 | T | C | CEU |
| CD | | CD_6 | IRGM | rs1000113 | chr5 | 150220269 | T | C | CEU |
| CD | | CD_7 | NOD2 (CARD15) | rs17221417 | chr16 | 49297083 | G | C | CEU |

FIG. 25A (cont.)

| Condition | Sub Type | Locus | Gene (or chr.loc on B36) | TEST SNP | B36 Chr | B36 location | Test Risk allele (plus, R) | Test Non Risk allele (plus, N) | Ethnicity/ Race-distr |
|---|---|---|---|---|---|---|---|---|---|
| CD |  | CD_8 | PTPN2 | rs2542151 | chr18 | 12769947 | G | T | CEU |
| CD |  | CD_9 | ZNF365 | rs10761659 | chr10 | 64115570 | G | A | CEU |
| CelD |  | CelD_4 | HLA-DQ8:1 |  |  |  |  |  | CEU |
| CelD |  | CelD_1 | IL2-IL22 locus | rs6840978 | chr4 | 123774157 | C | T | CEU |
| CelD |  | CelD_3 | CTLA4 | rs11571315 | chr2 | 204439146 | T | C | CEU |
| CelD |  | CelD_2 | HLA-DQ2.5 | rs2187668 | chr6 | 32713862 | T | C | CEU |
| CRC |  | CRC_1 | 8q24_R3 | rs6983267 | chr8 | 128482487 | G | T | CEU |
| GD |  | GD_2 | DRB1*0301 DQAl*0501 |  |  |  |  |  | CEU |
| GD |  | GD_1 | CTLA4 | rs3087243 | chr2 | 204447164 | G | A | CEU |
| HEM |  | HEM_1 | HFE | rs1800562 | chr6 | 26201120 | A | G | CEU |
| HEM |  | HEM_2 | HFE | rs129128 | chr6 | 26233321 | C | T | CEU |
| MI |  | MI_1 | THBS4 | rs1866389 | chr5 | 79397021 | G | C | CEU |
| MI |  | MI_2 | 9p21 | rs1333049 | chr9 | 22115503 | C | G | CEU |
| MI |  | MI_3 | MTHFD1L | rs6922269 | chr6 | 151294678 | A | G | CEU |
| MS |  | MS_3 | DRB1 |  |  |  |  |  | CEU |
| MS |  | MS_1 | IL7R | rs6897932 | chr5 | 35910332 | C | T | CEU |
| MS |  | MS_2 | IL2R | rs12722489 | chr10 | 6142018 | C | T | CEU |
| OA | OAK | OA_1 | GDF5 | rs4911178 | chr20 | 33416034 | A | G | CHB |
| PC |  | PC_5 | 17q12 |  |  |  |  |  | CEU |
| PC |  | PC_1 | 8q24_R1 | rs4242384 | chr8 | 128587736 | C | A | CEU |
| PC |  | PC_2 | 8q24_R3 | rs6983267 | chr8 | 128482487 | G | T | CEU |
| PC |  | PC_3 | 8q24_R2 | rs16901979 | chr8 | 128194098 | A | C | CEU |
| PC |  | PC_3 | 8q24_R2 | rs16901979 | chr8 | 128194098 | A | C | AfrAm |
| PC |  | PC_4 | TCF2 | rs17765344 | chr17 | 66618469 | A | G | CEU |
| PS |  | PS_3 | HLAC |  |  |  |  |  | CEU |
| PS |  | PS_1 | IL12B | rs6859018 | chr5 | 158669570 | G | A | CEU |

FIG. 25A (cont.)

| Condition | Sub Type | Locus | Gene (or chr.loc on B36) | TEST SNP | B36 Chr | B36 location | Test Risk allele (plus, R) | Test Non Risk allele (plus, N) | Ethnicity/ Race-distr |
|---|---|---|---|---|---|---|---|---|---|
| PS |  | PS_2 | IL23R | rs11209026 | chr1 | 67478546 | G | A | CEU |
| RA |  | RA_4 | HLADRB1 |  |  |  |  |  | CEU |
| RA |  | RA_5 | HLADRB1 |  |  |  |  |  | CEU |
| RA |  | RA_6 | HLADRB1 |  |  |  |  |  | CEU |
| RA | RA_Rfpos | RA_1 | PTPN22 | rs6679677 | chr1 | 114105331 | A | C | CEU |
| RA |  | RA_1 | PTPN22 | rs6679677 | chr1 | 114105331 | A | C | CEU |
| RA |  | RA_3 | PADI4 | rs11203367 | chr1 | 17530203 | T | C | CEU |
| RA |  | RA_3 | PADI4 | rs11203367 | chr1 | 17530203 | T | C | AS |
| RA |  | RA_2 | MHC | rs6452617 | chr6 | 32771829 | A | C | CEU |
| RLS | PLMS | RLS_3 | BTBD9 | rs6904723 | chr6 | 38544295 | G | T | CEU |
| RLS |  | RLS_1 | MEIS1 | rs2300478 | chr2 | 66634957 | G | A | CEU |
| RLS |  | RLS_2 | MAP2k5_LBXCOR1 | rs1026732 | chr15 | 65882139 | T | C | CEU |
| RLS |  | RLS_3 | BTBD9 | rs9296249 | chr6 | 38473819 |  |  | CEU |
| SLE |  | SLE_2 | IRF5 |  |  |  |  |  | CEU |
| SLE |  | SLE_3 | IRF5 |  |  |  |  |  | CEU |
| SLE |  | SLE_4 | HLA DRB1 |  |  |  |  |  | CEU |
| SLE |  | SLE_5 | HLA DRB1 |  |  |  |  |  | CEU |
| SLE |  | SLE_1 | IRF5 | rs12531711 | chr7 | 128404702 | G | A | CHB |
| T2D |  | T2D_12 | SLC30A8 | rs4506565 | chr10 | 114746031 | T | A | CEU |
| T2D |  | T2D_10 | TCF7L2 | rs10012946 | chr4 | 6344251 | C | T | CEU |
| T2D |  | T2D_11 | WFS1 | rs7756992 | chr6 | 20787688 | G | A | CEU |
| T2D |  | T2D_2 | CDKAL1 | rs7756992 | chr6 | 20787688 | G | A | CHB |
| T2D |  | T2D_2 | CDKAL1 | rs10811661 | chr9 | 22124094 | T | C | CEU |
| T2D |  | T2D_3 | CDKN2A/B | rs12288738 | chr11 | 41868875 | T | C | CEU |
| T2D |  | T2D_4 | Chr11.41871942 |  |  |  |  |  | CEU |
| T2D |  | T2D_5 | FTO | rs8050136 | chr16 | 52373776 | A | C | CEU |

FIG. 25A (cont.)

| Condition | Sub Type | Locus | Gene (or chr.loc on B36) | TEST SNP | B36 Chr | B36 location | Test Risk allele (plus, R) | Test Non Risk allele (plus, N) | Ethnicity/ Race-distr |
|---|---|---|---|---|---|---|---|---|---|
| T2D | | T2D_6 | HHEX | rs1111875 | chr10 | 94452862 | C | T | CEU |
| T2D | | T2D_7 | IGF2BP2 | rs4402960 | chr3 | 186994381 | T | G | CEU |
| T2D | | T2D_8 | KCNJ11 | rs5215 | chr11 | 17365206 | C | T | CEU |
| T2D | | T2D_9 | PPARG | rs1801282 | chr3 | 12368125 | C | G | CEU |
| XFG | | XFG_1 | LOXL1 | rs2165241 | chr15 | 72009255 | T | C | CEU |

FIG. 25B

| Condition | Published SNP | Published Risk allele (plus) | Published Non Risk allele (plus) | UNITS for effect estimate | Effect Estimate | Genotypic risk: risk homoz (RR vs NN) | RR confidence interval |
|---|---|---|---|---|---|---|---|
| AD | rs4420638 | G | A | OR (95%CI) | genotypic | 17.99 | 8.95, 36.19 |
| AMD | rs2230199 | C | G | OR (95%CI) | genotypic | 2.6 | 1.6, 4.1 |
| AMD | rs1061170 | C | T | OR (95%CI) | genotypic | 6.3 | 3.8, 10.4 |
| AMD | rs9332739 | G | C | OR (95%CI) | allelic | | |
| AMD | rs1410996 | G | A | OR (95%CI) | allelic | | |
| AMD | rs10490924 | T | G | OR (95%CI) | genotypic | 10.57 | |
| AMD | rs641153 | G | A | OR (95%CI) | genotypic | 6.98 | 0.72, 67.50 |
| BC | rs13387042 | A | G | OR (95%CI) | allelic | | |
| BC | rs3803662 | A | G | OR (95%CI) | allelic | | |
| BC | rs2981582 | A | G | OR (95%CI) | genotypic | 1.63 | 1.53, 1.72 |
| BC | rs889312 | C | A | OR (95%CI) | genotypic | 1.27 | 1.19, 1.36 |
| BC | rs3817198 | C | T | OR (95%CI) | genotypic | 1.17 | 1.08, 1.25 |
| BC | rs1045485 | G | C | OR (95%CI) | genotypic | 1.35 | 1.15, 1.61 |
| BC | rs13387042 | A | G | OR (95%CI) | genotypic | 1.44 | 1.30, 1.58 |
| BC | rs3803662 | A | G | OR (95%CI) | genotypic | 1.64 | 1.45, 1.85 |
| BMIOB | rs9939609 | G | T | OR (95%CI) | genotypic | 1.74 | 1.60, 1.89 |
| BMIOB | rs9291171 | C | A | OR (95%CI) | genotypic | 1.53 | 1.12, 2.10 |
| CD | rs2066845 | C | G | OR (95%CI) | genotypic | 12.13 | |
| CD | rs5743293 | C | - | OR (95%CI) | genotypic | 34.66 | 21.79, 47.53 |
| CD | rs10883365 | G | A | OR (95%CI) | genotypic | 1.62 | 1.37, 1.92 |
| CD | rs17234657 | G | T | OR (95%CI) | genotypic | 2.32 | 1.59, 3.39 |
| CD | rs10210302 | T | C | OR (95%CI) | genotypic | 1.85 | 1.56, 2.21 |
| CD | rs9858542 | A | G | OR (95%CI) | genotypic | 1.84 | 1.49, 2.26 |
| CD | rs11805303 | T | C | OR (95%CI) | genotypic | 1.86 | 1.54, 2.24 |
| CD | rs1000113 | T | C | OR (95%CI) | genotypic | 1.92 | 0.92, 4.00 |
| CD | rs17221417 | G | C | OR (95%CI) | genotypic | 1.92 | 1.58, 2.34 |

FIG. 25B (cont.)

| Condition | Published SNP | Published Risk allele (plus) | Published Non Risk allele (plus) | UNITS for effect estimate | Effect Estimate | Genotypic risk: risk homoz (RR vs NN) | RR confidence interval |
|---|---|---|---|---|---|---|---|
| CD | rs2542151 | G | T | OR (95%CI) | genotypic | 2.01 | 1.46, 2.76 |
| CD | rs10761659 | G | A | OR (95%CI) | genotypic | 1.55 | 1.30, 1.84 |
| CeID | DQA1*0301 DQB1*0302 | DQA1*0301 DQB1*0302 | not DQA1*0301 DQB1*0302 | | | | |
| CeID | rs6840978 | C | T | OR (95%CI) | allelic | | |
| CeID | rs231779 | T | C | OR (95%CI) | allelic | | |
| CeID | DQA1*0501 DQB1*0201 | T | C | OR (95%CI) | allelic | | |
| CRC | rs6983267 | G | T | OR (95%CI) | genotypic | 1.47 | 1.25, 1.74 |
| GD | DRB1*0301 DQA1*0501 | DRB1*0301 DQA1*0501 | not DRB1*0301 DQA1*0501 | OR (95%CI) | allelic | | |
| GD | rs3087243 | G | A | OR (95%CI) | genotypic | 2.32 | 1.71, 3.15 |
| HEM | rs1800562 | A | G | | multilocus | | |
| HEM | rs1799945 | G | C | | multilocus | | |
| MI | rs1866389 | G | C | OR (95%CI) | genotypic | 3.07 | 1.32, 7.13 |
| MI | rs10757278 | G | A | OR (95%CI) | genotypic | 1.72 | 1.45, 2.03 |
| MI | rs6922269 | A | G | OR (95%CI) | genotypic | 1.53 | 1.28, 1.83 |
| MS | DRB1*1501 | DRB1*1501 | not DRB1*1501 | OR (95%CI) | genotypic | 5.43 | 4.12, 7.16 |
| MS | rs6897932 | C | T | OR (95%CI) | genotypic | 1.8 | 1.37, 2.35 |
| MS | rs12722489 | C | T | OR (95%CI) | genotypic | 1.37 | 1.03, 1.80 |
| OA | rs143383 | A | G | OR (95%CI) | genotypic | 2.04 | 1.16, 3.58 |
| PC | rs4430796 | A | G | OR (95%CI) | genotypic | 1.48 | 1.32, 1.66 |
| PC | rs1447295 | A | C | OR (95%CI) | genotypic | 2.23 | 1.58, 3.14 |
| PC | rs6983267 | G | T | OR (95%CI) | genotypic | 1.58 | 1.40, 1.78 |
| PC | rs16901979 | A | C | OR (95%CI) | allelic | | |
| PC | rs16901979 | A | C | OR (95%CI) | allelic | | |
| PS | rs1859962 | G | T | OR (95%CI) | genotypic | 1.45 | 1.29, 1.62 |
| PS | HLAC*0602 | HLAC*0602 | not HLAC*0602 | OR (95%CI) | allelic | | |
| PS | rs3212227 | T | G | OR (95%CI) | genotypic | 2.55 | 1.52, 4.28 |

FIG. 25B (cont.)

| Condition | Published SNP | Published Risk allele (plus) | Published Non Risk allele (plus) | UNITS for effect estimate | Effect Estimate | Genotypic risk: risk homoz (RR vs NN) | RR confidence interval |
|---|---|---|---|---|---|---|---|
| PS | rs11209026 | G | A | OR (95%CI) | allelic | | |
| RA | DRB1*0101 | DRB1*0101 | not DRB1*0101 | OR (95%CI) | allelic | | |
| RA | DRB1*0401 | DRB1*0401 | not DRB1*0401 | OR (95%CI) | allelic | | |
| RA | DRB1*0404 | DRB1*0404 | not DRB1*0404 | OR (95%CI) | allelic | | |
| RA | rs2476601 | A | G | OR (95%CI) | carrier | | 0.56, 9.14 |
| RA | rs2476601 | A | G | OR (95%CI) | genotypic | 2.26 | 1.66, 2.66 |
| RA | rs2240340 | T | C | OR (95%CI) | genotypic | 2.1 | 2.52, 4.03 |
| RA | rs2240340 | T | C | OR (95%CI) | genotypic | 3.19 | 4.31, 6.30 |
| RA | rs6457617 | T | C | OR (95%CI) | genotypic | 5.21 | 1.78, 3.74 |
| RLS | rs6904723 | A | T | OR (95%CI) | genotypic | 2.58 | 2.64, 4.18 |
| RLS | rs2300478 | G | C | OR (95%CI) | genotypic | 3.32 | 1.62, 2.66 |
| RLS | rs1026732 | G | A | OR (95%CI) | genotypic | 2.08 | 1.93, 4.20 |
| RLS | rs9296249 | T | C | OR (95%CI) | genotypic | 2.85 | |
| SLE | rs10954213 | A | G | OR (95%CI) | allelic | | |
| SLE | rs2004640 | T | G | OR (95%CI) | allelic | | |
| SLE | DRB1*0301 | DRB1*0301 | not DRB1*0301 | OR (95%CI) | allelic | | |
| SLE | DRB1*1501 | DRB1*1501 | not DRB1*1501 | OR (95%CI) | allelic | | |
| SLE | rs2070197 | C | T | OR (95%CI) | allelic | | |
| T2D | rs13266634 | C | T | OR (95%CI) | allelic | | 1.56, 2.27 |
| T2D | rs4506565 | T | A | OR (95%CI) | genotypic | 1.88 | 1.10, 1.30 |
| T2D | rs10010131 | G | A | OR (95%CI) | genotypic | 1.19 | 1.31, 1.72 |
| T2D | rs7756992 | G | A | OR (95%CI) | genotypic | 1.5 | 1.21, 1.90 |
| T2D | rs7756992 | G | A | OR (95%CI) | genotypic | 1.52 | 1.13, 1.71 |
| T2D | rs10811661 | T | C | OR (95%CI) | genotypic | 1.39 | 1.33, 5.11 |
| T2D | rs9300039 | C | A | OR (95%CI) | genotypic | 2.61 | 1.33, 1.68 |
| T2D | rs8050136 | A | C | OR (95%CI) | genotypic | 1.49 | |

FIG. 25B (cont.)

| Condition | Published SNP | Published Risk allele (plus) | Published Non Risk allele (plus) | UNITS for effect estimate | Effect Estimate | Genotypic risk: risk homoz (RR vs NN) | RR confidence interval |
|---|---|---|---|---|---|---|---|
| T2D | rs1111875 | C | T | OR (95%CI) | genotypic | 1.2 | 1.10, 1.31 |
| T2D | rs4402960 | T | G | OR (95%CI) | genotypic | 1.21 | 1.10, 1.34 |
| T2D | rs5219 | T | C | OR (95%CI) | genotypic | 1.22 | 1.04, 1.44 |
| T2D | rs1801282 | C | G | OR (95%CI) | genotypic | 1.53 | 1.08, 2.16 |
| XFG | rs2165241 | T | C | OR (95%CI) | genotypic | 16.54 | 9.40, 29.11 |

FIG. 25C

| Condition | Genotypic risk: heteroz (RN vs NN) | RN confidence interval | Genotypic risk: nonrisk homoz (NN vs NN) | Carrier Risk (RR or RN vs NN) | RR or RN confidence interval | Allelic Risk (R vs N) | R confidence interval |
|---|---|---|---|---|---|---|---|
| AD | 4.00 | 3.00, 5.34 | 1.00 | | | | |
| AMD | 1.70 | 1.3, 2.1 | 1.00 | | | | |
| AMD | 3.10 | 2.0, 4.6 | 1.00 | | | | |
| AMD | | | | | | 2.78 | 2.08, 4.76 |
| AMD | | | | | | 3.16 | |
| AMD | 2.72 | | 1.00 | | | | |
| AMD | 2.33 | 0.23, 23.25 | 1.00 | | | | |
| BC | 1.23 | 1.18, 1.28 | | | | 1.22 | 1.14, 1.31 |
| BC | 1.13 | 1.09, 1.18 | 1.00 | | | 1.32 | 1.22, 1.42 |
| BC | 1.06 | 1.02, 1.11 | 1.00 | | | | |
| BC | 1.12 | 1.06, 1.18 | 1.00 | | | | |
| BC | 1.11 | 1.03, 1.20 | 1.00 | | | 1.2 | 1.14, 1.26 |
| BC | 1.27 | 1.19, 1.36 | 1.00 | | | 1.28 | 1.21, 1.35 |
| BMIOB | 1.31 | 1.23, 1.39 | 1.00 | | | | |
| BMIOB | 1.24 | 1.04, 1.47 | 1.00 | | | | |
| CD | 3.05 | 3.21, 5.89 | | | | | |
| CD | 4.55 | 1.03, 1.39 | 1.00 | | | | |
| CD | 1.20 | 1.34, 1.76 | 1.00 | | | | |
| CD | 1.54 | 1.01, 1.41 | 1.00 | | | | |
| CD | 1.19 | 0.96, 1.24 | 1.00 | | | | |
| CD | 1.09 | 1.22, 1.58 | 1.00 | | | | |
| CD | 1.39 | 1.31, 1.82 | 1.00 | | | | |
| CD | 1.54 | 1.13, 1.46 | 1.00 | | | | |
| CD | 1.29 | | 1.00 | | | | |

FIG. 25C (cont.)

| Condition | Genotypic risk: heteroz (RN vs NN) | RN confidence interval | Genotypic risk: nonrisk homoz (NN vs NN) | Carrier Risk (RR or RN vs NN) | RR or RN confidence interval | Allelic Risk (R vs N) | R confidence interval |
|---|---|---|---|---|---|---|---|
| CD | 1.30 | 1.13, 1.48 | 1.00 | | | | |
| CD | 1.23 | 1.05, 1.45 | 1.00 | | | | |
| CeID | | | | | | | |
| CeID | | | | | | 1.42 | 1.28, 1.59 |
| CeID | | | | | | 1.24 | 1.04, 1.49 |
| CeID | | | | | | 7.04 | 6.08, 8.15 |
| CRC | 1.04 | 0.90, 1.20 | 1 | | | | |
| GD | 1.59 | 1.19, 2.13 | 1 | | | 2.72 | 1.91, 3.87 |
| HEM | | | | | | | |
| HEM | | | | | | | |
| MI | 1.16 | 0.78, 1.73 | 1.00 | | | | |
| MI | 1.28 | 1.14, 1.45 | 1.00 | | | | |
| MI | 1.23 | 1.11, 1.36 | 1 | | | | |
| MS | 2.92 | 2.42, 3.51 | 1 | | | | |
| MS | 1.46 | 1.11, 1.92 | 1 | | | | |
| MS | 1.06 | 0.80, 1.41 | 1 | | | | |
| OA | 1.27 | 0.71, 2.28 | 1.00 | | | | |
| PC | 1.24 | 1.13, 1.36 | 1.00 | | | | |
| PC | 1.43 | 1.29, 1.59 | 1.00 | | | | |
| PC | 1.26 | 1.13, 1.41 | 1.00 | | | | |
| PC | | | | | | 1.79 | 1.53, 2.11 |
| PC | 1.33 | 1.21, 1.44 | 1.00 | | | 1.34 | 1.09, 1.64 |
| PS | | | | | | 3.1 | 2.37, 4.08 |
| PS | 1.47 | 0.86, 2.5 | 1 | | | | |

FIG. 25C (cont.)

| Condition | Genotypic risk: heteroz (RN vs NN) | RN confidence interval | Genotypic risk: nonrisk homoz (NN vs NN) | Carrier Risk (RR or RN vs NN) | RR or RN confidence interval | Allelic Risk (R vs N) | R confidence interval |
|---|---|---|---|---|---|---|---|
| PS |  |  |  |  |  | 1.59 | 1.27, 2.00 |
| RA |  |  |  |  |  | 1.1 |  |
| RA |  |  |  |  |  | 6.1 |  |
| RA |  |  |  |  |  | 4.6 |  |
| RA |  |  |  | 1.71 | 1.25, 2.34 |  |  |
| RA | 1.69 | 1.23, 2.32 | 1.00 |  |  |  |  |
| RA | 1.12 | 0.91, 1.98 | 1 |  |  |  |  |
| RA | 1.32 | 1.14, 1.53 | 1 |  |  |  |  |
| RA | 2.36 | 1.97, 2.84 | 1.00 |  |  |  |  |
| RLS | 1.86 | 1.30, 2.67 | 1 |  |  |  |  |
| RLS | 1.82 | 1.59, 2.09 | 1 |  |  |  |  |
| RLS | 1.44 | 1.12, 1.86 | 1 |  |  |  |  |
| RLS | 1.67 | 1.45, 1.92 |  |  |  |  |  |
| SLE |  |  |  |  |  | 1.44 | 1.14, 1.81 |
| SLE |  |  |  |  |  | 1.62 | 1.30, 2.01 |
| SLE |  |  |  |  |  | 2 | 1.6, 2.4 |
| SLE |  |  |  |  |  | 1.4 | 1.2, 1.7 |
| SLE |  |  |  |  |  | 2.04 | 1.52, 2.74 |
| T2D | 1.36 | 1.20, 1.54 | 1.00 |  |  |  |  |
| T2D | 1.03 | 0.95, 1.12 | 1 |  |  |  |  |
| T2D | 1.15 | 1.06, 1.24 | 1.00 |  |  |  |  |
| T2D | 1.27 | 1.05, 1.55 | 1.00 |  |  |  |  |
| T2D | 1.16 | 0.94, 1.43 | 1.00 |  |  |  |  |
| T2D | 1.80 | 0.91, 3.57 | 1.00 |  |  |  |  |
| T2D | 1.15 | 1.06, 1.26 | 1.00 |  |  | 1.18 | 1.09, 1.29 |

FIG. 25C (cont.)

| Condition | Genotypic risk: heteroz (RN vs NN) | RN confidence interval | Genotypic risk: nonrisk homoz (NN vs NN) | Carrier Risk (RR or RN vs NN) | RR or RN confidence interval | Allelic Risk (R vs N) | R confidence interval |
|---|---|---|---|---|---|---|---|
| T2D | 1.06 | 0.98, 1.16 | 1.00 | | | | |
| T2D | 1.16 | 1.09, 1.24 | 1.00 | | | | |
| T2D | 1.12 | 0.98, 1.28 | 1.00 | | | | |
| T2D | 1.30 | 0.91, 1.86 | 1.00 | | | | |
| XFG | 3.72 | 2.07, 6.68 | 1 | | | | |

FIG. 25D

| Condition | Seminal publication | Direct or tag snp | Published SNP B36 Chr | Published SNP B36 location | Published Minor allele (plus) | Published Major allele (plus) |
|---|---|---|---|---|---|---|
| AD | Coon. J Clin Psychiatry 68:4. 2007 | TAG | chr19 | 50114786 | G | A |
| AMD | Yates, NEJM 357:553. 2007 | | chr11 | 6669387 | C | G |
| AMD | Yates, NEJM 357:553. 2007 | | chr1 | 194925860 | C | T |
| AMD | Gold. Nat Genet 38:45. 2006 | | chr6 | 32011783 | C | G |
| AMD | Maller. NatGen 38:1055. 2006 | TAG | chr1 | 194963556 | A | G |
| AMD | Jakobsdottir. AJHG 77:389. 2005 | DIRECT | chr10 | 124204438 | T | G |
| AMD | Gold. Nat Genet 38:45. 2006 | TAG | chr6 | 32022159 | A | G |
| BC | Stacey. NatGen 39:865. 2007 | TAG | chr2 | 217614077 | G | A |
| BC | Stacey. NatGen 39:865. 2007 | DIRECT | chr16 | 51143842 | A | G |
| BC | Easton. Nature 447:1087. 2007 | DIRECT | chr10 | 123342307 | A | G |
| BC | Easton. Nature 447:1087. 2007 | TAG | chr5 | 56067641 | C | A |
| BC | Easton. Nature 447:1087. 2007 | DIRECT | chr11 | 1865582 | C | T |
| BC | Cox. NatGen 39:352. 2007 | TAG | chr2 | 201857834 | C | G |
| BC | Stacey. NatGen 39:865. 2007 | TAG | chr2 | 217614077 | G | A |
| BC | Stacey. NatGen 39:865. 2007 | DIRECT | chr6 | 51143842 | A | G |
| BMIOB | Frayling. Science 316:889. 2007 | DIRECT | chr16 | 52378028 | A | T |
| BMIOB | Dahlman. AJHG 80:1115. 2007 | DIRECT | chr4 | 73200490 | G | A |
| CD | Pascoe. EJHG 15:864. 2007 | | chr16 | 49314041 | C | G |
| CD | Pascoe. EJHG 15:864. 2007 | | chr16 | 49321283 | C | - |
| CD | WTCCC. NATURE 447:661. 2007 | DIRECT | chr10 | 101277754 | G | A |
| CD | WTCCC. NATURE 447:661. 2007 | DIRECT | chr5 | 40437266 | G | T |
| CD | WTCCC. NATURE 447:661. 2007 | DIRECT | chr2 | 233823578 | C | T |
| CD | WTCCC. NATURE 447:661. 2007 | DIRECT | chr3 | 49676987 | A | G |
| CD | WTCCC. NATURE 447:661. 2007 | DIRECT | chr1 | 67448104 | T | C |
| CD | WTCCC. NATURE 447:661. 2007 | DIRECT | chr5 | 150220269 | T | C |
| CD | WTCCC. NATURE 447:661. 2007 | TAG | chr16 | 49297083 | G | C |

FIG. 25D (cont.)

| Condition | Seminal publication | Direct or tag snp | Published SNP B36 Chr | Published SNP B36 location | Published Minor allele (plus) | Published Major allele (plus) |
|---|---|---|---|---|---|---|
| CD | WTCCC. Nature 447:661. 2007 | DIRECT | chr18 | 12769947 | G | T |
| CD | WTCCC. Nature 447:661. 2007 | DIRECT | chr10 | 64115570 | A | G |
| CeID | | | chr6 | | | |
| CeID | van Heel. Nat Genet 39:827. 2007 | DIRECT | chr4 | 123774157 | T | C |
| CeID | Hunt. EJHG 13:440. 2005; van Heel Nat Genet 39:827. 2007 | TAG | chr2 | 204442732 | T | C |
| CeID | van Heel Nat Genet 39:827. 2007 | TAG | chr6 | | T | C |
| CeID | Haiman. NatGen July 8. 2007 | DIRECT | chr8 | 128482487 | G | T |
| CRC | Heward. J Clin Endocr Metab 83:3394, 1998. | | chr6 | | | |
| GD | Ueda. Nature 423:506. 2003 | DIRECT | chr2 | 204447164 | A | G |
| GD | Burke. Gen Med 2:271. 2000 | DIRECT | chr6 | 26201120 | A | G |
| HEM | Burke. Gen Med 2:271. 2000 | TAG | chr6 | 26199158 | G | C |
| HEM | Wessel. AHJ 147:905. 2004 | DIRECT | chr5 | 79397021 | C | G |
| MI | Helgadottir. Science 3:16-1491. 2007 | TAG | chr9 | 22114477 | G | A |
| MI | Samani. NEJM July 2007 | DIRECT | chr6 | 151294678 | A | G |
| MS | Ramagopalan. PlosGen 3:1607. 2007 | | chr6 | | | |
| MS | Gregory. NatGen AOP 7/29/07 | DIRECT | chr5 | 35910332 | T | C |
| MS | Intl MS Cons. NEJM 7/29/07 | DIRECT | chr10 | 6142018 | T | C |
| OA | Miyamoto. NatGen 39:539. 2007 | TAG | chr20 | 33489397 | G | A |
| PC | Gudmundsson. NatGen 39:977. 2007 | | chr17 | 33172153 | A | G |
| PC | Yeager. NatGen 39:645. 2007 | TAG | chr8 | 128554220 | A | C |
| PC | Yeager. NatGen 39:645. 2007 | DIRECT | chr8 | 128482487 | G | T |
| PC | Gudmundsson. NatGen 39:631. 2007 | DIRECT | chr8 | 128194098 | A | C |
| PC | Gudmundsson. NatGen 39:631. 2007 | DIRECT | chr8 | 128194098 | A | C |
| PC | Gudmundsson. NatGen 39:977. 2007 | TAG | chr17 | 66620348 | G | T |
| PS | Cargill. AJHG 80:273. 2007 | | chr6 | | | |
| PS | Cargill. AJHG 80:273. 2007 | TAG | chr5 | 158675528 | G | T |

FIG. 25D (cont.)

| Condition | Seminal publication | Direct or tag snp | Published SNP B36 Chr | Published SNP B36 location | Published Minor allele (plus) | Published Major allele (plus) |
|---|---|---|---|---|---|---|
| PS | Cargill. AJHG 80:273. 2007 | DIRECT | chr1 | 67478546 | A | G |
| RA | The Genetic Basis of Common Diseases, 2ed. Ed: R. King, J. Rotter, A. Motulsky. 2002 | | chr6 | | | |
| RA | The Genetic Basis of Common Diseases, 2ed. Ed: R. King, J. Rotter, A. Motulsky. 2002 | | chr6 | | | |
| RA | The Genetic Basis of Common Diseases, 2ed. Ed: R. King, J. Rotter, A. Motulsky. 2002 | | chr6 | | | |
| RA | Begovich. AJHG. 75:330. 2004 | TAG | chr1 | 114179091 | A | G |
| RA | Begovich. AJHG. 75:330. 2004 | TAG | chr1 | 114179091 | A | G |
| RA | Lee, Rheumlot 27:827. 2007 | TAG | chr1 | 17535226 | T | C |
| RA | Lee, Rheumlot 27:827. 2007 | TAG | chr1 | 17535226 | T | C |
| RA | WTCCC. Nature 447:661. 2007 | TAG | chr6 | | T | C |
| RLS | Stefansson. NEJM 357. July 18, 2007 | DIRECT | chr6 | 38544295 | C | A |
| RLS | Winkelman. Nat Genet July 2007 | DIRECT | chr2 | 66634957 | G | T |
| RLS | Winkelman. Nat Genet July 2007 | DIRECT | chr15 | 65882139 | A | G |
| RLS | Winkelman. Nat Genet July 2007 | DIRECT | chr6 | 38473819 | C | T |
| SLE | Graham. PNAS 104:6758. 2007 | | chr7 | 128376663 | G | A |
| SLE | Graham. PNAS 104:6758. 2007 | | chr7 | 128365537 | G | T |
| SLE | Graham. EJHG 15:823. 2007 | | chr6 | | | |
| SLE | Graham. EJHG 15:823. 2007 | | chr6 | | | |
| SLE | Graham. PNAS 104:6758. 2007 | TAG | chr7 | 128376236 | C | T |
| T2D | Scott. Science 316:1341. 2007 | | chr8 | 118253964 | T | C |
| T2D | WTCCC. Nature 447:661. 2007 | DIRECT | chr10 | 114746031 | T | A |
| T2D | Sandhu. NatGen July 1, 2007 | TAG | chr4 | 6343816 | A | G |
| T2D | Steinthorsdottir. Nat Genet 39:770. 2007 | DIRECT | chr6 | 20787688 | G | A |

FIG. 25D (cont.)

| Condition | Seminal publication | Direct or tag snp | Published SNP B36 Chr | Published SNP B36 location | Published Minor allele (plus) | Published Major allele (plus) |
|---|---|---|---|---|---|---|
| T2D | Steinthorsdottir. Nat Genet 39:770. 2007 | DIRECT | ch6r | 20787688 | G | A |
| T2D | Scott. Science 316:1341. 2007; Zeggini. Science 316:1336.2007 | DIRECT | chr9 | 22124094 | C | T |
| T2D | Scott. Science 316:1341. 2007 | TAG | chr11 | 41871942 | A | C |
| T2D | Zeggini. Science 316:1336.2007 | DIRECT | chr16 | 52373776 | A | C |
| T2D | Scott. Science 316:1341. 2007 | DIRECT | chr10 | 94452862 | T | C |
| T2D | Scott. Science 316:1341. 2007 | DIRECT | chr3 | 186994381 | T | G |
| T2D | Scott. Science 316:1341. 2007 | TAG | chr11 | 17366148 | T | C |
| T2D | Scott. Science 316:1341. 2007 | DIRECT | chr3 | 12368125 | G | C |
| XFG | Thorleifsson. Science Express Aug 9, 2007 | DIRECT | chr15 | 72009255 | T | C |

GENETIC ANALYSIS SYSTEMS AND METHODS

CROSS-REFERENCE TO RELATED APPLICATIONS

This application is a U.S. National Stage (§371) entry of International Application No. PCT/US07/86138 filed Nov. 30, 2007 which claims priority to U.S. Provisional Application No. 60/868,066 filed Nov. 30, 2006 and to U.S. Provisional Application No. 60/951,123 filed Jul. 20, 2007 and to U.S. Provisional Application No. 60/972,198 filed Sep. 13, 2007 and to U.S. Provisional Application No. 60/985,622 filed Nov. 5, 2007 and to U.S. Provisional Application No. 60/989,685 filed Nov. 21, 2007 and a Continuation to U.S. application Ser. No. 11/781,679, filed Jul. 23, 2007 now abandoned which claims priority to U.S. Provisional Application No. 60/868,066 filed Nov. 30, 2006 and to U.S. Provisional Application No. 60/951,123 filed Jul. 20, 2007, which disclosures are herein incorporated by reference in their entirety.

BACKGROUND OF THE INVENTION

Sequencing of the human genome and other recent developments in human genomics has revealed that the genomic makeup between any two humans has over 99.9% similarity. The relatively small number of variations in DNA between individuals gives rise to differences in phenotypic traits, and is related to many human diseases, susceptibility to various diseases, and response to treatment of disease. Variations in DNA between individuals occur in both coding and non-coding regions, and include changes in bases at a particular locus in genomic DNA sequences, as well as insertions and deletions of DNA. Changes that occur at single base positions in the genome are referred to as single nucleotide polymorphisms, or "SNPs."

While SNPs are relatively rare in the human genome, they account for a majority of DNA sequence variations between individuals, occurring approximately once every 1,200 base pairs in the human genome (see International HapMap Project, www.hapmap.org). As more human genetic information becomes available, the complexity of SNPs is beginning to be understood. In turn, the occurrences of SNPs in the genome are becoming correlated to the presence of and/or susceptibility to various diseases and conditions.

As these correlations and other advances in human genetics are being made, medicine and personal health in general are moving toward a customized approach in which a patient will make appropriate medical and other choices in consideration of his or her genomic information, among other factors. Thus, there is a need to provide individuals and their caregivers with information specific to the individual's personal genome toward providing personalized medical and other decisions.

SUMMARY OF THE INVENTION

The present invention provides a method of assessing an individual's genotype correlations comprising: a) obtaining a genetic sample of the individual, b) generating a genomic profile for the individual, c) determining the individual's genotype correlations with phenotypes by comparing the individual's genomic profile to a current database of human genotype correlations with phenotypes, d) reporting the results from step c) to the individual or a health care manager of the individual, e) updating the database of human genotype correlations with an additional human genotype correlation as the additional human genotype correlation becomes known, f) updating the individual's genotype correlations by comparing the individual's genomic profile from step c) or a portion thereof to the additional human genotype correlation and determining an additional genotype correlation of the individual, and g) reporting the results from step f) to the individual or the health care manager of the individual.

The present invention further provides a business method of assessing genotype correlations of an individual comprising: a) obtaining a genetic sample of the individual; b) generating a genomic profile for the individual; c) determining the individual's genotype correlations by comparing the individual's genomic profile to a database of human genotype correlations; d) providing results of the determining of the individual's genotype correlations to the individual in a secure manner; e) updating the database of human genotype correlations with an additional human genotype correlation as the additional human genotype correlation becomes known; f) updating the individual's genotype correlations by comparing the individual's genomic profile or a portion thereof to the additional human genotype correlation and determining an additional genotype correlation of the individual; and g) providing results of the updating of the individual's genotype correlations to the individual of the health care manager of the individual.

Another aspect of the present invention is a method generating a phenotype profile for an individual comprising: a) providing a rule set comprising rules, each rule indicating a correlation between at least one genotype and at least one phenotype, b) providing a data set comprising genomic profiles of each of a plurality of individuals, wherein each genomic profile comprises a plurality of genotypes; c) periodically updating the rule set with at least one new rule, wherein the at least one new rule indicates a correlation between a genotype and a phenotype not previously correlated with each other in the rule set; d) applying each new rule to the genomic profile of at least one of the individuals, thereby correlating at least one genotype with at least one phenotype for the individual, and optionally, e) generating a report comprising the phenotype profile of the individual.

The present invention also provides a system comprising a) a rule set comprising rules, each rule indicating a correlation between at least one genotype and at least one phenotype; b) code that periodically updates the rule set with at least one new rule, wherein the at least one new rule indicates a correlation between a genotype and a phenotype not previously correlated with each other in the rule set; c) a database comprising genomic profiles of a plurality of individuals; d) code that applies the rule set to the genomic profiles of individuals to determine phenotype profiles for the individuals; and e) code that generates reports for each individual.

Another aspect of the present invention is transmission over a network, in a secure or non-secure manner, the methods and systems described above.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 4 are tables of representative genotype correlations from published literature with test SNPs and effect estimates. A-I) represents single locus genotype correlations; J) represents a two locus genotype correlation; K) represents a three locus genotype correlation; L) is an index of the ethnicity and country abbreviations used in A-K; M) is an index of the abbreviations of the Short Phenotype Names in A-K, the heritability, and the references for the heritability.

FIG. 5A-J are tables of representative genotype correlations with effect estimates.

FIG. 6A-F are tables of representative genotype correlations and estimated relative risks.

FIG. 7 is a sample report.

FIG. 16: are illustrations of sample webpages from a personalized portal for a person's risk for prostate cancer.

FIG. 17: are illustrations of sample webpages from a personalized portal for an individual's risk for Crohn's disease.

FIG. 21: is a table of multilocus correlations.

FIG. 22: is a table of SNPs and phenotype correlations.

FIG. 23: is a table of phenotypes and prevalences.

FIG. 24: is a glossary for abbreviations in FIGS. 21, 22, and 25.

FIG. 25: is a table of SNPs and phenotype correlations.

DETAILED DESCRIPTION

Figure 1:
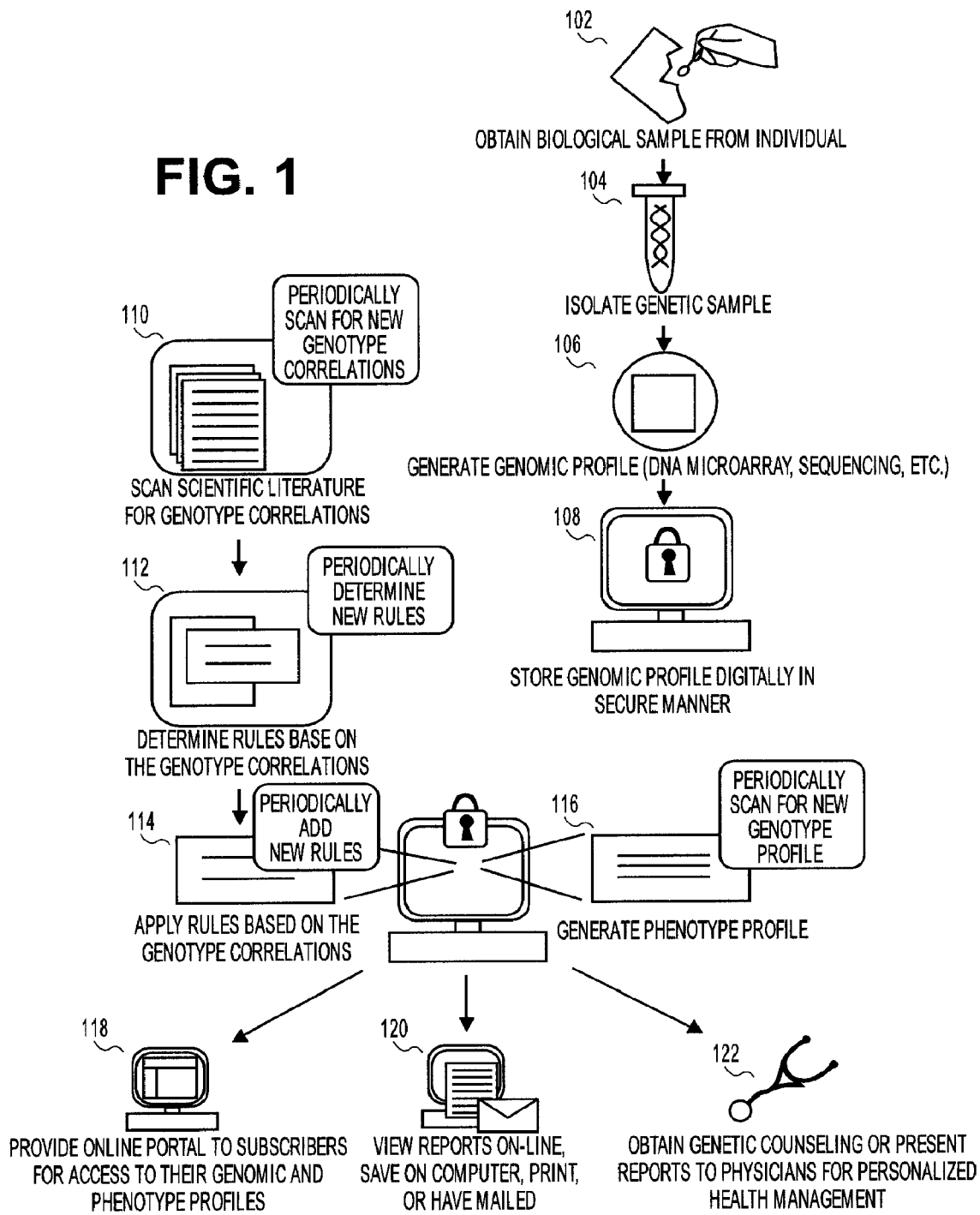
FIG. 1 is a flow chart illustrating aspects of the method herein.

The present invention provides methods and systems for generating phenotype profiles based on a stored genomic profile of an individual or group of individuals, and for readily generating original and updated phenotype profiles based on the stored genomic profiles. Genomic profiles are generated by determining genotypes from biological samples obtained from individuals. Biological samples obtained from individuals may be any sample from which a genetic sample may be derived. Samples may be from buccal swabs, saliva, blood, hair, or any other type of tissue sample. Genotypes may then be determined from the biological samples. Genotypes may be any genetic variant or biological marker, for example, single nucleotide polymorphisms (SNPs), haplotypes, or sequences of the genome. The genotype may be the entire genomic sequence of an individual. The genotypes may result from high-throughput analysis that generates thousands or millions of data points, for example, microarray analysis for most or all of the known SNPs. In other embodiments, genotypes may also be determined by high throughput sequencing.

The genotypes form a genomic profile for an individual. The genomic profile is stored digitally and is readily accessed at any point of time to generate phenotype profiles. Phenotype profiles are generated by applying rules that correlate or associate genotypes with phenotypes. Rules can be made based on scientific research that demonstrates a correlation between a genotype and a phenotype. The correlations may be curated or validated by a committee of one or more experts. By applying the rules to a genomic profile of an individual, the association between an individual's genotype and a phenotype may be determined. The phenotype profile for an individual will have this determination. The determination may be a positive association between an individual's genotype and a given phenotype, such that the individual has the given phenotype, or will develop the phenotype. Alternatively, it may be determined that the individual does not have, or will not develop, a given phenotype. In other embodiments, the determination may be a risk factor, estimate, or a probability that an individual has, or will develop a phenotype.

The determinations may be made based on a number of rules, for example, a plurality of rules may be applied to a genomic profile to determine the association of an individual's genotype with a specific phenotype. The determinations may also incorporate factors that are specific to an individual, such as ethnicity, gender, lifestyle (for example, diet and exercise habits), age, environment (for example, location of residence), family medical history, personal medical history, and other known phenotypes. The incorporation of the specific factors may be by modifying existing rules to encompass these factors. Alternatively, separate rules may be generated by these factors and applied to a phenotype determination for an individual after an existing rule has been applied.

Phenotypes may include any measurable trait or characteristic, such as susceptibility to a certain disease or response to a drug treatment. Other phenotypes that may be included are physical and mental traits, such as height, weight, hair color, eye color, sunburn susceptibility, size, memory, intelligence, level of optimism, and general disposition. Phenotypes may also include genetic comparisons to other individuals or organisms. For example, an individual may be interested in the similarity between their genomic profile and that of a celebrity. They may also have their genomic profile compared to other organisms such as bacteria, plants, or other animals.

Together, the collection of correlated phenotypes determined for an individual comprises the phenotype profile for the individual. The phenotype profile may be accessible by an on-line portal. Alternatively, the phenotype profile as it exists at a certain time may be provided in paper form, with subsequent updates also provided in paper form. The phenotype profile may also be provided by an on-line portal. The on-line portal may optionally be a secure on-line portal. Access to the phenotype profile may be provided to a subscriber, which is an individual who subscribes to the service that generates rules on correlations between phenotypes and genotypes, determines the genomic profile of an individual, applies the rules to the genomic profile, and generates a phenotype profile of the individual. Access may also be provided to non-subscribers, wherein they may have limited access to their phenotype profile and/or reports, or may have an initial report or phenotype profile generated, but updated reports will be generated only with purchase of a subscription. Health care managers and providers, such as caregivers, physicians, and genetic counselors may also have access to the phenotype profile.

In another aspect of the invention a genomic profile may be generated for subscribers and non-subscribers and stored digitally but access to the phenotype profile and reports may be limited to subscribers. In another variation, both subscribers and non-subscribers may access their genotype and phenotype profiles, but have limited access, or have a limited report generated for non-subscribers, whereas subscribers have full access and may have a full report generated. In another embodiment, both subscribers and non-subscribers may have full access initially, or full initial reports, but only subscribers may access updated reports based on their stored genomic profile.

In another aspect of the invention information about the association of multiple genetic markers with one or more diseases or conditions is combined and analyzed to produce a Genetic Composite Index (GCI) score. This score incorporates known risk factors, as well as other information and assumptions such as the allele frequencies and the prevalence of a disease. The GCI can be used to qualitatively estimate the association of a disease or a condition with the combined effect of a set of Genetic markers. The GCI score can be used to provide people not trained in genetics with a reliable (i.e., robust), understandable, and/or intuitive sense of what their individual risk of a disease is compared to a relevant population based on current scientific research. The GCI score may be used to generate GCI Plus scores. The GCI Plus score may contain all the GCI assumptions, including risk (such as lifetime risk), age-defined prevalence, and/or age-defined incidence of the condition. The lifetime risk for the individual may then be calculated as a GCI Plus score which is proportional to the individual's GCI score divided by the average GCI score. The average GCI score may be determined from a group of individuals of similar ancestral background, for example a group of Caucasians, Asians, East Indians, or other group with a common ancestral background. Groups may comprise of at least 5, 10, 15, 20, 25, 30, 35, 40, 45, 50, 55, or 60 individuals. In some embodiments, the average may be determined from at least 75, 80, 95, or 100 individuals. The GCI Plus score may be determined by determining the GCI score for an individual, dividing the GCI score by the average relative risk and multiplying by the lifetime risk for a condition or phenotype. For example, using data from FIG. 22 and/or FIG. 25 with information in FIG. 24 to calculate GCI Plus scores such as in FIG. 19.

The present invention encompasses using the GCI score as described herein, and one of ordinary skill in the art will readily recognize the use of GCI Plus scores or variations thereof, in place of GCI scores as described herein.

In one embodiment a GCI score is generated for each disease or condition of interest. These GCI scores may be collected to form a risk profile for an individual. The GCI scores may be stored digitally so that they are readily accessible at any point of time to generate risk profiles. Risk profiles may be broken down by broad disease classes, such as cancer, heart disease, metabolic disorders, psychiatric disorders, bone disease, or age on-set disorders. Broad disease classes may be further broken down into subcategories. For example for a broad class such as a cancer, sub-categories of cancer may be listed such as by type (sarcoma, carcinoma or leukemia, etc.) or by tissue specificity (neural, breast, ovaries, testes, prostate, bone, lymph nodes, pancreas, esophagus, stomach, liver, brain, lung, kidneys, etc.).

In another embodiment a GCI score is generated for an individual, which provides them with easily comprehended information about the individual's risk of acquiring or susceptibility to at least one disease or condition. In one embodiment multiple GCI scores are generated for different diseases or conditions. In another embodiment at least one GCI score is accessible by an on-line portal. Alternatively, at least one GCI score may be provided in paper form, with subsequent updates also provided in paper form. In one embodiment access to at least one GCI score is provided to a subscriber, which is an individual who subscribes to the service. In an alternative embodiment access is provided to non-subscribers, wherein they may have limited access to at least one of their GCI scores, or they may have an initial report on at least one of their GCI scores generated, but updated reports will be generated only with purchase of a subscription. In another embodiment health care managers and providers, such as caregivers, physicians, and genetic counselors may also have access to at least one of an individual's GCI scores.

There may also be a basic subscription model. A basic subscription may provide a phenotype profile where the subscriber may choose to apply all existing rules to their genomic profile, or a subset of the existing rules, to their genomic profile. For example, they may choose to apply only the rules for disease phenotypes that are actionable. The basic subscription may have different levels within the subscription class. For example, different levels may be dependent on the number of phenotypes a subscriber wants correlated to their genomic profile, or the number of people that may access their phenotype profile. Another level of basic subscription may be to incorporate factors specific to an individual, such as already known phenotypes such as age, gender, or medical history, to their phenotype profile. Still another level of the basic subscription may allow an individual to generate at least one GCI score for a disease or condition. A variation of this level may further allow an individual to specify for an automatic update of at least one GCI score for a disease or condition to be generated if their is any change in at least one GCI score due to changes in the analysis used to generate at least one GCI score. In some embodiments the individual may be notified of the automatic update by email, voice message, text message, mail delivery, or fax.

Subscribers may also generate reports that have their phenotype profile as well as information about the phenotypes, such as genetic and medical information about the phenotype. For example, the prevalence of the phenotype in the population, the genetic variant that was used for the correlation, the molecular mechanism that causes the phenotype, therapies for the phenotype, treatment options for the phenotype, and preventative actions, may be included in the report. In other embodiments, the reports may also include information such as the similarity between an individual's genotype and that of other individuals, such as celebrities or other famous people. The information on similarity may be, but are not limited to, percentage homology, number of identical variants, and phenotypes that may be similar. These reports may further contain at least one GCI score.

The report may also provide links to other sites with further information on the phenotypes, links to on-line support groups and message boards of people with the same phenotype or one or more similar phenotypes, links to an on-line genetic counselor or physician, or links to schedule telephonic or in-person appointments with a genetic counselor or physician, if the report is accessed on-line. If the report is in paper form, the information may be the website location of the aforementioned links, or the telephone number and address of the genetic counselor or physician. The subscriber may also choose which phenotypes to include in their phenotype profile and what information to include in their report. The phenotype profile and reports may also be accessible by an individual's health care manager or provider, such as a caregiver, physician, psychiatrist, psychologist, therapist, or genetic counselor. The subscriber may be able to choose whether the phenotype profile and reports, or portions thereof, are accessible by such individual's health care manager or provider.

The present invention may also include a premium level of subscription. The premium level of subscription maintains their genomic profile digitally after generation of an initial phenotype profile and report, and provides subscribers the opportunity to generate phenotype profiles and reports with updated correlations from the latest research. In another embodiment, subscribers have the opportunity to generate risk profile and reports with updated correlations from the latest research. As research reveals new correlations between genotypes and phenotypes, disease or conditions, new rules will be developed based on these new correlations and can be applied to the genomic profile that is already stored and being maintained. The new rules may correlate genotypes not previously correlated with any phenotype, correlate genotypes with new phenotypes, modify existing correlations, or provide the basis for adjustment of a GCI score based on a newly discovered association between a genotype and disease or condition. Subscribers may be informed of new correlations via e-mail or other electronic means, and if the phenotype is of interest, they may choose to update their phenotype profile with the new correlation. Subscribers may choose a subscription where they pay for each update, for a number of updates or an unlimited number of updates for a designated time period (e.g. three months, six months, or one year). Another subscription level may be where a subscriber has their phenotype profile or risk profile automatically updated, instead of where the individual chooses when to update their phenotype profile or risk profile, whenever a new rule is generated based on a new correlation.

In another aspect of the subscription, subscribers may refer non-subscribers to the service that generates rules on correlations between phenotypes and genotypes, determines the genomic profile of an individual, applies the rules to the genomic profile, and generates a phenotype profile of the individual. Referral by a subscriber may give the subscriber a reduced price on subscription to the service, or upgrades to their existing subscriptions. Referred individuals may have free access for a limited time or have a discounted subscription price.

Phenotype profiles and reports as well as risk profiles and reports may be generated for individuals that are human and non-human. For example, individuals may include other mammals, such as bovines, equines, ovines, canines, or felines. Subscribers, as used herein, are human individuals who subscribe to a service by purchase or payment for one or more services. Services may include, but are not limited to, one or more of the following: having their or another individual's, such as the subscriber's child or pet, genomic profile determined, obtaining a phenotype profile, having the phenotype profile updated, and obtaining reports based on their genomic and phenotype profile.

In another aspect of the invention, "field-deployed" mechanisms may be gathered from individuals to generate phenotype profiles for individuals. In preferred embodiments, an individual may have an initial phenotype profile generated based on genetic information. For example, an initial phenotype profile is generated that includes risk factors for different phenotypes as well as suggested treatments or preventative measures. For example, the profile may include information on available medication for a certain condition, and/or suggestions on dietary changes or exercise regimens. The individual may choose to see, or contact via a web portal or phone call, a physician or genetic counselor, to discuss their phenotype profile. The individual may decide to take a certain course of action, for example, take specific medications, change their diet, etc.

The individual may then subsequently submit biological samples to assess changes in their physical condition and possible change in risk factors. Individuals may have the changes determined by directly submitting biological samples to the facility (or associated facility, such as a facility contracted by the entity generating the genetic profiles and phenotype profiles us) that generates the genomic profiles and phenotype profiles. Alternatively, the individuals may use a "field-deployed" mechanism, wherein the individual may submit their saliva, blood, or other biological sample into a detection device at their home, analyzed by a third party, and the data transmitted to be incorporated into another phenotype profile. For example, an individual may have received an initial phenotype report based on their genetic data reporting the individual having an increased lifetime risk of myocardial infarction (MI). The report may also have suggestions on preventative measures to reduce the risk of MI, such as cholesterol lowering drugs and change in diet. The individual may choose to contact a genetic counselor or physician to discuss the report and the preventative measures and decides to change their diet. After a period of being on the new diet, the individual may see their personal physician to have their cholesterol level measured. The new information (cholesterol level) may be transmitted (for example, via the Internet) to the entity with the genomic information, and the new information used to generate a new phenotype profile for the individual, with a new risk factor for myocardial infarction, and/or other conditions.

The individual may also use a "field-deployed" mechanism, or direct mechanism, to determine their individual response to specific medications. For example, an individual may have their response to a drug measured, and the information may be used to determine more effective treatments. Measurable information include, but are not limited to, metabolite levels, glucose levels, ion levels (for example, calcium, sodium, potassium, iron), vitamins, blood cell counts, body mass index (BMI), protein levels, transcript levels, heart rate, etc., can be determined by methods readily available and can be factored into an algorithm to combine with initial genomic profiles to determine a modified overall risk estimate score.

The term "biological sample" refers to any biological sample that can be isolated from an individual, including samples from which genetic material may be isolated. As used herein, a "genetic sample" refers to DNA and/or RNA obtained or derived from an individual.

As used herein, the term "genome" is intended to mean the full complement of chromosomal DNA found within the nucleus of a human cell. The term "genomic DNA" refers to one or more chromosomal DNA molecules occurring naturally in the nucleus of a human cell, or a portion of the chromosomal DNA molecules.

The term "genomic profile" refers to a set of information about an individual's genes, such as the presence or absence of specific SNPs or mutations. Genomic profiles include the genotypes of individuals. Genomic profiles may also be substantially the complete genomic sequence of an individual. In some embodiments, the genomic profile may be at least 60%, 80%, or 95% of the complete genomic sequence of an individual. The genomic profile may be approximately 100% of the complete genomic sequence of an individual. In reference to a genomic profile, "a portion thereof" refers to the genomic profile of a subset of the genomic profile of an entire genome.

The term "genotype" refers to the specific genetic makeup of an individual's DNA. The genotype may include the genetic variants and markers of an individual. Genetic markers and variants may include nucleotide repeats, nucleotide insertions, nucleotide deletions, chromosomal translocations, chromosomal duplications, or copy number variations. Copy number variation may include microsatellite repeats, nucleotide repeats, centromeric repeats, or telomeric repeats. The genotypes may also be SNPs, haplotypes, or diplotypes. A haplotype may refer to a locus or an allele. A haplotype is also referred to as a set of single nucleotide polymorphisms (SNPs) on a single chromatid that are statistically associated. A diplotype is a set of haplotypes.

The term single nucleotide polymorphism or "SNP" refers to a particular locus on a chromosome which exhibits variability such as at least one percent (1%) with respect to the identity of the nitrogenous base present at such locus within the human population For example, where one individual might have adenosine (A) at a particular nucleotide position of a given gene, another might have cytosine (C), guanine (G), or thymine (T) at this position, such that there is a SNP at that particular position.

As used herein, the terminology "SNP genomic profile" refers to the base content of a given individual's DNA at SNP sites throughout the individual's entire genomic DNA sequence. A "SNP profile" can refer to an entire genomic profile, or may refer to a portion thereof, such as a more localized SNP profile which can be associated with a particular gene or set of genes.

The term "phenotype" is used to describe a quantitative trait or characteristic of an individual. Phenotypes include, but are not limited to, medical and non-medical conditions. Medical conditions include diseases and disorders. Phenotypes may also include physical traits, such as hair color, physiological traits, such as lung capacity, mental traits, such as memory retention, emotional traits, such as ability to control anger, ethnicity, such as ethnic background, ancestry, such as an individual's place of origin, and age, such as age expectancy or age of onset of different phenotypes. Phenotypes may also be monogenic, wherein it is thought that one gene may be correlated with a phenotype, or multigenic, wherein more than one gene is correlated with a phenotype.

A "rule" is used to define the correlation between a genotype and a phenotype. The rules may define the correlations by a numerical value, for example by a percentage, risk factor, or confidence score. A rule may incorporate the correlations of a plurality of genotypes with a phenotype. A "rule set" comprises more than one rule. A "new rule" may be a rule that indicates a correlation between a genotype and a phenotype for which a rule does not currently exist. A new rule may correlate an uncorrelated genotype with a phenotype. A new rule may also correlate a genotype that is already correlated with a phenotype to a phenotype it had not been previously correlated to. A "new rule" may also be an existing rule that is modified by other factors, including another rule. An existing rule may be modified due to an individual's known characteristics, such as ethnicity, ancestry, geography, gender, age, family history, or other previously determined phenotypes.

Use of "genotype correlation" herein refers to the statistical correlation between an individual's genotype, such as presence of a certain mutation or mutations, and the likelihood of being predisposed to a phenotype, such as a particular disease, condition, physical state, and/or mental state. The frequency with which a certain phenotype is observed in the presence of a specific genotype determines the degree of genotype correlation or likelihood of a particular phenotype. For example, as detailed herein, SNPs giving rise to the apolipoprotein E4 isoform are correlated with being predisposed to early onset Alzheimer's disease. Genotype correlations may also refer to correlations wherein there is not a predisposition to a phenotype, or a negative correlation. The genotype correlations may also represent an estimate of an individual to have a phenotype or be predisposed to have a phenotype. The genotype correlation may be indicated by a numerical value, such as a percentage, a relative risk factor, an effects estimate, or confidence score.

The term "phenotype profile" refers to a collection of a plurality of phenotypes correlated with a genotype or genotypes of an individual. Phenotype profiles may include information generated by applying one or more rules to a genomic profile, or information about genotype correlations that are applied to a genomic profile. Phenotype profiles may be generated by applying rules that correlate a plurality of genotypes with a phenotype. The probability or estimate may be expressed as a numerical value, such as a percentage, a numerical risk factor or a numerical confidence interval. The probability may also be expressed as high, moderate, or low. The phenotype profiles may also indicate the presence or absence of a phenotype or the risk of developing a phenotype. For example, a phenotype profile may indicate the presence of blue eyes, or a high risk of developing diabetes. The phenotype profiles may also indicate a predicted prognosis, effectiveness of a treatment, or response to a treatment of a medical condition.

The term risk profile refers to a collection of GCI scores for more than one disease or condition. GCI scores are based on analysis of the association between an individual's genotype with one or more diseases or conditions. Risk profiles may display GCI scores grouped into categories of disease. Further the Risk profiles may display information on how the GCI scores are predicted to change as the individual ages or various risk factors are adjusted. For example, the GCI scores for particular diseases may take into account the effect of changes in diet or preventative measures taken (smoking cessation, drug intake, double radical mastectomies, hysterectomies). The GCI scores may be displayed as a numerical measure, a graphical display, auditory feedback or any combination of the preceding.

As used herein, the term "on-line portal" refers to a source of information which can be readily accessed by an individual through use of a computer and internet website, telephone, or other means that allow similar access to information. The on-line portal may be a secure website. The website may provide links to other secure and non-secure websites, for example links to a secure website with the individual's phenotype profile, or to non-secure websites such as a message board for individuals sharing a specific phenotype.

The practice of the present invention may employ, unless otherwise indicated, conventional techniques and descriptions of molecular biology, cell biology, biochemistry, and immunology, which are within the skill of the art. Such conventional techniques include nucleic acid isolation, polymer array synthesis, hybridization, ligation, and detection of hybridization using a label. Specific illustrations of suitable techniques are exemplified and referenced herein. However, other equivalent conventional procedures can also be used. Other conventional techniques and descriptions can be found in standard laboratory manuals and texts such as Genome Analysis: A Laboratory Manual Series (Vols. I-IV), PCR Primer: A Laboratory Manual, Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000); Lehninger, Principles of Biochemistry 3rd Ed., W.H. Freeman Pub., New York, N.Y.; and Berg et al. (2002) Biochemistry, 5th Ed., W.H. Freeman Pub., New York, N.Y., all of which are herein incorporated in their entirety by reference for all purposes.

The methods of the present invention involve analysis of an individual's genomic profile to provide the individual with molecular information relating to a phenotype. As detailed herein, the individual provides a genetic sample, from which a personal genomic profile is generated. The data of the individual's genomic profile is queried for genotype correlations by comparing the profile against a database of established and validated human genotype correlations. The database of established and validated genotype correlations may be from peer-reviewed literature and further judged by a committee of one or more experts in the field, such as geneticists, epidemiologists, or statisticians, and curated. In preferred embodiments, rules are made based on curated genotype correlations and are applied to an individual's genomic profile to generate a phenotype profile. Results of the analysis of the individual's genomic profile, phenotype profile, along with interpretation and supportive information, are provided to the individual of the individual's health care manager, to empower personalized choices for the individual's health care.

A method of the invention is detailed as in FIG. 1, where an individual's genomic profile is first generated. An individual's genomic profile will contain information about an individual's genes based on genetic variations or markers. Genetic variations are genotypes, which make up genomic profiles. Such genetic variations or markers include, but are not limited to, single nucleotide polymorphisms, single and/or multiple nucleotide repeats, single and/or multiple nucleotide deletions, microsatellite repeats (small numbers of nucleotide repeats with a typical 5-1,000 repeat units), di-nucleotide repeats, tri-nucleotide repeats, sequence rearrangements (including translocation and duplication), copy number variations (both loss and gains at specific loci), and the like. Other genetic variations include chromosomal duplications and translocations as well as centromeric and telomeric repeats.

Genotypes may also include haplotypes and diplotypes. In some embodiments, genomic profiles may have at least 100,000, 300,000, 500,000, or 1,000,000 genotypes. In some embodiments, the genomic profile may be substantially the complete genomic sequence of an individual. In other embodiments, the genomic profile is at least 60%, 80%, or 95% of the complete genomic sequence of an individual. The genomic profile may be approximately 100% of the complete genomic sequence of an individual. Genetic samples that contain the targets include, but are not limited to, unamplified genomic DNA or RNA samples or amplified DNA (or cDNA). The targets may be particular regions of genomic DNA that contain genetic markers of particular interest.

In step 102 of FIG. 1, a genetic sample of an individual is isolated from a biological sample of an individual. Such biological samples include, but are not limited to, blood, hair, skin, saliva, semen, urine, fecal material, sweat, buccal, and various bodily tissues. In some embodiments, tissues samples may be directly collected by the individual, for example, a buccal sample may be obtained by the individual taking a swab against the inside of their cheek. Other samples such as saliva, semen, urine, fecal material, or sweat, may also be supplied by the individual themselves. Other biological samples may be taken by a health care specialist, such as a phlebotomist, nurse or physician. For example, blood samples may be withdrawn from an individual by a nurse. Tissue biopsies may be performed by a health care specialist, and kits are also available to health care specialists to efficiently obtain samples. A small cylinder of skin may be removed or a needle may be used to remove a small sample of tissue or fluids.

In some embodiments, kits are provided to individuals with sample collection containers for the individual's biological sample. The kit may also provide instructions for an individual to directly collect their own sample, such as how much hair, urine, sweat, or saliva to provide. The kit may also contain instructions for an individual to request tissue samples to be taken by a health care specialist. The kit may include locations where samples may be taken by a third party, for example kits may be provided to health care facilities who in turn collect samples from individuals. The kit may also provide return packaging for the sample to be sent to a sample processing facility, where genetic material is isolated from the biological sample in step 104.

A genetic sample of DNA or RNA may be isolated from a biological sample according to any of several well-known biochemical and molecular biological methods, see, e.g., Sambrook, et al., Molecular Cloning: A Laboratory Manual (Cold Spring Harbor Laboratory, New York) (1989). There are also several commercially available kits and reagents for isolating DNA or RNA from biological samples, such as those available from DNA Genotek, Gentra Systems, Qiagen, Ambion, and other suppliers. Buccal sample kits are readily available commercially, such as the MasterAmp™ Buccal Swab DNA extraction kit from Epicentre Biotechnologies, as are kits for DNA extraction from blood samples such as Extract-N-Amp™ from Sigma Aldrich. DNA from other tissues may be obtained by digesting the tissue with proteases and heat, centrifuging the sample, and using phenol-chloroform to extract the unwanted materials, leaving the DNA in the aqueous phase. The DNA can then be further isolated by ethanol precipitation.

In a preferred embodiment, genomic DNA is isolated from saliva. For example, using DNA self collection kit technology available from DNA Genotek, an individual collects a specimen of saliva for clinical processing. The sample conveniently can be stored and shipped at room temperature. After delivery of the sample to an appropriate laboratory for processing, DNA is isolated by heat denaturing and protease digesting the sample, typically using reagents supplied by the collection kit supplier at 50° C. for at least one hour. The sample is next centrifuged, and the supernatant is ethanol precipitated. The DNA pellet is suspended in a buffer appropriate for subsequent analysis.

In another embodiment, RNA may be used as the genetic sample. In particular, genetic variations that are expressed can be identified from mRNA. The term "messenger RNA" or "mRNA" includes, but is not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, a DNA amplified from the cDNA, an RNA transcribed from the amplified DNA, etc., are all derived from the mRNA transcript. RNA can be isolated from any of several bodily tissues using methods known in the art, such as isolation of RNA from unfractionated whole blood using the PAXgene™ Blood RNA System available from PreAnalytiX. Typically, mRNA will be used to reverse transcribe cDNA, which will then be used or amplified for gene variation analysis.

Prior to genomic profile analysis, a genetic sample will typically be amplified, either from DNA or cDNA reverse transcribed from RNA. DNA can be amplified by a number of methods, many of which employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., *Proc. Natl. Acad. Sci. USA* 86:1173-1177 (1989) and WO88/10315), self-sustained sequence replication (Guatelli et al., *Proc. Nat. Acad. Sci. USA*, 87:1874-1878 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) nucleic acid based sequence amplification (NABSA), rolling circle amplification (RCA), multiple displacement amplification (MDA) (U.S. Pat. Nos. 6,124,120 and 6,323,009) and circle-to-circle amplification (C2CA) (Dahl et al. *Proc. Natl. Acad. Sci* 101:4548-4553 (2004)). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 5,409,818, 4,988,617, 6,063,603 and 5,554,517 and in U.S. Ser. No. 09/854,317, each of which is incorporated herein by reference.

Generation of a genomic profile in step 106 is performed using any of several methods. Several methods are known in the art to identify genetic variations and include, but are not limited to, DNA sequencing by any of several methodologies, PCR based methods, fragment length polymorphism assays (restriction fragment length polymorphism (RFLP), cleavage fragment length polymorphism (CFLP)) hybridization methods using an allele-specific oligonucleotide as a template (e.g., TaqMan PCR method, the invader method, the DNA chip method), methods using a primer extension reaction, mass spectrometry (MALDI-TOF/MS method), and the like.

In one embodiment, a high density DNA array is used for SNP identification and profile generation. Such arrays are commercially available from Affymetrix and Illumina (see Affymetrix GeneChip® 500K Assay Manual, Affymetrix, Santa Clara, Calif. (incorporated by reference); Sentrix® humanHap650Y genotyping beadchip, Illumina, San Diego, Calif.).

Figure 2:
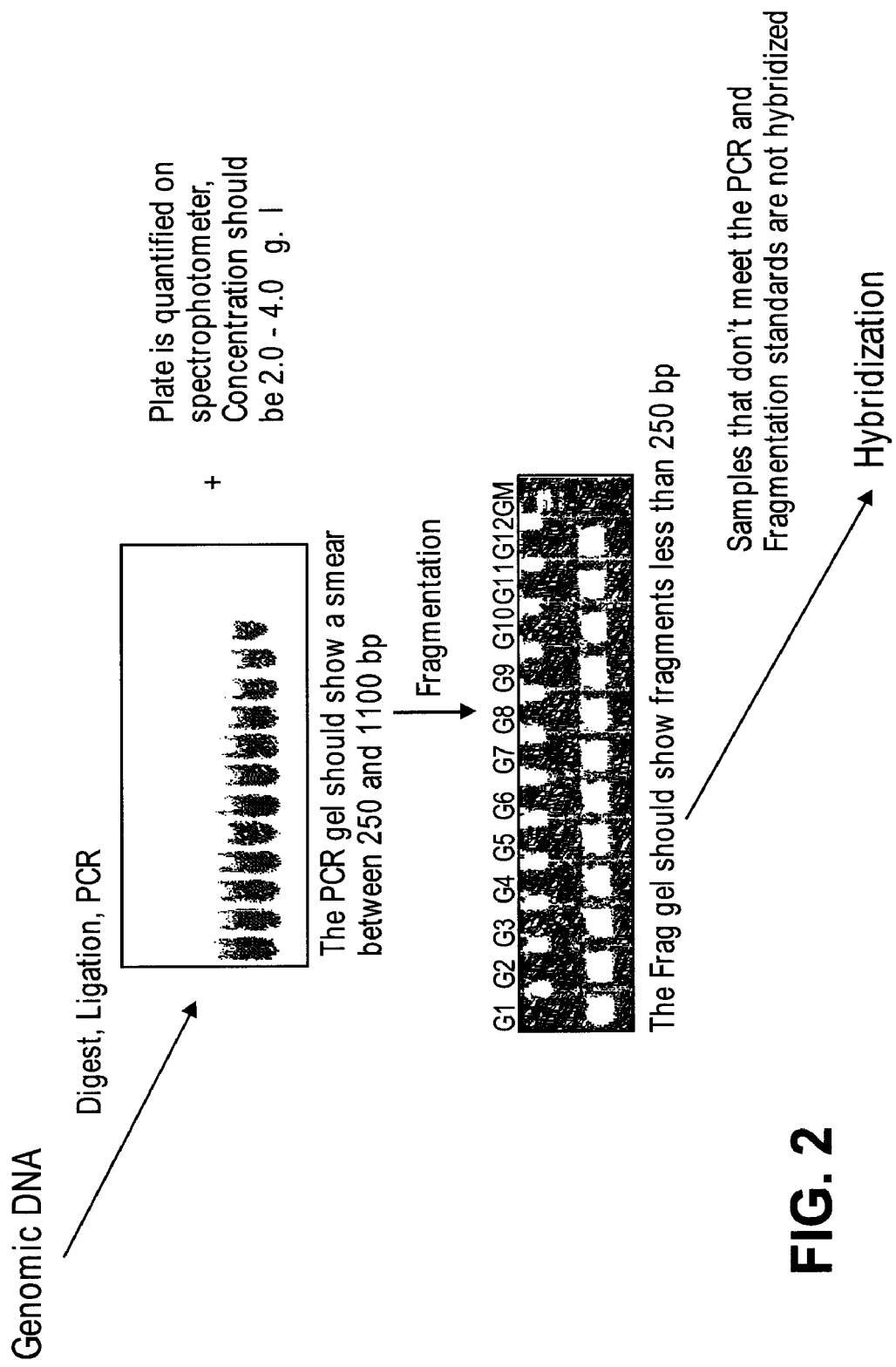
FIG. 2 is an example of a genomic DNA quality control measure.

For example, a SNP profile can be generated by genotyping more than 900,000 SNPs using the Affymetrix Genome Wide Human SNP Array 6.0. Alternatively, more than 500,000 SNPs through whole-genome sampling analysis may be determined by using the Affymetrix GeneChip Human Mapping 500K Array Set. In these assays, a subset of the human genome is amplified through a single primer amplification reaction using restriction enzyme digested, adaptor-ligated human genomic DNA. As shown in FIG. 2, the concentration of the ligated DNA may then be determined. The amplified DNA is then fragmented and the quality of the sample determined prior to continuing with step 106. If the samples meet the PCR and fragmentation standards, the sample is denatured, labeled, and then hybridized to a microarray consisting of small DNA probes at specific locations on a coated quartz surface. The amount of label that hybridizes to each probe as a function of the amplified DNA sequence is monitored, thereby yielding sequence information and resultant SNP genotyping.

Use of the Affymetrix GeneChip 500K Assay is carried out according to the manufacturer's directions. Briefly, isolated genomic DNA is first digested with either a NspI or StyI restriction endonuclease. The digested DNA is then ligated with a NspI or StyI adaptor oligonucleotide that respectively anneals to either the NspI or StyI restricted DNA. The adaptor-containing DNA following ligation is then amplified by PCR to yield amplified DNA fragments between about 200 and 1100 base pairs, as confirmed by gel electrophoresis. PCR products that meet the amplification standard are purified and quantified for fragmentation. The PCR products are fragmented with DNase I for optimal DNA chip hybridization. Following fragmentation, DNA fragments should be less than 250 base pairs, and on average, about 180 base pairs, as confirmed by gel electrophoresis. Samples that meet the fragmentation standard are then labeled with a biotin compound using terminal deoxynucleotidyl transferase. The labeled fragments are next denatured and then hybridized into a GeneChip 250K array. Following hybridization, the array is stained prior to scanning in a three step process consisting of a streptavidin phycoerythin (SAPE) stain, followed by an antibody amplification step with a biotinylated, anti-streptavidin antibody (goat), and final stain with streptavidin phycoerythin (SAPE). After labeling, the array is covered with an array holding buffer and then scanned with a scanner such as the Affymetrix GeneChip Scanner 3000.

Figure 3:
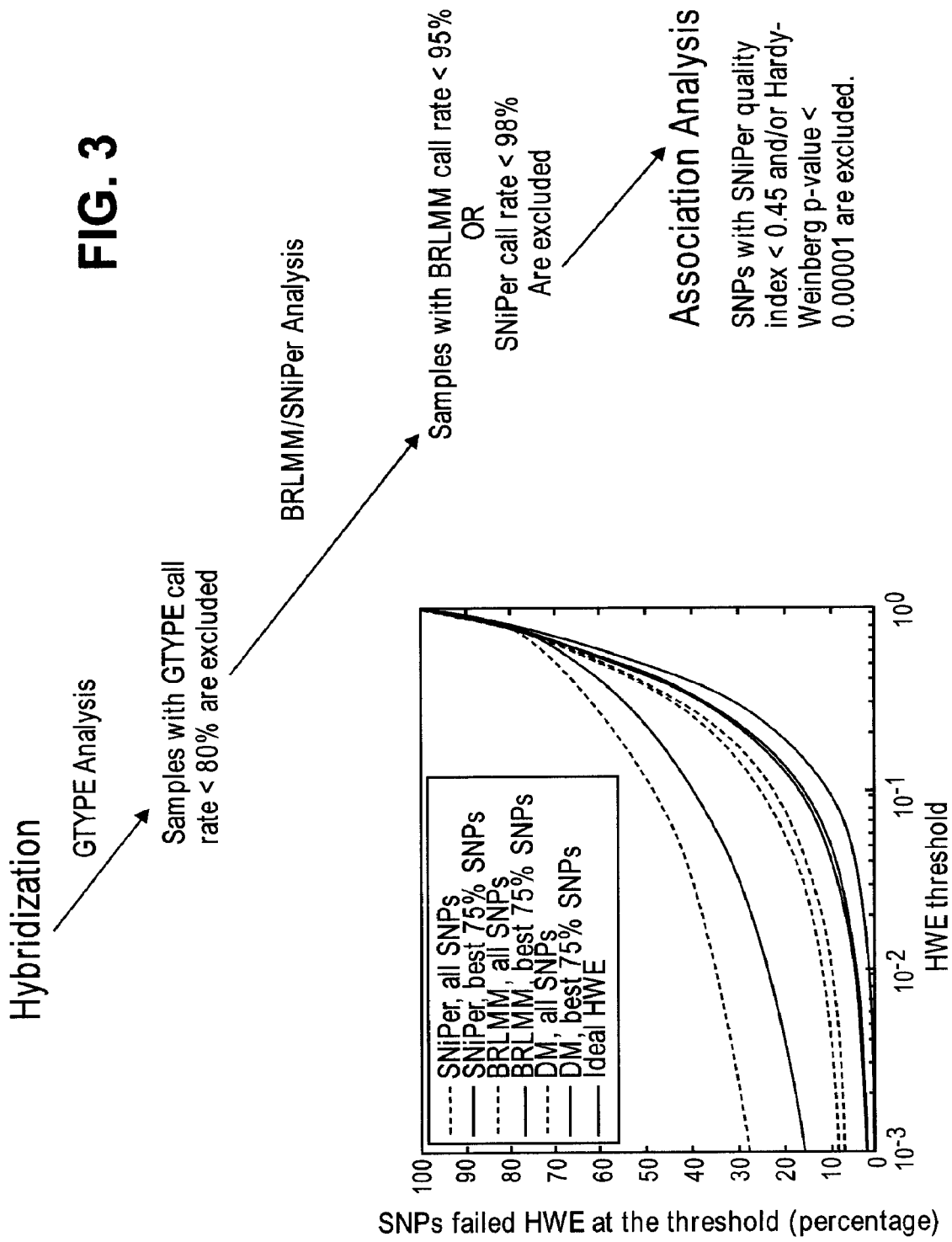
FIG. 3 is an example of a hybridization quality control measure.

Analysis of data following scanning of an Affymetrix GeneChip Human Mapping 500K Array Set is performed according to the manufacturer's guidelines, as shown in FIG. 3. Briefly, acquisition of raw data using GeneChip Operating Software (GCOS) occurs. Data may also be aquired using Affymetrix GeneChip Command Console™. The aquisition of raw data is followed by analysis with GeneChip Genotyping Analysis Software (GTYPE). For purposes of the present invention, samples with a GTYPE call rate of less than 80% are excluded. Samples are then examined with BRLMM and/or SNiPer algorithm analyses. Samples with a BRLMM call rate of less than 95% or a SNiPer call rate of less than 98% are excluded. Finally, an association analysis is performed, and samples with a SNiPer quality index of less than 0.45 and/or a Hardy-Weinberg p-value of less than 0.00001 are excluded.

As an alternative to or in addition to DNA microarray analysis, genetic variations such as SNPs and mutations can be detected by DNA sequencing. DNA sequencing may also be used to sequence a substantial portion, or the entire, genomic sequence of an individual. Traditionally, common DNA sequencing has been based on polyacrylamide gel fractionation to resolve a population of chain-terminated fragments (Sanger et al., *Proc. Natl. Acad. Sci. USA* 74:5463-5467 (1977)). Alternative methods have been and continue to be developed to increase the speed and ease of DNA sequencing. For example, high throughput and single molecule sequencing platforms are commercially available or under development from 454 Life Sciences (Branford, Conn.) (Margulies et al., *Nature* (2005) 437:376-380 (2005)); Solexa (Hayward, Calif.); Helicos BioSciences Corporation (Cambridge, Mass.) (U.S. application Ser. No. 11/167,046, filed Jun. 23, 2005), and Li-Cor Biosciences (Lincoln, Nebr.) (U.S. application Ser. No. 11/118031, filed Apr. 29, 2005).

After an individual's genomic profile is generated in step 106, the profile is stored digitally in step 108, such profile may be stored digitally in a secure manner. The genomic profile is encoded in a computer readable format to be stored as part of a data set and may be stored as a database, where the genomic profile may be "banked", and can be accessed again later. The data set comprises a plurality of data points, wherein each data point relates to an individual. Each data point may have a plurality of data elements. One data element is the unique identifier, used to identify the individual's genomic profile. It may be a bar code. Another data element is genotype information, such as the SNPs or nucleotide sequence of the individual's genome. Data elements corresponding to the genotype information may also be included in the data point. For example, if the genotype information includes SNPs identified by microarray analysis, other data elements may include the microarray SNP identification number, the SNP rs number, and the polymorphic nucleotide. Other data elements may be chromosome position of the genotype information, quality metrics of the data, raw data files, images of the data, and extracted intensity scores.

The individual's specific factors such as physical data, medical data, ethnicity, ancestry, geography, gender, age, family history, known phenotypes, demographic data, exposure data, lifestyle data, behavior data, and other known phenotypes may also be incorporated as data elements. For example, factors may include, but are not limited to, individual's: birthplace, parents and/or grandparents, relatives' ancestry, location of residence, ancestors' location of residence, environmental conditions, known health conditions, known drug interactions, family health conditions, lifestyle conditions, diet, exercise habits, marital status, and physical measurements, such as weight, height, cholesterol level, heart rate, blood pressure, glucose level and other measurements known in the art The above mentioned factors for an individual's relatives or ancestors, such as parents and grandparents, may also be incorporated as data elements and used to determine an individual's risk for a phenotype or condition.

The specific factors may be obtained from a questionnaire or from a health care manager of the individual. Information from the "banked" profile can then be accessed and utilized as desired. For example, in the initial assessment of an individual's genotype correlations, the individual's entire information (typically SNPs or other genomic sequences across, or taken from an entire genome) will be analyzed for genotype correlations. In subsequent analyses, either the entire information can be accessed, or a portion thereof, from the stored, or banked genomic profile, as desired or appropriate.

Comparison of Genomic Profile with Database of Genotype Correlations.

In step 110, genotype correlations are obtained from scientific literature. Genotype correlations for genetic variations are determined from analysis of a population of individuals who have been tested for the presence or absence of one or more phenotypic traits of interest and for genotype profile. The alleles of each genetic variation or polymorphism in the profile are then reviewed to determine whether the presence or absence of a particular allele is associated with a trait of interest. Correlation can be performed by standard statistical methods and statistically significant correlations between genetic variations and phenotypic characteristics are noted. For example, it may be determined that the presence of allele A1 at polymorphism A correlates with heart disease. As a further example, it might be found that the combined presence of allele A1 at polymorphism A and allele B1 at polymorphism B correlates with increased risk of cancer. The results of the analyses may be published in peer-reviewed literature, validated by other research groups, and/or analyzed by a committee of experts, such as geneticists, statisticians, epidemiologists, and physicians, and may also be curated.

In FIGS. 4, 5, and 6 are examples of correlations between genotypes and phenotypes from which rules to be applied to genomic profiles may be based. For example, in FIGS. 4A and B, each row corresponds to a phenotype/locus/ethnicity, wherein FIGS. 4C through I contains further information about the correlations for each of these rows. As an example, in FIG. 4A, the "Short Phenotype Name" of BC, as noted in FIG. 4M, an index for the names of the short phenotypes, is an abbreviation for breast cancer. In row BC_4, which is the generic name for the locus, the gene LSP1 is correlated to breast cancer. The published or functional SNP identified with this correlation is rs3817198, as shown in FIG. 4C, with the published risk allele being C, the nonrisk allele being T. The published SNP and alleles are identified through publications such as seminal publications as in FIGS. 4E-G. In the example of LSP1 in FIG. 4E, the seminal publication is Easton et al., Nature 447:713-720 (2007). FIGS. 22 and 25 further list correlations. The correlations in FIGS. 22 and 25 may be used to calculate an individual's risk for a condition or phenotype, for example, for calculating a GCI or GCI Plus score. The GCI or GCI Plus score may also incorporate information such as a condition's prevalence, for example in FIG. 23.

Alternatively, the correlations may be generated from the stored genomic profiles. For example, individuals with stored genomic profiles may also have known phenotype information stored as well. Analysis of the stored genomic profiles and known phenotypes may generate a genotype correlation. As an example, 250 individuals with stored genomic profiles also have stored information that they have previously been diagnosed with diabetes. Analysis of their genomic profiles is performed and compared to a control group of individuals without diabetes. It is then determined that the individuals previously diagnosed with diabetes have a higher rate of having a particular genetic variant compared to the control group, and a genotype correlation may be made between that particular genetic variant and diabetes.

In step 112, rules are made based on the validated correlations of genetic variants to particular phenotypes. Rules may be generated based on the genotypes and phenotypes correlated as listed in Table 1, for example. Rules based on correlations may incorporate other factors such as gender (e.g. FIG. 4) or ethnicity (FIGS. 4 and 5), to generate effects estimates, such as those in FIGS. 4 and 5. Other measures resulting from rules may be estimated relative risk increase such as in FIG. 6. The effects estimates and estimated relative risk increase may be from the published literature, or calculated from the published literature. Alternatively, the rules may be based on correlations generated from stored genomic profiles and previously known phenotypes. In some embodiments, the rules are based on correlations in FIGS. 22 and 25.

In a preferred embodiment, the genetic variants will be SNPs. While SNPs occur at a single site, individuals who carry a particular SNP allele at one site often predictably carry specific SNP alleles at other sites. A correlation of SNPs and an allele predisposing an individual to disease or condition occurs through linkage disequilibrium, in which the non-random association of alleles at two or more loci occur more or less frequently in a population than would be expected from random formation through recombination.

Other genetic markers or variants, such as nucleotide repeats or insertions, may also be in linkage disequilibrium with genetic markers that have been shown to be associated with specific phenotypes. For example, a nucleotide insertion is correlated with a phenotype and a SNP is in linkage disequilibrium with the nucleotide insertion. A rule is made based on the correlation between the SNP and the phenotype. A rule based on the correlation between the nucleotide insertion and the phenotype may also be made. Either rules or both rules may be applied to a genomic profile, as the presence of one SNP may give a certain risk factor, the other may give another risk factor, and when combined may increase the risk.

Through linkage disequilibrium, a disease predisposing allele cosegregates with a particular allele of a SNP or a combination of particular alleles of SNPs. A particular combination of SNP alleles along a chromosome is termed a haplotype, and the DNA region in which they occur in combination can be referred to as a haplotype block. While a haplotype block can consist of one SNP, typically a haplotype block represents a contiguous series of 2 or more SNPs exhibiting low haplotype diversity across individuals and with generally low recombination frequencies. An identification of a haplotype can be made by identification of one or more SNPs that lie in a haplotype block. Thus, a SNP profile typically can be used to identify haplotype blocks without necessarily requiring identification of all SNPs in a given haplotype block.

Genotype correlations between SNP haplotype patterns and diseases, conditions or physical states are increasingly becoming known. For a given disease, the haplotype patterns of a group of people known to have the disease are compared to a group of people without the disease. By analyzing many individuals, frequencies of polymorphisms in a population can be determined, and in turn these frequencies or genotypes can be associated with a particular phenotype, such as a disease or a condition. Examples of known SNP-disease correlations include polymorphisms in Complement Factor H in age-related macular degeneration (Klein et al., *Science:* 308: 385-389, (2005)) and a variant near the INSIG2 gene associated with obesity (Herbert et al., *Science:* 312:279-283 (2006)). Other known SNP correlations include polymorphisms in the 9p21 region that includes CDKN2A and B, such as) such as rs10757274, rs2383206, rs13333040, rs2383207, and rs10116277 correlated to myocardial infarction (Helgadottir et al., *Science* 316:1491-1493 (2007); McPherson et al., *Science* 316:1488-1491 (2007))

The SNPs may be functional or non-functional. For example, a functional SNP has an effect on a cellular function, thereby resulting in a phenotype, whereas a non-functional SNP is silent in function, but may be in linkage disequilibrium with a functional SNP. The SNPs may also be synonymous or non-synonymous. SNPs that are synonymous are SNPs in which the different forms lead to the same polypeptide sequence, and are non-functional SNPs. If the SNPs lead to different polypeptides, the SNP is non-synonymous and may or may not be functional. SNPs, or other genetic markers, used to identify haplotypes in a diplotype, which is 2 or more haplotypes, may also be used to correlate phenotypes associated with a diplotype. Information about an individual's haplotypes, diplotypes, and SNP profiles may be in the genomic profile of the individual.

In preferred embodiments, for a rule to be generated based on a genetic marker in linkage disequilibrium with another genetic marker that is correlated with a phenotype, the genetic marker may have a $r^2$ or D' score, scores commonly used in the art to determine linkage disequilibrium, of greater than 0.5. In preferred embodiments, the score is greater than 0.6, 0.7, 0.8, 0.90, 0.95 or 0.99. As a result, in the present invention, the genetic marker used to correlate a phenotype to an individual's genomic profile may be the same as the functional or published SNP correlated to a phenotype, or different. For example, using BC_4, the test SNP and published SNP are the same, as are the test risk and nonrisk alleles are the same as the published risk and nonrisk alleles (FIGS. 4A and C). However, for BC_5, CASP8 and its correlation to breast cancer, the test SNP is different from its functional or published SNP, as are the test risk and nonrisk alleles to the published risk and nonrisk alleles. The test and published alleles are oriented relative to the plus strand of the genome, and from these columns, it can be inferred the homozygous risk or nonrisk genotype, which may generate a rule to be applied to the genomic profile of individuals such as subscribers. In some embodiments, the test SNP may not yet be identified, but using the published SNP information, allelic differences or SNPs may be identified based on another assay, such as TaqMan. For example, AMD_5 in FIG. 25A, the published SNP is rs1061170 but a test SNP has not been identified. The test SNP may be identified by LD analysis with the published SNP. Alternatively, the test SNP may not be used, and instead, TaqMan or other comparable assay, will be used to assess an individual's genome having the test SNP.

The test SNPs may be "DIRECT" or "TAG" SNPs (FIGS. 4E-G, FIG. 5). Direct SNPs are the test SNPs that are the same as the published or functional SNP, such as for BC_4. Direct SNPs may also be used for FGFR2 correlation with breast cancer, using the SNP rs1073640 in Europeans and Asians, where the minor allele is A and the other allele is G (Easton et al., *Nature* 447:1087-1093 (2007)). Another published or functional SNP for FGFR2 correlation to breast cancer is rs1219648, also in Europeans and Asians (Hunter et al., *Nat. Genet.* 39:870-874 (2007)). Tag SNPs are where the test SNP is different from that of the functional or published SNP, as in for BC_5. Tag SNPs may also be used for other genetic variants such as SNPs for CAMTA1 (rs4908449), 9p21 (rs10757274, rs2383206, rs13333040, rs2383207, rs10116277), COL1A1 (rs1800012), FVL (rs6025), HLA-DQA1 (rs4988889, rs2588331), eNOS (rs1799983), MTHFR (rs1801133), and APC (rs28933380).

Databases of SNPs are publicly available from, for example, the International HapMap Project (see www.hapmap.org, *The International HapMap Consortium, Nature* 426:789-796 (2003), and *The International HapMap Consortium, Nature* 437:1299-1320 (2005)), the Human Gene Mutation Database (HGMD) public database (see www.hgmd.org), and the Single Nucleotide Polymorphism database (dbSNP) (see www.ncbi.nlm.nih.gov/SNP/). These databases provide SNP haplotypes, or enable the determination of SNP haplotype patterns. Accordingly, these SNP databases enable examination of the genetic risk factors underlying a wide range of diseases and conditions, such as cancer, inflammatory diseases, cardiovascular diseases, neurodegenerative diseases, and infectious diseases. The diseases or conditions may be actionable, in which treatments and therapies currently exist. Treatments may include prophylactic treatments as well as treatments that ameliorate symptoms and conditions, including lifestyle changes.

Many other phenotypes such as physical traits, physiological traits, mental traits, emotional traits, ethnicity, ancestry, and age may also be examined. Physical traits may include height, hair color, eye color, body, or traits such as stamina, endurance, and agility. Mental traits may include intelligence, memory performance, or learning performance. Ethnicity and ancestry may include identification of ancestors or ethnicity, or where an individual's ancestors originated from. The age may be a determination of an individual's real age, or the age in which an individual's genetics places them in relation to the general population. For example, an individual's real age is 38 years of age, however their genetics may determine their memory capacity or physical well-being may be of the average 28 year old. Another age trait may be a projected longevity for an individual.

Other phenotypes may also include non-medical conditions, such as "fun" phenotypes. These phenotypes may include comparisons to well known individuals, such as foreign dignitaries, politicians, celebrities, inventors, athletes, musicians, artists, business people, and infamous individuals, such as convicts. Other "fun" phenotypes may include comparisons to other organisms, such as bacteria, insects, plants, or non-human animals. For example, an individual may be interested to see how their genomic profile compares to that of their pet dog, or to a former president.

At step 114, the rules are applied to the stored genomic profile to generate a phenotype profile of step 116. For example, information in FIG. 4, 5, or 6 may form the basis of rules, or tests, to apply to an individual's genomic profile. The rules may encompass the information on test SNP and alleles, and the effect estimates of FIG. 4, where the UNITS for effect estimate is the units of the effect estimate, such as OR, or odds-ratio (95% confidence interval) or mean. The effects estimate may be a genotypic risk (FIGS. 4C-G) in preferred embodiments, such as the risk for homozygotes (homoz or RR), risk heterozygotes (heteroz or RN), and nonrisk homozygotes (homoz or NN). In other embodiments, the effect estimate may be carrier risk, which is RR or RN vs NN. In yet other embodiments, the effect estimate may be based on the allele, an allelic risk such as R vs. N. There may also be two locus (FIG. 4J) or three locus (FIG. 4K) genotypic effect estimate (e.g. RRRR, RRNN, etc for the 9 possible genotype combinations for a two locus effect estimate). The test SNP frequency in the public HapMap is also noted in FIGS. 4H and I.

Figure 15A:
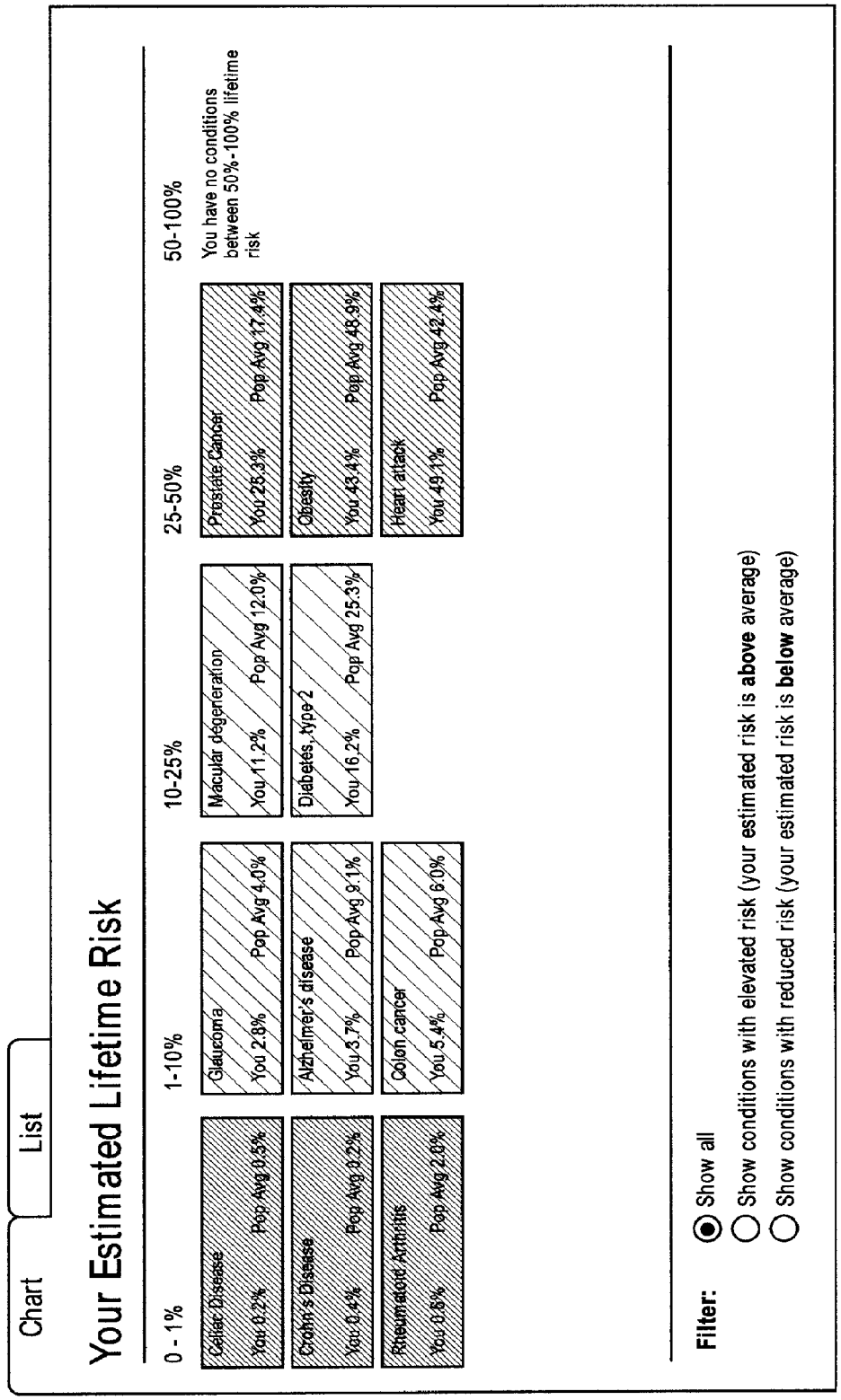
FIG. 15: are illustrations of sample webpages from a personalized portal.
Figure 15B:
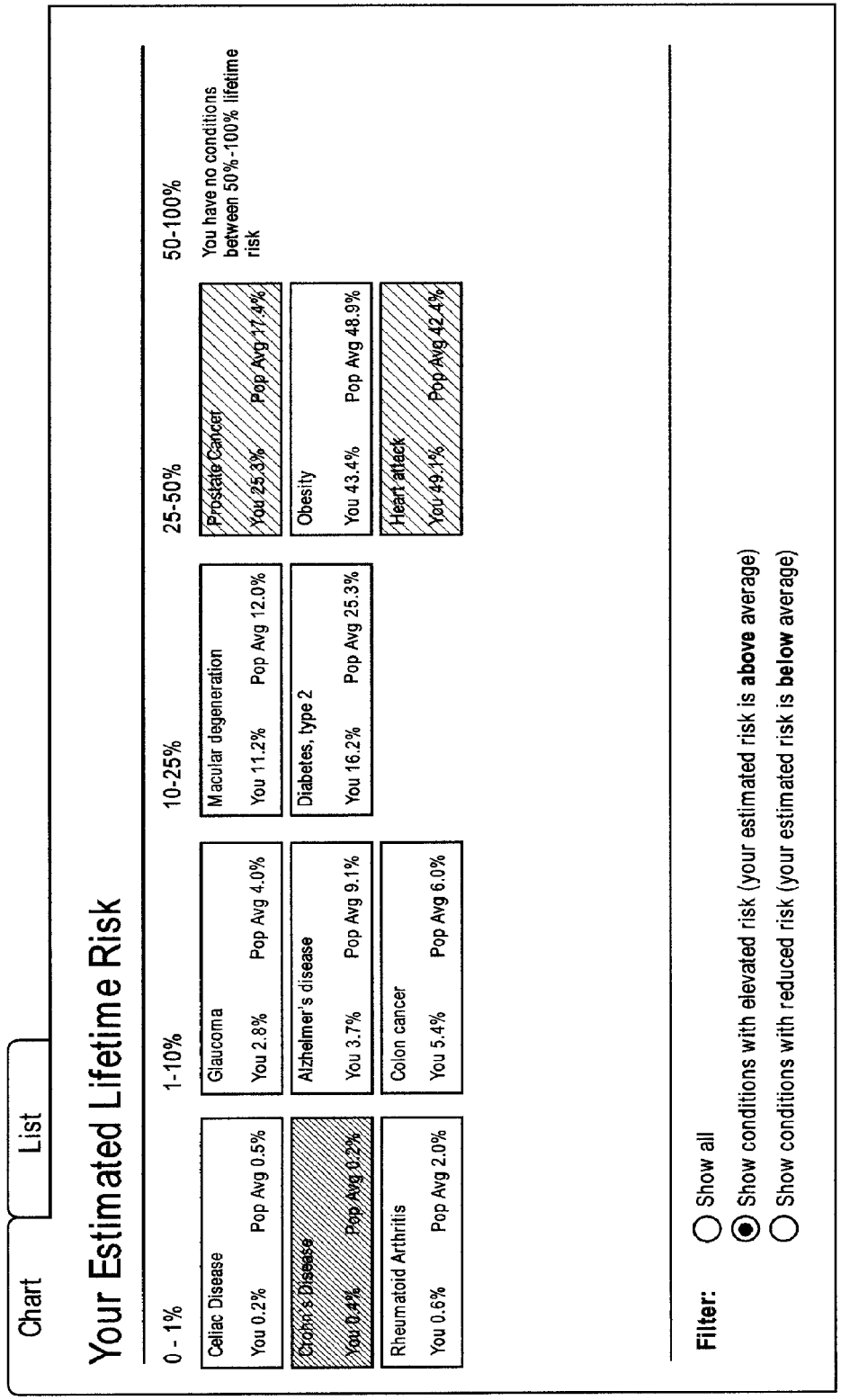

In other embodiments, information from FIGS. 21, 22, 23, and/or 25 may be used to generate information to apply to an individual's genomic profile. For example, the information may be used to generate GCI or GCI Plus scores for an individual (for example, FIG. 19). The scores may be used to generate information on genetic risks, such as estimated lifetime risk, for one or more conditions in the phenotype profile of an individual (for example, FIG. 15). the methods allow calculating estimated lifetime risks or relative risks for one or more phenotypes or conditions as listed in FIG. 22 or 25. The risk for a single condition may be based on one or more SNP. For example, an estimated risk for a phenotype or condition may be based on at least 2, 3, 4, 5, 6, 7, 8, 9, 10, 11, or 12 SNPs, wherein the SNPs for estimating a risk may be published SNPs, test SNPs, or both (for example, FIG. 25).

The estimated risk for a condition may be based on the SNPs as listed in FIG. 22 or 25. In some embodiments, the risk for a condition may be based on at least one SNP. For example, assessment of an individual's risk for Alzheimers (AD), colorectal cancer (CRC), osteoarthritis (OA) or exfoliation glaucoma (XFG), may be based on 1 SNP (for example, rs4420638 for AD, rs6983267 for CRC, rs4911178 for OA and rs2165241 for XFG). For other conditions, such as obesity (BMIOB), Graves' disease (GD), or hemochromatosis (HEM), an individual's estimated risk may be based on at least 1 or 2 SNPs (for example, rs9939609 and/or rs9291171 for BMIOB; DRB1*0301 DQA1*0501 and/or rs3087243 for GD; rs1800562 and/or rs129128 for HEM). For conditions such as, but not limited to, myocardial infarction (MI), multiple sclerosis (MS), or psoriasis (PS), 1, 2, or 3 SNPs may be used to assess an individual's risk for the condition (for example, rs1866389, rs1333049, and/or rs6922269 for MI; rs6897932, rs12722489, and/or DRB1*1501 for MS; rs6859018, rs11209026, and/or HLAC*0602 for PS). For estimating an individual's risk of restless legs syndrome (RLS) or celiac disease (CelD), 1, 2, 3, or 4 SNPs (for example, rs6904723, rs2300478, rs1026732, and/or rs9296249 for RLS; rs6840978, rs11571315, rs2187668, and/or DQA1*0301 DQB1*0302 for CelD). For prostate cancer (PC) or lupus (SLE), 1, 2, 3, 4, or 5 SNPs may be used to estimate an individual's risk for PC or SLE (for example, rs4242384, rs6983267, rs16901979, rs17765344, and/or rs4430796 for PC; rs12531711, rs10954213, rs2004640, DRB1*0301, and/or DRB1*1501 for SLE). For estimating an individual's lifetime risk of macular degeneration (AMD) or rheumatoid arthritis (RA), 1, 2, 3, 4, 5, or 6 SNPs, may be used (for example, rs10737680, rs10490924, rs541862, rs2230199, rs1061170, and/or rs9332739 for AMD; rs6679677, rs11203367, rs6457617, DRB*0101, DRB1*0401, and/or DRB1*0404 for RA). For estimating an individual's lifetime risk of breast cancer (BC), 1, 2, 3, 4, 5, 6 or 7 SNPs may be used (for example, rs3803662, rs2981582, rs4700485, rs3817198, rs17468277, rs6721996, and/or rs3803662). For estimating an individual's lifetime risk of Crohn's disease (CD) or Type 2 diabetes (T2D), 1, 2, 3, 4, 5, 6, 7, 8, 9, 10, or 11 SNPs may be used (for example, rs2066845, rs5743293, rs10883365, rs17234657, rs10210302, rs9858542, rs11805303, rs1000113, rs17221417, rs2542151, and/or rs10761659 for CD; rs13266634, rs4506565, rs10012946, rs7756992, rs10811661, rs12288738, rs8050136, rs1111875, rs4402960, rs5215, and/or rs1801282 for T2D). In some embodiments, the SNPs used as a basis for determining risk may be in linkage disequilibrium with the SNPs as mentioned above, or listed in FIG. 22 or 25.

The phenotype profile of an individual may comprise a number of phenotypes. In particular, the assessment of a patient's risk of disease or other conditions such as likely drug response including metabolism, efficacy and/or safety, by the methods of the present invention allows for prognostic or diagnostic analysis of susceptibility to multiple, unrelated diseases and conditions, whether in symptomatic, presymptomatic or asymptomatic individuals, including carriers of one or more disease/condition predisposing alleles. Accordingly, these methods provide for general assessment of an individual's susceptibility to disease or condition without any preconceived notion of testing for a specific disease or condition. For example, the methods of the present invention allow for assessment of an individual's susceptibility to any of the several conditions listed in Tables 1, FIG. 4, 5, or 6, based on the individual's genomic profile. Furthermore, the methods allow assessments of an individual's estimated lifetime risk or relative risk for one or more phenotype or condition, such as those in FIG. 22 or 25.

The assessment preferably provides information for 2 or more of these conditions, and more preferably, 3, 4, 5, 10, 20, 50, 100 or even more of these conditions. In preferred embodiments, the phenotype profile results from the application of at least 20 rules to the genomic profile of an individual. In other embodiments, at least 50 rules are applied to the genomic profile of an individual. A single rule for a phenotype may be applied for monogenic phenotypes. More than one rule may also be applied for a single phenotype, such as a multigenic phenotype or a monogenic phenotype wherein multiple genetic variants within a single gene affects the probability of having the phenotype.

Following an initial screening of an individual patient's genomic profile, updates of an individual's genotype correlations are made (or are available) through comparisons to additional nucleotide variants, such as SNPs, when such additional nucleotide variants become known. For example, step 110 may be performed periodically, for example, daily, weekly, or monthly by one or more people of ordinary skill in the field of genetics, who scan scientific literature for new genotype correlations. The new genotype correlations may then be further validated by a committee of one or more experts in the field. Step 112 may then also be periodically updated with new rules based on the new validated correlations.

The new rule may encompass a genotype or phenotype without an existing rule. For example, a genotype not correlated with any phenotype is discovered to correlate with a new or existing phenotype. A new rule may also be for a correlation between a phenotype for which no genotype has previously been correlated to. New rules may also be determined for genotypes and phenotypes that have existing rules. For example, a rule based on the correlation between genotype A and phenotype A exists. New research reveals genotype B correlates with phenotype A, and a new rule based on this correlation is made. Another example is phenotype B is discovered to be associated with genotype A, and thus a new rule may be made.

Rules may also be made on discoveries based on known correlations but not initially identified in published scientific literature. For example, it may be reported genotype C is correlated with phenotype C. Another publication reports genotype D is correlated with phenotype D. Phenotype C and D are related symptoms, for example phenotype C may be shortness of breath, and phenotype D is small lung capacity. A correlation between genotype C and phenotype D, or genotype D with phenotype C, may be discovered and validated through statistical means with existing stored genomic profiles of individuals with genotypes C and D, and phenotypes C and D, or by further research. A new rule may then be generated based on the newly discovered and validated correlation. In another embodiment, stored genomic profiles of a number of individuals with a specific or related phenotype may be studied to determine a genotype common to the individuals, and a correlation may be determined. A new rule may be generated based on this correlation.

Rules may also be made to modify existing rules. For example, correlations between genotypes and phenotypes may be partly determined by a known individual characteristic, such as ethnicity, ancestry, geography, gender, age, family history, or any other known phenotypes of the individual. Rules based on these known individual characteristics may be made and incorporated into an existing rule, to provide a modified rule. The choice of modified rule to be applied will be dependent on the specific individual factor of an individual. For example, a rule may be based on the probability an individual who has phenotype E is 35% when the individual has genotype E. However, if an individual is of a particular ethnicity, the probability is 5%. A new rule may be generated based on this result and applied to individuals with that particular ethnicity. Alternatively, the existing rule with a determination of 35% may be applied, and then another rule based on ethnicity for that phenotype is applied. The rules based on known individual characteristics may be determined from scientific literature or determined based on studies of stored genomic profiles. New rules may be added and applied to genomic profiles in step 114, as the new rules are developed, or they may be applied periodically, such as at least once a year.

Information of an individual's risk of disease can also be expanded as technology advances allow for finer resolution SNP genomic profiles. As indicated above, an initial SNP genomic profile readily can be generated using microarray technology for scanning of 500,000 SNPs. Given the nature of haplotype blocks, this number allows for a representative profile of all SNPs in an individual's genome. Nonetheless, there are approximately 10 million SNPs estimated to occur commonly in the human genome (the International HapMap Project; www.hapmap.org). As technological advances allow for practical, cost-efficient resolution of SNPs at a finer level of detail, such as microarrays of 1,000,000, 1,500,000, 2,000,000, 3,000,000, or more SNPs, or whole genomic sequencing, more detailed SNP genomic profiles can be generated. Likewise, cost-efficient analysis of finer SNP genomic profiles and updates to the master database of SNP-disease correlations will be enabled by advances in computational analytical methodology.

After generation of phenotype profile at step 116, a subscriber or their health care manager may access their genomic or phenotype profiles via an on-line portal or website as in step 118. Reports containing phenotype profiles and other information related to the phenotype and genomic profiles may also be provided to the subscriber or their health care manager, as in steps 120 and 122. The reports may be printed, saved on the subscriber's computer, or viewed on-line.

A sample on-line report is shown in FIG. 7. The subscriber may choose to display a single phenotype, or more than one phenotype. The subscriber may also have different viewing options, for example, as shown in FIG. 7, a "Quick View" option. The phenotype may be a medical condition and different treatments and symptoms in the quick report may link to other web pages that contain further information about the treatment. For example, by clicking on a drug, it will lead to website that contains information about dosages, costs, side effects, and effectiveness. It may also compare the drug to other treatments. The website may also contain a link leading to the drug manufacturer's website. Another link may provide an option for the subscriber to have a pharmacogenomic profile generated, which would include information such as their likely response to the drug based on their genomic profile. Links to alternatives to the drug may also be provided, such as preventative action such as fitness and weight loss, and links to diet supplements, diet plans, and to nearby health clubs, health clinics, health and wellness providers, day spas and the like may also be provided. Educational and informational videos, summaries of available treatments, possible remedies, and general recommendations may also be provided.

The on-line report may also provide links to schedule in-person physician or genetic counseling appointments or to access an on-line genetic counselor or physician, providing the opportunity for a subscriber to ask for more information regarding their phenotype profile. Links to on-line genetic counseling and physician questions may also be provided on the on-line report.

Reports may also be viewed in other formats such as a comprehensive view for a single phenotype, wherein more detail for each category is provided. For example, there may be more detailed statistics about the likelihood of the subscriber developing the phenotype, more information about the typical symptoms or phenotypes, such as sample symptoms for a medical condition, or the range of a physical non-medical condition such as height, or more information about the gene and genetic variant, such as the population incidence, for example in the world, or in different countries, or in different age ranges or genders. For example, FIG. 15 shows a summary of estimated lifetime risks for a number of conditions. The individual may view more information for a specific condition, such as prostate cancer (FIG. 16) or Crohn's disease (FIG. 17).

In another embodiment, the report may be of a "fun" phenotype, such as the similarity of an individual's genomic profile to that of a famous individual, such as Albert Einstein. The report may display a percentage similarity between the individual's genomic profile to that of Einstein's, and may further display a predicted IQ of Einstein and that of the individual's. Further information may include how the genomic profile of the general population and their IQ compares to that of the individual's and Einstein's.

Figure 15C:
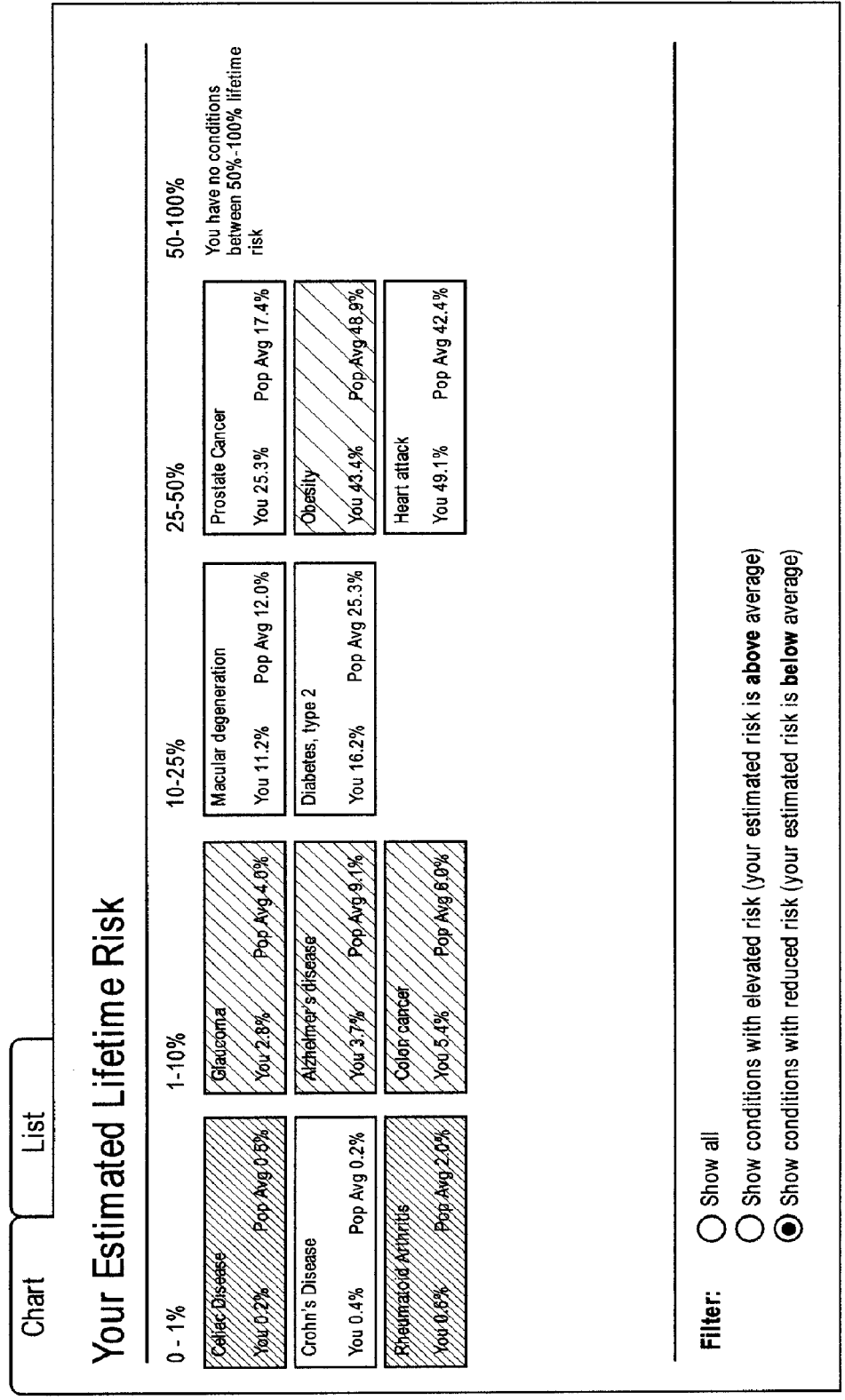

In another embodiment, the report may display all phenotypes that have been correlated to the subscriber's genomic profile. In other embodiments, the report may display only the phenotypes that are positively correlated with an individual's genomic profile. In other formats, the individual may choose to display certain subgroups of phenotypes, such as only medical phenotypes, or only actionable medical phenotypes. For example, actionable phenotypes and their correlated genotypes, may include Crohn's disease (correlated with IL23R and CARD 15), Type 1 diabetes (correlated with HLA-DR/DQ), lupus (correlated HLA-DRB1), psoriasis (HLA-C), multiple sclerosis (HLA-DQA1), Graves disease (HLA-DRB1), rheumatoid arthritis (HLA-DRB1), Type 2 diabetes (TCF7L2), breast cancer (BRCA2), colon cancer (APC), episodic memory (KIBRA), and osteoporosis (COL1A1). The individual may also choose to display subcategories of phenotypes in their report, such as only inflammatory diseases for medical conditions, or only physical traits for non-medical conditions. In some embodiments, the individual may choose to show all conditions an estimated risk was calculated for the individual by highlighting those conditions (for example, FIG. 15A, D), highlighting only conditions with an elevated risk (FIG. 15B), or only conditions with a reduced risk (FIG. 15C).

Information submitted by and conveyed to an individual may be secure and confidential, and access to such information may be controlled by the individual. Information derived from the complex genomic profile may be supplied to the individual as regulatory agency approved, understandable, medically relevant and/or high impact data. Information may also be of general interest, and not medically relevant. Information can be securely conveyed to the individual by several means including, but not restricted to, a portal interface and/or mailing. More preferably, information is securely (if so elected by the individual) provided to the individual by a portal interface, to which the individual has secure and confidential access. Such an interface is preferably provided by on-line, internet website access, or in the alternative, telephone or other means that allow private, secure, and readily available access. The genomic profiles, phenotype profiles, and reports are provided to an individual or their health care manager by transmission of the data over a network.

Figure 8:
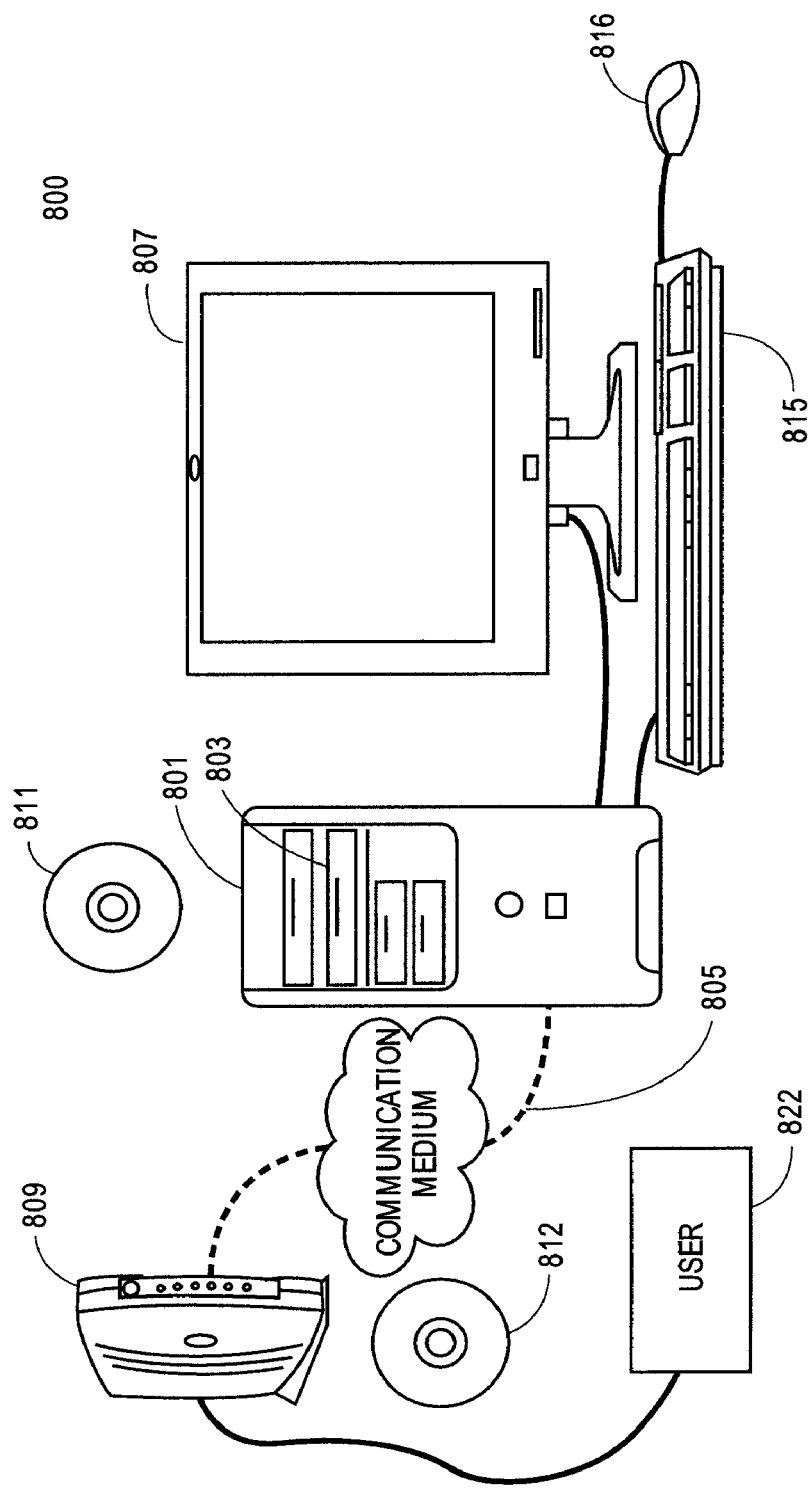
FIG. 8 is a schematic of a system for the analysis and transmission of genomic and phenotype profiles over a network.

Accordingly, FIG. 8 is a block diagram showing a representative example logic device through which a phenotype profile and report may be generated. FIG. 8 shows a computer system (or digital device) 800 to receive and store genomic profiles, analyze genotype correlations, generate rules based on the analysis of genotype correlations, apply the rules to the genomic profiles, and produce a phenotype profile and report. The computer system 800 may be understood as a logical apparatus that can read instructions from media 811 and/or network port 805, which can optionally be connected to server 809 having fixed media 812. The system shown in FIG. 8 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 822. The receiving party 822 can be but is not limited to an individual, a subscriber, a health care provider or a health care manager. In one embodiment, a computer-readable medium includes a medium suitable for transmission of a result of an analysis of a biological sample or a genotype correlation. The medium can include a result regarding a phenotype profile of an individual subject, wherein such a result is derived using the methods described herein.

A personal portal will preferably serve as the primary interface with an individual for receiving and evaluating genomic data. A portal will enable individuals to track the progress of their sample from collection through testing and results. Through portal access, individuals are introduced to relative risks for common genetic disorders based on their genomic profile. The subscriber may choose which rules to apply to their genomic profile through the portal.

In one embodiment, one or more web pages will have a list of phenotypes and next to each phenotype a box in which a subscriber may select to include in their phenotype profile. The phenotypes may be linked to information on the phenotype, to help the subscriber make an informed choice about the phenotype they want included in their phenotype profile. The webpage may also have phenotypes organized by disease groups, for example as actionable diseases or not. For example, a subscriber may choose actionable phenotypes only, such as HLA-DQA1 and celiac disease. The subscriber may also choose to display pre or post symptomatic treatments for the phenotypes. For example, the individual may choose actionable phenotypes with pre-symptomatic treatments (outside of increased screening), for celiac disease, a pre-symptomatic treatment of gluten free diet. Another example may be Alzheimer's, the pre-symptomatic treatment of statins, exercise, vitamins, and mental activity. Thrombosis is another example, with a pre-symptomatic treatment of avoid oral contraceptives and avoid sitting still for long periods of time. An example of a phenotype with an approved post symptomatic treatment is wet AMD, correlated with CFH, wherein individuals may obtain laser treatment for their condition.

The phenotypes may also be organized by type or class of disease or conditions, for example neurological, cardiovascular, endocrine, immunological, and so forth. Phenotypes may also be grouped as medical and non-medical phenotypes. Other groupings of phenotypes on the webpage may be by physical traits, physiological traits, mental traits, or emotional traits. The webpage may further provide a section in which a group of phenotypes are chosen by selection of one box. For example, a selection for all phenotypes, only medically relevant phenotypes, only non-medically relevant phenotypes, only actionable phenotypes, only non-actionable phenotypes, different disease group, or "fun" phenotypes. "Fun" phenotypes may include comparisons to celebrities or other famous individuals, or to other animals or even other organisms. A list of genomic profiles available for comparison may also be provided on the webpage for selection by the subscriber to compare to the subscriber's genomic profile.

The on-line portal may also provide a search engine, to help the subscriber navigate the portal, search for a specific phenotype, or search for specific terms or information revealed by their phenotype profile or report. Links to access partner services and product offerings may also be provided by the portal. Additional links to support groups, message boards, and chat rooms for individuals with a common or similar phenotype may also be provided. The on-line portal may also provide links to other sites with more information on the phenotypes in a subscriber's phenotype profile. The on-line portal may also provide a service to allow subscribers to share their phenotype profile and reports with friends, families, or health care managers. Subscribers may choose which phenotypes to show in the phenotype profile they want shared with their friends, families, or health care managers.

The phenotype profiles and reports provide a personalized genotype correlation to an individual. The genotype correlations provided to an individual can be used in determining personal health care and lifestyle choices. If a strong correlation is found between a genetic variant and a disease for which treatment is available, detection of the genetic variant may assist in deciding to begin treatment of the disease and/or monitoring of the individual. In the case where a statistically significant correlation exists but is not regarded as a strong correlation, an individual can review the information with a personal physician and decide an appropriate, beneficial course of action. Potential courses of action that could be beneficial to an individual in view of a particular genotype correlation include administration of therapeutic treatment, monitoring for potential need of treatment or effects of treatment, or making life-style changes in diet, exercise, and other personal habits/activities. For example, an actionable phenotype such as celiac disease may have a pre-symptomatic treatment of a gluten-free diet. Likewise, genotype correlation information could be applied through pharmacogenomics to predict the likely response an individual would have to treatment with a particular drug or regimen of drugs, such as the likely efficacy or safety of a particular drug treatment.

Subscribers may choose to provide the genomic and phenotype profiles to their health care managers, such as a physician or genetic counselor. The genomic and phenotype profiles may be directly accessed by the healthcare manager, by the subscriber printing out a copy to be given to the healthcare manager, or have it directly sent to the healthcare manager through the on-line portal, such as through a link on the on-line report.

Delivery of this pertinent information will empower patients to act in concert with their physician. In particular, discussions between patients and their physicians can be empowered through an individual's portal and links to medical information, and the ability to tie patient's genomic information into their medical records. Medical information may include prevention and wellness information. The information provided to the individual patient by the present invention will enable patients to make informed choices for their health care. In this manner, patients will be able to make choices that may help them avoid and/or delay diseases that their individual genomic profile (inherited DNA) makes more likely. In addition, patients will be able to employ a treatment regime that personally fits their specific medical needs. Individuals also will have the ability to access their genotype data should they develop an illness and need this information to help their physician form a therapeutic strategy.

Genotype correlation information could also be used in cooperation with genetic counseling to advise couples considering reproduction, and potential genetic concerns to the mother, father and/or child. Genetic counselors may provide information and support to subscribers with phenotype profiles that display an increased risk for specific conditions or diseases. They may interpret information about the disorder, analyze inheritance patterns and risks of recurrence, and review available options with the subscriber. Genetic counselors may also provide supportive counseling refer subscribers to community or state support services. Genetic counseling may be included with specific subscription plans. In some embodiments, genetic counseling may be scheduled within 24 hours of request and available during of hours such as evenings, Saturdays, Sundays, and/or holidays.

An individual's portal will also facilitate delivery of additional information beyond an initial screening. Individuals will be informed about new scientific discoveries that relate to their personal genetic profile, such as information on new treatments or prevention strategies for their current or potential conditions. The new discoveries may also be delivered to their healthcare managers. In preferred embodiments, the subscribers, or their healthcare providers are informed of new genotype correlations and new research about the phenotypes in the subscriber's phenotype profiles, by e-mail. In other embodiments, e-mails of "fun" phenotypes are sent to subscribers, for example, an e-mail may inform them that their genomic profile is 77% identical to that of Abraham Lincoln and that further information is available via an on-line portal.

The present invention also provides a system of computer code for generating new rules, modifying rules, combining rules, periodically updating the rule set with new rules, maintaining a database of genomic profile securely, applying the rules to the genomic profiles to determine phenotype profiles, and for generating reports. Computer code for notifying subscribers of new or revised correlations new or revised rules, and new or revised reports, for example with new prevention and wellness information, information about new therapies in development, or new treatments available.

Business Method

Figure 9:
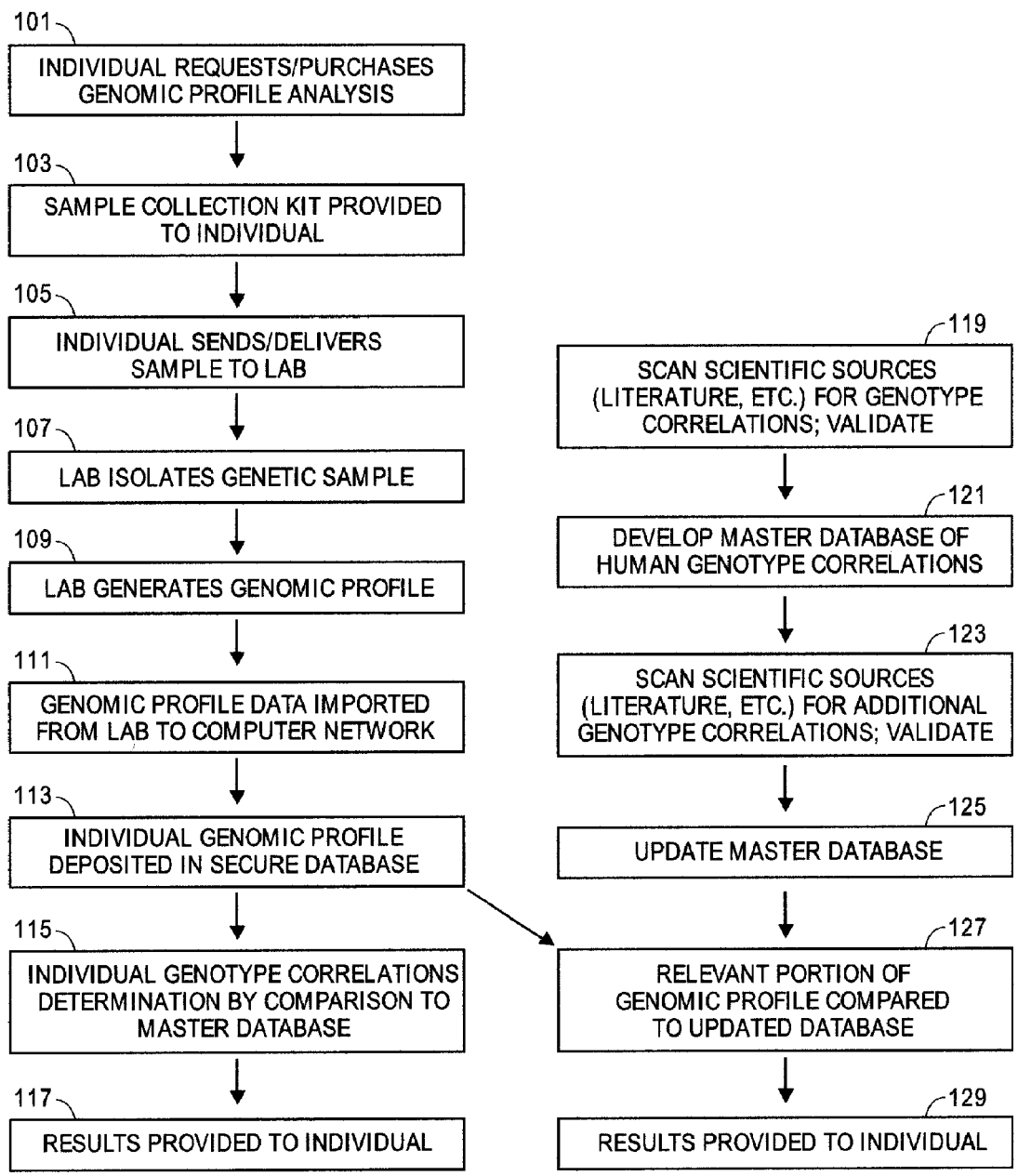
FIG. 9 is a flow chart illustrating aspects of the business method herein

The present invention provides a business method of assessing an individual's genotype correlations based on comparison of the patient's genome profile against a clinically-derived database of established, medically relevant nucleotide variants. The present invention further provides a business method for using the stored genomic profile of the individual for assessing new correlations that were not initially known, to generate updated phenotype profiles for an individual, without the requirement of the individual submitting another biological sample. A flow chart illustrating the business method is in FIG. 9.

A revenue stream for the subject business method is generated in part at step 101, when an individual initially requests and purchases a personalized genomic profile for genotype correlations for a multitude of common human diseases, conditions, and physical states. A request and purchase can be made through any number of sources, including but not limited to, an on-line web portal, an on-line health service, and an individual's personal physician or similar source of personal medical attention. In an alternative embodiment, the genomic profile may be provided free, and the revenue stream is generated at a later step, such as step 103.

A subscriber, or customer, makes a request for purchase of a phenotype profile. In response to a request and purchase, a customer is provided a collection kit for a biological sample used for genetic sample isolation at step 103. When a request is made on-line, by telephone, or other source in which a collection kit is not readily physically available to the customer, a collection kit is provided by expedited delivery, such as courier service that provides same-day or overnight delivery. Included in the collection kit is a container for a sample, as well as packaging materials for expedited delivery of the sample to a laboratory for genomic profile generation. The kit may also include instructions for sending the sample to the sample processing facility, or laboratory, and instructions for accessing their genomic profile and phenotype profile, which may occur through an on-line portal.

As detailed above, genomic DNA can be obtained from any of a number of types of biological samples. Preferably, genomic DNA is isolated from saliva, using a commercially available collection kit such as that available from DNA Genotek. Use of saliva and such a kit allows for a non-invasive sample collection, as the customer conveniently provides a saliva sample in a container from a collection kit and then seals the container. In addition, a saliva sample can be stored and shipped at room temperature.

After depositing a biological sample into a collection or specimen container, a customer will deliver the sample to a laboratory for processing at step 105. Typically, the customer may use packaging materials provided in the collection kit to deliver/send the sample to a laboratory by expedited delivery, such as same-day or overnight courier service.

The laboratory that processes the sample and generates the genomic profile may adhere to appropriate governmental agency guidelines and requirements. For example, in the United States, a processing laboratory may be regulated by one or more federal agencies such as the Food and Drug Administration (FDA) or the Centers for Medicare and Medicaid Services (CMS), and/or one or more state agencies. In the United States, a clinical laboratory may be accredited or approved under the Clinical Laboratory Improvement Amendments of 1988 (CLIA).

At step 107, the laboratory processes the sample as previously described to isolate the genetic sample of DNA or RNA. Analysis of the isolated genetic sample and generation of a genomic profile is then performed at step 109. Preferably, a genomic SNP profile is generated. As described above, several methodologies may be used to generate a SNP profile. Preferably, a high density array, such as the commercially available platforms from Affymetrix or Illumina, is used for SNP identification and profile generation. For example, a SNP profile may be generated using an Affymetrix GeneChip assay, as described above in more detail. As technology evolves, there may be other technology vendors who can generate high density SNP profiles. In another embodiment, a genomic profile for a subscriber will be the genomic sequence of the subscriber.

Following generation of an individual's genomic profile, the genotype data is preferably encrypted, imported at step 111, and deposited into a secure database or vault at step 113, where the information is stored for future reference. The genomic profile and related information may be confidential, with access to this proprietary information and the genomic profile limited as directed by the individual and/or his or her personal physician. Others, such as family and the genetic counselor of the individual may also be permitted access by the subscriber.

The database or vault may be located on-site with the processing laboratory. Alternatively, the database may be located at a separate location. In this scenario, the genomic profile data generated by the processing lab can be imported at step 111 to a separate facility that contains the database.

After an individual's genomic profile is generated, the individual's genetic variations are then compared against a clinically-derived database of established, medically relevant genetic variants in step 115. Alternatively, the genotype correlations may not be medically relevant but still incorporated into the database of genotype correlations, for example, physical traits such as eye color, or "fun" phenotypes such as genomic profile similarity to a celebrity.

The medically relevant SNPs may have been established through the scientific literature and related sources. The non-SNP genetic variants may also be established to be correlated with phenotypes. Generally, the correlation of SNPs to a given disease is established by comparing the haplotype patterns of a group of people known to have the disease to a group of people without the disease. By analyzing many individuals, frequencies of polymorphisms in a population can be determined, and in turn these genotype frequencies can be associated with a particular phenotype, such as a disease or a condition. Alternatively, the phenotype may be a non-medical condition.

The relevant SNPs and non-SNP genetic variants may also be determined through analysis of the stored genomic profiles of individuals rather than determined by available published literature. Individuals with stored genomic profiles may disclose phenotypes that have previously been determined. Analysis of the genotypes and disclosed phenotypes of the individuals may be compared to those without the phenotypes to determine a correlation that may then be applied to other genomic profiles. Individuals that have their genomic profiles determined may fill out questionnaires about phenotypes that have previously been determined. Questionnaires may contain questions about medical and non-medical conditions, such as diseases previously diagnosed, family history of medical conditions, lifestyle, physical traits, mental traits, age, social life, environment and the like.

In one embodiment, an individual may have their genomic profile determined free of charge if they fill out a questionnaire. In some embodiments, the questionnaires are to be filled out periodically by the individuals in order to have free access to their phenotype profile and reports. In other embodiments, the individuals that fill out the questionnaires may be entitled to a subscription upgrade, such that they have more access than their previous subscription level, or they may purchase or renew a subscription at a reduced cost.

All information deposited in the database of medically relevant genetic variants at step 121 is first approved by a research/clinical advisory board for scientific accuracy and importance, coupled with review and oversight by an appropriate governmental agency if warranted at step 119. For example, in the United States, the FDA may provide oversight through approval of algorithms used for validation of genetic variant (typically SNP, transcript level, or mutation) correlative data. At step 123, scientific literature and other relevant sources are monitored for additional genetic variant-disease or condition correlations, and following validation of their accuracy and importance, along with governmental agency review and approval, these additional genotype correlations are added to the master database at step 125.

The database of approved, validated medically-relevant genetic variants, coupled with a genome-wide individual profile, will advantageously allow genetic risk-assessment to be performed for a large number of diseases or conditions. Following compilation of an individual's genomic profile, individual genotype correlations can be determined through comparison of the individual's nucleotide (genetic) variants or markers with a database of human nucleotide variants that have been correlated to a particular phenotype, such as a disease, condition, or physical state. Through comparison of an individual's genomic profile to the master database of genotype correlations, the individual can be informed whether they are found to be positive or negative for a genetic risk factor, and to what degree. An individual will receive relative risk and/or predisposition data on a wide range of scientifically validated disease states (e.g., Alzheimer's, cardiovascular disease, blood clotting). For example, genotype correlations in Table 1 may be included. In addition, SNP disease correlations in the database may include, but are not limited to, those correlations shown in FIG. 4. Other correlations from FIGS. 5 and 6 may also be included. The subject business method therefore provides analysis of risk to a multitude of diseases and conditions without any preconceived notion of what those diseases and conditions might entail.

In other embodiments, the genotype correlations that are coupled to the genome wide individual profile are non-medically relevant phenotypes, such as "fun" phenotypes or physical traits such as hair color. In preferred embodiments, a rule or rule set is applied to the genomic profile or SNP profile of an individual, as described above. Application of the rules to a genomic profile generates a phenotype profile for the individual.

Accordingly, the master database of human genotype correlations is expanded with additional genotype correlations as new correlations become discovered and validated. An update can be made by accessing pertinent information from the individual's genomic profile stored in a database as desired or appropriate. For example, a new genotype correlation that becomes known may be based on a particular gene variant. Determination of whether an individual may be susceptible to that new genotype correlation can then be made by retrieving and comparing just that gene portion of the individual's entire genomic profile.

The results of the genomic query preferably are analyzed and interpreted so as to be presented to the individual in an understandable format. At step 117, the results of an initial screening are then provided to the patient in a secure, confidential form, either by mailing or through an on-line portal interface, as detailed above.

The report may contain the phenotype profile as well as genomic information about the phenotypes in the phenotype profile, for example basic genetics about the genes involved or the statistics of the genetic variants in different populations. Other information based on the phenotype profile that may be included in the report are prevention strategies, wellness information, therapies, symptom awareness, early detection schemes, intervention schemes, and refined identification and sub-classification of the phenotypes. Following an initial screening of an individual's genomic profile, controlled, moderated updates are or can be made.

Updates of an individual's genomic profile are made or are available in conjunction with updates to the master database as new genotype correlations emerge and are both validated and approved. New rules based on the new genotype correlations may be applied to the initial genomic profile to provide updated phenotype profiles. An updated genotype correlation profile can be generated by comparing the relevant portion of the individual's genomic profile to a new genotype correlation at step 127. For example, if a new genotype correlation is found based on variation in a particular gene, then that gene portion of the individual's genomic profile can be analyzed for the new genotype correlation. In such a case, one or more new rules may be applied to generate an updated phenotype profile, rather than an entire rule set with rules that had already been applied. The results of the individual's updated genotype correlations are provided in a secure manner at step 129.

Initial and updated phenotype profiles may be a service provided to subscribers or customers. Varying levels of subscriptions to genomic profile analysis and combinations thereof can be provided. Likewise, subscription levels can vary to provide individuals choices of the amount of service they wish to receive with their genotype correlations. Thus, the level of service provided would vary with the level of service subscription purchased by the individual.

An entry level subscription for a subscriber may include a genomic profile and an initial phenotype profile. This may be a basic subscription level. Within the basic subscription level may be varying levels of service. For example, a particular subscription level could provide references for genetic counseling, physicians with particular expertise in treating or preventing a particular disease, and other service options. Genetic counseling may be obtained on-line or by telephone. In another embodiment, the price of the subscription may depend on the number of phenotypes an individual chooses for their phenotype profile. Another option may be whether the subscriber chooses to access on-line genetic counseling.

In another scenario, a subscription could provide for an initial genome-wide, genotype correlation, with maintenance of the individual's genomic profile in a database; such database may be secure if so elected by the individual. Following this initial analysis, subsequent analyses and additional results could be made upon request and additional payment by the individual. This may be a premium level of subscription.

In one embodiment of the subject business method, updates of an individual's risks are performed and corresponding information made available to individuals on a subscription basis. The updates may be available to subscribers who purchase the premium level of subscription. Subscription to genotype correlation analysis can provide updates with a particular category or subset of new genotype correlations according to an individual's preferences. For example, an individual might only wish to learn of genotype correlations for which there is a known course of treatment or prevention. To aid an individual in deciding whether to have an additional analysis performed, the individual can be provided with information regarding additional genotype correlations that have become available. Such information can be conveniently mailed or e-mailed to a subscriber.

Within the premium subscription, there may be further levels of service, such as those mentioned in the basic subscription. Other subscription models may be provided within the premium level. For example, the highest level may provide a subscriber to unlimited updates and reports. The subscriber's profile may be updated as new correlations and rules are determined. At this level, subscribers may also permit access to unlimited number of individuals, such as family members and health care managers. The subscribers may also have unlimited access to on-line genetic counselors and physicians.

The next level of subscription within the premium level may provide more limited aspects, for example a limited number of updates. The subscriber may have a limited number of updates for their genomic profile within a subscription period, for example, 4 times a year. In another subscription level, the subscriber may have their stored genomic profile updated once a week, once a month, or once a year. In another embodiment, the subscriber may only have a limited number of phenotypes they may choose to update their genomic profile against.

A personal portal will also conveniently allow an individual to maintain a subscription to risk or correlation updates and information updates or alternatively, make requests for updated risk assessment and information. As described above, varying subscription levels could be provided to allow individuals choices of various levels of genotype correlation results and updates and may different subscription levels may be chosen by the subscriber via their personal portal.

Any of these subscription options will contribute to the revenue stream for the subject business method. The revenue stream for the subject business method will also be added by the addition of new customers and subscribers, wherein the new genomic profiles are added to the database.

TABLE 1

Representative genes having genetic variants correlated with a phenotype.

| Gene | Phenotype |
|---|---|
| A2M | Alzheimer's Disease |
| ABCA1 | cholesterol, HDL |
| ABCB1 | HIV |
| ABCB1 | epilepsy |
| ABCB1 | kidney transplant complications |
| ABCB1 | digoxin, serum concentration |
| ABCB1 | Crohn's disease; ulcerative colitis |
| ABCB1 | Parkinson's disease |
| ABCC8 | Type 2 diabetes |
| ABCC8 | diabetes, type 2 |
| ABO | myocardial infarct |
| ACADM | medium-chain acyl-CoA dehydrogenase deficiency |
| ACDC | Type 2, diabetes |
| ACE | Type 2 diabetes |
| ACE | hypertension |
| ACE | Alzheimer's Disease |
| ACE | myocardial infarction |
| ACE | cardiovascular |
| ACE | left ventricular hypertrophy |
| ACE | coronary artery disease |
| ACE | atherosclerosis, coronary |
| ACE | retinopathy, diabetic |
| ACE | systemic lupus erythematosus |
| ACE | blood pressure, arterial |
| ACE | erectile dysfunction |
| ACE | Lupus |
| ACE | polycystic kidney disease |
| ACE | stroke |
| ACP1 | diabetes, type 1 |
| ACSM1 (LIP)c | cholesterol levels |
| ADAM33 | asthma |
| ADD1 | hypertension |
| ADD1 | blood pressure, arterial |
| ADH1B | alcohol abuse |
| ADH1C | alcohol abuse |
| ADIPOQ | diabetes, type 2 |
| ADIPOQ | obesity |
| ADORA2A | panic disorder |
| ADRB1 | hypertension |
| ADRB1 | heart failure |
| ADRB2 | asthma |
| ADRB2 | hypertension |
| ADRB2 | obesity |
| ADRB2 | blood pressure, arterial |
| ADRB2 | Type 2 Diabetes |
| ADRB3 | obesity |
| ADRB3 | Type 2 Diabetes |
| ADRB3 | hypertension |
| AGT | hypertension |
| AGT | Type 2 diabetes |
| AGT | Essential Hypertension |
| AGT | myocardial infarction |
| AGTR1 | hypertension |
| AGTR2 | hypertension |

TABLE 1-continued

Representative genes having genetic variants correlated with a phenotype.

| Gene | Phenotype |
|---|---|
| AHR | breast cancer |
| ALAD | lead toxicity |
| ALDH2 | alcoholism |
| ALDH2 | alcohol abuse |
| ALDH2 | colorectal cancer |
| ALDRL2 | Type 2 diabetes |
| ALOX5 | asthma |
| ALOX5AP | asthma |
| APBB1 | Alzheimer's Disease |
| APC | colorectal cancer |
| APEX1 | lung cancer |
| APOA1 | atherosclerosis, coronary |
| APOA1 | cholesterol, HDL |
| APOA1 | coronary artery disease |
| APOA1 | Type 2 diabetes |
| APOA4 | Type 2 diabetes |
| APOA5 | triglycerides |
| APOA5 | atherosclerosis, coronary |
| APOB | hypercholesterolemia |
| APOB | obesity |
| APOB | cardiovascular |
| APOB | coronary artery disease |
| APOB | coronary heart disease |
| APOB | Type 2 diabetes |
| APOC1 | Alzheimer's Disease |
| APOC3 | triglycerides |
| APOC3 | Type 2 Diabetes |
| APOE | Alzheimer's Disease |
| APOE | Type 2 diabetes |
| APOE | multiple sclerosis |
| APOE | atherosclerosis, coronary |
| APOE | Parkinson's disease |
| APOE | coronary heart disease |
| APOE | myocardial infarction |
| APOE | stroke |
| APOE | Alzheimer's disease |
| APOE | coronary artery disease |
| APP | Alzheimer's Disease |
| AR | prostate cancer |
| AR | breast cancer |
| ATM | breast cancer |
| ATP7B | Wilson disease |
| ATXN8OS | spinocerebellar ataxia |
| BACE1 | Alzheimer's Disease |
| BCHE | Alzheimer's Disease |
| BDKRB2 | hypertension |
| BDNF | Alzheimer's Disease |
| BDNF | bipolar disorder |
| BDNF | Parkinson's disease |
| BDNF | schizophrenia |
| BDNF | memory |
| BGLAP | bone density |
| BRAF | thyroid cancer |
| BRCA1 | breast cancer |
| BRCA1 | breast cancer; ovarian cancer |
| BRCA1 | ovarian cancer |
| BRCA2 | breast cancer |
| BRCA2 | breast cancer; ovarian cancer |
| BRCA2 | ovarian cancer |
| BRIP1 | breast cancer |
| C4A | systemic lupus erythematosus |
| CALCR | bone density |
| CAMTA1 | episodic memory |
| CAPN10 | diabetes, type 2 |
| CAPN10 | Type 2 diabetes |
| CAPN3 | muscular dystrophy |
| CARD15 | Crohn's disease |
| CARD15 | Crohn's disease; ulcerative colitis |
| CARD15 | Inflammatory Bowel Disease |
| CART | obesity |
| CASR | bone density |
| CCKAR | schizophrenia |
| CCL2 | systemic lupus erythematosus |
| CCL5 | HIV |
| CCL5 | asthma |

TABLE 1-continued

Representative genes having genetic variants correlated with a phenotype.

| Gene | Phenotype |
|---|---|
| CCND1 | colorectal cancer |
| CCR2 | HIV |
| CCR2 | HIV infection |
| CCR2 | hepatitis C |
| CCR2 | myocardial infarct |
| CCR3 | Asthma |
| CCR5 | HIV |
| CCR5 | HIV infection |
| CCR5 | hepatitis C |
| CCR5 | asthma |
| CCR5 | multiple sclerosis |
| CD14 | atopy |
| CD14 | asthma |
| CD14 | Crohn's disease |
| CD14 | Crohn's disease; ulcerative colitis |
| CD14 | periodontitis |
| CD14 | Total IgE |
| CDH1 | prostate cancer |
| CDH1 | colorectal cancer |
| CDKN2A | melanoma |
| CDSN | psoriasis |
| CEBPA | leukemia, myeloid |
| CETP | atherosclerosis, coronary |
| CETP | coronary heart disease |
| CETP | hypercholesterolemia |
| CFH | macular degeneration |
| CFTR | cystic fibrosis |
| CFTR | pancreatitis |
| CFTR | Cystic Fibrosis |
| CHAT | Alzheimer's Disease |
| CHEK2 | breast cancer |
| CHRNA7 | schizophrenia |
| CMA1 | atopic dermatitis |
| CNR1 | schizophrenia |
| COL1A1 | bone density |
| COL1A1 | osteoporosis |
| COL1A2 | bone density |
| COL2A1 | Osteoarthritis |
| COMT | schizophrenia |
| COMT | breast cancer |
| COMT | Parkinson's disease |
| COMT | bipolar disorder |
| COMT | obsessive compulsive disorder |
| COMT | alcoholism |
| CR1 | systemic lupus erythematosus |
| CRP | C-reactive protein |
| CST3 | Alzheimer's Disease |
| CTLA4 | Type 1 diabetes |
| CTLA4 | Graves' disease |
| CTLA4 | multiple sclerosis |
| CTLA4 | rheumatoid arthritis |
| CTLA4 | systemic lupus erythematosus |
| CTLA4 | lupus erythematosus |
| CTLA4 | celiac disease |
| CTSD | Alzheimer's Disease |
| CX3CR1 | HIV |
| CXCL12 | HIV |
| CXCL12 | HIV infection |
| CYBA | atherosclerosis, coronary |
| CYBA | hypertension |
| CYP11B2 | hypertension |
| CYP11B2 | left ventricular hypertrophy |
| CYP17A1 | breast cancer |
| CYP17A1 | prostate cancer |
| CYP17A1 | endometriosis |
| CYP17A1 | endometrial cancer |
| CYP19A1 | breast cancer |
| CYP19A1 | prostate cancer |
| CYP19A1 | endometriosis |
| CYP1A1 | lung cancer |
| CYP1A1 | breast cancer |
| CYP1A1 | Colorectal Cancer |
| CYP1A1 | prostate cancer |
| CYP1A1 | esophageal cancer |
| CYP1A1 | endometriosis |
| CYP1A1 | cytogenetic studies |
| CYP1A2 | schizophrenia |
| CYP1A2 | colorectal cancer |
| CYP1B1 | breast cancer |
| CYP1B1 | glaucoma |
| CYP1B1 | prostate cancer |
| CYP21A2 | 21-hydroxylase deficiency |
| CYP21A2 | congenital adrenal hyperplasia |
| CYP21A2 | adrenal hyperplasia, congenital |
| CYP2A6 | smoking behavior |
| CYP2A6 | nicotine |
| CYP2A6 | lung cancer |
| CYP2C19 | H. pylori infection |
| CYP2C19 | phenytoin |
| CYP2C19 | gastric disease |
| CYP2C8 | malaria, plasmodium falciparum |
| CYP2C9 | anticoagulant complications |
| CYP2C9 | warfarin sensitivity |
| CYP2C9 | warfarin therapy, response to |
| CYP2C9 | colorectal cancer |
| CYP2C9 | phenytoin |
| CYP2C9 | acenocoumarol response |
| CYP2C9 | coagulation disorder |
| CYP2C9 | hypertension |
| CYP2D6 | colorectal cancer |
| CYP2D6 | Parkinson's disease |
| CYP2D6 | CYP2D6 poor metabolizer phenotype |
| CYP2E1 | lung cancer |
| CYP2E1 | colorectal cancer |
| CYP3A4 | prostate cancer |
| CYP3A5 | prostate cancer |
| CYP3A5 | esophageal cancer |
| CYP46A1 | Alzheimer's Disease |
| DBH | schizophrenia |
| DHCR7 | Smith-Lemli-Opitz syndrome |
| DISC1 | schizophrenia |
| DLST | Alzheimer's Disease |
| DMD | muscular dystrophy |
| DRD2 | alcoholism |
| DRD2 | schizophrenia |
| DRD2 | smoking behavior |
| DRD2 | Parkinson's disease |
| DRD2 | tardive dyskinesia |
| DRD3 | schizophrenia |
| DRD3 | tardive dyskinesia |
| DRD3 | bipolar disorder |
| DRD4 | attention deficit hyperactivity disorder |
| DRD4 | schizophrenia |
| DRD4 | novelty seeking |
| DRD4 | ADHD |
| DRD4 | personality traits |
| DRD4 | heroin abuse |
| DRD4 | alcohol abuse |
| DRD4 | alcoholism |
| DRD4 | personality disorders |
| DTNBP1 | schizophrenia |
| EDN1 | hypertension |
| EGFR | lung cancer |
| ELAC2 | prostate cancer |
| ENPP1 | Type 2 diabetes |
| EPHB2 | prostate cancer |
| EPHX1 | lung cancer |
| EPHX1 | colorectal cancer |
| EPHX1 | cytogenetic studies |
| EPHX1 | chronic obstructive pulmonary disease/COPD |
| ERBB2 | breast cancer |
| ERCC1 | lung cancer |
| ERCC1 | colorectal cancer |
| ERCC2 | lung cancer |
| ERCC2 | cytogenetic studies |
| ERCC2 | bladder cancer |
| ERCC2 | colorectal cancer |
| ESR1 | bone density |
| ESR1 | bone mineral density |
| ESR1 | breast cancer |

TABLE 1-continued

Representative genes having genetic variants correlated with a phenotype.

| Gene | Phenotype |
|---|---|
| ESR1 | endometriosis |
| ESR1 | osteoporosis |
| ESR2 | bone density |
| ESR2 | breast cancer |
| estrogen receptor | bone mineral density |
| F2 | coronary heart disease |
| F2 | stroke |
| F2 | thromboembolism, venous |
| F2 | preeclampsia |
| F2 | thrombosis |
| F5 | thromboembolism, venous |
| F5 | preeclampsia |
| F5 | myocardial infarct |
| F5 | stroke |
| F5 | stroke, ischemic |
| F7 | atherosclerosis, coronary |
| F7 | myocardial infarct |
| F8 | hemophilia |
| F9 | hemophilia |
| FABP2 | Type 2 diabetes |
| FAS | Alzheimer's Disease |
| FASLG | multiple sclerosis |
| FCGR2A | systemic lupus erythematosus |
| FCGR2A | lupus erythematosus |
| FCGR2A | periodontitis |
| FCGR2A | rheumatoid arthritis |
| FCGR2B | lupus erythematosus |
| FCGR2B | systemic lupus erythematosus |
| FCGR3A | systemic lupus erythematosus |
| FCGR3A | lupus erythematosus |
| FCGR3A | periodontitis |
| FCGR3A | arthritis |
| FCGR3A | rheumatoid arthritis |
| FCGR3B | periodontitis |
| FCGR3B | periodontal disease |
| FCGR3B | lupus erythematosus |
| FGB | fibrinogen |
| FGB | myocardial infarction |
| FGB | coronary heart disease |
| FLT3 | leukemia, myeloid |
| FLT3 | leukemia |
| FMR1 | Fragile X syndrome |
| FRAXA | Fragile X Syndrome |
| FUT2 | H. pylori infection |
| FVL | Factor V Leiden |
| G6PD | G6PD deficiency |
| G6PD | hyperbilirubinemia |
| GABRA5 | bipolar disorder |
| GBA | Gaucher disease |
| GBA | Parkinson's disease |
| GCGR (FAAH, ML4R, UCP2) | body mass/obesity |
| GCK | Type 2 diabetes |
| GCLM (F12, TLR4) | atherosclerosis, myocardial infarction |
| GDNF | schizophrenia |
| GHRL | obesity |
| GJB1 | Charcot-Marie-Tooth disease |
| GJB2 | deafness |
| GJB2 | hearing loss, sensorineural nonsyndromic |
| GJB2 | hearing loss, sensorineural |
| GJB2 | hearing loss/deafness |
| GJB6 | hearing loss, sensorineural nonsyndromic |
| GJB6 | hearing loss/deafness |
| GNAS | hypertension |
| GNB3 | hypertension |
| GPX1 | lung cancer |
| GRIN1 | schizophrenia |
| GRIN2B | schizophrenia |
| GSK3B | bipolar disorder |
| GSTM1 | lung cancer |
| GSTM1 | colorectal cancer |
| GSTM1 | breast cancer |
| GSTM1 | prostate cancer |
| GSTM1 | cytogenetic studies |
| GSTM1 | bladder cancer |
| GSTM1 | esophageal cancer |
| GSTM1 | head and neck cancer |
| GSTM1 | leukemia |
| GSTM1 | Parkinson's disease |
| GSTM1 | stomach cancer |
| GSTP1 | Lung cancer |
| GSTP1 | colorectal cancer |
| GSTP1 | breast cancer |
| GSTP1 | cytogenetic studies |
| GSTP1 | prostate cancer |
| GSTT1 | lung cancer |
| GSTT1 | colorectal cancer |
| GSTT1 | breast cancer |
| GSTT1 | prostate cancer |
| GSTT1 | Bladder Cancer |
| GSTT1 | cytogenetic studies |
| GSTT1 | asthma |
| GSTT1 | benzene toxicity |
| GSTT1 | esophageal cancer |
| GSTT1 | head and neck cancer |
| GYS1 | Type 2 diabetes |
| HBB | thalassemia |
| HBB | thalassemia, beta |
| HD | Huntington's disease |
| HFE | Hemochromatosis |
| HFE | iron levels |
| HFE | colorectal cancer |
| HK2 | Type 2 diabetes |
| HLA | rheumatoid arthritis |
| HLA | Type 1 diabetes |
| HLA | Behcet's Disease |
| HLA | celiac disease |
| HLA | psoriasis |
| HLA | Graves disease |
| HLA | multiple sclerosis |
| HLA | schizophrenia |
| HLA | asthma |
| HLA | diabetes mellitus |
| HLA | Lupus |
| HLA-A | leukemia |
| HLA-A | HIV |
| HLA-A | diabetes, type 1 |
| HLA-A | graft-versus-host disease |
| HLA-A | multiple sclerosis |
| HLA-B | leukemia |
| HLA-B | Behcet's Disease |
| HLA-B | celiac disease |
| HLA-B | diabetes, type 1 |
| HLA-B | graft-versus-host disease |
| HLA-B | sarcoidosis |
| HLA-C | psoriasis |
| HLA-DPA1 | measles |
| HLA-DPB1 | diabetes, type 1 |
| HLA-DPB1 | Asthma |
| HLA-DQA1 | diabetes, type 1 |
| HLA-DQA1 | celiac disease |
| HLA-DQA1 | cervical cancer |
| HLA-DQA1 | asthma |
| HLA-DQA1 | multiple sclerosis |
| HLA-DQA1 | diabetes, type 2; diabetes, type 1 |
| HLA-DQA1 | lupus erythematosus |
| HLA-DQA1 | pregnancy loss, recurrent |
| HLA-DQA1 | psoriasis |
| HLA-DQB1 | diabetes, type 1 |
| HLA-DQB1 | celiac disease |
| HLA-DQB1 | multiple sclerosis |
| HLA-DQB1 | cervical cancer |
| HLA-DQB1 | lupus erythematosus |
| HLA-DQB1 | pregnancy loss, recurrent |
| HLA-DQB1 | arthritis |
| HLA-DQB1 | asthma |
| HLA-DQB1 | HIV |
| HLA-DQB1 | lymphoma |
| HLA-DQB1 | tuberculosis |
| HLA-DQB1 | rheumatoid arthritis |

TABLE 1-continued

Representative genes having genetic variants correlated with a phenotype.

| Gene | Phenotype |
|---|---|
| HLA-DQB1 | diabetes, type 2 |
| HLA-DQB1 | graft-versus-host disease |
| HLA-DQB1 | narcolepsy |
| HLA-DQB1 | arthritis, rheumatoid |
| HLA-DQB1 | cholangitis, sclerosing |
| HLA-DQB1 | diabetes, type 2; diabetes, type 1 |
| HLA-DQB1 | Graves' disease |
| HLA-DQB1 | hepatitis C |
| HLA-DQB1 | hepatitis C, chronic |
| HLA-DQB1 | malaria |
| HLA-DQB1 | malaria, plasmodium falciparum |
| HLA-DQB1 | melanoma |
| HLA-DQB1 | psoriasis |
| HLA-DQB1 | Sjogren's syndrome |
| HLA-DQB1 | systemic lupus erythematosus |
| HLA-DQB1 | diabetes, type 1 |
| HLA-DRB1 | multiple sclerosis |
| HLA-DRB1 | systemic lupus erythematosus |
| HLA-DRB1 | rheumatoid arthritis |
| HLA-DRB1 | cervical cancer |
| HLA-DRB1 | arthritis |
| HLA-DRB1 | celiac disease |
| HLA-DRB1 | lupus erythematosus |
| HLA-DRB1 | sarcoidosis |
| HLA-DRB1 | HIV |
| HLA-DRB1 | tuberculosis |
| HLA-DRB1 | Graves' disease |
| HLA-DRB1 | lymphoma |
| HLA-DRB1 | psoriasis |
| HLA-DRB1 | asthma |
| HLA-DRB1 | Crohn's disease |
| HLA-DRB1 | graft-versus-host disease |
| HLA-DRB1 | hepatitis C, chronic |
| HLA-DRB1 | narcolepsy |
| HLA-DRB1 | sclerosis, systemic |
| HLA-DRB1 | Sjogren's syndrome |
| HLA-DRB1 | Type 1 diabetes |
| HLA-DRB1 | arthritis, rheumatoid |
| HLA-DRB1 | cholangitis, sclerosing |
| HLA-DRB1 | diabetes, type 2; diabetes, type 1 |
| HLA-DRB1 | H. pylori infection |
| HLA-DRB1 | hepatitis C |
| HLA-DRB1 | juvenile arthritis |
| HLA-DRB1 | leukemia |
| HLA-DRB1 | malaria |
| HLA-DRB1 | melanoma |
| HLA-DRB1 | pregnancy loss, recurrent |
| HLA-DRB3 | psoriasis |
| HLA-G | pregnancy loss, recurrent |
| HMOX1 | atherosclerosis, coronary |
| HNF4A | diabetes, type 2 |
| HNF4A | type 2 diabetes |
| HSD11B2 | hypertension |
| HSD17B1 | breast cancer |
| HTR1A | depressive disorder, major |
| HTR1B | alcohol dependence |
| HTR1B | alcoholism |
| HTR2A | memory |
| HTR2A | schizophrenia |
| HTR2A | bipolar disorder |
| HTR2A | depression |
| HTR2A | depressive disorder, major |
| HTR2A | suicide |
| HTR2A | Alzheimer's Disease |
| HTR2A | anorexia nervosa |
| HTR2A | hypertension |
| HTR2A | obsessive compulsive disorder |
| HTR2C | schizophrenia |
| HTR6 | Alzheimer's Disease |
| HTR6 | schizophrenia |
| HTRA1 | wet age-related macular degeneration |
| IAPP | Type 2 Diabetes |
| IDE | Alzheimer's Disease |
| IFNG | tuberculosis |
| IFNG | Type 1 diabetes |
| IFNG | graft-versus-host disease |
| IFNG | hepatitis B |
| IFNG | multiple sclerosis |
| IFNG | asthma |
| IFNG | breast cancer |
| IFNG | kidney transplant |
| IFNG | kidney transplant complications |
| IFNG | longevity |
| IFNG | pregnancy loss, recurrent |
| IGFBP3 | breast cancer |
| IGFBP3 | prostate cancer |
| IL10 | systemic lupus erythematosus |
| IL10 | asthma |
| IL10 | graft-versus-host disease |
| IL10 | HIV |
| IL10 | kidney transplant |
| IL10 | kidney transplant complications |
| IL10 | hepatitis B |
| IL10 | juvenile arthritis |
| IL10 | longevity |
| IL10 | multiple sclerosis |
| IL10 | pregnancy loss, recurrent |
| IL10 | rheumatoid arthritis |
| IL10 | tuberculosis |
| IL12B | Type 1 diabetes |
| IL12B | asthma |
| IL13 | asthma |
| IL13 | atopy |
| IL13 | chronic obstructive pulmonary disease/COPD |
| IL13 | Graves' disease |
| IL1A | periodontitis |
| IL1A | Alzheimer's Disease |
| IL1B | periodontitis |
| IL1B | Alzheimer's Disease |
| IL1B | stomach cancer |
| IL1R1 | Type 1 diabetes |
| IL1RN | stomach cancer |
| IL2 | asthma; eczema; allergic disease |
| IL4 | Asthma |
| IL4 | atopy |
| IL4 | HIV |
| IL4R | asthma |
| IL4R | atopy |
| IL4R | Total serum IgE |
| IL6 | Bone Mineralization |
| IL6 | kidney transplant |
| IL6 | kidney transplant complications |
| IL6 | Longevity |
| IL6 | multiple sclerosis |
| IL6 | bone density |
| IL6 | bone mineral density |
| IL6 | Colorectal Cancer |
| IL6 | juvenile arthritis |
| IL6 | rheumatoid arthritis |
| IL9 | asthma |
| INHA | premature ovarian failure |
| INS | Type 1 diabetes |
| INS | Type 2 diabetes |
| INS | diabetes, type 1 |
| INS | obesity |
| INS | prostate cancer |
| INSIG2 | obesity |
| INSR | Type 2 diabetes |
| INSR | hypertension |
| INSR | polycystic ovary syndrome |
| IPF1 | diabetes, type 2 |
| IRS1 | Type 2 diabetes |
| IRS1 | diabetes, type 2 |
| IRS2 | diabetes, type 2 |
| ITGB3 | myocardial infarction |
| ITGB3 | atherosclerosis, coronary |
| ITGB3 | coronary heart disease |
| ITGB3 | myocardial infarct |
| KCNE1 | EKG, abnormal |
| KCNE2 | EKG, abnormal |

TABLE 1-continued

Representative genes having genetic variants correlated with a phenotype.

| Gene | Phenotype |
| --- | --- |
| KCNH2 | EKG, abnormal |
| KCNH2 | long QT syndrome |
| KCNJ11 | diabetes, type 2 |
| KCNJ11 | Type 2 Diabetes |
| KCNN3 | schizophrenia |
| KCNQ1 | EKG, abnormal |
| KCNQ1 | long QT syndrome |
| KIBRA | episodic memory |
| KLK1 | hypertension |
| KLK3 | prostate cancer |
| KRAS | colorectal cancer |
| LDLR | hypercholesterolemia |
| LDLR | hypertension |
| LEP | obesity |
| LEPR | obesity |
| LIG4 | breast cancer |
| LIPC | atherosclerosis, coronary |
| LPL | Coronary Artery Disease |
| LPL | hyperlipidemia |
| LPL | triglycerides |
| LRP1 | Alzheimer's Disease |
| LRP5 | bone density |
| LRRK2 | Parkinson's disease |
| LRRK2 | Parkinsons disease |
| LTA | type 1 diabetes |
| LTA | Asthma |
| LTA | systemic lupus erythematosus |
| LTA | sepsis |
| LTC4S | Asthma |
| MAOA | alcoholism |
| MAOA | schizophrenia |
| MAOA | bipolar disorder |
| MAOA | smoking behavior |
| MAOA | personality disorders |
| MAOB | Parkinson's disease |
| MAOB | smoking behavior |
| MAPT | Parkinson's disease |
| MAPT | Alzheimer's Disease |
| MAPT | dementia |
| MAPT | Frontotemporal dementia |
| MAPT | progressive supranuclear palsy |
| MC1R | melanoma |
| MC3R | obesity |
| MC4R | obesity |
| MECP2 | Rett syndrome |
| MEFV | Familial Mediterranean Fever |
| MEFV | amyloidosis |
| MICA | Type 1 diabetes |
| MICA | Behcet's Disease |
| MICA | celiac disease |
| MICA | rheumatoid arthritis |
| MICA | systemic lupus erythematosus |
| MLH1 | colorectal cancer |
| MME | Alzheimer's Disease |
| MMP1 | Lung Cancer |
| MMP1 | ovarian cancer |
| MMP1 | periodontitis |
| MMP3 | myocardial infarct |
| MMP3 | ovarian cancer |
| MMP3 | rheumatoid arthritis |
| MPO | lung cancer |
| MPO | Alzheimer's Disease |
| MPO | breast cancer |
| MPZ | Charcot-Marie-Tooth disease |
| MS4A2 | asthma |
| MS4A2 | atopy |
| MSH2 | colorectal cancer |
| MSH6 | colorectal cancer |
| MSR1 | prostate cancer |
| MTHFR | colorectal cancer |
| MTHFR | Type 2 diabetes |
| MTHFR | neural tube defects |
| MTHFR | homocysteine |
| MTHFR | thromboembolism, venous |
| MTHFR | atherosclerosis, coronary |
| MTHFR | Alzheimer's Disease |
| MTHFR | esophageal cancer |
| MTHFR | preeclampsia |
| MTHFR | pregnancy loss, recurrent |
| MTHFR | stroke |
| MTHFR | thrombosis, deep vein |
| MT-ND1 | diabetes, type 2 |
| MTR | colorectal cancer |
| MT-RNR1 | hearing loss, sensorineural nonsyndromic |
| MTRR | neural tube defects |
| MTRR | homocysteine |
| MT-TL1 | diabetes, type 2 |
| MUTYH | colorectal cancer |
| MYBPC3 | cardiomyopathy |
| MYH7 | cardiomyopathy |
| MYOC | glaucoma, primary open-angle |
| MYOC | glaucoma |
| NAT1 | colorectal cancer |
| NAT1 | Breast Cancer |
| NAT1 | bladder cancer |
| NAT2 | colorectal cancer |
| NAT2 | bladder cancer |
| NAT2 | breast cancer |
| NAT2 | Lung Cancer |
| NBN | breast cancer |
| NCOA3 | breast cancer |
| NCSTN | Alzheimer's Disease |
| NEUROD1 | Type 1 diabetes |
| NF1 | neurofibromatosis1 |
| NOS1 | Asthma |
| NOS2A | multiple sclerosis |
| NOS3 | hypertension |
| NOS3 | coronary heart disease |
| NOS3 | atherosclerosis, coronary |
| NOS3 | coronary artery disease |
| NOS3 | myocardial infarction |
| NOS3 | acute coronary syndrome |
| NOS3 | blood pressure, arterial |
| NOS3 | preeclampsia |
| NOS3 | nitric oxide |
| NOS3 | Alzheimer's Disease |
| NOS3 | asthma |
| NOS3 | Type 2 diabetes |
| NOS3 | cardiovascular disease |
| NOS3 | Behcet's Disease |
| NOS3 | erectile dysfunction |
| NOS3 | kidney failure, chronic |
| NOS3 | lead toxicity |
| NOS3 | left ventricular hypertrophy |
| NOS3 | pregnancy loss, recurrent |
| NOS3 | retinopathy, diabetic |
| NOS3 | stroke |
| NOTCH4 | schizophrenia |
| NPY | alcohol abuse |
| NQO1 | lung cancer |
| NQO1 | colorectal cancer |
| NQO1 | benzene toxicity |
| NQO1 | bladder cancer |
| NQO1 | Parkinson's Disease |
| NR3C2 | hypertension |
| NR4A2 | Parkinson's disease |
| NRG1 | schizophrenia |
| NTF3 | schizophrenia |
| OGG1 | lung cancer |
| OGG1 | colorectal cancer |
| OLR1 | Alzheimer's Disease |
| OPA1 | glaucoma |
| OPRM1 | alcohol abuse |
| OPRM1 | substance dependence |
| OPTN | glaucoma, primary open-angle |
| P450 | drug metabolism |
| PADI4 | rheumatoid arthritis |
| PAH | phenylketonuria/PKU |
| PAI1 | coronary heart disease |
| PAI1 | asthma |

TABLE 1-continued

Representative genes having genetic variants correlated with a phenotype.

| Gene | Phenotype |
| --- | --- |
| PALB2 | breast cancer |
| PARK2 | Parkinson's disease |
| PARK7 | Parkinson's disease |
| PDCD1 | lupus erythematosus |
| PINK1 | Parkinson's disease |
| PKA | memory |
| PKC | memory |
| PLA2G4A | schizophrenia |
| PNOC | schizophrenia |
| POMC | obesity |
| PON1 | atherosclerosis, coronary |
| PON1 | Parkinson's disease |
| PON1 | Type 2 Diabetes |
| PON1 | atherosclerosis |
| PON1 | coronary artery disease |
| PON1 | coronary heart disease |
| PON1 | Alzheimer's Disease |
| PON1 | longevity |
| PON2 | atherosclerosis, coronary |
| PON2 | preterm delivery |
| PPARG | Type 2 Diabetes |
| PPARG | obesity |
| PPARG | diabetes, type 2 |
| PPARG | Colorectal Cancer |
| PPARG | hypertension |
| PPARGC1A | diabetes, type 2 |
| PRKCZ | Type 2 diabetes |
| PRL | systemic lupus erythematosus |
| PRNP | Alzheimer's Disease |
| PRNP | Creutzfeldt-Jakob disease |
| PRNP | Jakob-Creutzfeldt disease |
| PRODH | schizophrenia |
| PRSS1 | pancreatitis |
| PSEN1 | Alzheimer's Disease |
| PSEN2 | Alzheimer's Disease |
| PSMB8 | Type 1 diabetes |
| PSMB9 | Type 1 diabetes |
| PTCH | skin cancer, non-melanoma |
| PTGIS | hypertension |
| PTGS2 | colorectal cancer |
| PTH | bone density |
| PTPN11 | Noonan syndrome |
| PTPN22 | rheumatoid arthritis |
| PTPRC | multiple sclerosis |
| PVT1 | end stage renal disease |
| RAD51 | breast cancer |
| RAGE | retinopathy, diabetic |
| RB1 | retinoblastoma |
| RELN | schizophrenia |
| REN | hypertension |
| RET | thyroid cancer |
| RET | Hirschsprung's disease |
| RFC1 | neural tube defects |
| RGS4 | schizophrenia |
| RHO | retinitis pigmentosa |
| RNASEL | prostate cancer |
| RYR1 | malignant hyperthermia |
| SAA1 | amyloidosis |
| SCG2 | hypertension |
| SCG3 | obesity |
| SCGB1A1 | asthma |
| SCN5A | Brugada syndrome |
| SCN5A | EKG, abnormal |
| SCN5A | long QT syndrome |
| SCNN1B | hypertension |
| SCNN1G | hypertension |
| SERPINA1 | COPD |
| SERPINA3 | Alzheimer's Disease |
| SERPINA3 | COPD |
| SERPINA3 | Parkinson's disease |
| SERPINE1 | myocardial infarct |
| SERPINE1 | Type 2 Diabetes |
| SERPINE1 | atherosclerosis, coronary |
| SERPINE1 | obesity |
| SERPINE1 | preeclampsia |
| SERPINE1 | stroke |
| SERPINE1 | hypertension |
| SERPINE1 | pregnancy loss, recurrent |
| SERPINE1 | thromboembolism, venous |
| SLC11A1 | tuberculosis |
| SLC22A4 | Crohn's disease; ulcerative colitis |
| SLC22A5 | Crohn's disease; ulcerative colitis |
| SLC2A1 | Type 2 diabetes |
| SLC2A2 | Type 2 diabetes |
| SLC2A4 | Type 2 diabetes |
| SLC3A1 | cystinuria |
| SLC6A3 | attention deficit hyperactivity disorder |
| SLC6A3 | Parkinson's disease |
| SLC6A3 | smoking behavior |
| SLC6A3 | alcoholism |
| SLC6A3 | schizophrenia |
| SLC6A4 | depression |
| SLC6A4 | depressive disorder, major |
| SLC6A4 | schizophrenia |
| SLC6A4 | suicide |
| SLC6A4 | alcoholism |
| SLC6A4 | bipolar disorder |
| SLC6A4 | personality traits |
| SLC6A4 | attention deficit hyperactivity disorder |
| SLC6A4 | Alzheimer's Disease |
| SLC6A4 | personality disorders |
| SLC6A4 | panic disorder |
| SLC6A4 | alcohol abuse |
| SLC6A4 | affective disorder |
| SLC6A4 | anxiety disorder |
| SLC6A4 | smoking behavior |
| SLC6A4 | depressive disorder, major; bipolar disorder |
| SLC6A4 | heroin abuse |
| SLC6A4 | irritable bowel syndrome |
| SLC6A4 | migraine |
| SLC6A4 | obsessive compulsive disorder |
| SLC6A4 | suicidal behavior |
| SLC7A9 | cystinuria |
| SNAP25 | ADHD |
| SNCA | Parkinson's disease |
| SOD1 | ALS/amyotrophic lateral sclerosis |
| SOD2 | breast cancer |
| SOD2 | lung cancer |
| SOD2 | prostate cancer |
| SPINK1 | pancreatitis |
| SPP1 | multiple sclerosis |
| SRD5A2 | prostate cancer |
| STAT6 | asthma |
| STAT6 | Total IgE |
| SULT1A1 | breast cancer |
| SULT1A1 | colorectal cancer |
| TAP1 | Type 1 diabetes |
| TAP1 | lupus erythematosus |
| TAP2 | Type 1 diabetes |
| TAP2 | diabetes, type 1 |
| TBX21 | asthma |
| TBXA2R | asthma |
| TCF1 | diabetes, type 2 |
| TCF1 | Type 2 diabetes |
| TF | Alzheimer's Disease |
| TGFB1 | breast cancer |
| TGFB1 | kidney transplant |
| TGFB1 | kidney transplant complications |
| TH | schizophrenia |
| THBD | myocardial infarction |
| TLR4 | asthma |
| TLR4 | Crohn's disease; ulcerative colitis |
| TLR4 | sepsis |
| TNF | asthma |
| TNFA | cerebrovascular disease |
| TNF | Type 1 diabetes |
| TNF | rheumatoid arthritis |
| TNF | systemic lupus erythematosus |
| TNF | kidney transplant |
| TNF | psoriasis |

TABLE 1-continued

Representative genes having genetic variants correlated with a phenotype.

| Gene | Phenotype |
|---|---|
| TNF | sepsis |
| TNF | Type 2 Diabetes |
| TNF | Alzheimer's Disease |
| TNF | Crohn's disease |
| TNF | diabetes, type 1 |
| TNF | hepatitis B |
| TNF | kidney transplant complications |
| TNF | multiple sclerosis |
| TNF | schizophrenia |
| TNF | celiac disease |
| TNF | obesity |
| TNF | pregnancy loss, recurrent |
| TNFRSF11B | bone density |
| TNFRSF1A | rheumatoid arthritis |
| TNFRSF1B | Rheumatoid Arthritis |
| TNFRSF1B | systemic lupus erythematosus |
| TNFRSF1B | arthritis |
| TNNT2 | cardiomyopathy |
| TP53 | lung cancer |
| TP53 | breast cancer |
| TP53 | Colorectal Cancer |
| TP53 | prostate cancer |
| TP53 | cervical cancer |
| TP53 | ovarian cancer |
| TP53 | smoking |
| TP53 | esophageal cancer |
| TP73 | lung cancer |
| TPH1 | suicide |
| TPH1 | depressive disorder, major |
| TPH1 | suicidal behavior |
| TPH1 | schizophrenia |
| TPMT | thiopurine methyltransferase activity |
| TPMT | leukemia |
| TPMT | inflammatory bowel disease |
| TPMT | thiopurine S-methyltransferase phenotype |
| TSC1 | tuberous sclerosis |
| TSC2 | tuberous sclerosis |
| TSHR | Graves' disease |
| TYMS | colorectal cancer |
| TYMS | stomach cancer |
| TYMS | esophageal cancer |
| UCHL1 | Parkinson's disease |
| UCP1 | obesity |
| UCP2 | obesity |
| UCP3 | obesity |
| UGT1A1 | hyperbilirubinemia |
| UGT1A1 | Gilbert syndrome |
| UGT1A6 | colorectal cancer |
| UGT1A7 | colorectal cancer |
| UTS2 | diabetes, type 2 |
| VDR | bone density |
| VDR | prostate cancer |
| VDR | bone mineral density |
| VDR | Type 1 diabetes |
| VDR | osteoporosis |
| VDR | bone mass |
| VDR | breast cancer |
| VDR | lead toxicity |
| VDR | tuberculosis |
| VDR | Type 2 diabetes |
| VEGF | breast cancer |
| Vit D rec | idiopathic short stature |
| VKORC1 | warfarin therapy, response to |
| WNK4 | hypertension |
| XPA | lung cancer |
| XPC | lung cancer |
| XPC | cytogenetic studies |
| XRCC1 | lung cancer |
| XRCC1 | cytogenetic studies |
| XRCC1 | breast cancer |
| XRCC1 | bladder cancer |
| XRCC2 | breast cancer |
| XRCC3 | breast cancer |
| XRCC3 | cytogenetic studies |
| XRCC3 | lung cancer |
| XRCC3 | bladder cancer |
| ZDHHC8 | schizophrenia |

The Genetic Composite Index (GCI)

The etiology of many conditions or diseases is attributed to both genetic and environmental factors. Recent advances in genotyping technology has provided opportunities to identify new associations between diseases and genetic markers across an entire genome. Indeed, many recent studies have discovered such associations, in which a specific allele or genotype is correlated with an increased risk for a disease. Some of these studies involve the collection of a set of test cases and a set of controls, and the comparison of allele distribution of genetic markers between the two populations. In some of these studies the association between a specific genetic markers and a disease is measure in isolation from other genetic markers, which are treated as background and are not accounted for in the statistical analysis.

Genetic markers and variants may include SNPs, nucleotide repeats, nucleotide insertions, nucleotide deletions, chromosomal translocations, chromosomal duplications, or copy number variations. Copy number variation may include microsatellite repeats, nucleotide repeats, centromeric repeats, or telomeric repeats.

In one aspect of the present invention information about the association of multiple genetic markers with one or more diseases or conditions is combined and analyzed to produce a GCI score. The GCI score can be used to provide people not trained in genetics with a reliable (i.e., robust), understandable, and/or intuitive sense of what their individual risk of disease is compared to a relevant population based on current scientific research. In one embodiment a method for generating a robust GCI score for the combined effect of different loci is based on a reported individual risk for each locus studied. For example a disease or condition of interest is identified and then informational sources, including but not limited to databases, patent publications and scientific literature, are queried for information on the association of the disease of condition with one or more genetic loci. These informational sources are curated and assessed using quality criteria. In some embodiments the assessment process involves multiple steps. In other embodiments the informational sources are assessed for multiple quality criteria. The information derived from informational sources is used to identify the odds ratio or relative risk for one or more genetic loci for each disease or condition of interest.

In an alternative embodiment the odds ratio (OR) or relative risk (RR) for at least one genetic loci is not available from available informational sources. The RR is then calculated using (1) reported OR of multiple alleles of same locus, (2) allele frequencies from data sets, such as the HapMap data set, and/or (3) disease/condition prevalence from available sources (e.g., CDC, National Center for Health Statistics, etc.) to derive RR of all alleles of interest. In one embodiment the ORs of multiple alleles of same locus are estimated separately or independently. In a preferred embodiment the ORs of multiple alleles of same locus are combined to account for dependencies between the ORs of the different alleles. In some embodiments established disease models (including, but not limited to models such as the multiplicative, additive, Harvard-modified, dominant effect) are used to generate an intermediate score that represents the risk of an individual according to the model chosen.

In another embodiment a method is used that analyzes multiple models for a disease or condition of interest and which correlates the results obtained from these different models; this minimizes the possible errors that may be introduced by choice of a particular disease model. This method minimizes the influence of reasonable errors in the estimates of prevalence, allele frequencies and ORs obtained from informational sources on the calculation of the relative risk. Because of the "linearity" or monotonic nature of the effect of a prevalence estimate on the RR, there is little or no effect of incorrectly estimating the prevalence on the final rank score; provided that the same model is applied consistently to all individuals for which a report is generated.

In another embodiment a method is used that takes into account environmental/behavioral/demographic data as additional "loci." In a related embodiment such data may be obtained from informational sources, such as medical or scientific literature or databases (e.g., associations of smoking w/lung cancer, or from insurance industry health risk assessments). In one embodiment a GCI score is produced for one or more complex diseases. Complex diseases may be influenced by multiple genes, environmental factors, and their interactions. A large number of possible interactions needs to be analyzed when studying complex diseases. In one embodiment a procedure is used to correct for multiple comparisons, such as the Bonferroni correction. In an alternative embodiment the Simes's test is used to control the overall significance level (also known as the "familywise error rate") when the tests are independent or exhibit a special type of dependence (Sarkar S. (1998)). Some probability inequalities for ordered MTP2 random variables: a proof of the Simes conjecture. Ann Stat 26:494-504). Simes's test rejects the global null hypothesis that all K test-specific null hypotheses are true if $p_{(k)} \leq \alpha k/K$ for any k in 1, . . . , K. (Simes R J (1986) An improved Bonferroni procedure for multiple tests of significance. Biometrika 73:751-754.).

Other embodiments that can be used in the context of multiple-gene and multiple-environmental-factor analysis control the false-discovery rate—that is, the expected proportion of rejected null hypotheses that are falsely rejected. This approach is particularly useful when a portion of the null hypotheses can be assumed false, as in microarray studies. Devlin et al. (2003, Analysis of multilocus models of association. Genet Epidemiol 25:36-47) proposed a variant of the Benjamini and Hochberg (1995, Controlling the false discovery rate: a practical and powerful approach to multiple testing. J R Stat Soc Ser B 57:289-300) step-up procedure that controls the false-discovery rate when testing a large number of possible gene×gene interactions in multilocus association studies. The Benjamini and Hochberg procedure is related to Simes's test; setting k*=maxk such that p(k)≤αk/K, it rejects all k* null hypotheses corresponding to $p_{(1)}, \ldots, p_{(k)}$. In fact, the Benjamini and Hochberg procedure reduces to Simes's test when all null hypotheses are true (Benjamini Y, Yekutieli D (2001) The control of the false discovery rate in multiple testing under dependency. Ann Stat 29:1165-1188).

In some embodiments an individual is ranked in comparison to a population of individuals based on their intermediate score to produce a final rank score, which may be represented as rank in the population, such as the $99^{th}$ percentile or $99^{th}$, $98^{th}$, $97^{th}$, $96^{th}$, $95^{th}$, $94^{th}$, $93^{rd}$, $92^{nd}$, $91^{st}$, $90^{th}$, $89^{th}$, $88^{th}$, $87^{th}$, $86^{th}$, $85^{th}$, $84^{th}$, $83^{rd}$, $82^{nd}$, $81^{st}$, $80^{th}$, $79^{th}$, $78^{th}$, $77^{th}$, $76^{th}$, $75^{th}$, $74^{th}$, $73^{rd}$, $72^{nd}$, $71^{st}$, $70^{th}$, $69^{th}$, $65^{th}$, $60^{th}$, $55^{th}$, $50^{th}$, $45^{th}$, $40^{th}$, $40^{th}$, $35^{th}$, $30^{th}$, $25^{th}$, $20^{th}$, $15^{th}$, $10^{th}$, $5^{th}$, or $0^{th}$. Percentile. In another embodiment the rank may score may be displayed as a range, such as the $100^{th}$ to $95^{th}$ percentile, the $95^{th}$ to $85^{th}$ percentile, the $85^{th}$ to $60^{th}$ percentile, or any subrange between the $100^{th}$ and $0^{th}$ percentile. In yet another embodiment the individual is ranked in quartiles, such as the top $75^{th}$ quartile, or the lowest $25^{th}$ quartile. In a further embodiment the individual is ranked in comparison to the mean or median score of the population.

In one embodiment the population to which the individual is compared to includes a large number of people from various geographic and ethnic backgrounds, such as a global population. In other embodiments the population to which an individual is compared to is limited to a particular geography, ancestry, ethnicity, sex, age (fetal, neonate, child, adolescent, teenager, adult, geriatric individual) disease state (such as symptomatic, asymptomatic, carrier, early-onset, late onset). In some embodiments the population to which the individual is compared is derived from information reported in public and/or private informational sources.

Figure 18:
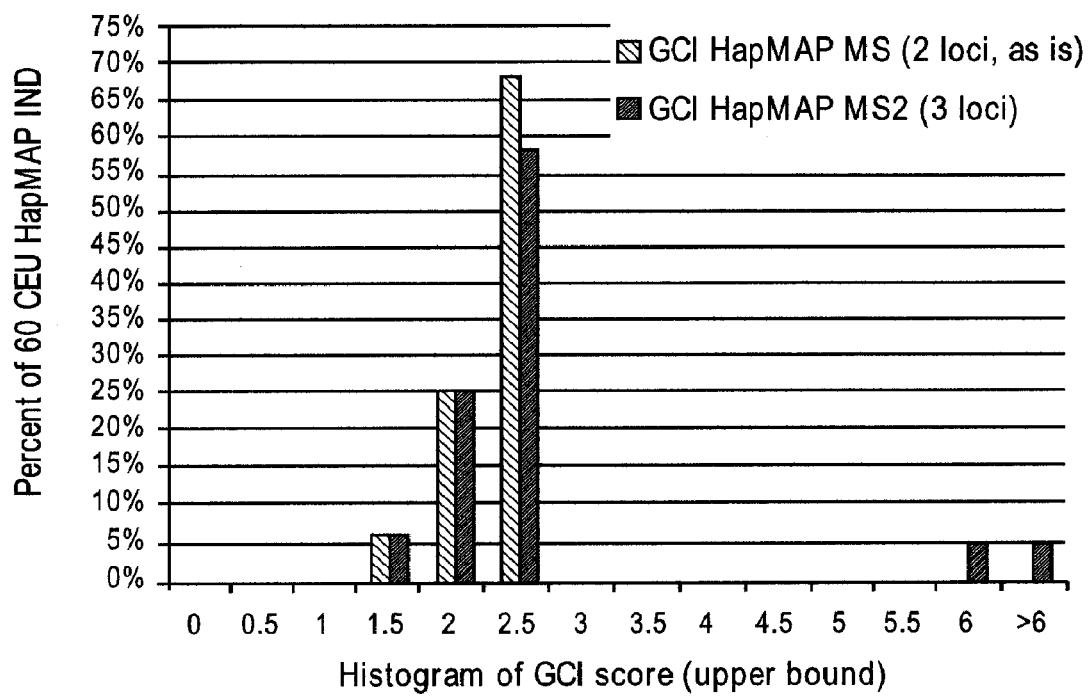
FIG. 18: is a histogram of GCI scores for Multiple Sclerosis based on the HapMAP using 2 SNPs.
Figure 19:
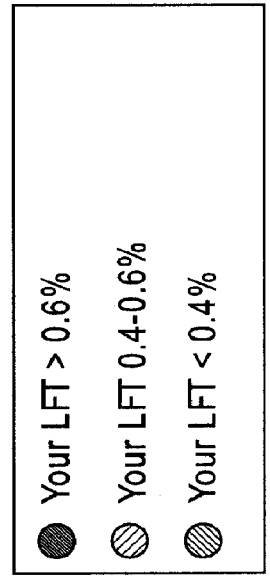
FIG. 19: is an individuals' lifetime risk for Multiple Sclerosis using GCI Plus.
Figure 20:
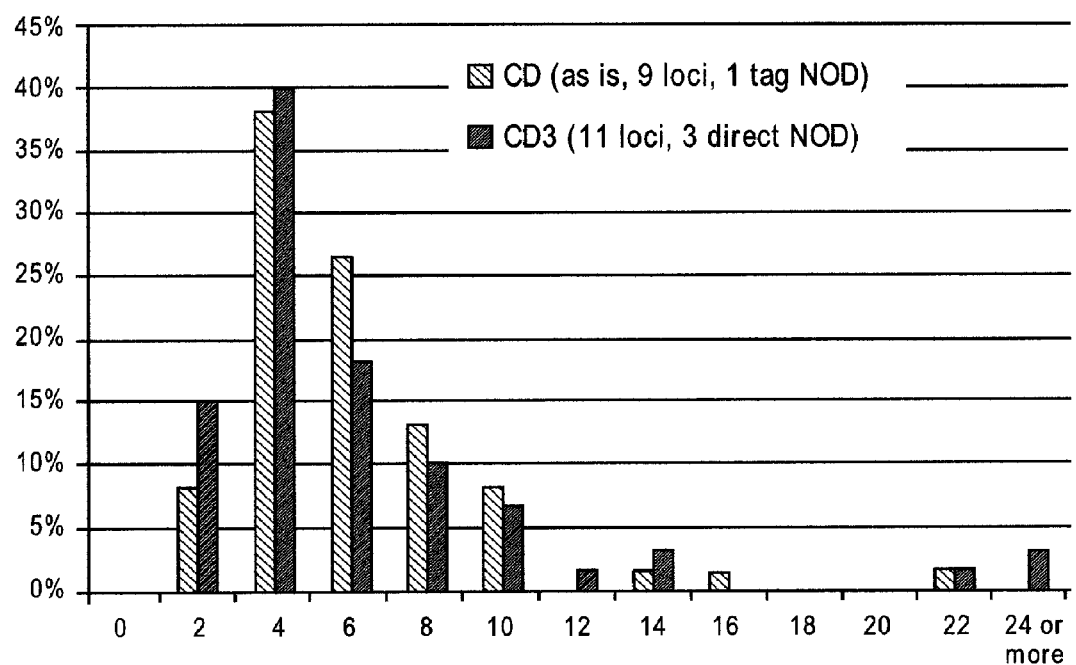
FIG. 20: is a histogram of GCI scores for Crohn's disease.

In one embodiment an individual's GCI score, or GCI Plus score, is visualized using a display. In some embodiments a screen (such as a computer monitor or television screen) is used to visualize the display, such as a personal portal with relevant information. In another embodiment the display is a static display such as a printed page. In one embodiment the display may include but is not limited to one or more of the following: bins (such as 1-5, 6-10, 11-15, 16-20, 21-25, 26-30, 31-35, 36-40, 41-45, 46-50, 51-55, 56-60, 61-65, 66-70, 71-75, 76-80, 82-85, 86-90, 91-95, 96-100), a color or grayscale gradient, a thermometer, a gauge, a pie chart, a histogram or a bar graph. For example, FIGS. 18 and 19 are different displays for MS and FIG. 20 is for Crohn's disease). In another embodiment a thermometer is used to display GCI score and disease/condition prevalence. In another embodiment a thermometer displays a level that changes with the reported GCI score, for example, FIGS. 15-17, the color corresponds to the risk. The thermometer may display a colorimetric change as the GCI score increases (such as changing from blue, for a lower GCI score, progressively to red, for a higher GCI score). In a related embodiment a thermometer displays both a level that changes with the reported GCI score and a colorimetric change as the risk rank increases In an alternative embodiment an individual's GCI score is delivered to an individual by using auditory feedback. In one embodiment the auditory feedback is a verbalized instruction that the risk rank is high or low. In another embodiment the auditory feedback is a recitation of a specific GCI score such as a number, a percentile, a range, a quartile or a comparison with the mean or median GCI score for a population. In one embodiment a live human delivers the auditory feedback in person or over a telecommunications device, such as a phone (landline, cellular phone or satellite phone) or via a personal portal. In another embodiment the auditory feedback is delivered by an automated system, such as a computer. In one embodiment the auditory feedback is delivered as part of an interactive voice response (IVR) system, which is a technology that allows a computer to detect voice and touch tones using a normal phone call. In another embodiment an individual may interact with a central server via an IVR system. The IVR system may respond with pre-recorded or dynamically generated audio to interact with individuals and provide them with auditory feedback of their risk rank. In one example an individual may call a number that is answered by an IVR system. After optionally entering an identification code, a security code or undergoing voice-recognition protocols the IVR system asks the subject to select options from a menu, such as a touch tone or voice menu. One of these options may provide an individual with his or her risk rank.

In another embodiment an individual's GCI score is visualized using a display and delivered using auditory feedback, such as over a personal portal. This combination may include a visual display of the GCI score and auditory feedback, which discusses the relevance of the GCI score to the individual's overall health and possible preventive measures, may be advised.

In one example the GCI score is generated using a multi-step process. Initially, for each condition to be studied, the relative risks from the odds ratios for each of the Genetic markers is calculated. For every prevalence value p=0.01, 0.02, . . . , 0.5, the GCI score of the HapMap CEU population is calculated based on the prevalence and on the HapMap allele frequency. If the GCI scores are invariant under the varying prevalence, then the only assumption taken into account is that there is a multiplicative model. Otherwise, it is determined that the model is sensitive to the prevalence. The relative risks and the distribution of the scores in the HapMap population, for any combination of no-call values, are obtained. For each new individual, the individual's score is compared to the HapMap distribution and the resulting score is the individual's rank in this population. The resolution of the reported score may be low due to the assumptions made during the process. The population will be partitioned into quantiles (3-6 bins), and the reported bin would be the one in which the individual's rank falls. The number of bins may be different for different diseases based on considerations such as the resolution of the score for each disease. In case of ties between the scores of different HapMap individuals, the average rank will be used.

In one embodiment a higher GCI score is interpreted as an indication of an increased risk for acquiring or being diagnosed with a condition or disease. In another embodiment mathematical models are used to derive the GCI score. In some embodiments the GCI score is based on a mathematical model that accounts for the incomplete nature of the underlying information about the population and/or diseases or conditions. In some embodiments the mathematical model includes certain at least one presumption as part of the basis for calculating the GCI score, wherein said presumption includes, but is not limited to: a presumption that the odds ratio values are given; a presumption that the prevalence of the condition is known; a presumption that the genotype frequencies in the population are known; and a presumption that the customers are from the same ancestry background as the populations used for the studies and as the HapMap; a presumption that the amalgamated risk is a product of the different risk factors of the individual genetic markers. In some embodiments, the GCI may also include a presumption that the multi-genotypic frequence of a genotype is the product of frequencies of the alleles of each of the SNPs or individual genetic markers (for example, the different SNPs or genetic markers are independent across the population).

The Multiplicative Model

In one embodiment a GCI score is computed under the assumption that the risk attributed to the set of Genetic markers is the product of the risks attributed to the individual Genetic markers. This means that the different Genetic markers attribute independently of the other Genetic markers to the risk of the disease. Formally, there are k Genetic markers with risk alleles $r_1, \ldots, r_k$ and non-risk alleles $n_1, \ldots, n_k$. In SNP i, we denote the three possible genotype values as $r_i r_i$, $n_i r_i$, and $n_i n_i$. The genotype information of an individual can be described by a vector, $(g_1, \ldots, g_k)$, where $g_i$ can be 0, 1, or 2, according to the number of risk alleles in position i. We denote by $\lambda_1^i$ the relative risk of a heterozygous genotype in position i compared to a homozygous non-risk allele at the same position. In other words, we define $$\lambda_1^i = \frac{P(D|n_i r_i)}{P(D|n_i n_i)}.$$

Similarly, we denote the relative risk of an $r_i r_i$ genotype as $$\lambda_2^i = \frac{P(D|r_i r_i)}{P(D|n_i n_i)}.$$

Under the multiplicative model we assume that the risk of an individual with a genotype $(g_1, \ldots, g_k)$ is $$GCI(g_1, \ldots, g_k) = \prod_{i=1}^{k} \lambda_{g_i}^i.$$

The multiplicative model has been previously used in the literature in order to simulate case-control studies, or for visualization purposes.

Estimating the Relative Risk.

In another embodiment the relative risks for different Genetic markers are known and the multiplicative model can be used for risk assessment. However, in some embodiments involving association studies the study design prevents the reporting of the relative risks. In some case-control studies the relative risk cannot be calculated directly from the data without further assumptions. Instead of reporting the relative risks, it is customary to report the odds ratio (OR) of the genotype, which are the odds of carrying the disease given the risk genotype (either $r_i r_i$ or $n_i r_i$) vs. the odds of not carrying the disease given the risk genotypes. Formally, $$OR_i^1 = \frac{P(D|n_i r_i)}{P(D|n_i r_i)} \cdot \frac{1 - P(D|n_i n_i)}{1 - P(D|n_i r_i)}$$

$$OR_i^2 = \frac{P(D|r_i r_i)}{P(D|n_i n_i)} \cdot \frac{1 - P(D|n_i n_i)}{1 - P(D|r_i r_i)}$$

Finding the relative risks from the odds ratio may require additional assumptions. Such as the presumption that the allele frequencies in an entire population $a = f_{n_i n_i}$, $b = f_{n_i r_i}$, and $c = f_{r_i r_i}$ are known or estimated (these could be estimated from current datasets such as the HapMap dataset which includes 120 chromosomes), and/or that the prevalence of the disease p=p(D) is known. From the preceding three equations can be derived:

$$p = a \cdot P(D \mid n_i n_i) + b \cdot P(D \mid n_i r_i) + c \cdot P(D \mid r_i r_i)$$

$$OR_i^1 = \frac{P(D|n_i r_i)}{P(D|n_i r_i)} \cdot \frac{1 - P(D|n_i n_i)}{1 - P(D|n_i r_i)}$$

$$OR_i^2 = \frac{P(D|r_i r_i)}{P(D|n_i n_i)} \cdot \frac{1 - P(D|n_i n_i)}{1 - P(D|r_i r_i)}$$

By the definition of the relative risk, after dividing by the term $pP(D|n_i n_i)$, the first equation can be rewritten as:

$$\frac{1}{P(D|n_i n_i|)} = \frac{a + b\lambda_1^i + c\lambda_2^i}{p},$$

and therefore, the last two equations can be rewritten as:

$$OR_i^1 = \lambda_1^i \cdot \frac{(a-p) + b\lambda_1^i + c\lambda_2^i}{a + (b-p)\lambda_1^i + c\lambda_2^i} \quad (1)$$

$$OR_i^2 = \lambda_2^i \cdot \frac{(a-p) + b\lambda_1^i + c\lambda_2^i}{a + b\lambda_1^i + (c-p)\lambda_2^i}$$

Note that when a=1 (non-risk allele frequency is 1), Equation system 1 is equivalent to the Zhang and Yu formula in Zhang J and Yu K. (What's the relative risk? A method of correcting the odds ratio in cohort studies of common outcomes. *JAMA*, 280:1690-1, 1998), which is incorporated by reference in its entirety. In contrast to the Zhang and Yu formula, some embodiments of the present invention take into consideration the allele frequency in the population, which may affect the relative risk. Further some embodiments take into account the interdependence of the relative risks. As opposed to computing each of the relative risks independently.

Equation system 1 can be rewritten as two quadratic equations, with at most four possible solutions. A gradient descent algorithm can be used to solve these equations, where the starting point is set to be the odds ratio, e.g., $\lambda_1^i = OR_1^i$, and $\lambda_2^i = OR_2^i$.

For example:

$$f_1(\lambda_1, \lambda_2) = OR_i^1(a + (b-p)\lambda_1^i + c\lambda_2^i) - \lambda_1^i \cdot ((a-p) + b\lambda_1^i + c\lambda_2^i)$$

$$f_2(\lambda_1, \lambda_2) = OR_i^2(a + b\lambda_1^i + (c-p)\lambda_2^i) - \lambda_2^i \cdot ((a-p) + b\lambda_1^i + c\lambda_2^i)$$

Finding the solution of these equations is equivalent to finding the minimum of the function $g(\lambda_1, \lambda_2) = f_1(\lambda_1, \lambda_2)^2 + f_2(\lambda_1, \lambda_2)^2$.

Thus, $$\frac{dg}{d\lambda_1} = 2f_1(\lambda_1, \lambda_2) \cdot b \cdot (\lambda_2 - OR_2) +$$

$$2f_2(\lambda_1, \lambda_2)(2b\lambda_1 + c\lambda_2 + a - OR_1 b - p + OR_1 p)$$

$$\frac{dg}{d\lambda_2} = 2f_1(\lambda_1, \lambda_2) \cdot c \cdot (\lambda_1 - OR_1) +$$

$$2f_1(\lambda_1, \lambda_2)(2c\lambda_2 + b\lambda_1 + a - OR_2 c - p + OR_2 p)$$

In this example we begin by setting $x_0 = OR_1$, $y_0 = OR_2$. We will set the values [epsilon]=$10^{-10}$ to be a tolerance constant through the algorithm. In iteration i, we define $$\gamma = \min\left\{0.001, \frac{x_{i-1}}{[\text{epsilon}] + 10\left|\frac{dg}{d\lambda_1}(x_{i-1}, y_{i-1})\right|}, \frac{y_{i-1}}{[\text{epsilon}] + 10\left|\frac{dg}{d\lambda_2}(x_{i-1}, y_{i-1})\right|}\right\}.$$

We then set $$x_i = x_{i-1} - \gamma \frac{dg}{d\lambda_1}(x_{i-1}, y_{i-1})$$

$$y_i = y_{i-1} - \gamma \frac{dg}{d\lambda_2}(x_{i-1}, y_{i-1})$$

There iterations are repeated until $g(x_i, y_i)$<tolerance, where tolerance is set to $10^{-7}$ in the supplied code.

Figure 10:
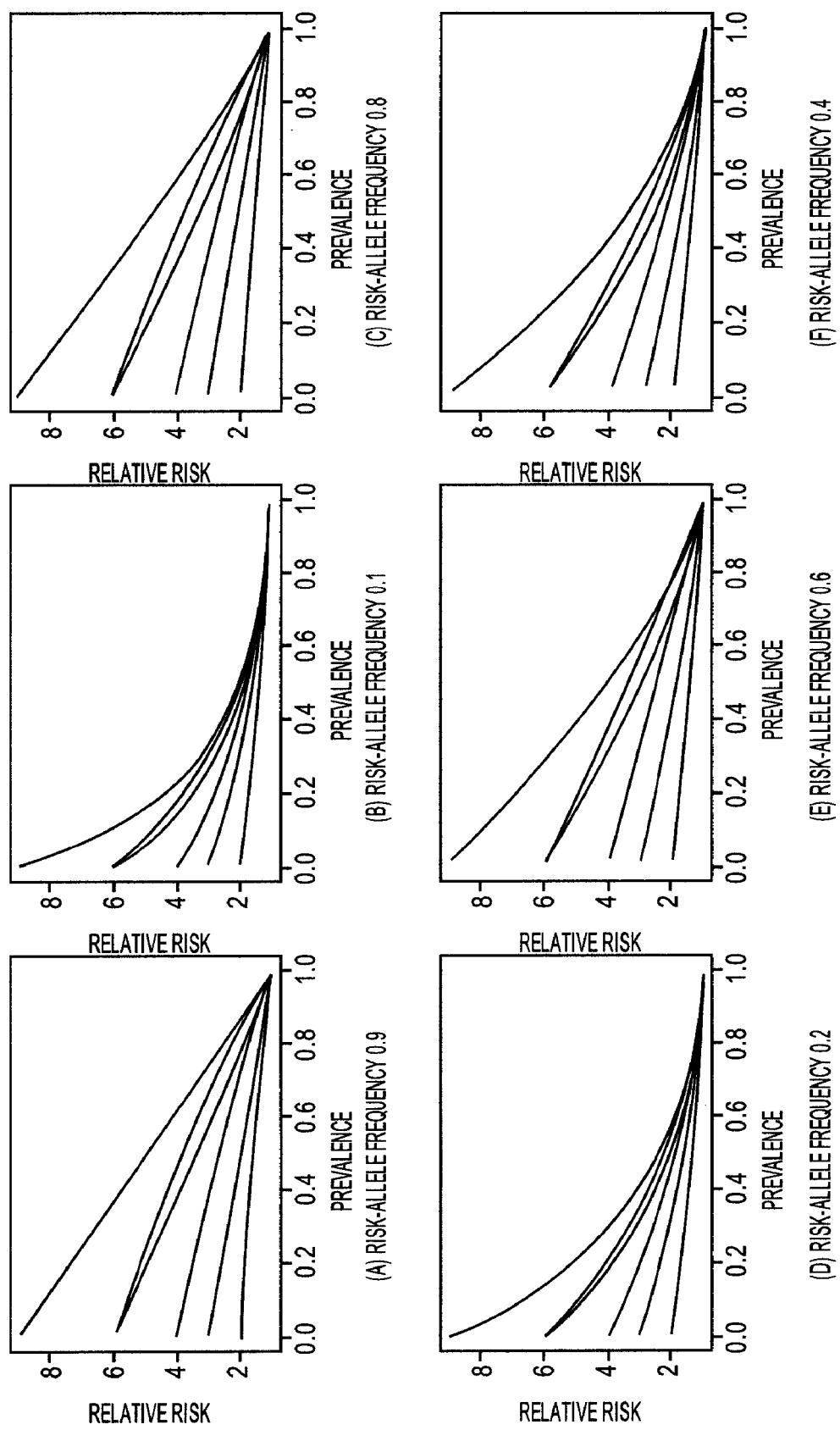
FIG. 10: The effect of the estimate of the prevalence on the relative risk estimations. Each of the plots correspond to a different value of the allele frequencies in the populations, assuming Hardy-Weinberg Equilibrium. The two black lines correspond to odds ratio of 9 and 6, the two red lines correspond to 6 and 4, and the two blue lines correspond to odds ratio of 3 and 2.

In this example these equations give the correct solution for different values of a, b, c, p, $OR_1$, and $OR_2$. FIG. 10

Robustness of the Relative Risk Estimation.

Figure 11:
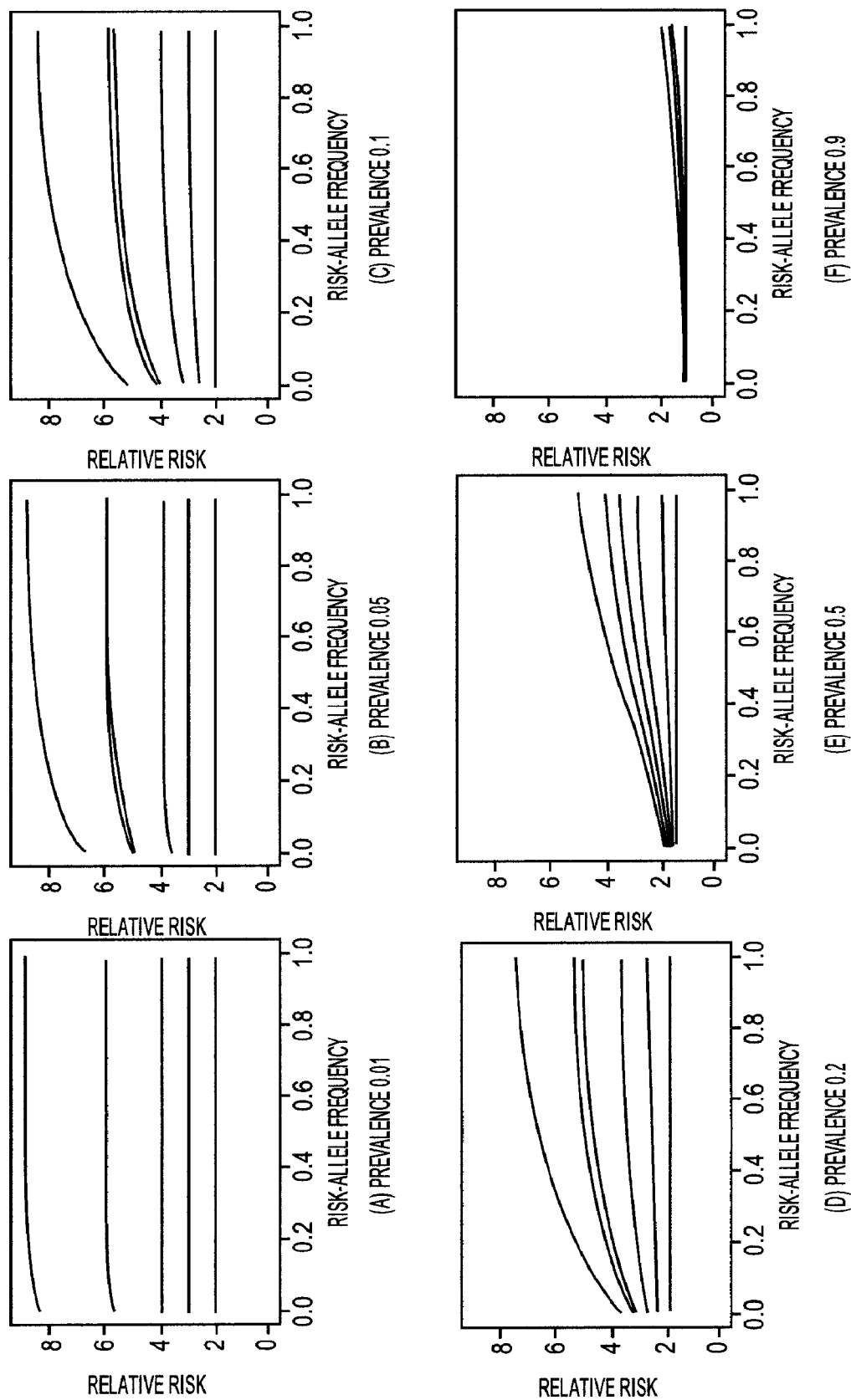
FIG. 11: The effect of the estimate of the allele frequencies on the relative risk estimations. Each of the plots correspond to a different value of the prevalence in the populations. The two black lines correspond to odds ratio of 9 and 6, the two red lines correspond to 6 and 4, and the two blue lines correspond to odds ratio of 3 and 2.

In some embodiments the effect of different parameters (prevalence, allele frequencies, and odds ratio errors) on the estimates of the relative risks is measured. In order to measure the effect of the allele frequency and prevalence estimates on the relative risk values, the relative risk from a set of values of different odds ratios and different allele frequencies is computed (under HWE), and the results of these calculations is plotted for prevalence values ranging from 0 to 1. FIG. 10. Additionally, for fixed values of the prevalence, the resulting relative risks can be plotted as a function of the risk-allele frequencies. FIG. 11. In cases when p=0, $\lambda_1 = OR_1$, and $\lambda_2 = OR_2$, and when p=1, $\lambda_1 = \lambda_2 = 0$. This can be computed directly from the equations. Additionally, in some embodiments when the risk allele frequency is high, $\lambda_1$ gets closer to a linear function, and $\lambda_2$ gets closer to a concave function with a bounded second derivative. In the limit, when c=1, $\lambda_2 = OR_2 + p(1 - OR_2)$, and $$\lambda_i = OR_i - \frac{(OR_i - 1)pOR_i}{OR_2(1-p) + pOR_1}.$$

If $OR_1 \approx OR_2$ the latter is close to a linear function as well. When risk-allele frequency is low, $\lambda_1$ and $\lambda_2$ approach the behavior of the function $1/p$. In the limit, when c=0, $$\lambda_1 = \frac{OR_1}{1 - p + pOR_1}, \lambda_2 = \frac{OR_2}{1 - p + pOR_2}.$$

This indicates that for high risk-allele frequencies, incorrect estimates of the prevalence will not significantly affect the resulting relative risk. Further, for low risk-allele frequency, if a prevalence value of p'=αp is substituted for the correct prevalence p, then the resulting relative risks will be off by a factor of $$\frac{1}{\alpha}$$

at most. This is illustrated in sections (c) and (d) of FIG. 11. Note that for high risk-allele frequencies the two graphs are quite similar and while there is a higher deviation in the difference in the values of the relative risks for low allele frequencies, this deviation is less than a factor of 2.

Calculating the GCI Score

In one embodiment the Genetic Composite Index is calculated by using a reference set that represents the relevant population. This reference set may be one of the populations in the HapMap, or anther genotype dataset.

In this embodiment the GCI is computed as follows. For each of the k risk loci, the relative risk is calculated from the odds ratio using the equation system 1. Then, the multiplicative score for each individual in the reference set is calculated. The GCI of an individual with a multiplicative score of s is the fraction of all individuals in the reference dataset with a score of s'≤s. For instance, if 50% of the individuals in the reference set have a multiplicative score smaller than s, the final GCI score of the individual would be 0.5.

Other Models

In one embodiment the multiplicative model is used. In alternative embodiments other models that may be used for the purpose of determining the GCI score. Other suitable models include but are not limited to:

The Additive Model. Under the additive model the risk of an individual with a genotype $(g_1, \ldots, g_k)$ is presumed to be $$GCI(g_1, \ldots, g_k) = \sum_{i=1}^{k} \lambda_{g_i}^i.$$

Generalized Additive Model. Under the generalized additive model it is presumed that there is a function $f$ such that the risk of an individual with a genotype $(g_1, \ldots, g_k)$ is $$GCI(g_1, \ldots, g_k) = \sum_{i=1}^{k} f(\lambda_{g_i}^i).$$

Harvard Modified Score (Het). This score was derived from G. A Colditz et al., so that the score that applies to genetic markers (Harvard report on cancer prevention volume 4: Harvard cancer risk index. *Cancer Causes and Controls*, 11:477-488, 2000 which is herein incorporated in its entirety). The Het score is essentially a generalized additive score, although the function $f$ operates on the odds ratio values instead of the relative risks. This may be useful in cases where the relative risk is difficult to estimate. In order to define the function $f$, an intermediate function g, is defined as:

$$g(x) = \begin{cases} 0 & 1 < x \le 1.09 \\ 5 & 1.09 < x \le 1.49 \\ 10 & 1.49 < x \le 2.99 \\ 25 & 2.99 < x \le 6.99 \\ 50 & 6.99 < x \end{cases}$$

Next the quantity $$het = \sum_{i=1}^{k} p_{het}^i g(OR_1^i)$$

is calculated, where $p_{het}^i$ is the frequency of heterozygous individuals in SNP i across the reference population. The function $f$ is then defined as $f(x)=g(x)/het$, and the Harvard Modified Score (Het) is simply defined as $$\sum_{i=1}^{k} f(OR_{g_i}^i).$$

The Harvard Modified Score (Hom). This score is similar to the Het score, except that the value het is replaced by the value $$hom = \sum_{i=1}^{k} p_{hom}^i g(OR_1^i),$$

where $p_{hom}^i$ is the frequency of individuals with homozygous risk-allele.

The Maximum-Odds Ratio. In this model, it is presumed that one of the Genetic markers (one with a maximal odds ratio) gives a lower bound on the combined risk of the entire panel. Formally, the score of an individual with genotypes $(g_1, \ldots, g_k)$ is $GCI(g_1, \ldots, g_k) = \max_{i=1}^{k} OR_{g_i}^i$.

A Comparison between the Scores

In one Example the GCI score was calculated based on multiple models across the HapMap CEU population, for 10 SNPs associated with T2D. The relevant SNPs were rs7754840, rs4506565, rs7756992, rs10811661, rs12804210, rs8050136, rs1111875, rs4402960, rs5215, rs1801282. For each of these SNPs, an odds ratio for three possible genotypes is reported in the literature. The CEU population consists of thirty mother-father-child trios. Sixty parents from this population were used in order to avoid dependencies. One of the individuals that had a no-call in one of the 10 SNPs was excluded, resulting in a set of 59 individuals. The GCI rank for each of the individuals was then calculated using several different models.

Figure 12:
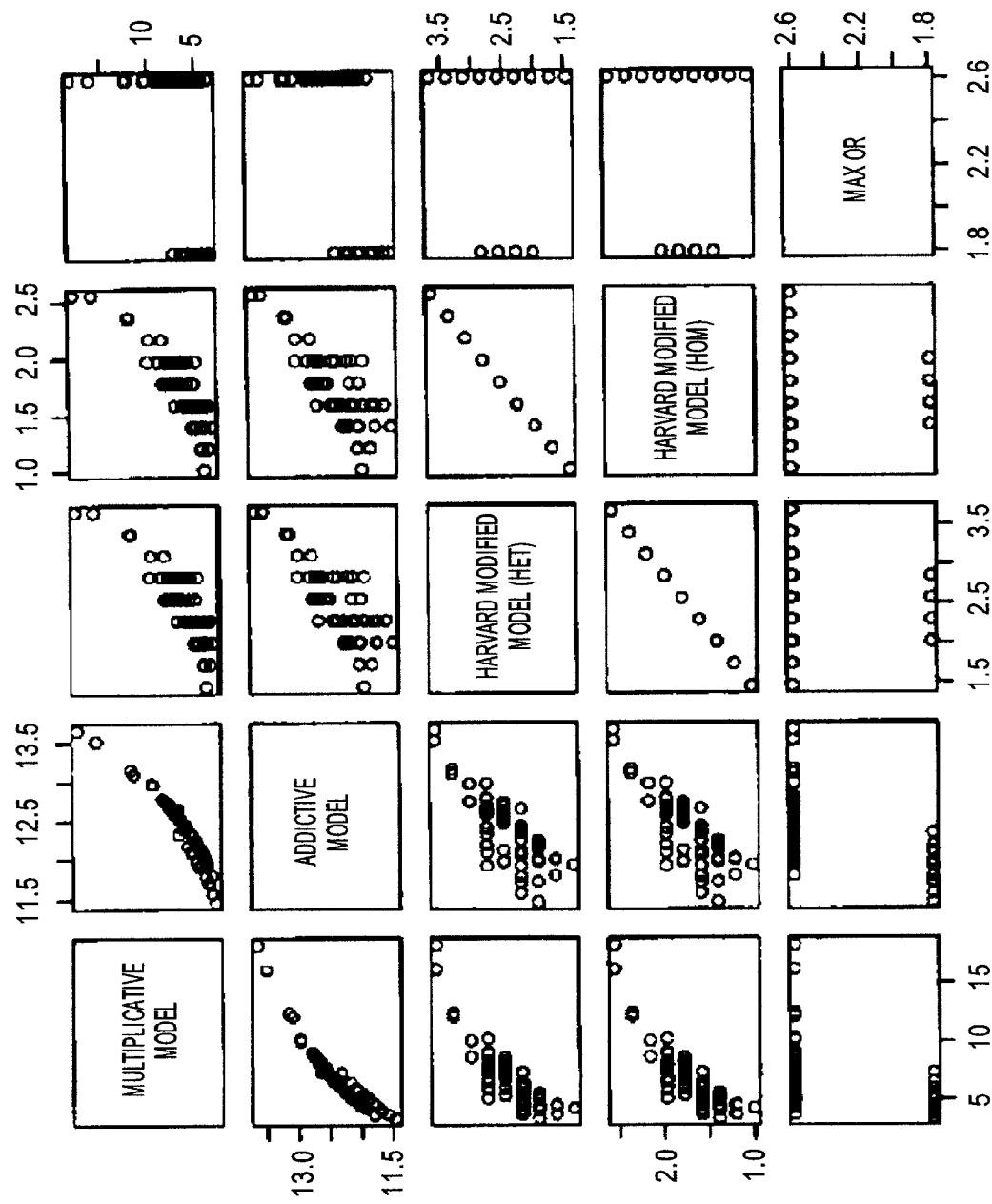
FIG. 12: Pairwise Comparison of the absolute values of the different models
Figure 13:
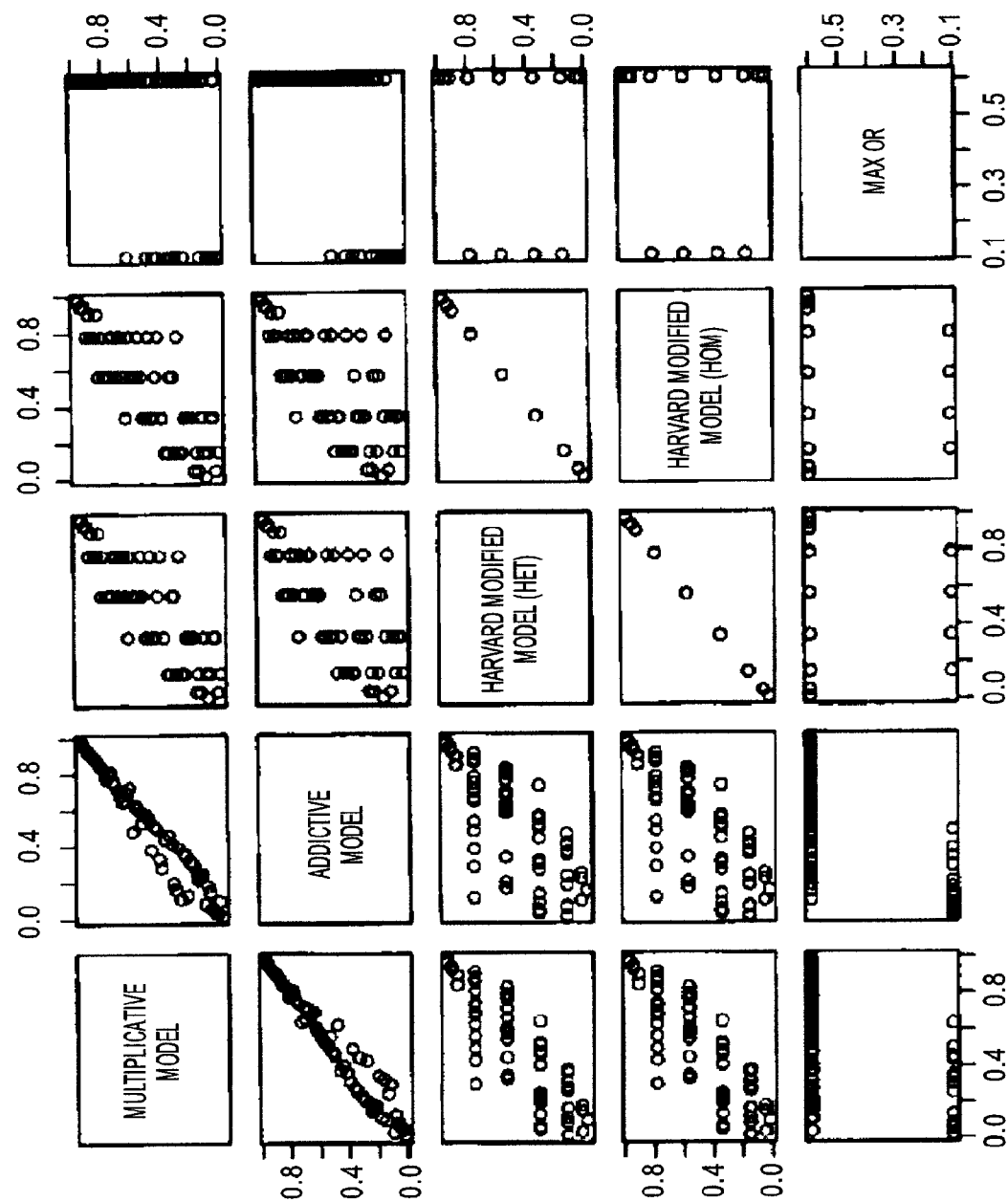
FIG. 13: Pairwise Comparison of the ranked values (GCI scores) based on the different models. The Spearman correlations between the different pairs are given in Table 2.

It was observed that for this dataset different models produced highly correlated results. FIGS. 12 & 13. The Spearman correlation was calculated between each pair of models (Table 2), which showed that the Multiplicative and Additive model had a correlation coefficient of 0.97, and thus the GCI score would be robust using either the additive or multiplicative models. Similarly, the correlation between the Harvard modified scores and the multiplicative model was 0.83, and the correlation coefficient between the Harvard scores and the additive model was 0.7. However, using the maximum odds ratio as the genetic score yielded a dichotomous score which was defined by one SNP. Overall these results indicate score ranking provided a robust framework that minimized model dependency.

TABLE 2

The Spearman correlations for the score distributions on the CEU data between model pairs.

|  | Multiplicative | Additive | Harv-Het | Harv-Hom | MAX OR |
| --- | --- | --- | --- | --- | --- |
| Mult | 1 | 0.97 | 0.83 | 0.83 | 0.42 |
| Additive | 0.97 | 1. | 0.7 | 0.7 | 0.6 |
| Harv-Het | 0.83 | 0.7 | 1 | 1 | 0 |
| Harv-Hom | 0.83 | 0.7 | 1 | 1 | 0 |
| MAX OR | 0.42 | 0.6 | 0 | 0 | 1 |

Figure 14:
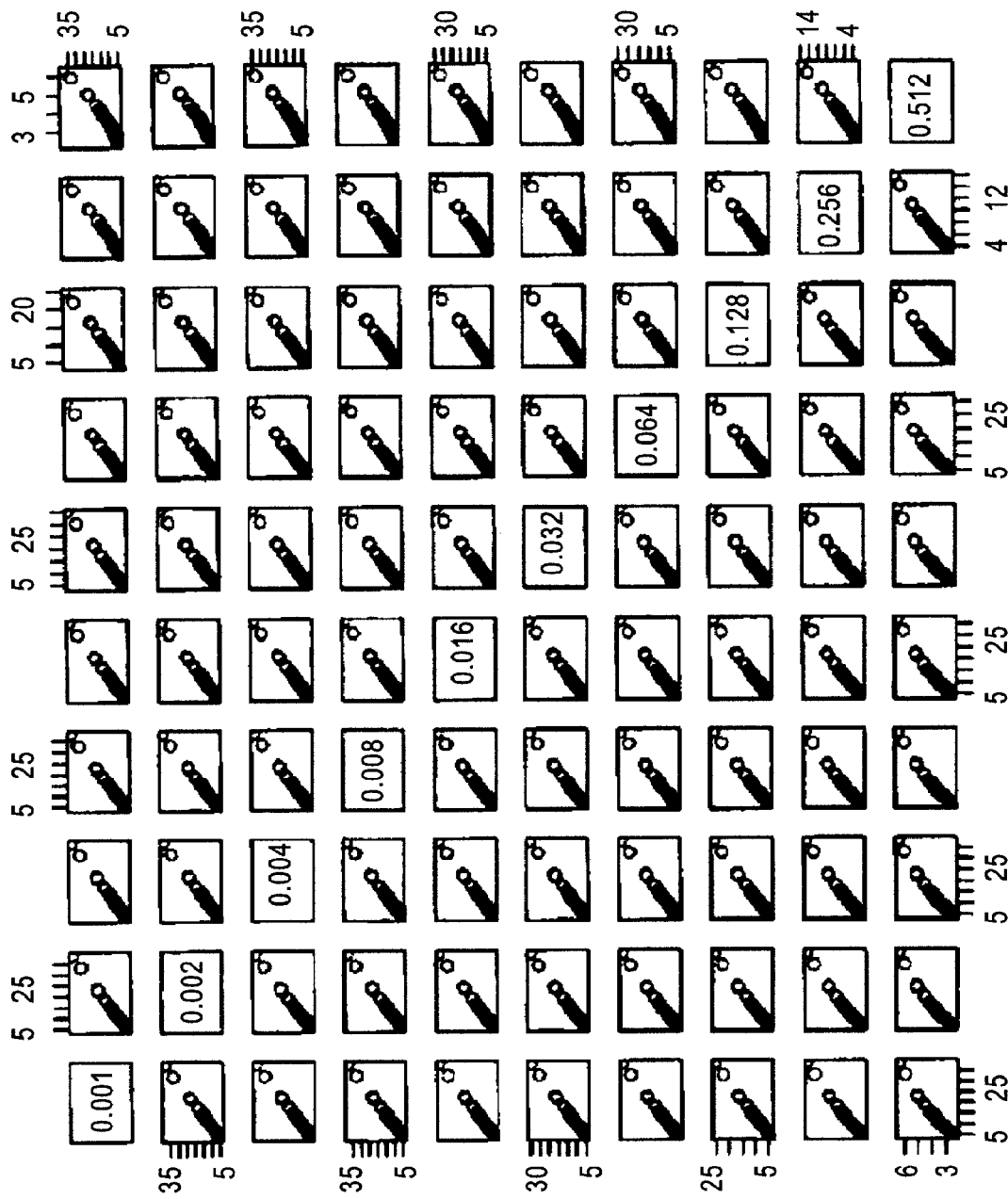
FIG. 14: Effect of Prevalence Reporting on the GCI score. The Spearman correlation between any two prevalence values is at least 0.99.

The effect of variation in the prevalence of T2D on the resulting distribution was measured. The prevalence values from 0.001 to 0.512 was varied (FIG. 14). For the case of T2D, it was observed that different prevalence values result in the same order of individuals (Spearman correlation>0.99), therefore an artificially fixed value of prevalence 0.01 could be presumed.

Extending the Model to an Arbitrary Number of Variants

In another embodiment the model can be extended to the situations where an arbitrary number of possible variants occur. Previous considerations dealt with situations where there were three possible variants (nn, nr, rr). Generally, when a multi-SNP association is known, an arbitrary number of variants may be found in the population. For example, when an interaction between two Genetic markers is associated with a condition, there are nine possible variants. This results in eight different odds ratios values.

To generalize the initial formula, it may be assumed that there are k+1 possible variants $\alpha_0, \ldots, \alpha_k$, with frequencies $f_0, f_1, \ldots, f_k$, measured odds ratios of 1, $OR_1, \ldots, OR_k$, and unknown relative risk values 1, $\lambda_1, \ldots, \lambda_k$. Further it may be assumed that all relative risks and odds ratios are measured with respect to $\alpha_0$, and thus, $$\lambda_i = \frac{P(D \mid a_i)}{P(D \mid a_o)}, \quad \text{and} \quad OR_i = \frac{P(D \mid a_i)}{P(D \mid a_o)} \cdot \frac{1 - P(D \mid a_i)}{1 - P(D \mid a_o)}.$$

Based on:

$$p = \sum_{i=0}^{k} f_i P(D \mid a_i),$$

It is determined that $$OR_i = \lambda_i \frac{\sum_{i=0}^{k} f_i \lambda_i - p}{\sum_{i=0}^{k} f_i \lambda_i - \lambda_i p}.$$

Further if it is set that $$C = \sum_{i} f_i \lambda_i,$$

this results in the equation:

$$\lambda_i = \frac{C \cdot OR_i}{C - p + OR_i p},$$

and thus, $$C = \sum_{i=0}^{k} f_i \lambda_i = \sum_{i=0}^{k} \frac{C \cdot OR_i f_i}{C - p + OR_i p},$$

or $$1 = \sum_{i=0}^{k} \frac{OR_i f_i}{C - p + OR_i p}.$$

The latter is an equation with one variable (C). This equation can produce many different solutions (essentially, up to k+1 different solutions). Standard optimization tools such as gradient descent can be used to find the closest solution to $C_0 = \Sigma f_i t_i$.

The present invention uses a robust scoring framework for the quantification of risk factors. While different genetic models may result in different scores, the results are usually correlated. Therefore the quantification of risk factors is generally not dependent on the model used.

Estimating Relative Risk Case Control Studies

A method that estimates the relative risks from the odds ratios of multiple alleles in a case-control study is also provided in the present invention. In contrast to previous approaches, the method takes into consideration the allele frequencies, the prevalence of the disease, and the dependencies between the relative risks of the different alleles. The performance of the approach on simulated case-control studies was measured, and found to be extremely accurate.

Methods

In the case where a specific SNP is tested for association with a disease D, R and N denote the risk and non-risk alleles of this particular SNP. P(RR|D), P(RN|D) and P(NN|D) denote the probability of getting affected by the disease given that a person is homozygous for the risk allele, heterozygous, or homozygous for the non-risk allele respectively. $f_{RR}$, $f_{RN}$ and $f_{NN}$ are used to denote the frequencies of the three genotypes in the population. Using these definitions, the relative risks are defined as $$\lambda_{RR} = \frac{P(D \mid RR)}{P(D \mid NN)}$$

$$\lambda_{RN} = \frac{P(D \mid RN)}{P(D \mid NN)}$$

In a case-control study, the values P(RR|D), P(RR|~D) can be estimated, i.e., the frequency of RR among the cases and the controls, as well as P(RN|D), P(RN|~D), P(NN|D), and P(NN|~D), i.e., the frequency of RN and NN among the cases and the controls. In order to estimate the relative risk, Bayes law can be used to get:

$$\lambda_{RR} = \frac{P(RR \mid D) f_{NN}}{P(NN \mid D) f_{RR}}$$

$$\lambda_{RN} = \frac{P(D \mid RN) f_{NN}}{P(D \mid NN) f_{RR}}$$

Thus, if the frequencies of the genotypes are known, one can use those to calculate the relative risks. The frequencies of the genotypes in the population cannot be calculated from the case-control study itself, since they depend on the prevalence of disease in the population. In particular, if the prevalence of the disease is p(D), then:

$$f_{RR} = P(RR \mid D) p(D) + P(RR \mid \sim D)(1 - p(D))$$

$$f_{RN} = P(RN \mid D) p(D) + P(RN \mid \sim D)(1 - p(D))$$

$$f_{NN} = P(NN \mid D) p(D) + P(NN \mid \sim D)(1 - p(D))$$

When p(D) is small enough, the frequencies of the genotypes can be approximated by the frequencies of the genotypes in the control population, but this would not be an accurate estimate when the prevalence is high. However, if a reference dataset is given (e.g., the HapMap [cite]), one can estimate the genotype frequencies based on the reference dataset.

Most current studies do not use a reference dataset to estimate the relative risk, and only the odds-ratio is reported. The odds-ratio can be written as $$OR_{RR} = \frac{P(RR \mid D) P(NN \mid \sim D)}{P(NN \mid D) P(RR \mid \sim D)}$$

-continued
$$OR_{RN} = \frac{P(RN \mid D)P(NN \mid \sim D)}{P(NN \mid D)P(RN \mid \sim D)}$$

The odds ratios are typically advantageous since there is usually no need to have an estimate of the allele frequencies in the population; in order to calculate the odds ratios typically what is needed is the genotype frequencies in the cases and in the controls.

In some situations, the genotype data itself is not available, but the summary data, such as the odds-ratios are available. This is the case when meta-analysis is being performed based on results from previous case-control studies. In this case, how to find the relative risks from the odds ratios is demonstrated. Using the fact that the following equation holds:

$$p(D) = f_{RR}P(D|RR) + f_{RN}P(D|RN) + f_{NN}P(D|NN)$$

If this equation is divided by P(D|NN), we get $$\frac{p(D)}{p(D \mid NN)} = f_{RR}\lambda_{RR} + f_{RN}\lambda_{RN} + f_{NN}$$

This allows the odds ratios to be written in the following way:

$$OR_{RR} = \frac{P(D \mid RR)(1 - P(D \mid NN))}{P(D \mid NN)(1 - P(D \mid RR))}$$

$$= \lambda_{RR} \frac{\frac{p(D)}{p(D \mid NN)} - p(D)}{\frac{p(D)}{p(D \mid NN)} - p(D)\lambda_{RR}}$$

$$= \lambda_{RR} \frac{f_{RR}\lambda_{RR} + f_{RN}\lambda_{RN} + f_{NN} - p(D)}{f_{RR}\lambda_{RR} + f_{RN}\lambda_{RN} + f_{NN} - p(D)\lambda_{RR}}$$

By a similar calculation, the following system of equations results:

$$OR_{RR} = \lambda_{RR} \frac{f_{RR}\lambda_{RR} + f_{RN}\lambda_{RN} + f_{NN} - p(D)}{f_{RR}\lambda_{RR} + f_{RN}\lambda_{RN} + f_{NN} - p(D)\lambda_{RR}} \quad \text{Equation 1}$$

$$OR_{RN} = \lambda_{RN} \frac{f_{RR}\lambda_{RR} + f_{RN}\lambda_{RN} + f_{NN} - p(D)}{f_{RR}\lambda_{RR} + f_{RN}\lambda_{RN} + f_{NN} - p(D)\lambda_{RN}}$$

If the odds-ratios, the frequencies of the genotypes in the populations, and the prevalence of the disease are known, the relative risks can be found by solving this set of equations.

Note that these are two quadratic equations, and thus they have a maximum of four solutions. However, as shown below that there is typically one possible solution to this equation.

Note that when $f_{NN}=1$, Equation system 1 is equivalent to the Zhang and Yu formula; however, here the allele frequency in the population is taken into account. Furthermore, our method takes into account the fact that the two relative risks depend on each other, while previous methods suggest to compute each of the relative risks independently.

Relative risks for multi-allelic loci. If multi-markers or other multi-allelic variants are considered, the calculation is complicated slightly. $a_0, a_1, \ldots, a_k$ is denoted by the possible k+1 alleles, where $a_0$ is the non-risk allele. Allele frequencies $f_0, f_1, f_2, \ldots, f_k$ in the population for the k+1 possible alleles are assumed. For allele i, the relative risk and odds-ratios are defined as $$\lambda_i = \frac{P(D \mid a_i)}{P(D \mid a_0)}$$

$$OR_i = \frac{P(D \mid a_i)(1 - P(D \mid a_0))}{P(D \mid a_0)(1 - P(D \mid a_i))} = \lambda_i \frac{1 - P(D \mid a_0)}{1 - P(D \mid a_i)}$$

The following equation holds for the prevalence of the disease:

$$p(D) = \sum_{i=0}^{k} f_i P(D \mid a_i)$$

Thus, by dividing both sides of the equation by $p(D|a_0)$, we get:

$$\frac{p(D)}{p(D \mid a_0)} = \sum_{i=0}^{k} f_i \lambda_i$$

Resulting in:

$$OR_i = \lambda_i \frac{\sum_{i=0}^{k} f_i \lambda_i - p(D)}{\sum_{i=0}^{k} f_i \lambda_i - \lambda_i p(D)},$$

By setting $$C = \sum_{i=0}^{k} f_i \lambda_i,$$

the result is $$\lambda_i = C \cdot \frac{OR_i}{p(D)OR_i + C - p(D)}.$$

Thus, by the definition of C, it is:

$$1 = \sum_{i=0}^{k} f_i \frac{\lambda_i}{C} = \sum_{i=0}^{k} \frac{f_i OR_i}{p(D)OR_i + C - p(D)}.$$

This is a polynomial equation with one variable C. Once C is determined, the relative risks are determined. The polynomial is of degree k+1, and thus we expect to have at most k+1 solutions. However, since the right-hand side of the equation is a strictly decreasing as a function of C, there can typically only be one solution to this equation. Finding this solution is easy using a binary search, since the solution is bounded between C=1 and $$C = \sum_{i=0}^{k} OR_i.$$

Robustness of the Relative Risk Estimation. The effect of each of the different parameters (prevalence, allele frequencies, and odds ratio errors) on the estimates of the relative risks was measured. In order to measure the effect of the allele frequency and prevalence estimates on the relative risk values, the relative risk was calculated from a set of values of different odds ratios, different allele frequencies (under HWE), and plotted the results of these calculations for a prevalence values ranging from 0 to 1.

Additionally, for fixed values of the prevalence, the resulting relative risks as a function of the risk-allele frequencies was plotted. Evidently, in all cases when $p(D)=0$, $\lambda_{RR}=OR_{RR}$, and $\lambda_{RN}=OR_{RN}$, and when $p(D)=1$, $\lambda_{RR}=\lambda_{RN}=0$. This can be computed directly from Equation 1. Additionally, when the risk allele frequency is high, $\lambda_{RR}$ approaches a linear behavior, and $\lambda_{RN}$ approaches a concave function with a bounded second derivative. When the risk-allele frequency is low, $\lambda_{RR}$ and $\lambda_{RN}$ approach the behavior of the function $1/p(D)$. This means that for high risk-allele frequency, wrong estimates of the prevalence will not affect the resulting relative risk by much.

The following examples illustrate and explain the invention. The scope of the invention is not limited by these examples.

Example I

Generation and Analysis of SNP Profile

The individual is provided a sample tube in the kit, such as that available from DNA Genotek, into which the individual deposits a sample of saliva (approximately 4 mls) from which genomic DNA will be extracted. The saliva sample is sent to a CLIA certified laboratory for processing and analysis. The sample is typically sent to the facility by overnight mail in a shipping container that is conveniently provided to the individual in the collection kit.

In a preferred embodiment, genomic DNA is isolated from saliva. For example, using DNA self collection kit technology available from DNA Genotek, an individual collects a specimen of about 4 ml saliva for clinical processing. After delivery of the sample to an appropriate laboratory for processing, DNA is isolated by heat denaturing and protease digesting the sample, typically using reagents supplied by the collection kit supplier at 50° C. for at least one hour. The sample is next centrifuged, and the supernatant is ethanol precipitated. The DNA pellet is suspended in a buffer appropriate for subsequent analysis.

The individual's genomic DNA is isolated from the saliva sample, according to well known procedures and/or those provided by the manufacturer of a collection kit. Generally, the sample is first heat denatured and protease digested. Next, the sample is centrifuged, and the supernatant is retained. The supernatant is then ethanol precipitated to yield a pellet containing approximately 5-16 ug of genomic DNA. The DNA pellet is suspended in 10 mM Tris pH 7.6, 1 mM EDTA (TE). A SNP profile is generated by hybridizing the genomic DNA to a commercially available high density SNP array, such as those available from Affymetrix or Illumina, using instrumentation and instructions provided by the array manufacturer. The individual's SNP profile is deposited into a secure database or vault.

The patient's data structure is queried for risk-imparting SNPs by comparison to a clinically-derived database of established, medically relevant SNPs whose presence in a genome correlates to a given disease or condition. The database contains information of the statistical correlation of particular SNPs and SNP haplotypes to particular diseases or conditions. For example, as shown in Example III, polymorphisms in the apolipoprotein E gene give rise to differing isoforms of the protein, which in turn correlate with a statistical likelihood of developing Alzheimer's Disease. As another example, individuals possessing a variant of the blood clotting protein Factor V known as Factor V Leiden have an increased tendency to clot. A number of genes in which SNPs have been associated to a disease or condition phenotype are shown in Table 1. The information in the database is approved by a research/clinical advisory board for its scientific accuracy and importance, and may be reviewed with governmental agency oversight. The database is continually updated as more SNP-disease correlations emerge from the scientific community.

The results of the analysis of an individual's SNP profile is securely provided to patient by an on-line portal or mailings. The patient is provided interpretation and supportive information, such as the information shown for Factor V Leiden in Example IV. Secure access to the individual's SNP profile information, such as through an on-line portal, will facilitate discussions with the patient's physician and empower individual choices for personalized medicine.

Example II

Update of Genotype Correlations

In response to a request for an initial determination of an individual's genotype correlations, a genomic profile is generated, genotype correlations are made, and the results are provided to the individual as described in Example I. Following an initial determination of an individual's genotype correlations, subsequent, updated correlations are or can be determined as additional genotype correlations become known. The subscriber has a premium level subscription and their genotype profile and is maintained in a secure database. The updated correlations are performed on the stored genotype profile.

For example, an initial genotype correlation, such as described above in Example I, could have determined that a particular individual does not have ApoE4 and thus is not predisposed to early-onset Alzheimer's Disease, and that this individual does not have Factor V Leiden. Subsequent to this initial determination, a new correlation could become known and validated, such that polymorphisms in a given gene, hypothetically gene XYZ, are correlated to a given condition, hypothetically condition 321. This new genotype correlation is added to the master database of human genotype correlations. An update is then provided to the particular individual by first retrieving the relevant gene XYZ data from the particular individual's genomic profile stored in a secure database. The particular individual's relevant gene XYZ data is compared to the updated master database information for gene XYZ. The particular individual's susceptibility or genetic predisposition to condition 321 is determined from this comparison. The results of this determination are added to the particular individual's genotype correlations. The updated results of whether or not the particular individual is susceptible or genetically predisposed to condition 321 is provided to the particular individual, along with interpretative and supportive information.

Example III

Correlation of ApoE4 Locus and Alzheimer's Disease

The risk of Alzheimer's disease (AD) has been shown to correlate with polymorphisms in the apolipoprotein E (APOE) gene, which gives rise to three isoforms of APOE referred to as ApoE2, ApoE3, and ApoE4. The isoforms vary from one another by one or two amino acids at residues 112 and 158 in the APOE protein. ApoE2 contains 112/158 cys/cys; ApoE3 contains 112/158 cys/arg; and ApoE4 contains 112/158 arg/arg. As shown in Table 3, the risk of Alzheimer's disease onset at an earlier age increases with the number of APOE ε4 gene copies. Likewise, as shown in Table 3, the relative risk of AD increases with number of APOE ε4 gene copies.

TABLE 3

Prevalence of AD Risk Alleles (Corder et al., Science: 261: 921-3, 1993)

| APOE ε4 Copies | Prevalence | Alzheimer's Risk | Onset Age |
|---|---|---|---|
| 0 | 73% | 20% | 84 |
| 1 | 24% | 47% | 75 |
| 2 | 3% | 91% | 68 |

TABLE 4

Relative Risk of AD with ApoE4 (Farrer et al., JAMA: 278: 1349-56, 1997)

| APOE Genotype | Odds Ratio |
|---|---|
| ε2ε2 | 0.6 |
| ε2ε3 | 0.6 |
| ε3ε3 | 1.0 |
| ε2ε4 | 2.6 |
| ε3ε4 | 3.2 |
| ε4ε4 | 14.9 |

Example IV

Information for Factor V Leiden Positive Patient

The following information is exemplary of information that could be supplied to an individual having a genomic SNP profile that shows the presence of the gene for Factor V Leiden. The individual may have a basic subscription in which the information may be supplied in an initial report.
What is Factor V Leiden?
Factor V Leiden is not a disease, it is the presence of a particular gene that is passed on from one's parents. Factor V Leiden is a variant of the protein Factor V (5) which is needed for blood clotting. People who have a Factor V deficiency are more likely to bleed badly while people with Factor V Leiden have blood that has an increased tendency to clot.
People carrying the Factor V Leiden gene have a five times greater risk of developing a blood clot (thrombosis) than the rest of the population. However, many people with the gene will never suffer from blood clots. In Britain and the United States, 5 percent of the population carry one or more genes for Factor V Leiden, which is far more than the number of people who will actually suffer from thrombosis.
How do You get Factor V Leiden?
The genes for the Factor V are passed on from one's parents. As with all inherited characteristics, one gene is inherited from the mother and one from the father. So, it is possible to inherit: —two normal genes or one Factor V Leiden gene and one normal gene -or two Factor V Leiden genes. Having one Factor V Leiden gene will result in a slightly higher risk of developing a thrombosis, but having two genes makes the risk much greater.
What are the Symptoms of Factor V Leiden?
There are no signs, unless you have a blood clot (thrombosis).
What are the Danger Signals?
The most common problem is a blood clot in the leg. This problem is indicated by the leg becoming swollen, painful and red. In rarer cases a blood clot in the lungs (pulmonary thrombosis) may develop, making it hard to breathe. Depending on the size of the blood clot this can range from being barely noticeable to the patient experiencing severe respiratory difficulty. In even rarer cases the clot might occur in an arm or another part of the body. Since these clots formed in the veins that take blood to the heart and not in the arteries (which take blood from the heart), Factor V Leiden does not increase the risk of coronary thrombosis.
What can be Done to Avoid Blood Clots?
Factor V Leiden only slightly increases the risk of getting a blood clot and many people with this condition will never experience thrombosis. There are many things one can do to avoid getting blood clots. Avoid standing or sitting in the same position for long periods of time. When traveling long distances, it is important to exercise regularly—the blood must not 'stand still'. Being overweight or smoking will greatly increase the risk of blood clots. Women carrying the Factor V Leiden gene should not take the contraceptive pill as this will significantly increase the chance of getting thrombosis. Women carrying the Factor V Leiden gene should also consult their doctor before becoming pregnant as this can also increase the risk of thrombosis.
How does a Doctor Find Out if You have Factor V Leiden?
The gene for Factor V Leiden can be found in a blood sample.
A blood clot in the leg or the arm can usually be detected by an ultrasound examination.
Clots can also be detected by X-ray after injecting a substance into the blood to make the clot stand out. A blood clot in the lung is harder to find, but normally a doctor will use a radioactive substance to test the distribution of blood flow in the lung, and the distribution of air to the lungs. The two patterns should match—a mismatch indicates the presence of a clot.
How is Factor V Leiden Treated?
People with Factor V Leiden do not need treatment unless their blood starts to clot, in which case a doctor will prescribe blood-thinning (anticoagulant) medicines such as warfarin (e.g. Marevan) or heparin to prevent further clots. Treatment will usually last for three to six months, but if there are several clots it could take longer. In severe cases the course of drug treatment may be continued indefinitely; in very rare cases the blood clots may need to be surgically removed.
How is Factor V Leiden Treated during Pregnancy?
Women carrying two genes for Factor V Leiden will need to receive treatment with a heparin coagulant medicine during pregnancy. The same applies to women carrying just one gene for Factor V Leiden who have previously had a blood clot themselves or who have a family history of blood clots.

All women carrying a gene for Factor V Leiden may need to wear special stockings to prevent clots during the last half of pregnancy. After the birth of the child they may be prescribed the anticoagulant drug heparin.

Prognosis

The risk of developing a clot increases with age, but in a survey of people over the age of 100 who carry the gene, it was found that only a few had ever suffered from thrombosis. The National Society for Genetic Counselors (NSGC) can provide a list of genetic counselors in your area, as well as information about creating a family history. Search their on-line database at www.nsgc.org/consumer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method of generating at least one Genetic Composite Index (GCI) score, wherein said GCI score represents an estimation of an individual's risk to a phenotype comprising:
   a) obtaining a genetic sample from said individual;
   b) generating a genomic profile from said genetic sample;
   c) determining at least two relative risks (RR) or odds ratios (OR) for a phenotype by comparing said individual's genomic profile to a current database of human genotype correlations wherein a human genotype correlation is a correlation between a genetic variant and a phenotype, wherein phenotype is selected from Alzheimers (AD), colorectal cancer (CRC), osteoarthritis (OA), exfoliation glaucoma (XFG), obesity (BMIOB), Graves Disease (GD), hemochromatosis (HEM), myocardial infarction (MI), multiple sclerosis (MS), psoriasis (PS), restless legs syndrome (RLS), celiac disease (CelD), prostate cancer (PC), lupus (SLE), macular degeneration (AMD), rheumatoid arthritis (RA), breast cancer (BC), Crohn's disease (CD), Type 2 diabetes (T2D), and a combination thereof, wherein the RR or OR are determined by $$OR_i^1 = \frac{P(D|n_i r_i|)}{P(D|n_i r_i|)} \cdot \frac{1 - P(D|n_i n_i|)}{1 - P(D|n_i r_i|)};$$

and wherein the genomic variant is selected from SNP is:rs4420638 when said phenotype is AD; rs6983267 when said phenotype is CRC; rs4911178 when said phenotype is OA; rs2165241 when said phenotype is XFG; rs9939609 or rs9291171 when said phenotype is BMIOB; rs3087243, DRBI*0301 DQA1*0501 when said phenotype is GD; rs1800562 or rs129128 when said phenotype is HEM; rs1866389, rs1333049, or rs6922269 when said phenotype is MI; rs6897932, rs12722489, or DRB1*1501 when said phenotype is MS; rs6859018, rs11209026, or HLAC*0602 when said phenotype is PS; rs6904723, rs2300478, rs1026732, or rs9296249 when said phenotype is RLS; rs6840978, rs11571315, rs2187668, or DQA1*0301 DQB1*0302 when said phenotype is CelD; rs4242384, rs6983267, rs16901979, rs17765344, or rs4430796 when said phenotype is PC; rs12531711, rs10954213, rs2004640, DRB1*0301, or DRB1*1501 when said phenotype is SLE; rs10737680, rs10490924, rs541862, rs2230199, rs1061170, or rs9332739 when said phenotype is AMD; rs6679677, rs11203367, rs6457617, DRB*0101, DRB1*0401, or DRB1*0404 when said phenotype is RA; rs3803662, rs2981582, rs4700485, rs3817198, rs17468277, rs6721996, or rs3803662 when said phenotype is BC; rs2066845, rs5743293, rs10883365, rs17234657, rs10210302, rs9858542, rs11805303, rs1000113, rs17221417, rs2542151, or rs10761659 when said phenotype is CD; rs13266634, rs4506565, rs10012946, rs7756992, rs10811661, rs12288738, rs8050136, rs1111875, rs4402960, rs5215, or rs1801282 when said phenotype is T2D;
   d) calculating at least one GCI score from said at least two relative risks or odds ratios using $$GCI(g_1, \ldots, g_k) = \prod_{i=1}^{k} \lambda_{g_i}^i;$$

e) reporting said at least one GCI score; and
   f) providing genetic counseling to the individual based on said at least one GCI score.

2. The method of claim 1, wherein a third party obtains said genetic sample.

3. The method of claim 1, wherein said generating of a genomic profile is by a third party.

4. The method of claim 1, wherein said reporting comprises transmission of said results over a network.

5. The method of claim 1, wherein said genomic profile is of said individual's entire genome.

6. The method of claim 1, wherein said method comprises determining said at least two relative risks or odds ratios from 10 or more genotype correlations.

7. The method of claim 1, further comprising generating a GCI Plus score.

8. The method of claim 1, wherein said genetic sample is from a biological sample selected from said group consisting of blood, hair, skin, saliva, semen, urine, fecal material, sweat, and buccal sample.

9. The method of claim 1, wherein said genotype correlations are correlations of single nucleotide polymorphisms to phenotypes that are not medical conditions.

10. The method of claim 1, wherein said genomic profile is generated using a high density DNA microarray, DNA sequencing, or PCR based method.

11. The method of claim 1, wherein said results further comprises incorporating a characteristic of said individual selected from physical data, medical data, demographic data, exposure data, lifestyle data, behavior data, ethnicity, ancestry, geography, gender, age, family history, and previously determined phenotypes.

12. The method of claim 1, wherein said genomic profile comprises a genetic marker in linkage disequilibrium with a genetic variant correlated with a phenotype.

13. The method of claim 1, wherein said GCI score is an estimated lifetime risk.

14. The method of claim 1, wherein said genomic profile comprises at least 100,000 genetic variants.

15. The method of claim 1, wherein said genomic profile comprises at least 400,000 genetic variants.

16. The method of claim 1, further comprising reporting information on said phenotype, wherein said information is selected from the group consisting of: prevention strategy, wellness information, therapy, symptom awareness, early detection scheme, intervention scheme, and refined identification and sub-classification of said phenotype.

17. The method of claim 11, wherein said individual's physical data is selected from the group consisting of: blood pressure, heart rate, glucose level, metabolite level, ion level, weight, height, cholesterol level, vitamin level, blood cell count, body mass index (BMI), protein level, and transcript level.

18. The method of claim 1, further comprising:
   f) updating said database with at least one human genotype correlation;
   g) generating at least one additional relative risk or odds ratio for said phenotype by comparing said individual's genomic profile to said at least one human genotype correlation of step f);
   h) calculating at least one updated Genetic Composite Index (GCI) from said at least one additional relative risk or odds ratio determined in step g); and,
   i) reporting said results from step h) to said individual or a health care manager of said individual.

19. The method of claim 1, wherein the reporting of said at least one GCI score comprises electronic transmission.

20. The method of claim 19, wherein the reporting comprises transmission of said at least one GCI score via an online portal.

21. The method of claim 19, wherein the reporting comprises transmission of said at least one GCI score over a network.

\* \* \* \* \*